United States Patent
Darowski et al.

(10) Patent No.: US 12,038,441 B2
(45) Date of Patent: Jul. 16, 2024

(54) CAR-T REPORTER BASED DIAGNOSTIC ASSAYS TO DETECT TUMOR ANTIGENS IN CANCER PATIENTS

(71) Applicant: Hoffmann-La Roche Inc., Little Falls, NJ (US)

(72) Inventors: Diana Darowski, Gerbrunn (DE); Camille Loise Sophie Delon, Oberengstringen (CH); Lydia Jasmin Hanisch, Birmensdorf (CH); Christian Jost, Zurich (CH); Christian Klein, Bonstetten (CH); Ekkehard Moessner, Kreuzlingen (CH); Vesna Pulko, Zurich (CH); Wei Xu, Urdorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 783 days.

(21) Appl. No.: 17/061,795

(22) Filed: Oct. 2, 2020

(65) Prior Publication Data

US 2021/0018509 A1    Jan. 21, 2021

Related U.S. Application Data

(63) Continuation of application No. PCT/EP2019/058215, filed on Apr. 2, 2019.

(30) Foreign Application Priority Data

Apr. 4, 2018 (EP) .................................. 18165605

(51) Int. Cl.
*G01N 33/574* (2006.01)
(52) U.S. Cl.
CPC .............................. *G01N 33/57492* (2013.01)
(58) Field of Classification Search
CPC ....... G01N 33/57492; G01N 33/57484; G01N 33/56972
See application file for complete search history.

(56) References Cited

FOREIGN PATENT DOCUMENTS

| JP | 2017-522879 A | 8/2017 |
| WO | 2015/143224 A1 | 9/2015 |
| WO | 2016/014535 A1 | 1/2016 |
| WO | 2017/091546 A1 | 6/2017 |

OTHER PUBLICATIONS

Cheng, Z., "Reporter Gene Immunotherapy Bioassays" Poster BEBPA 2016, ( Sep. 30, 2016).
"International Preliminary Report on Patentability—PCT/EP2019/058215" (Report Issuance Date: Oct. 6, 2020—Chapter I; w\Written Opinion), :pp. 1-7 (Oct. 15, 2020).
"International Search Report—PCT/EP2019/058215":pp. 1-6 (Apr. 26, 2019).
Li, S., et al., "An ultrasensitive bioluminogenic probe of γ-Glutamyltranspeptidase in vivo and in human serum for tumor diagnosis" Biosens Bioelectron 98:325-329 (Dec. 15, 2017).
Rodgers, D., et al., "Switch-mediated activation and retargeting of CAR-T cells for B-cell malignancies" PNAS USA 113(4):E459-E468 (Jan. 12, 2016).
Santos, E.B., et al., "Sensitive in vivo imaging of T cells utilizing a membrane bound Gaussia princeps luciferase enzyme" Nat Med 15(3):338-344 (Feb. 15, 2009).
Schroten, C., et al., "T cell activation upon exposure to patient-derived tumor tissue: A functional assay to select patients for adoptive T cell therapy" J Immunol Methods 359(1-2):11-20 (Jul. 31, 2010).
Tamada, K., et al., "Redirecting Gene-Modified T Cells toward Various Cancer Types Using Tagged Antibodies" Clin Cancer Res 18(23):6436-6445 (Dec. 1, 2012).

*Primary Examiner* — Elly-Gerald Stoica
(74) *Attorney, Agent, or Firm* — Jonathan Aumais

(57) ABSTRACT

The present invention generally relates to diagnostic assays using cell cultures, in particular to chimeric antigen receptor (CAR) expressing reporter cell assays to analyze samples, in particular patient samples, to diagnose cancer by quantifying the expression of tumor antigens and/or predicting clinical response to cancer immunotherapies. A further aspect of the present invention is to improve safety of e.g., cancer immunotherapies.

18 Claims, 36 Drawing Sheets

Specification includes a Sequence Listing.

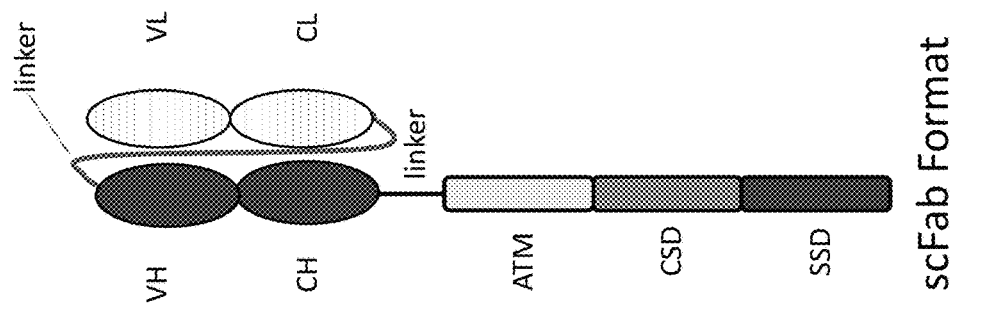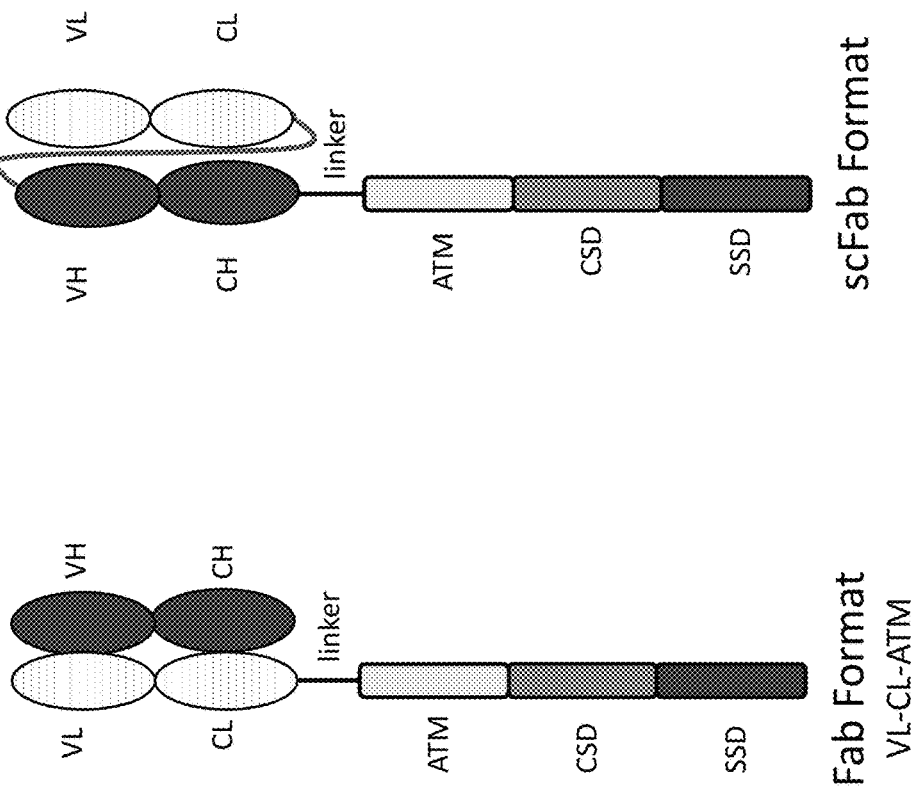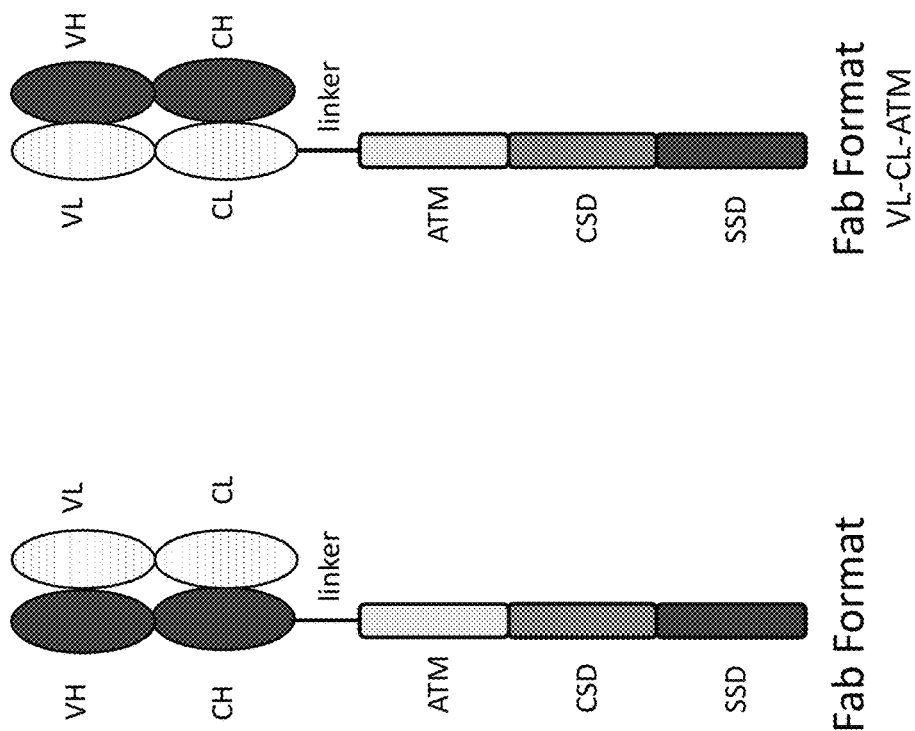

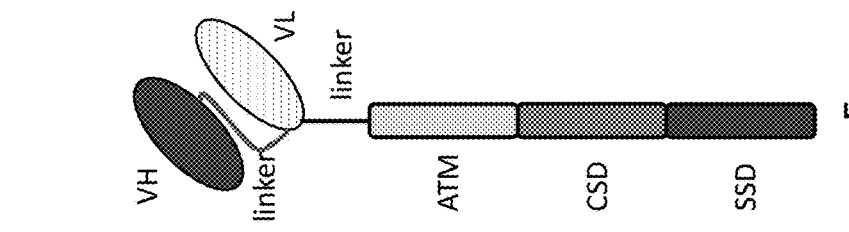
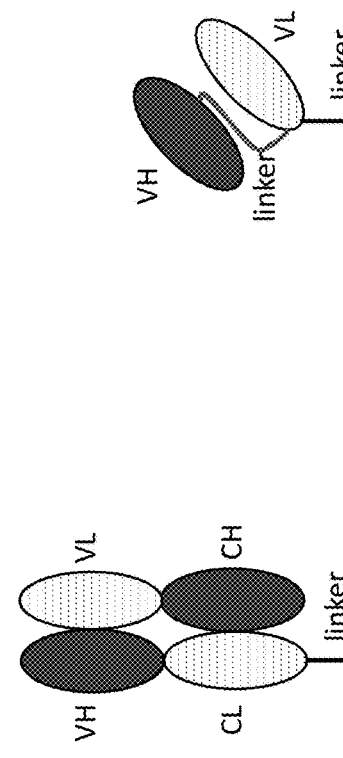
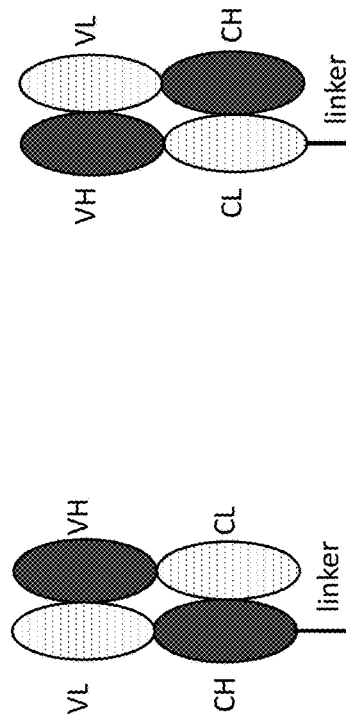
ATM = anchoring transmembrane domain; CSD = co-stimulatory signaling domain; SSD = stimulatory signaling domain

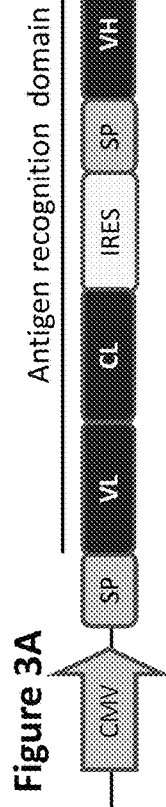
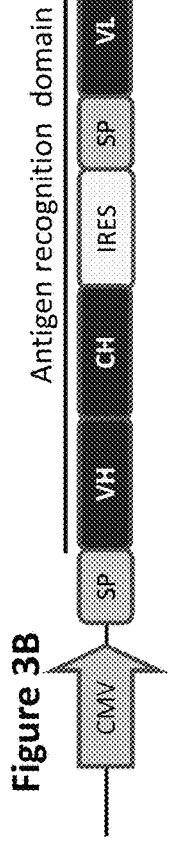
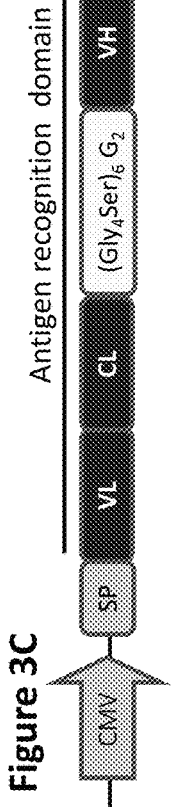
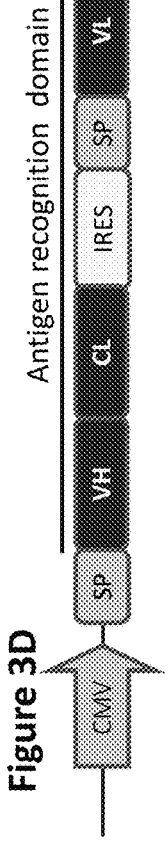
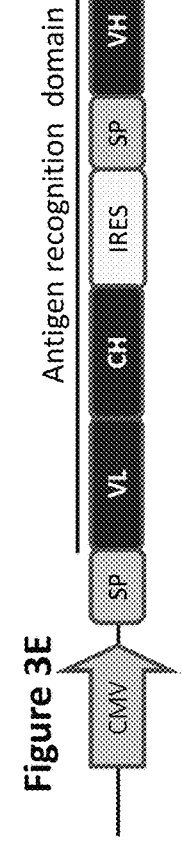
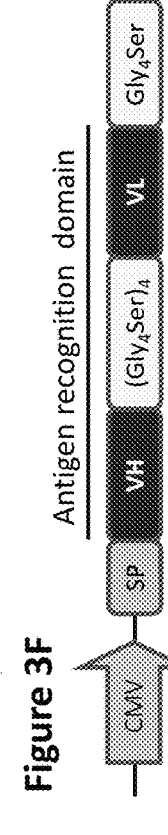
CMV = Cytomegalovirus promotor, SP= Signal peptide, VH = variable heavy chain, VL = variable light chain, TM = transmembrane domain, IRES= internal ribosomal entry site

Digoxigenin

*Synonym:* *3β,12β,14β,21-Tetrahydroxy-20(22)-norcholenic acid lactone, 3β,12β,14-Trihydroxy-5β,20(22)-cardenolide, 5β,20(22)-Cardenolide-3β,12β,14-triol, Lanadigigenin*

CAR-T REPORTER BASED DIAGNOSTIC ASSAYS TO DETECT TUMOR ANTIGENS IN CANCER PATIENTS

CROSS REFERENCE TO RELATED APPLICATIONS

This application is a continuation of International Application No. PCT/EP2019/058215, filed Apr. 2, 2019, which claims benefit to European Patent Application No. 18165605.9, filed Apr. 4, 2018, which are incorporated herein by reference in its entirety.

SEQUENCE LISTING

This application contains a Sequence Listing which has been submitted electronically in ASCII format and is hereby incorporated by reference in its entirety. Said ASCII copy, created on Sep. 23, 2020, is named P34755_US_Sequence_listing and is 168,243 bytes in size.

FIELD OF THE INVENTION

The present invention generally relates to diagnostic assays using cell cultures, in particular to chimeric antigen receptor (CAR) expressing reporter cell assays to analyze samples, in particular patient samples, to diagnose cancer by quantifying the expression of tumor antigens and/or predicting clinical response to cancer immunotherapies. A further aspect of the present invention is to improve safety of e.g., cancer immunotherapies.

BACKGROUND

Cancer is one of the leading causes for death throughout all age cohorts. Cancer is an abnormal stage of cells which leads to uncontrolled proliferation of one or more cell populations. Ultimately, the proliferation leads to aberration of normal biological function leading to a plurality of clinical and non-clinical symptoms. Tumor cells typically display one or several of properties which distinguish the tumor cells from normal cells, such as morphology, expression of fetal antigens, lack of contact inhibition and growth-factor independence.

Unfortunately, most cancers are asymptomatic at an early stage of the disease leading to the challenging situation that, e.g., for lung cancers, only 15% are found at an early, still localized stage. However, for such early diagnosed patents, the five-year survival rate can be as high as 85% whereas only 2% of such patients survive 5 years after the cancer has spread to other organs. Despite of decades of encouraging improvements to cancer therapy, the most significant predictor for successful treatment of cancer remains early detection and classification of the disease.

Typically, the immune system does not alarm and trigger recognition of tumor cells owing to the nature of these cells originated from the "self". Cancer immunotherapies are aimed to harness the immune system to target tumor cells by recognizing unique proteins exclusively expressed by tumors, and simultaneously engaging immune cell action e.g. via antibody-dependent cytotoxicity (ADCC) or T cell cytotoxicity which enables destruction of the tumor cells. This engagement can be achieved via classical ADCC-competent and/or T cell bispecific antibodies, or T cells engineered to express the native T-cell receptor (TCR-T) recognizing the tumor antigen or an artificial chimeric antigen (CAR-T). The antibodies recognize either conventional tumor surface proteins or protein-derived peptides presented in the context of MHC complex (pMHC). In either approach, not all the patients respond to the therapies in the clinics as the density of the tumor antigens expressed on the tumor cell surface or pMHC varies largely among patients across all cancer types.

Therefore, a valid tool to detect and quantify the amount of tumor antigens (surface and/or pMHC) would warrant a better diagnosis of cancer patients, and could predict the likelihood of the clinical response to the respective cancer immunotherapies. Furthermore, cancer immunotherapies can sometimes trigger unwanted immune response targeting normal tissues. Early prediction of the safety of immunotherapies would be helpful for the physicians to monitor the potential lethal side effect in patients.

The detection of tumor antigens in diverse body fluids remains of utmost importance given, e.g., that the presence of already a very small number of viable tumor cells in lymph or blood may indicate an important hall mark in the disease progression. Immunological diagnostic assays provide an important tool towards this end capable of detecting a variety of disease conditions. However, such assays may not always be sensitive and/or specific enough to reliably detect tumor cells, e.g., in the context of MHC-presented protein-derived peptides.

Accordingly, there remains a need for highly sensitive and robust diagnostic assays to detect cancer antigens suitable for the use in detecting malignant cells and/or to predict on-target off-tissue effects to improve safety of immunotherapies and to predict response of a patent to a particular immunotherapeutic.

The present inventors developed a highly flexible assay with an integrative and straight-forward readout feasible for high-throughput formats to screen tumor antigens in cancer patients applicable to both classical surface cancer antigens and MHC complex presented protein-derived peptides. This invention applies to diagnosis of cancer patients, prediction of the clinical response to the immunotherapies, and safety measurement of the immunotherapies.

SUMMARY OF THE INVENTION

The present invention generally relates to diagnostic assays for determining the presence of a target antigen, e.g., a tumor target antigen and/or a tumor cell in a sample, particularly in a sample derived from a patient, and combines the detection of target antigen with the activation of reporter cells in response to tumor cells. The assays of the present invention are suitable to screen patient samples and allow precise measurement of antigen density in the context of surface antigens and/or MHC presented protein-derived peptides. The assays of the present invention are further useful for predicting the likelihood of the clinical response to cancer immunotherapies.

Accordingly, herein provided is a diagnostic assay for determining the presence of a tumor cell in a sample, the diagnostic assay comprising the steps of:
  a) contacting the sample with an antigen binding molecule comprising an antigen binding domain and a recognition domain, wherein the antigen binding domain comprises a target antigen binding moiety capable of specific binding to the tumor cell;
  b) contacting the sample with a chimeric antigen receptor (CAR) expressing reporter T (CAR-T) cell wherein the reporter CAR-T cell comprises:

i. a CAR capable of specific binding to the recognition domain, wherein the CAR is operationally coupled to a response element;
ii. a reporter gene under the control of the response element; and
c) determining T cell activation by measuring the expression of the reporter gene to establish the presence of the tumor cell.

In one embodiment, the antigen binding domain is a Fab fragment and the recognition domain is an Fc domain.

In one embodiment, the antigen binding molecule is an IgG class antibody, particularly an IgG1 or IgG4 isotype antibody.

In one embodiment, the recognition domain is a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.

In one embodiment, the mutant Fc domain comprises an amino acid substitution at a position selected from the group consisting of residue 117, 118, 136, 180, 193, 212, 214, and 318 of human IgG1 Fc (SEQ ID NO:132), in particular wherein the mutant human IgG1 Fc comprises the amino acid substitution leucine to alanine at residue 117, leucine to alanine at residue 118, isoleucine to alanine at position 136, asparagine to alanine at residue 180, histidine to alanine at residue 193, proline to glycine at residue 212, proline to glycine at residue 214, and/or or histidine to alanine at residue 318 of human IgG1 Fc (SEQ ID NO:132).

In one embodiment, the mutant Fc domain comprises an amino acid substitution at the position of residue 212 of human IgG1 Fc (SEQ ID NO:132), in particular wherein the mutant Fc domain comprises the amino acid substitution proline to glycine at residue 212 of human IgG1 Fc (SEQ ID NO:132).

In one embodiment, the recognition domain comprises a tag, wherein the CAR is capable of specific binding to the recognition domain comprising the tag but not capable of specific binding to the recognition domain not comprising the tag.

In one embodiment, the tag is a hapten molecule, particularly wherein the hapten molecule is selected from the group consisting of Biotin, Digoxigenin (DIG) and Fluorescein (FITC).

In one embodiment, the tag is a polypeptide tag, particularly wherein the polypeptide tag is selected from the group consisting of myc-tag, HA-tag, AviTag, FLAG-tag, His-tag, GCN4-tag, and NE-tag.

In one embodiment the CAR comprises at least one intracellular stimulatory signaling and/or co-stimulatory signaling domain.

In one embodiment, activation of the intracellular signaling and/or co-signaling domain leads to activation of the response element.

In one embodiment, activation of the response element leads to expression of the reporter gene.

In one embodiment, the sample is a patient sample derived from an individual suffering from a disease, in particular wherein the disease is cancer.

In one embodiment, provided is a diagnostic kit for determining the presence of a tumor cell in a sample, the diagnostic kit comprising:
(a) an antigen binding molecule capable of specific binding to a tumor cell; and
(b) a transduced T cell comprising (i) a CAR capable of specific binding to the antigen binding molecule and (ii) a reporter gene under the control of the response element, wherein the CAR is operationally coupled to a response element.

In one embodiment, provided is a kit as described herein for use in the diagnosis of cancer.

SHORT DESCRIPTION OF THE FIGURES

FIG. 1A to 1B depicts schematic representations of diagnostic Jurkat NFAT reporter CAR-T cell assays. FIG. 1A depicts one embodiment of the diagnostic Jurkat NFAT reporter CAR-T cell assay. The target antigen bound IgG which is digoxigeninylated at the Fc (recognition domain) can be recognized by the anti-Digoxigenin CAR expressing Jurkat NFAT reporter T cell. This recognition leads to the activation of the cell which can be detected by measuring luminescence (cps). FIG. 1B depicts another embodiment of the diagnostic Jurkat NFAT reporter CAR-T cell assay. TAA bound IgG harboring the P329G mutation can be recognized by the anti-P329G CAR expressing Jurkat NFAT reporter T cell. This recognition leads to the activation of the cell which can be detected by measuring luminescence (cps).

FIG. 2A to 2F depicts the architecture of different CAR formats used in the present invention. FIG. 2A shows the architecture of the Fab format. Depicted is the extracellular domain comprising an antigen binding moiety which consists of an Ig heavy chain fragment and an Ig light chain. Attached to the heavy chain, a linker connects the antigen recognition domain with an anchoring transmembrane domain (ATD) which is fused to an intracellular co-stimulatory signaling domain (CSD) which in turn is fused to a stimulatory signaling domain (SSD). FIG. 2B shows the architecture of the Fab format with heavy and light chain swap. Depicted is the extracellular domain comprising an antigen binding moiety which consists of an Ig heavy chain fragment and an Ig light chain. Attached to the light chain constant domain, a linker connects the antigen recognition domain with an anchoring transmembrane domain (ATD) which is fused to an intracellular co-stimulatory signaling domain (CSD) which in turn is fused to a stimulatory signaling domain (SSD). FIG. 2C shows the architecture of the scFab format. Depicted is the extracellular domain comprising an antigen binding moiety which consists of an Ig heavy chain fragment and an Ig light chain, both connected by a linker. Attached to the heavy chain, a linker connects the antigen recognition domain with an anchoring transmembrane domain (ATD) which is fused to an intracellular co-stimulatory signaling domain (CSD) which in turn is fused to a stimulatory signaling domain (SSD). FIG. 2D shows the architecture of the crossFab format with VH-VL swap. Depicted is the extracellular domain comprising an antigen binding moiety which consists of an Ig heavy chain fragment and an Ig light chain wherein the VH and VL domains are exchanged. Attached to the heavy chain constant domain, a linker connects the antigen recognition domain with an anchoring transmembrane domain (ATD) which is fused to an intracellular co-stimulatory signaling domain (CSD) which in turn is fused to a stimulatory signaling domain (SSD). FIG. 2E shows the architecture of the crossFab format with CH-CL swap. Depicted is the extracellular domain comprising an antigen binding moiety which consists of an Ig heavy chain fragment and an Ig light chain wherein the CH and CL domains are exchanged. Attached to the light chain constant domain, a linker connects the antigen recognition domain with an anchoring transmembrane domain (ATD) which is fused to an intracellular co-stimulatory signaling domain (CSD) which in turn is fused to a stimulatory signaling domain (SSD). FIG. 2F shows the architecture of the classic scFv format with an extracellular antigen recognition domain, consisting of a variable heavy and variable light chain, both connected by a linker. Attached to the variable light chain, a linker connects the antigen recognition domain with an anchoring transmembrane domain (ATD) which is fused to an intracellular co-stimulatory signaling domain (CSD) which in turn is fused to a stimulatory signaling domain (SSD).

FIG. 3A to 3F depicts a schematic representation illustrating the modular composition of exemplary expression constructs encoding CARs used according to the invention. FIG. 3A and FIG. 3B depict exemplary Fab formats. FIG. 3C depicts an exemplary scFab format. FIG. 3D and FIG. 3E depict exemplary crossFab formats. FIG. 3F depicts a classic scFv format.

Figure 6B:
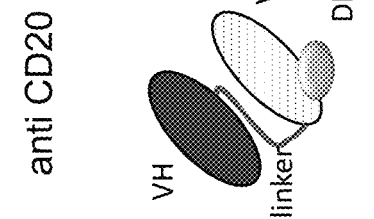
Figure 6A:

FIG. 6A and FIG. 6B depicts alternative digoxigenylated antigen binding molecules which are recognized by an anti-Digoxigenin CAR. In this embodiment, the target antigen binding domain and the recognition domain are the same domain, i.e., the Digoxigenin hapten tag is coupled to the antigen binding domain wherein the antigen binding domain exerts also the function of the recognition domain. FIG. 6A depicts an digoxigeninylated Fab molecule which can be recognized by an anti-Digoxigenin CAR. FIG. 6B depicts an digoxigenylated scFv molecule which can be recognized by an anti-Digoxigenin CAR.

Figure 7:

FIG. 7 depicts a Western Blot confirming successful digoxigenylation of the anti-CD20 targeting antibody GA101. Digoxigeninylation was detected by anti-Digoxigenin-AP Fab fragments by Western Blot analysis.

Figure 8:
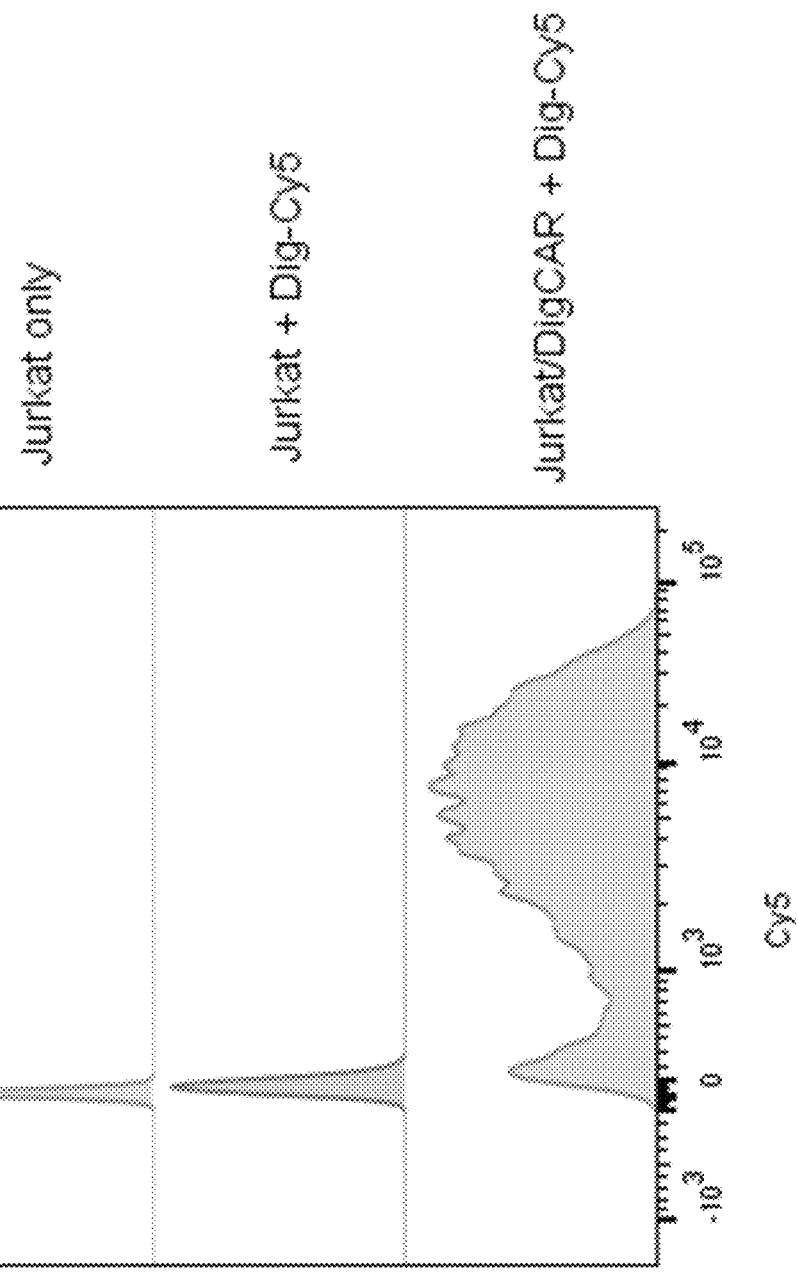

FIG. 8 depicts surface detection of anti-Digoxigenin-ds-scFv on Jurkat NFAT reporter cells.

Figure 9:
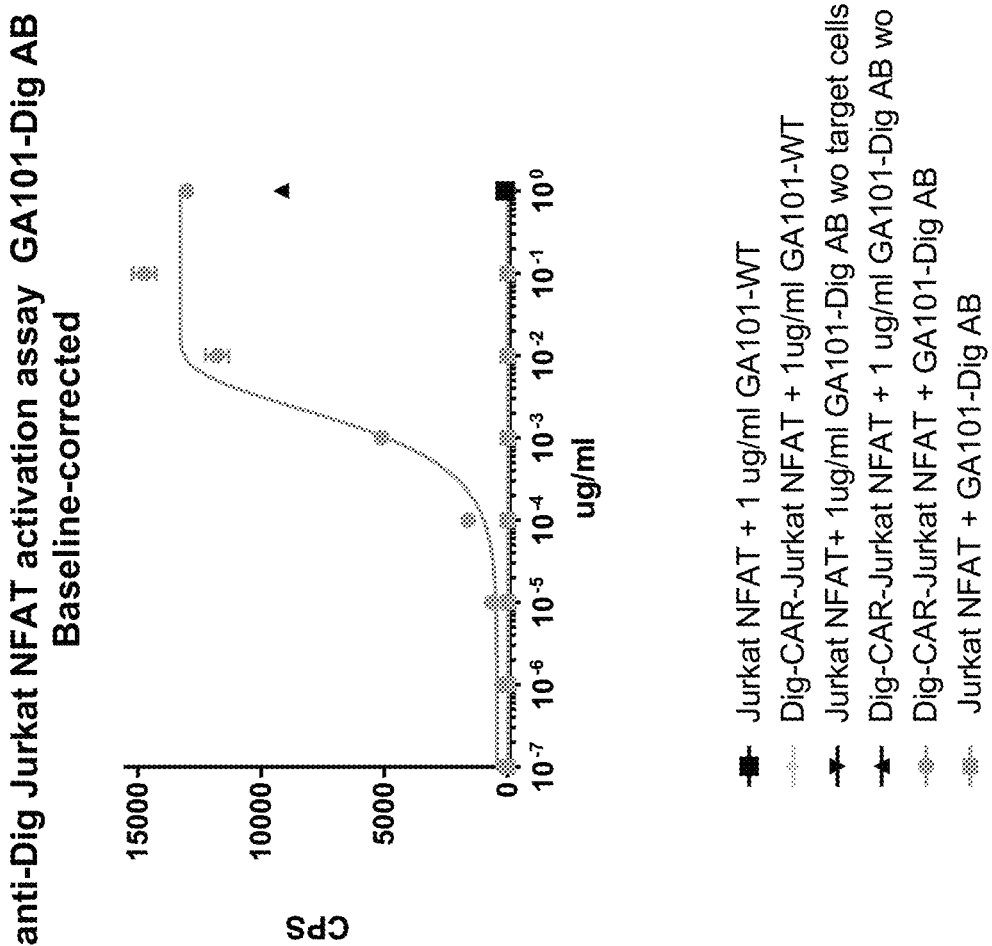

FIG. 9 depicts the diagnostic Jurkat NFAT reporter CAR-T cell assay using CD20 expressing SUDHDL4 tumor cells as target cells and an anti-CD20 IgG antibody (GA101) digoxigeninylated with a ten times molar excess of Digoxigenin-3-O-methylcarbonyl-e-aminocaproic acid-N-hydroxysuccinimide ester. The antibody recognizes on the one hand the tumor associated antigen and on the other hand is recognized by Jurkat NFAT reporter CAR-T cells. A sorted pool of anti-Digoxigenin-ds-scFv-CD28ATDCD28CSD-CD3zSSD expressing Jurkat NFAT reporter CAR-T cells was used as effector cells.

Figure 10:
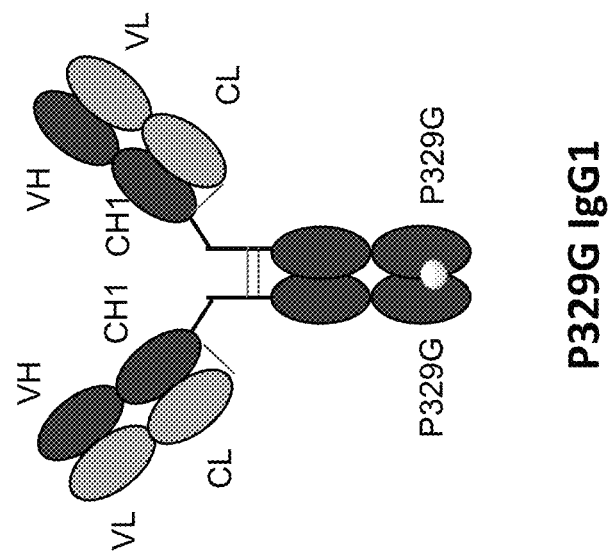

FIG. 10 depicts an exemplary IgG1 molecule harboring the P329G mutation in the Fc domain which is recognized by an anti-P329G CAR used according to the invention.

Figure 11A:
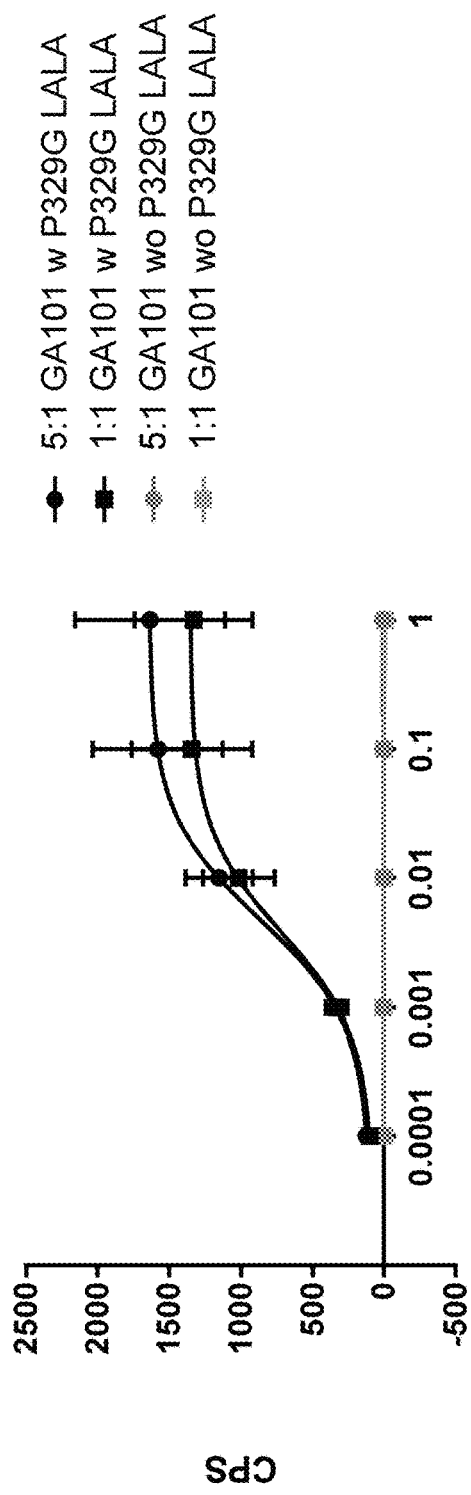
Figure 11B:
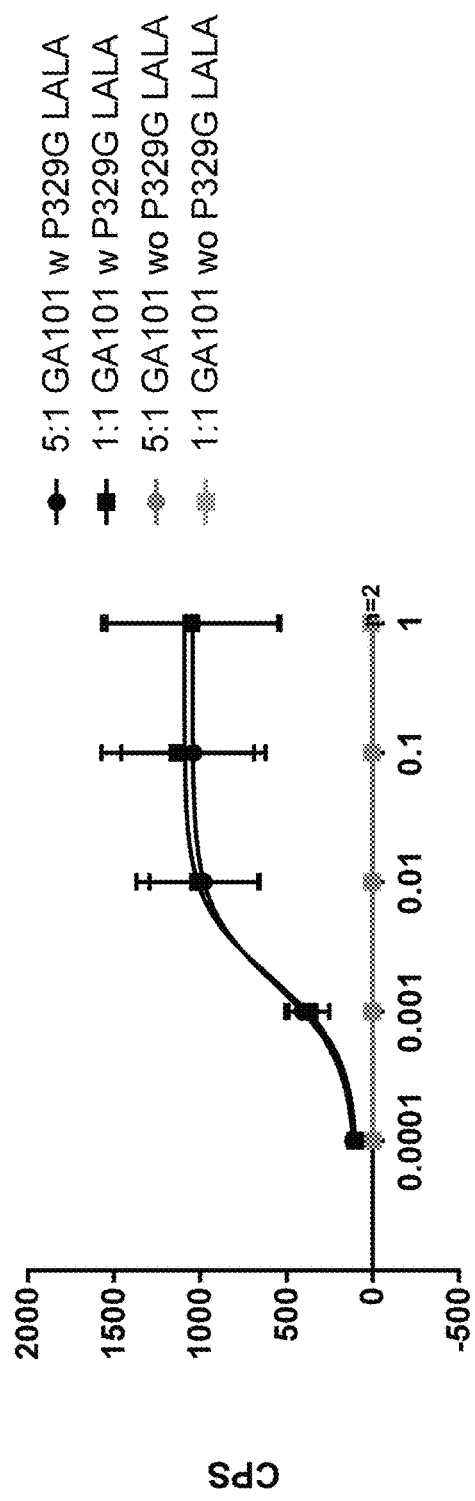

FIG. 11A and FIG. 11B depicts a diagnostic Jurkat NFAT reporter CAR-T cell assay using CD20 expressing SUDHDL4 tumor cells as target cells. An anti-CD20 IgG antibody (GA101) harboring the P329G mutation was used, which on one hand recognizes the tumor associated antigen and on the other hand is recognized by the Jurkat NFAT reporter CAR-T cells. In FIG. 11A a sorted pool of anti-P329G-ds-Fab-CD28ATD-CD28CSD-CD3zSSD expressing Jurkat NFAT reporter CAR-T cell was used as reporter cells. In FIG. 11B a sorted pool of anti-P329G-ds-scFv-CD28ATD-CD28CSD-CD3zSSD expressing Jurkat NFAT reporter CAR-T cells was used as reporter cells.

Figure 12A:
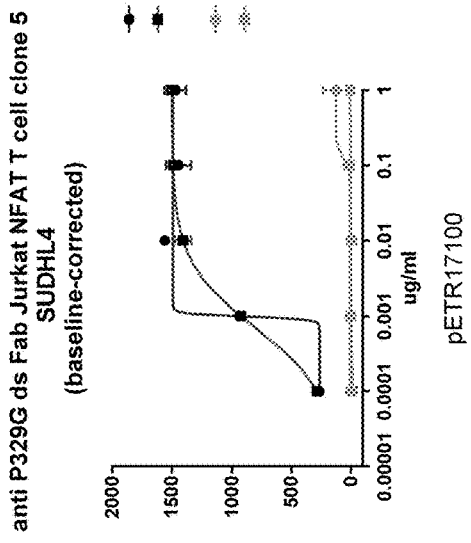
Figure 12B:
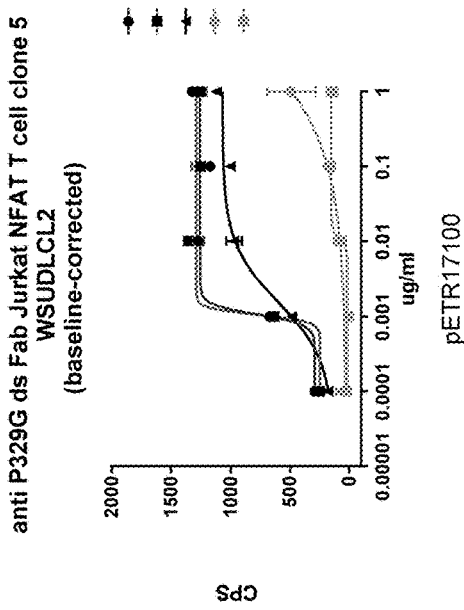
Figure 12C:
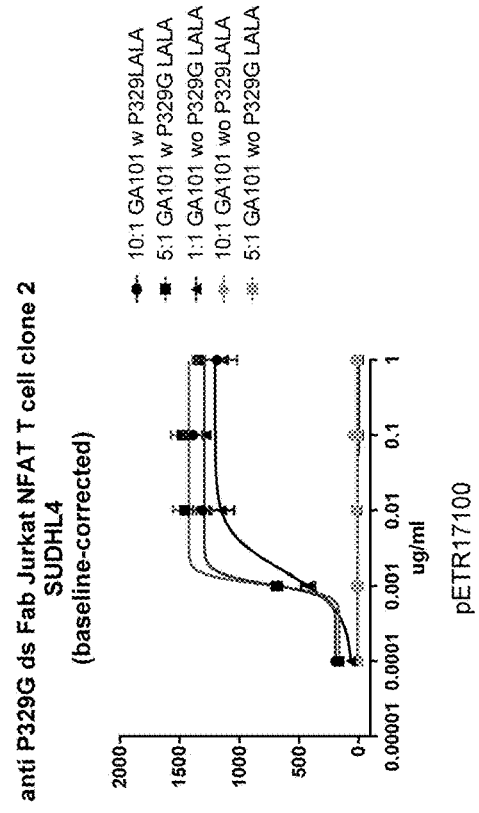
Figure 12D:
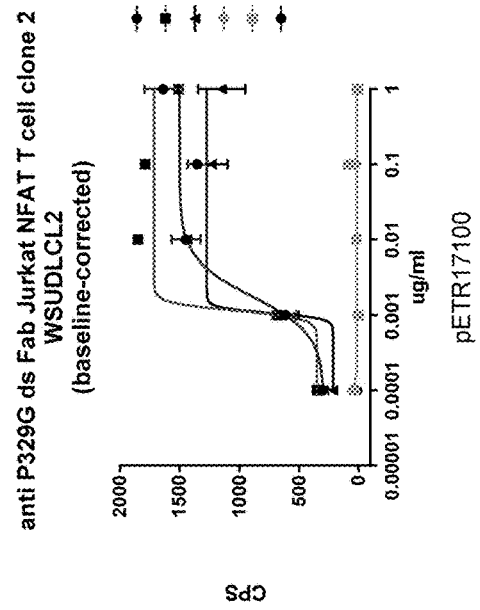

FIG. 12A to 12D depicts a diagnostic Jurkat NFAT reporter CAR-T cell assay using CD20 tumor cells as target cells. An anti-CD20 IgG antibody (GA101) harboring the P329G mutation was used which recognizes the tumor associated antigen and is recognized by the Jurkat NFAT reporter CAR-T cells used according to the invention. In FIG. 12A the single clone 5 of anti-P329G-ds-Fab-CD28ATD-CD28CSD-CD3zSSD expressing Jurkat NFAT reporter CAR-T cells was used as reporter cells and WSUDLCL2 cells as tumor cells. In FIG. 12B the single clone 2 of anti-P329G-ds-Fab-CD28ATD-CD28CSD-CD3zSSD expressing Jurkat NFAT reporter CAR-T cells was used as reporter cells and WSUDLCL2 cells as tumor cells. In FIG. 12C the single clone 5 of anti-P329G-ds-Fab-CD28ATD-CD28CSD-CD3zSSD expressing Jurkat NFAT reporter CAR-T cells was used as reporter cells and SUDHL4 cells as tumor cells. In FIG. 12D the single clone 2 of anti-P329G-ds-Fab-CD28ATD-CD28CSD-CD3zSSD expressing Jurkat NFAT reporter CAR-T cells was used as reporter cells and SUDHL4 as tumor cells.

Figure 13A:
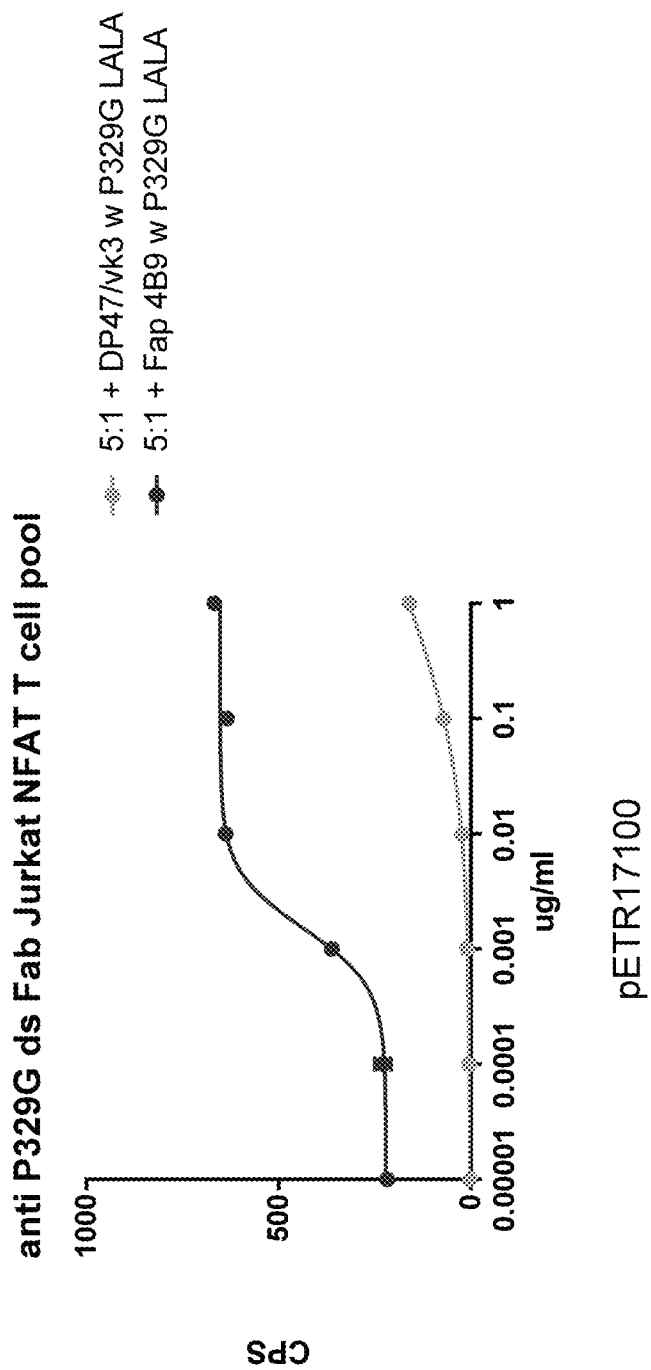
Figure 13B:
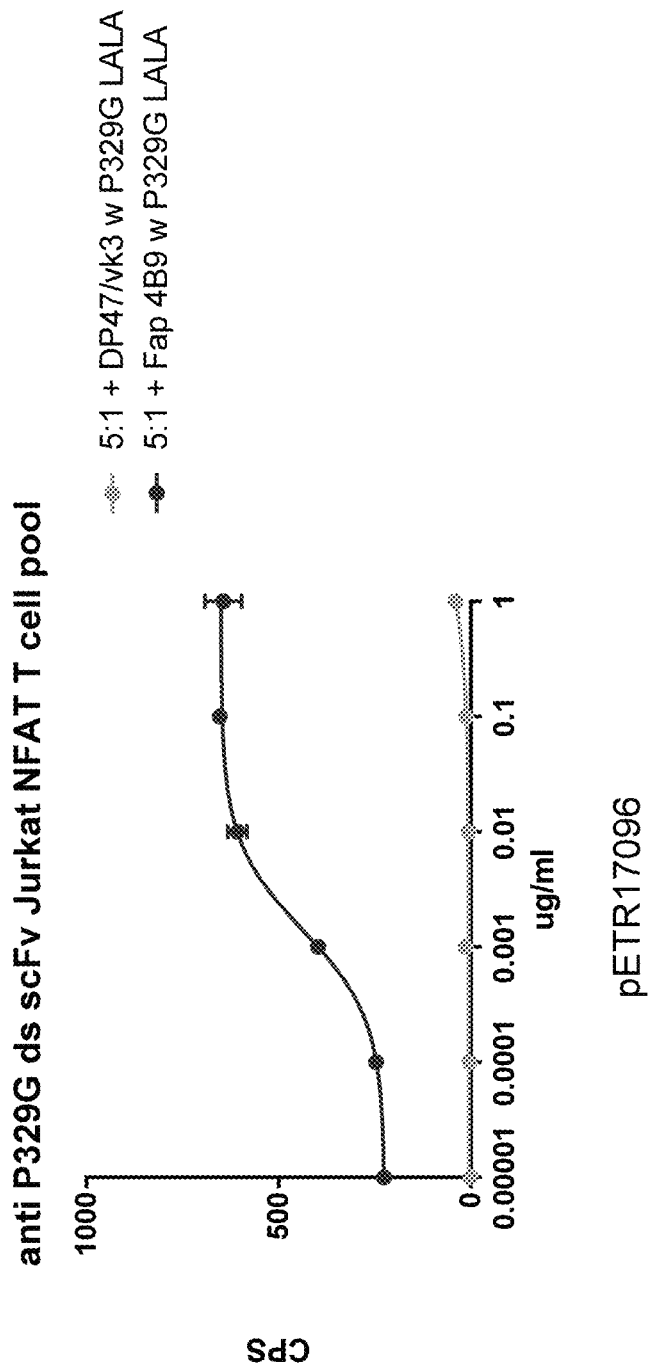
Figure 13C:
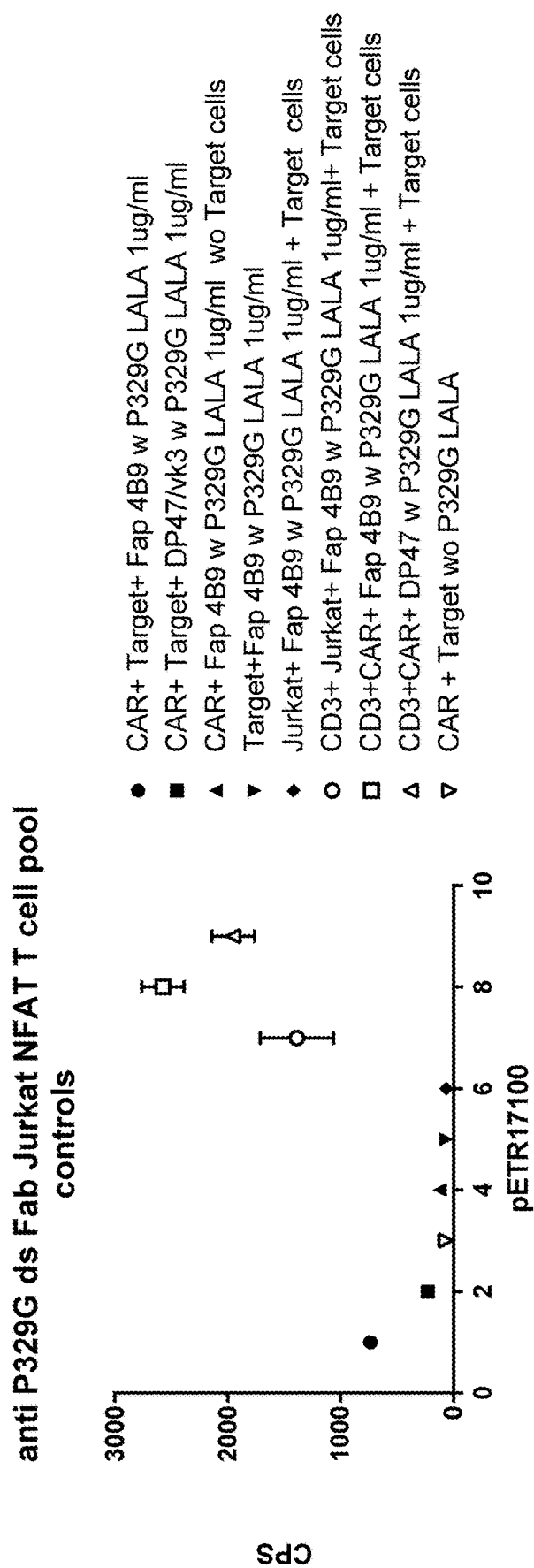
Figure 13D:
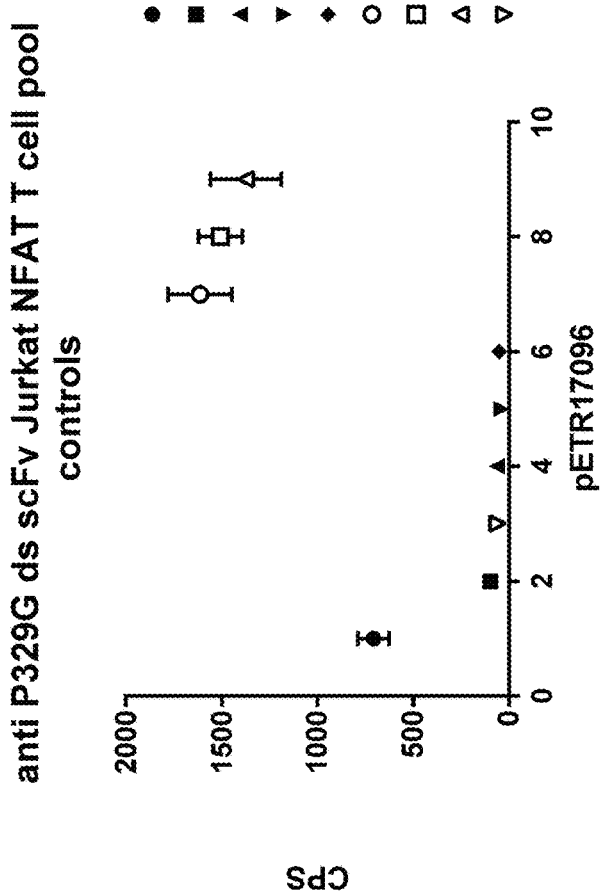
Figure 14A:
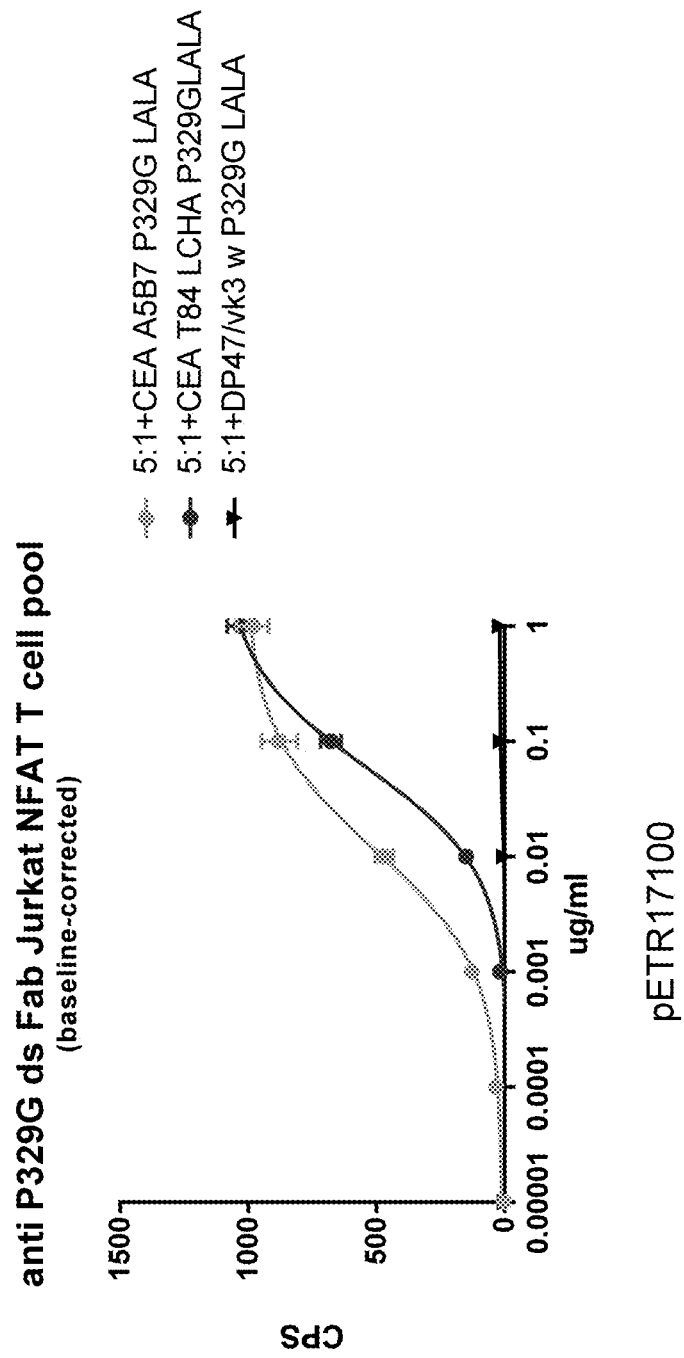

FIG. 13A to 13D depicts a diagnostic Jurkat NFAT reporter CAR-T cell assay performed using adherent FAP expressing NIH/3T3-huFAP cl 19 tumor cells as target cells. The anti-FAP IgG antibody clone 4B9 harboring the P329G mutation was used which the tumor associated antigen and is recognized by the Jurkat NFAT reporter CAR-T cells. IgG DP47/vk3 harboring P329G mutation was included as isotype control. In FIG. 13A a sorted pool of anti-P329G-ds-Fab-CD28ATD-CD28CSD-CD3zSSD expressing Jurkat NFAT reporter CAR-T cells was used as reporter cells. In FIG. 13B a sorted pool of anti-P329G-ds-scFv-CD28ATD-CD28CSD-CD3zSSD expressing Jurkat NFAT reporter CAR-T cells was used as reporter cells. In FIG. 13C a sorted pool of anti-P329G-ds-Fab-CD28ATD-CD28CSD-CD3zSSD expressing Jurkat NFAT reporter CAR-T cells was used as reporter cells. In FIG. 13D a sorted pool of anti-P329G-ds-scFv-CD28ATD-CD28CSD-CD3zSSD expressing Jurkat NFAT reporter CAR-T cells was used as reporter cells FIG. 14A to 14D depicts a diagnostic Jurkat NFAT reporter CAR-T cell assay using adherent CEA expressing MKN45 tumor cells as target cells. Either the anti-CEA IgG clone A5B7 or the anti-CEA IgG clone T84 LCHA both harboring the P329G mutation were used which recognize the tumor associated antigen and are recognized by the Jurkat NFAT reporter CAR-T cells. Further IgG DP47/vk3 harboring the P329G mutation was included as isotype control. In FIG. 14A and in FIG. 14B a sorted pool of anti-P329G-ds-Fab-CD28ATD-CD28CSD-CD3zSSD expressing NFAT T cells was used as reporter cells. In FIG. 14C and in FIG. 14D a sorted pool of anti-P329G-ds-scFv-CD28ATD-CD28CSD-CD3zSSD expressing NFAT T cells was used as reporter cells.

Figure 15A:
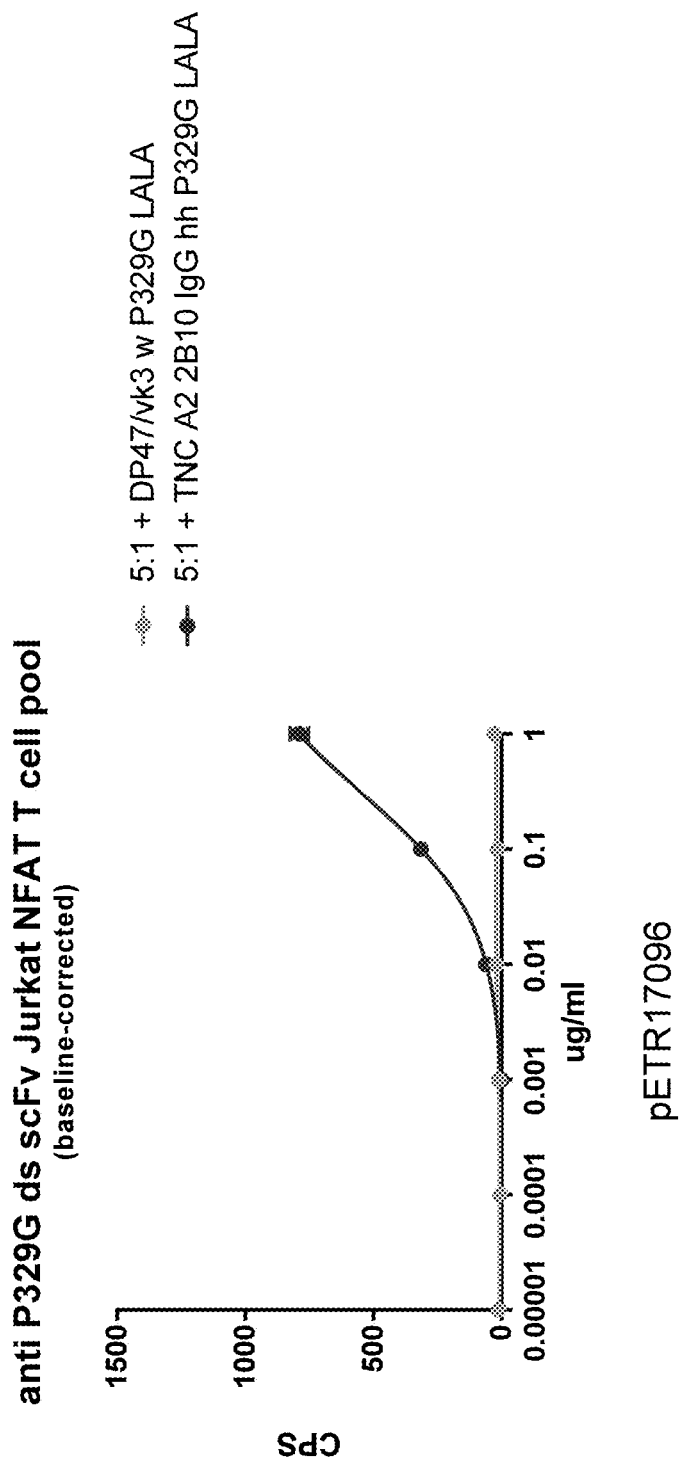
Figure 15B:
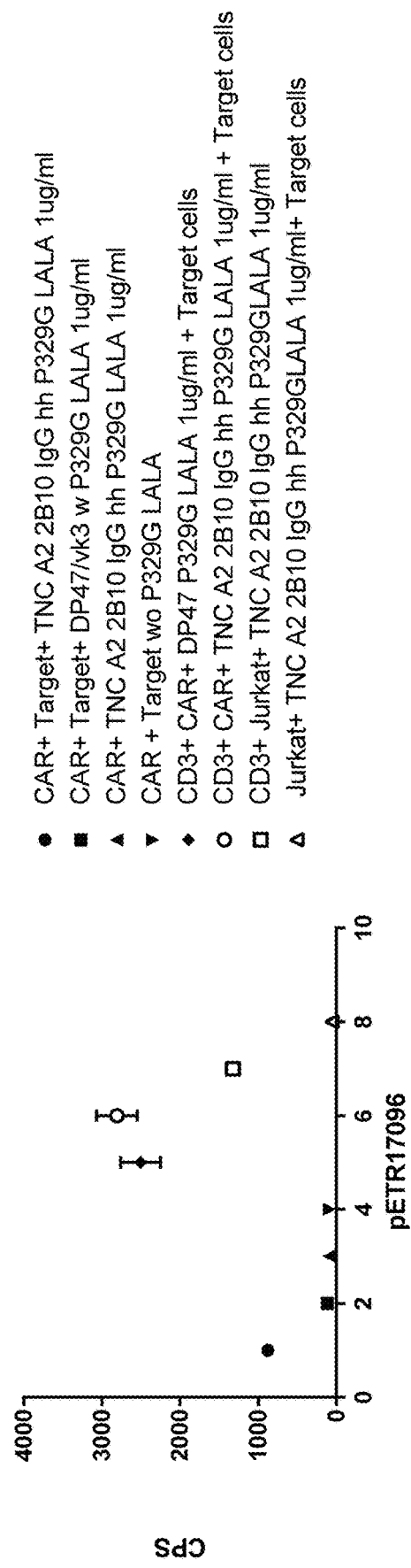
Figure 15C:
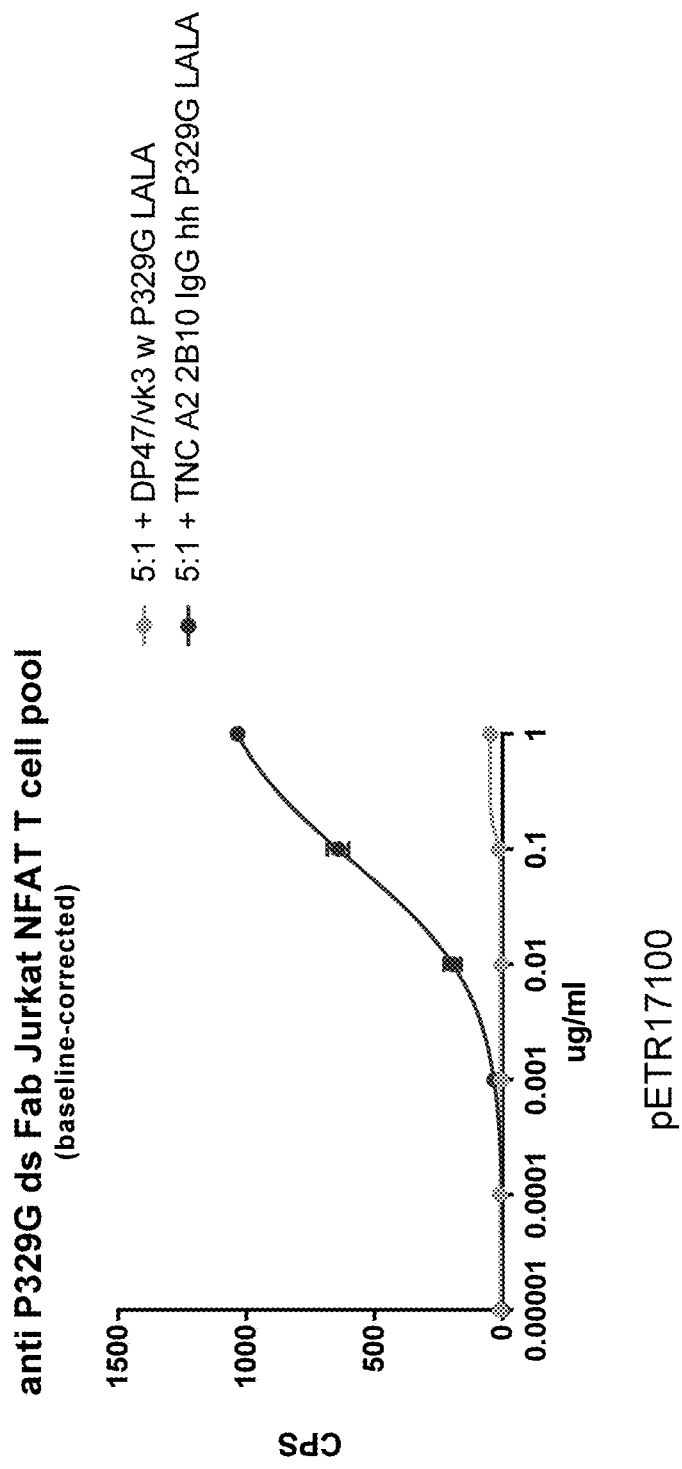

FIG. 15A to 15D depicts a diagnostic Jurkat NFAT reporter CAR-T cell assay using adherent TNC expressing CT26TNC cl 19 tumor cells as target cells. The anti-TNC IgG clone A2B10 harboring the P329G mutation was used as IgG antibody which recognizes the tumor associated antigen and is recognized by the Jurkat NFAT reporter CAR-T cells. Further IgG DP47/vk3 harboring P329G mutation was included as isotype control. In FIG. 15A and in FIG. 15B a sorted pool of anti-P329G-ds-scFv-CD28ATD-CD28CSD-CD3zSSD expressing NFAT T cells was used as reporter cells. In FIG. 15C and in FIG. 15D a sorted pool of anti-P329G-ds-Fab-CD28ATD-CD28CSD-CD3zSSD expressing NFAT T cells was used as reporter cells.

Figure 16A:
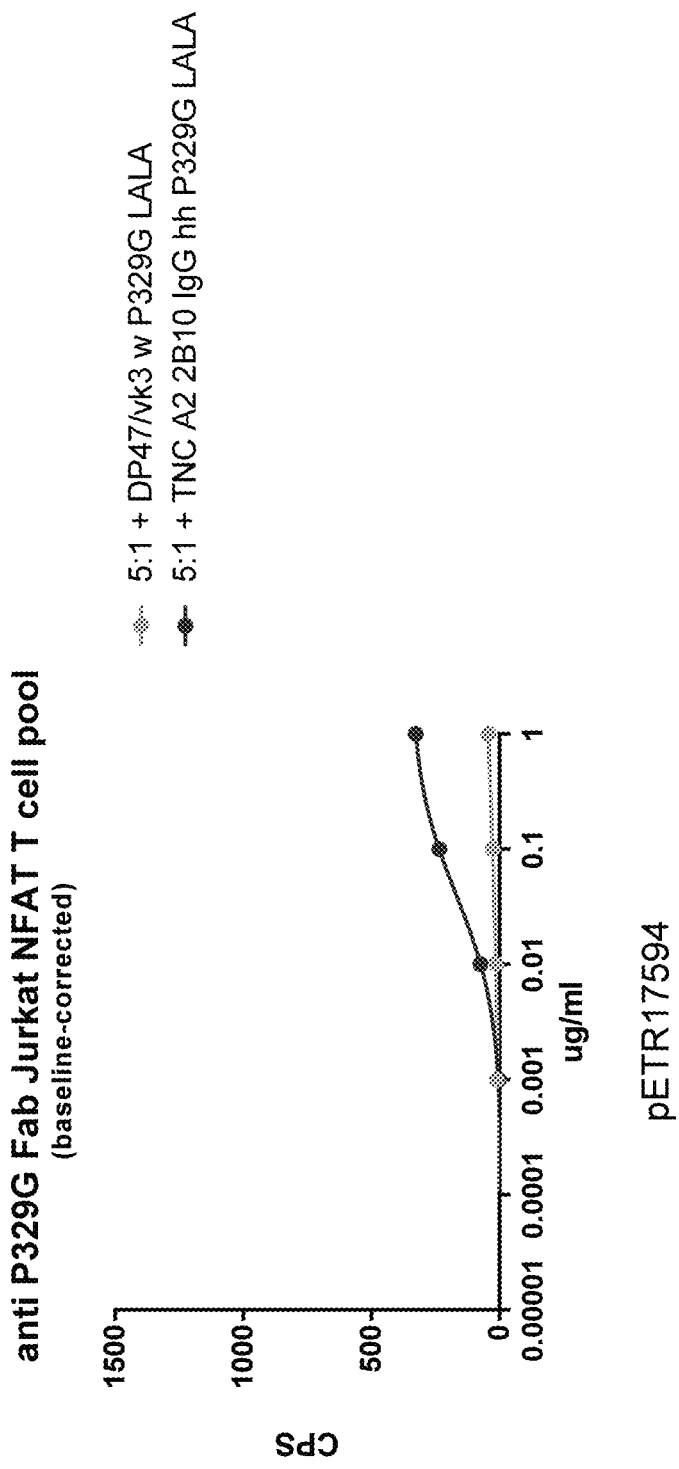
Figure 16B:
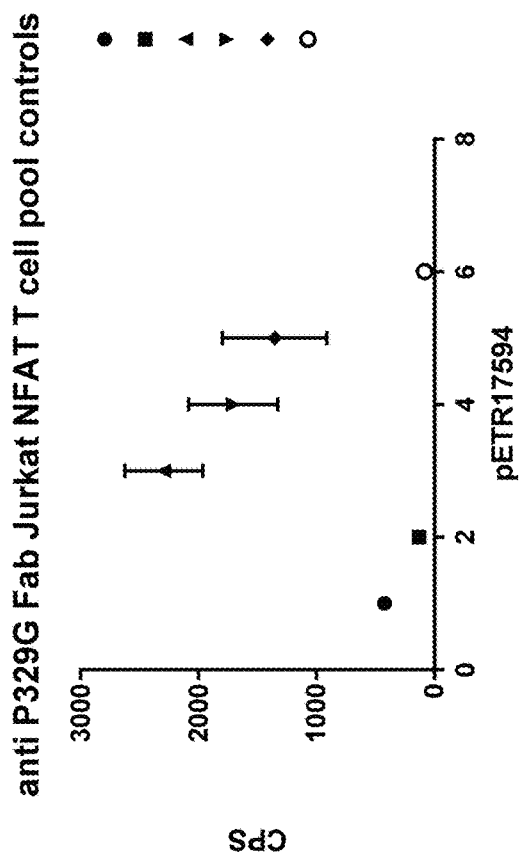

FIG. 16A and FIG. 16B depict a diagnostic Jurkat NFAT reporter CAR-T cell assay using adherent TNC expressing CT26TNC cl 19 tumor cells as target cells. The anti-TNC IgG clone A2B10 harboring the P329G mutation was used which recognizes the tumor associated antigen and is recognized by the Jurkat NFAT reporter CAR-T cells. Further IgG DP47/vk3 harboring P329G mutation was included as isotype control. A sorted pool of anti-P329G-Fab-CD28ATD-CD28CSD-CD3zSSD expressing Jurkat NFAT reporter CAR-T cells was used as reporter cells.

Figure 17:
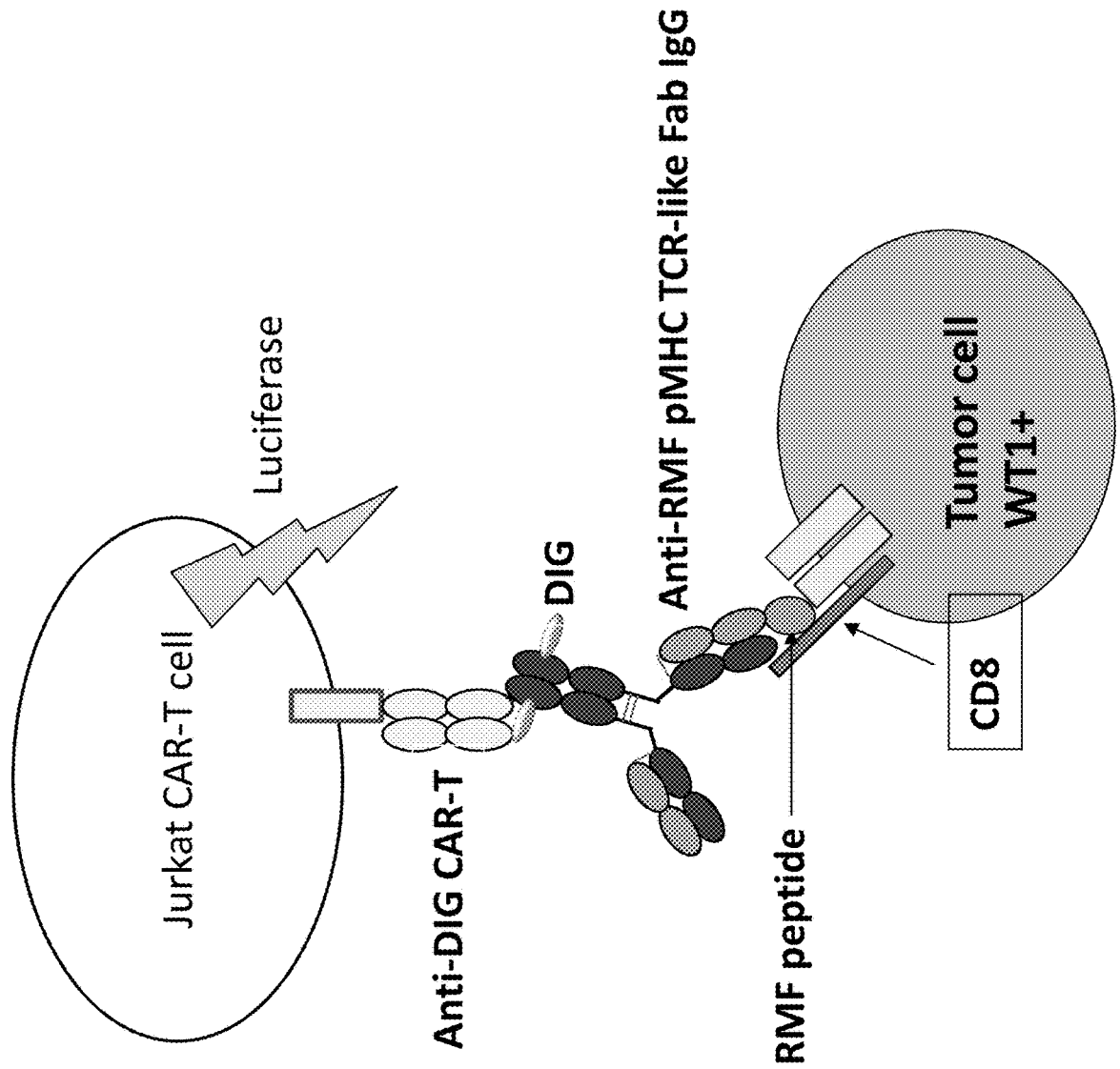
Figure 18A:
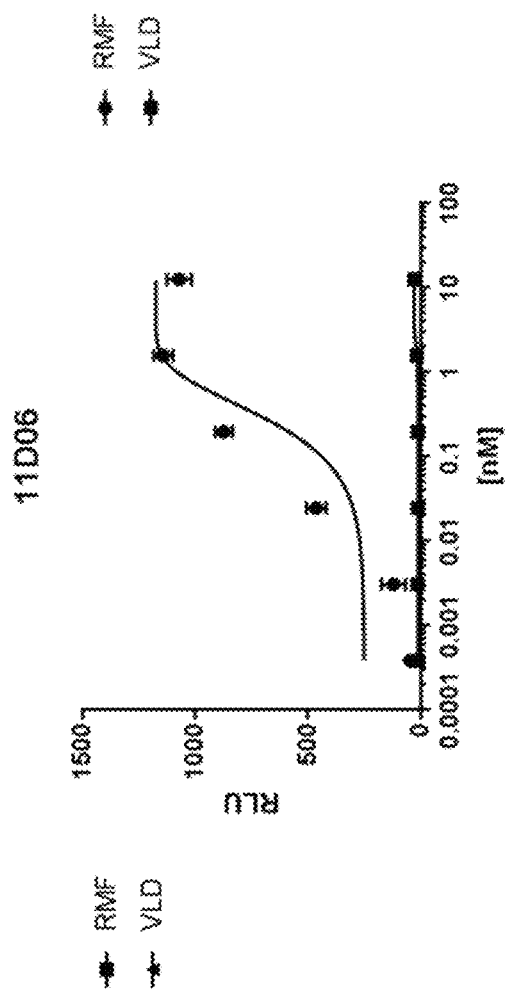
Figure 18B:
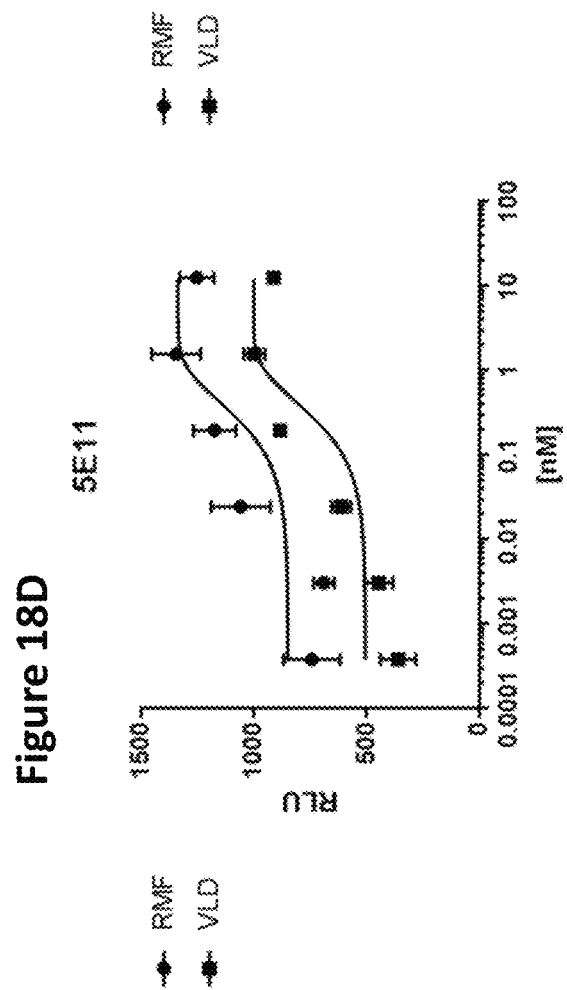
Figure 18C:
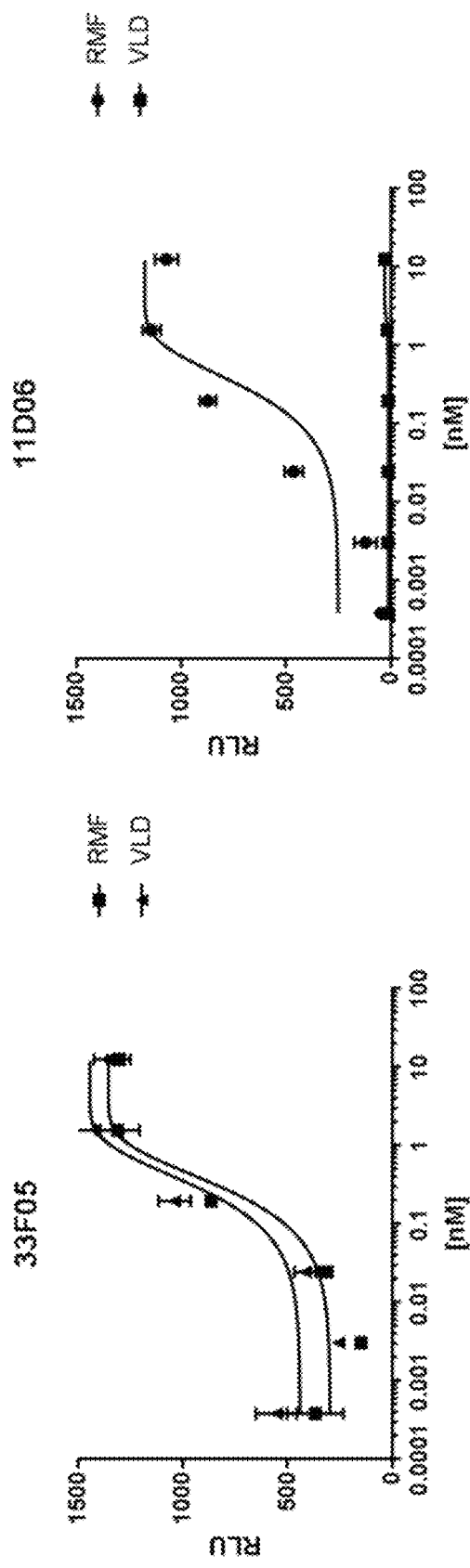
Figure 18D:
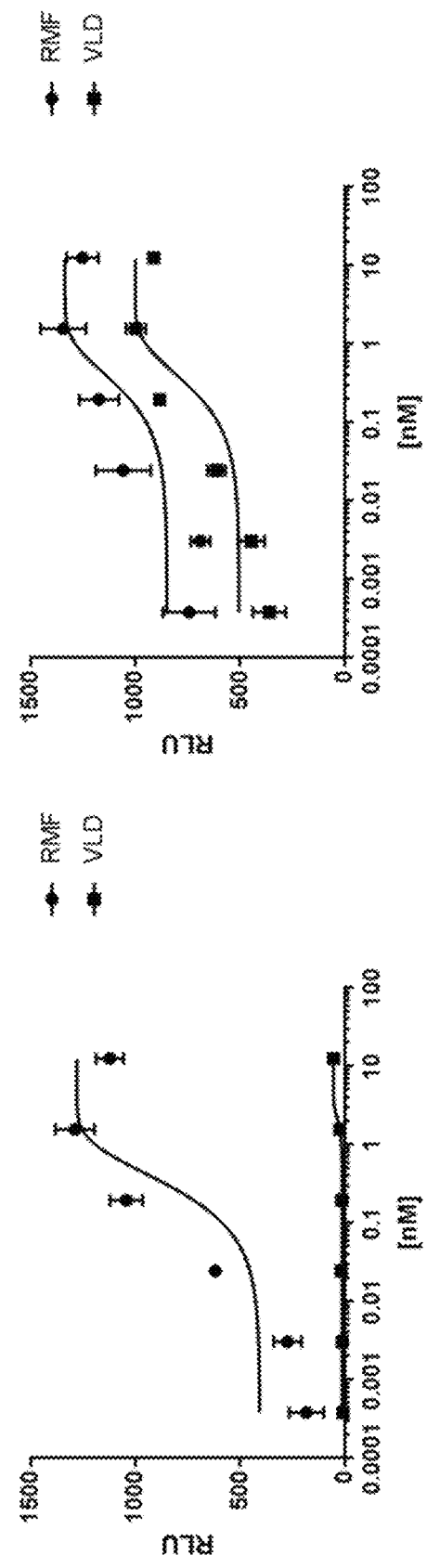

FIG. 17 depicts a schematic representation of a diagnostic reporter CAR-T cell assay for detection of a MHC presented peptide.

FIG. 18A to FIG. 18D depict activation of CAR-NFAT-signaling in Jurkat NFAT reporter CAR-T cells by HLA-A2/WT1-peptide-binding IgG (harboring the P329G mutation) variants to RMF- or VLD-peptide-pulsed T2 cells. As reporter cells, a sorted pool of Anti-P329G-ds-Fab-CD28ATD-CD28CSD-CD3zSSD expressing Jurkat NFAT reporter CAR-T cells were used. Each subfigure represents dilutions of the particular binder (33F05, 11D06, 33H09 and 5E11). Comparison of signals on RMF-peptide (target) vs. VLD-peptide (off-target) helps to assess specificity of activation.

Figure 19:
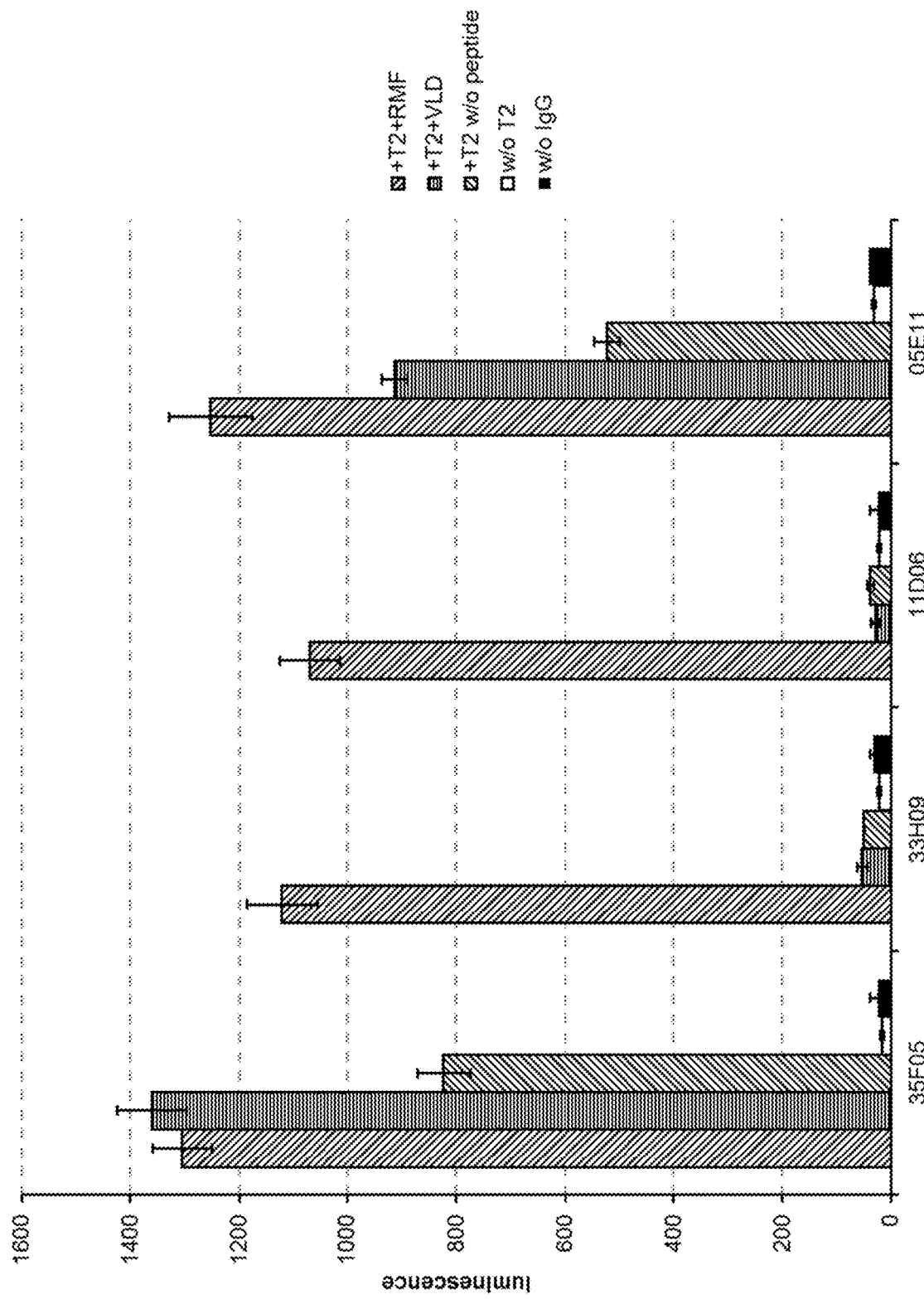

FIG. 19 depicts activation of CAR-NFAT-signaling in Jurkat NFAT reporter CAR-T cells to assess the specificity of selected WT1/HLA-A2-binders 33F05, 33H09, 11D06 and 5E11 upon incubation with T2 cells pulsed with RMF-peptide or VLD-peptide. Negative controls using Jurkat NFAT reporter CAR-T cells with unpulsed T2 cells, without T2 cells or without IgG are included. Activation (luciferase signal from Jurkat NFAT reporter CAR-T cells) was measured afterwards by adding luciferase substrate and measuring luminescence.

Figure 20A:
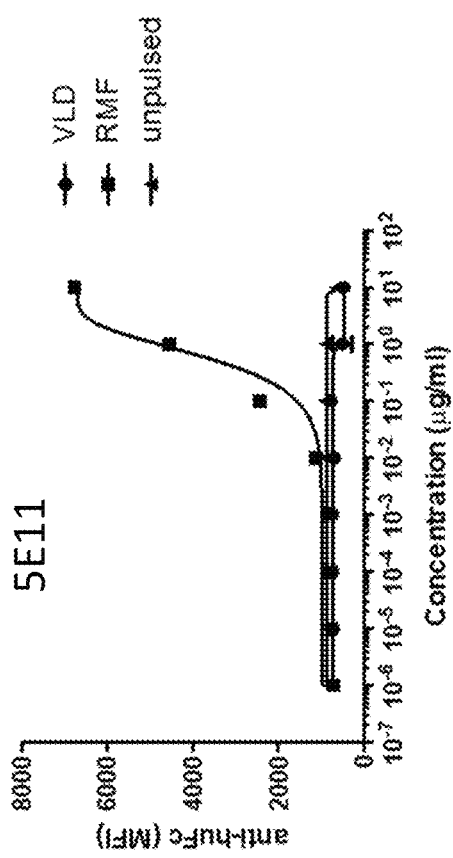
Figure 20B:
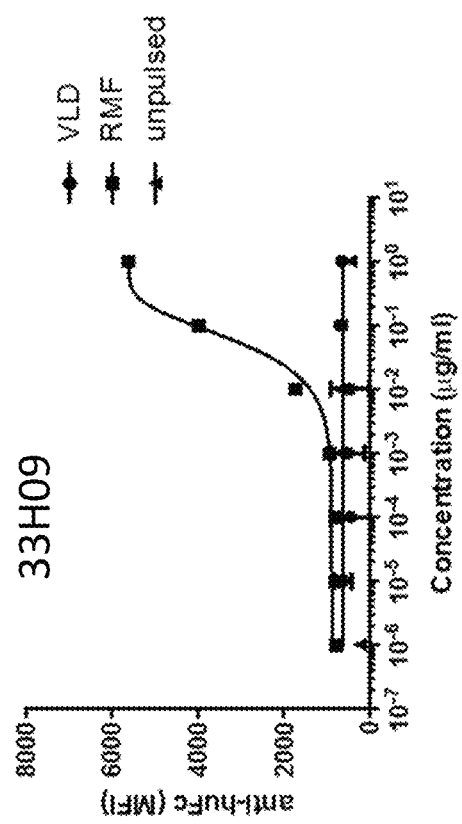

FIG. 20A and FIG. 20B depict assessment of specificity of WT1/HLA-binders 5E11 and 33H09 by FACS with T2 cells pulsed with RMF-peptide or VLD-peptide.

Figure 21:
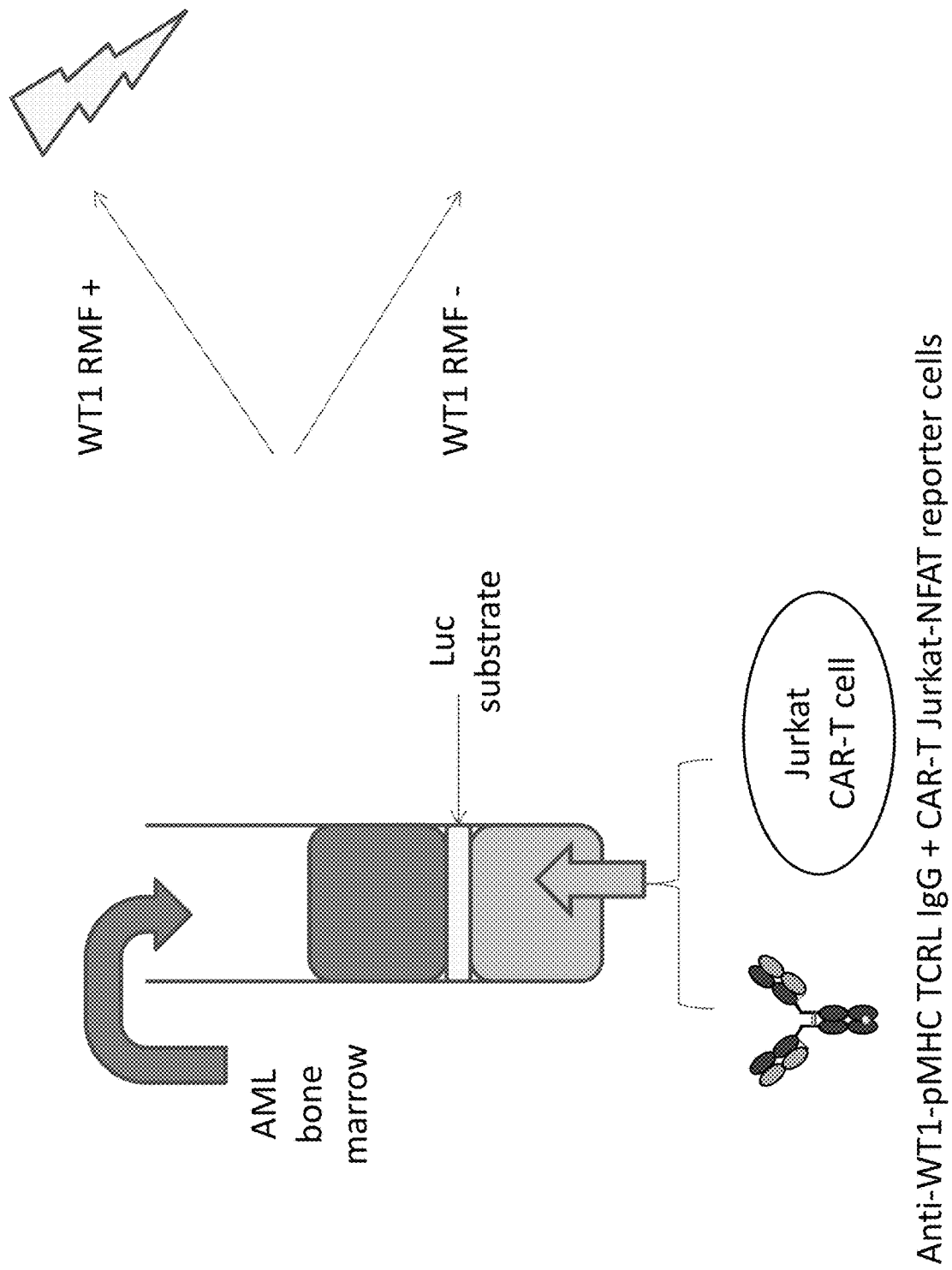

FIG. 21 depicts a schematic representation of a diagnostic reporter CAR-T cell assay transduced Jurkat NFAT reporter cells to detect WT1 positive cells in the bone marrow of an AML patient.

Figure 22A:
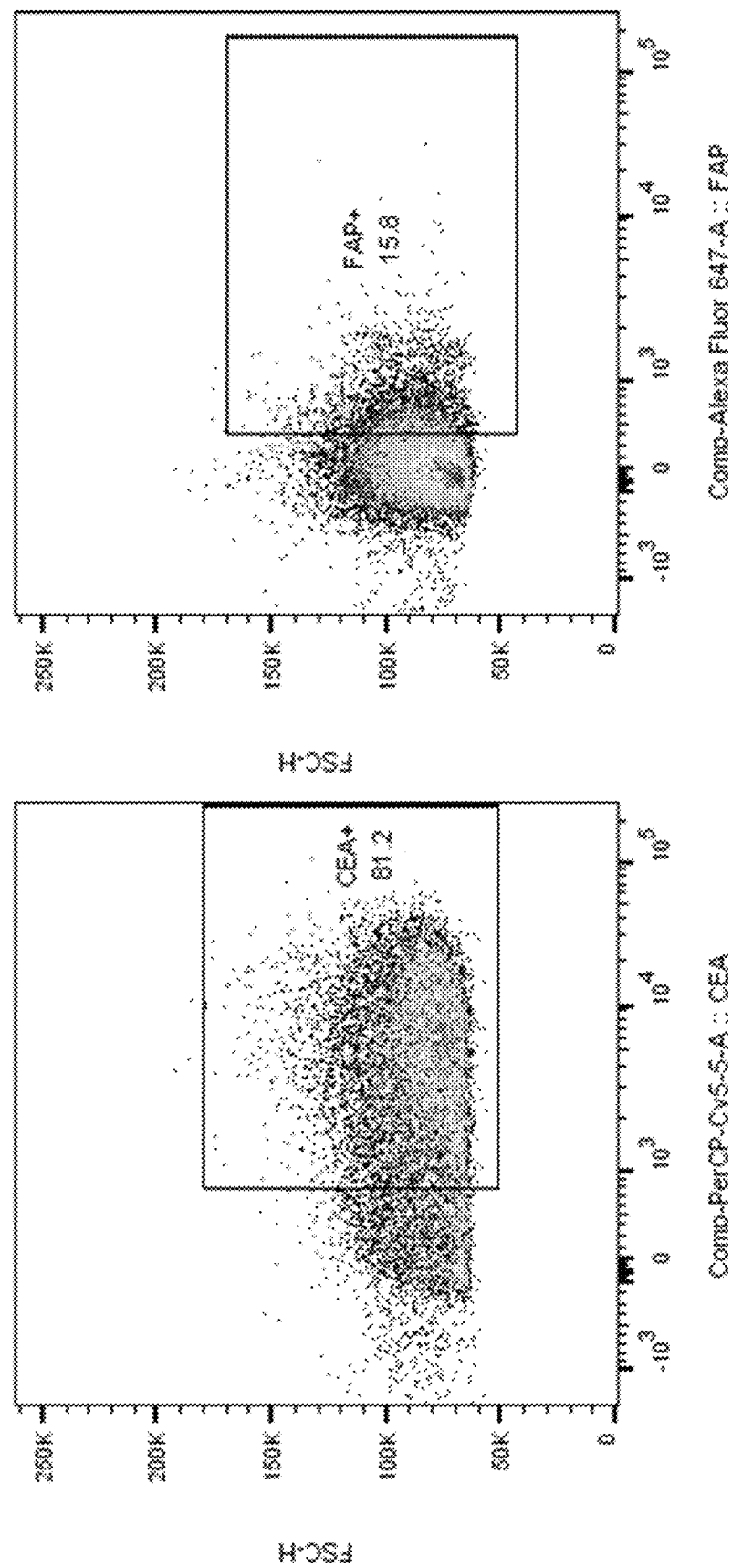
Figure 22B:
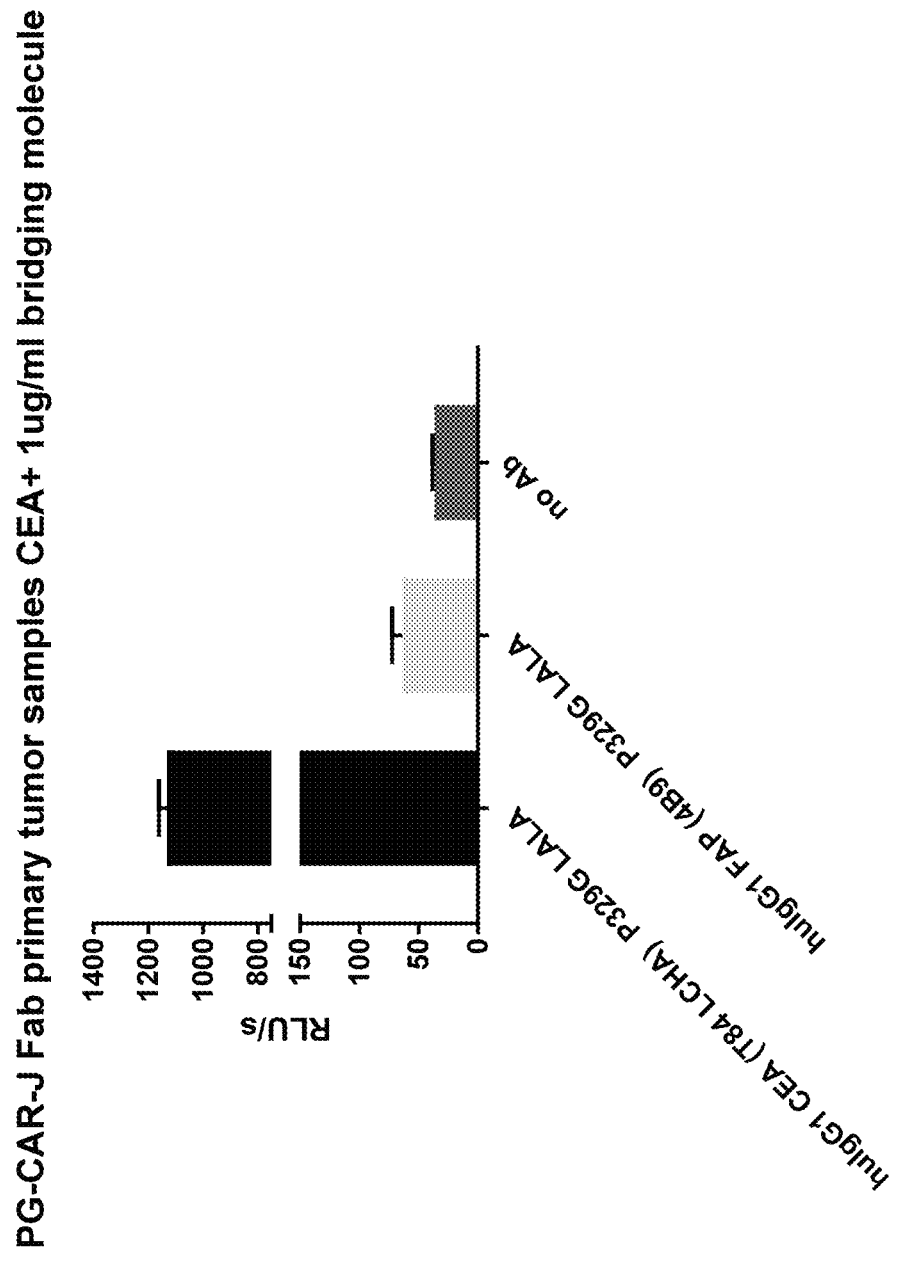
Figure 22C:
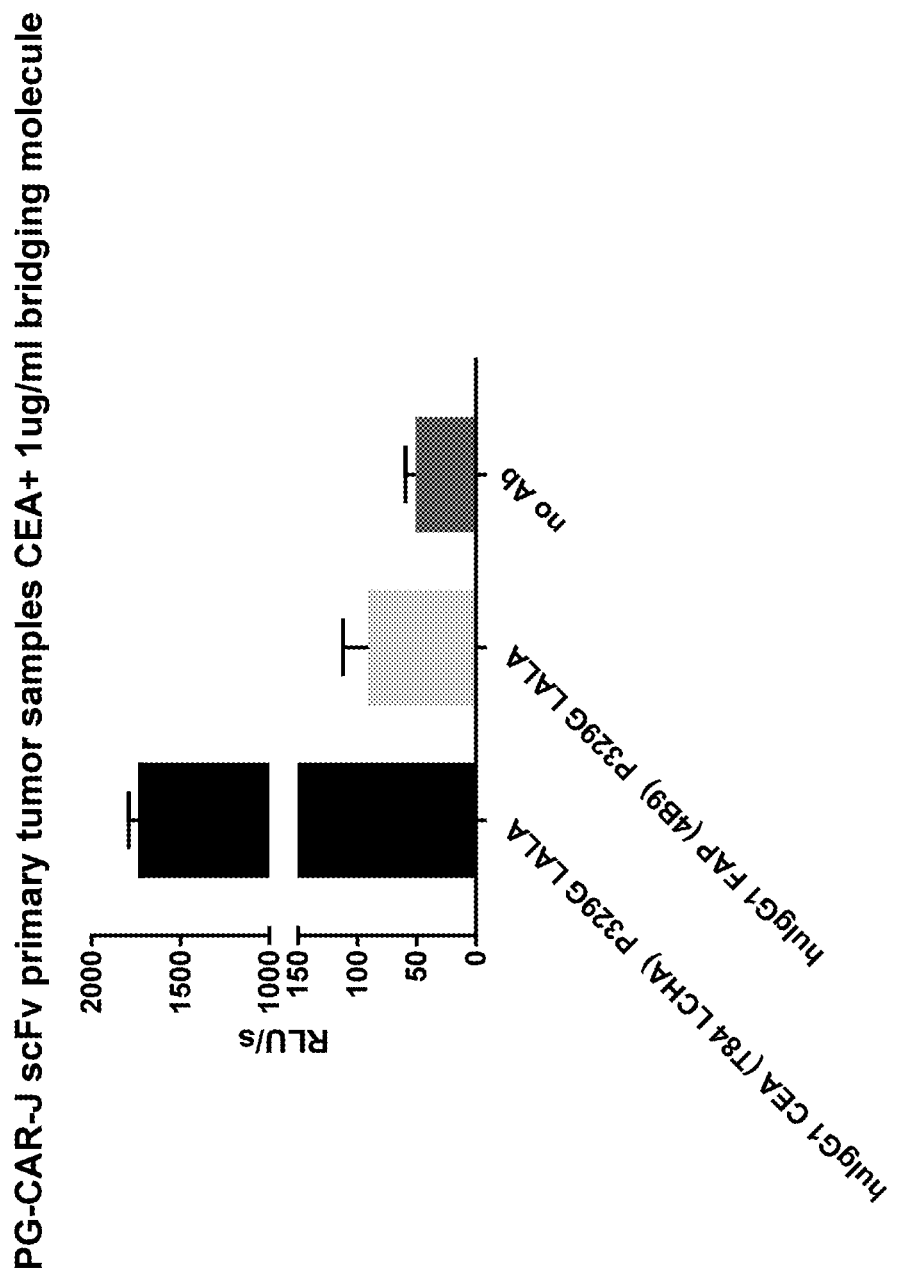

FIG. 22A to FIG. 22C depict activation of diagnostic reporter CAR-T cells upon contact with a CEA and FAP positive human lung metastasis of colon carcinoma and human IgG1 anti-CEA T84 LCHA or anti-FAP (4B9) antibodies with P329G LALA mutation. FIG. 22A depict a FACS plot showing expression levels of CEA and FAP antigens of the lung metastasis of colon carcinoma sample. FIG. 22B depicts activation of anti-P329G-ds-Fab-CD28ATD-CD28CSD-CD3zSSD expressing Jurkat NFAT reporter CAR-T cells. FIG. 22C depicts activation of anti-P329G-ds-scFv-CD28ATD-CD28C SD-CD3zSSD expressing Jurkat NFAT reporter CAR-T cells.

DETAILED DESCRIPTION

"Affinity" refers to the strength of the sum total of non-covalent interactions between a single binding site of a molecule (e.g., an antibody or a CAR) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen and/or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A preferred method for measuring affinity is Surface Plasmon Resonance (SPR) and a preferred temperature for the measurement is 25° C.

The term "amino acid" ("aa") refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics. Amino acid sequence deletions and insertions include amino- and/or carboxy-terminal deletions and insertions of amino acids. Particular amino acid mutations are amino acid substitutions. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

The term "antibody" herein is used in the broadest sense and encompasses various antibody structures, including but not limited to monoclonal antibodies, polyclonal antibodies, and antibody fragments so long as they exhibit the desired antigen-binding activity. Accordingly, in the context of the present invention, the term antibody relates to full immunoglobulin molecules as well as to parts of such immunoglobulin molecules. Furthermore, the term relates, as discussed herein, to modified and/or altered antibody molecules, in particular to modified antibody molecules. The term also relates to recombinantly or synthetically generated/synthesized antibodies. In the context of the present invention the term antibody is used interchangeably with the term immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, crossover Fab, Fab', Fab'-SH, F(ab')$_2$, diabodies, linear antibodies, single-domain antibodies, single-chain antibody molecules (e.g., scFv, scFab), and single-domain antibodies. For a review of certain antibody fragments, see Hudson et al., Nat Med 9, 129-134 (2003). For a review of scFv fragments, see e.g., Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody (Domantis, Inc., Waltham, MA; see e.g., U.S. Pat. No. 6,248,516 B1). Antibody fragments can be made by various techniques, including but not limited to proteolytic digestion of an intact antibody as well as production by recombinant host cells (e.g., E. coli or phage), as described herein.

As used herein, the term "antigen binding molecule" refers in its broadest sense to a molecule that specifically binds an antigenic determinant. Examples of antigen binding molecules are antibodies/immunoglobulins and derivatives, e.g., fragments, thereof. Furthermore, the term relates, as discussed herein, to modified and/or altered antigen binding molecules, in particular to modified antibody molecules. The term also relates to recombinantly or synthetically generated/synthesized antibodies. In the context of the present invention the antigen binding molecule is preferably an antibody or fragment thereof.

As used herein, the term "antigen binding moiety" refers to a polypeptide molecule that specifically binds to an antigenic determinant. In one embodiment, an antigen binding moiety is able to direct the entity to which it is attached (e.g., an immunoglobulin or a CAR) to a target site, for example to a specific type of tumor cell or tumor stroma bearing the antigenic determinant or to an immunoglobulin binding to the antigenic determinant on a tumor cell. In another embodiment an antigen binding moiety is able to activate signaling through its target antigen, for example signaling is activated upon binding of an antigenic determinant to a CAR on a T cell. In the context of the present invention, antigen binding moieties may be included in antibodies and fragments thereof as well as in antigen binding receptors (e.g., CARs) and fragments thereof as further defined herein. Antigen binding moieties include an antigen binding domain, e.g., comprising an immunoglobulin heavy chain variable region and an immunoglobulin light chain variable region.

In the context of the present invention the term "antigen binding receptor" relates to a molecule comprising an anchoring transmembrane domain and an extracellular domain comprising at least one antigen binding moiety. An antigen binding receptor (e.g., a CAR) can be made of polypeptide parts from different sources. Accordingly, it may be also understood as a "fusion protein" and/or a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. In the context of the present invention a CAR (chimeric antigen receptor) is understood to be an antigen binding receptor comprising an extracellular portion comprising an antigen binding moiety fused by a spacer sequence to an anchoring transmembrane domain which is itself fused to the intracellular signaling domains of e.g., CD3z and CD28.

An "antigen binding site" refers to the site, i.e., one or more amino acid residues, of an antigen binding molecule which provides interaction with the antigen. A native immunoglobulin molecule typically has two antigen binding sites, a Fab or a scFv molecule typically has a single antigen binding site.

The term "antigen binding domain" refers to the part of an antibody or an antigen binding receptor (e.g., a CAR) that comprises the area which specifically binds to and is complementary to part or all of an antigen. An antigen binding domain may be provided by, for example, one or more immunoglobulin variable domains (also called variable regions). Particularly, an antigen binding domain comprises an immunoglobulin light chain variable region (VL) and an immunoglobulin heavy chain variable region (VH).

The term "variable region" or "variable domain" refers to the domain of an immunoglobulin heavy or light chain that is involved in binding the antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co, page 91 (2007). A single VH or VL domain is usually sufficient to confer antigen-binding specificity.

The term "ATD" as used herein refers to "anchoring transmembrane domain" which defines a polypeptide stretch capable of integrating in (the) cellular membrane(s) of a cell. The ATD can be fused to further extracellular and/or intracellular polypeptide domains wherein these extracellular and/or intracellular polypeptide domains will be confined to the cell membrane as well. In the context of the antigen binding receptors as used in the present invention the ATD confers membrane attachment and confinement of the antigen binding receptor, e.g., a CAR used according to the present invention.

The term "bin ding to" as used in the context of the antigen binding receptors (e.g., CARs) and antibodies used according to the present invention defines a binding (interaction) of an "antigen-interaction-site" and an antigen with each other. The term "antigen-interaction-site" defines a motif of a polypeptide which shows the capacity of specific interaction with a specific antigen or a specific group of antigens. Said binding/interaction is also understood to define a "specific recognition". The term "specifically recognizing" means in accordance with this invention that the antigen binding receptor is capable of specifically interacting with and/or binding to the recognition domain, i.e., a modified molecule as defined herein whereas the non-modified molecule is not recognized. The antigen binding moiety of an antigen binding receptor (e.g., a CAR) can recognize, interact and/or bind to different epitopes on the same molecule. This term relates to the specificity of the antigen binding receptor, i.e., to its ability to discriminate between the specific regions of a modified molecule, i.e., a modified Fc domain, as defined herein. The specific interaction of the antigen-interaction-site with its specific antigen may result in an initiation of a signal, e.g., due to the induction of a change of the conformation of the polypeptide comprising the antigen, an oligomerization of the polypeptide comprising the antigen, an oligomerization of the antigen binding receptor, etc. Thus, a specific motif in the amino acid sequence of the antigen-interaction-site and the antigen bind to each other as a result of their primary, secondary or tertiary structure as well as the result of secondary modifications of said structure. The term binding to does not only relate to a linear epitope but may also relate to a conformational epitope, a structural epitope or a discontinuous epitope consisting of two regions of the target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the term "interacting with". The ability of the antigen binding moiety (e.g., a Fab or scFv domain) of a CAR or an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the target antigen as measured, in particular by SPR. In certain embodiments, an antigen binding moiety that binds to the target antigen, has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$M, e.g., from $10^{-9}$M to $10^{-13}$ M). An antigen binding moiety is said to "specifically bind" to a target antigen when the antigen binding moiety has a $K_D$ of 1 µM or less and such interaction is herein referred to as "specific binding". The antigen binding receptor (e.g., the CAR) used according to the invention specifically binds to/interacts with a recognition domain, e.g., an Fc domain, preferably a modified Fc domain. Cross-reactivity of a panel of constructs under investigation may be tested, for example, by assessing binding of a panel of antigen binding moieties under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the recognition domain of interest, e.g., a modified Fc domain as well as to parent non-modified Fc domain. Only those constructs (i.e., Fab fragments, scFvs and the like) that bind to the domain of interest but do not or do not essentially bind to structurally closely related domain, e.g., a non-modified Fc domain, are considered specific for the recognition domain of interest and selected for further studies in accordance with the method provided herein. These methods may comprise, inter alia, binding studies, blocking and competition studies with structurally and/or functionally closely related domains. The binding studies also comprise FACS analysis, surface plasmon resonance (SPR, e.g., with BIAcore), analytical ultracentrifugation, isothermal titration calorimetry, fluorescence anisotropy, fluorescence spectroscopy or by radiolabeled ligand binding assays.

The term "CDR" as employed herein relates to "complementary determining region", which is well known in the art. The CDRs are parts of immunoglobulins or antigen binding receptors that determine the specificity of said molecules and make contact with a specific ligand. The CDRs are the most variable part of the molecule and contribute to the antigen binding diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in "Kabat" (Sequences of Proteins of Immunological Interest", 5th edit. NIH Publication no. 91-3242 U.S. Department of Health and Human Services (1991); Chothia J. Mol. Biol. 196 (1987), 901-917) or "Chothia" (Nature 342 (1989), 877-883).

The term "CD3z" refers to T-cell surface glycoprotein CD3 zeta chain, also known as "T-cell receptor T3 zeta chain" and "CD247".

The term "chimeric antigen receptor" or "chimeric receptor" or "CAR" refers to an antigen binding receptor constituted of an extracellular portion of an antigen binding moiety (e.g., a scFv or a Fab) fused by a spacer sequence to intracellular signaling domains (e.g., of CD3z and CD28).

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and µ, respectively.

By a "crossover Fab molecule" (also termed "crossFab" or "crossover Fab fragment") is meant a Fab molecule wherein either the variable regions or the constant regions of the Fab heavy and light chain are exchanged, i.e., the crossFab fragment comprises a peptide chain composed of the light chain variable region and the heavy chain constant region, and a peptide chain composed of the heavy chain variable region and the light chain constant region. For clarity, in a crossFab fragment wherein the variable regions of the Fab light chain and the Fab heavy chain are exchanged, the peptide chain comprising the heavy chain constant region is referred to herein as the heavy chain of the crossover Fab molecule. Conversely, in a crossFab fragment wherein the constant regions of the Fab light chain and the Fab heavy chain are exchanged, the peptide chain comprising the heavy chain variable region is referred to herein as the heavy chain of the crossFab fragment. Accordingly, a crossFab fragment comprises a heavy or light chain composed of the heavy chain variable and the light chain constant regions (VH-CL), and a heavy or light chain composed of the light chain variable and the heavy chain constant regions (VL-CH1). In contrast thereto, by a "Fab" or "conventional Fab molecule" is meant a Fab molecule in its natural format, i.e., comprising a heavy chain composed of the heavy chain variable and constant regions (VH-CH1), and a light chain composed of the light chain variable and constant regions (VL-CL).

The term "CSD" as used herein refers to co-stimulatory signaling domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the terms "engineer", "engineered", "engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

A "Fab molecule" refers to a protein consisting of the VH and CH1 domain of the heavy chain (the "Fab heavy chain") and the VL and CL domain of the light chain (the "Fab light chain") of an antigen binding molecule.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the "EU numbering" system, also called the EU index, as described in Kabat et al., Sequences of Proteins of Immunological Interest, 5th Ed. Public Health Service, National Institutes of Health, Bethesda, MD, 1991. A subunit of an Fc domain as used herein refers to one of the two polypeptides forming the dimeric Fc domain, i.e., a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g., IgG 1 and IgG2), IgM, IgA, IgD, and IgE.) The full length antibodies used according to the invention can be from a single species e.g., human, or they can be chimerized or humanized antibodies. In some embodiments, the full length antibodies used according to the invention, comprise two antigen binding sites each formed by a pair of VH and VL, which both specifically bind to the same antigen. In further embodiments, the full length antibodies used according to the invention comprise two antigen binding sites each formed by a pair of VH and VL, wherein the two antigen binding sites bind to different antigens, e.g., wherein the antibodies are bispecific. The C-terminus of the heavy or light chain of said full length antibody denotes the last amino acid at the C-terminus of said heavy or light chain.

By "fused" is meant that the components (e.g., a Fab and a transmembrane domain) are linked by peptide bonds, either directly or via one or more peptide linkers.

The terms "host cell", "host cell line" and "host cell culture" are used interchangeably and refer to cells into which exogenous nucleic acid has been introduced, including the progeny of such cells. Host cells include "transformants" and "transformed cells" which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate an antibody used according to the present invention. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody and/or an antigen binding receptor or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of Kabat numbering to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antigen binding moiety variable region are according to the Kabat numbering system. The polypeptide sequences of the sequence listing are not numbered according to the Kabat numbering system. However, it is well within the ordinary skill of one in the art to convert the numbering of the sequences of the Sequence Listing to Kabat numbering.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

By "isolated nucleic acid" molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed below for polypeptides (e.g., ALIGN-2).

By an "isolated polypeptide" or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y; where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "nucleic acid molecule" relates to the sequence of bases comprising purine- and pyrimidine bases which are comprised by polynucleotides, whereby said bases represent the primary structure of a nucleic acid molecule. Herein, the term nucleic acid molecule includes DNA, cDNA, genomic DNA, RNA, synthetic forms of DNA and mixed polymers comprising two or more of these molecules. In addition, the term nucleic acid molecule includes both, sense and antisense strands. Moreover, the herein described nucleic acid molecule may contain non-natural or derivatized nucleotide bases, as will be readily appreciated by those skilled in the art.

As used herein "NFAT" refers to the "nuclear factor of activated T-cells" and is a family of transcription factors which is expressed in most immune cells. Activation of transcription factors of the NFAT family is dependent on calcium signaling. As an example, T cell activation through the T cell synapse results in calcium influx. Increased intracellular calcium levels activate the calcium-sensitive phosphatase, calcineurin, which rapidly dephosphorylates the serine-rich region (SRR) and SP-repeats in the amino termini of NFAT proteins. This results in a conformational change that exposes a nuclear localization signal promoting NFAT nuclear import and activation of target genes.

As used herein "NFAT pathway" refers to the stimuli that lead to modulation of activity of member of the NFAT family of transcription factors. NFAT DNA elements are known to the art and are herein also referred to as "response element of the NFAT pathway". Hence, a "receptor of the NFAT pathway" refers to a receptor which can trigger the modulation of activity of NFAT. Examples of a "receptor of the NFAT pathway" are e.g., T cell receptor and B cell receptor.

As used herein "NF-κB" refers to the "nuclear factor kappa-light-chain-enhancer of activated B cells" and is a transcription factor which is implicated in the regulation of many genes that code for mediators of apoptosis, viral replication, tumorigenesis, various autoimmune diseases and inflammatory responses. NFκB is present in almost all eukaryotic cells. Generally, it is located in the cytosol in an inactive state, since it forms a complex with inhibitory kappa B (IκB) proteins. Through the binding of ligands to integral membrane receptors (also referred to as "receptors of the NF-κB pathway", the IκB kinase (IKK) is activated. IKK is an enzyme complex which consists of two kinases and a regulatory subunit. This complex phosphorylates the IκB proteins, which leads to ubiquitination and therefore degradation of those proteins by the proteasome. Finally, the free NFκB is in an active state, translocates to the nucleus and binds to the κB DNA elements and induces transcription of target genes.

As used herein "NF-κB pathway" refers to the stimuli that lead to modulation of activity of NF-κB. For example activation of the Toll-like receptor signaling, TNF receptor signaling, T cell receptor and B cell receptor signaling through either binding of a ligand or an antibody result in activation of NF-κB. Subsequently, phosphorylated NF-κB dimers bind to κB DNA elements and induce transcription of target genes. κB DNA elements are known in the art and herein also referred to as "response element of the NF-κB pathway". Hence, a "receptor of the NF-κB pathway" refers to a receptor which can trigger the modulation of activity of NF-κB. Examples of a "receptor of the NF-κB pathway" are Toll-like receptors, TNF receptors, T cell receptor and B cell receptor.

As used herein "AP-1" refers to the "activator protein 1" and is a transcription factor which is involved a number of cellular processes including differentiation, proliferation, and apoptosis. AP-1 functions are dependent on the specific Fos and Jun subunits contributing to AP-1 dimers. AP-1 binds to a palindromic DNA motif (5'-TGA G/C TCA-3') to regulate gene expression.

The term "pharmaceutical composition" refers to a preparation which is in such form as to permit the biological activity of an active ingredient contained therein to be effective, and which contains no additional components which are unacceptably toxic to a subject to which the formulation would be administered. A pharmaceutical composition usually comprises one or more pharmaceutically acceptable carrier(s).

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, the term "polypeptide" refers to a molecule composed of monomers (amino acids) linearly linked by amide bonds (also known as peptide bonds). The term polypeptide refers to any chain of two or more amino acids, and does not refer to a specific length of the product. Thus, peptides, dipeptides, tripeptides, oligopeptides, protein, amino acid chain, or any other term used to refer to a chain of two or more amino acids, are included within the definition of polypeptide, and the term polypeptide may be used instead of, or interchangeably with any of these terms. The term polypeptide is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term nucleic acid molecule refers to any one or more nucleic acid segments, e.g., DNA or RNA fragments, present in a polynucleotide.

The term "protein with intrinsic fluorescence" refers to a protein capable of forming a highly fluorescent, intrinsic chromophore either through the cyclization and oxidation of internal amino acids within the protein or via the enzymatic addition of a fluorescent co-factor. The term "protein with intrinsic fluorescence" includes wild-type fluorescent proteins and mutants that exhibit altered spectral or physical properties. The term does not include proteins that exhibit weak fluorescence by virtue only of the fluorescence contribution of non-modified tyrosine, tryptophan, histidine and phenylalanine groups within the protein. Proteins with intrinsic fluorescence are known in the art, e.g., green fluorescent protein (GFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Oruro et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) and can be measured e.g., by live cell imaging (e.g., Incucyte) or fluorescent spectrophotometry.

"Reduced binding" refers to a decrease in affinity for the respective interaction, as measured for example by SPR. For clarity the term includes also reduction of the affinity to zero (or below the detection limit of the analytic method), i.e., complete abolishment of the interaction. Conversely, "increased binding" refers to an increase in binding affinity for the respective interaction.

The term "regulatory sequence" refers to DNA sequences, which are necessary to effect the expression of coding sequences to which they are ligated. The nature of such control sequences differs depending upon the organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

As used herein, a "reporter gene" means a gene whose expression can be assayed. In one preferred embodiment a "reporter gene" is a gene that encodes a protein the production and detection of which is used as a surrogate to detect indirectly the activity of the antibody or ligand to be tested. The reporter protein is the protein encoded by the reporter gene. Preferably, the reporter gene encodes an enzyme whose catalytic activity can be detected by a simple assay method or a protein with a property such as intrinsic fluorescence or luminescence so that expression of the reporter gene can be detected in a simple and rapid assay requiring minimal sample preparation. Non-limiting examples of enzymes whose catalytic activity can be detected are Luciferase, beta Galactosidase, Alkaline Phosphatase. Luciferase is a monomeric enzyme with a molecular weight (MW) of 61 kDa. It acts as a catalysator and is able to convert D-luciferin in the presence of Adenosine triphosphate (ATP) and Mg2+ to luciferyl adenylate. In addition, pyrophosphate (PPi) and adenosine monophosphate (AMP) are generated as byproducts. The intermediate luciferyl adenylate is then oxidized to oxyluciferin, carbon dioxide ($CO_2$) and light. Oxyluciferin is a bioluminescent product which can be quantitatively measured in a luminometer by the light released from the reaction. Luciferase reporter assays are commercially available and known in the art, e.g., Luciferase 1000 Assay System and ONE-Glo™ Luciferase Assay System.

A "response element" refers to a specific transcription factor binding element, or cis acting element which can be activated or silenced on binding of a certain transcription factor. In one embodiment the response element is a cis-acting enhancer element located upstream of a minimal promotor (e.g., a TATA box promotor) which drives expression of the reporter gene upon transcription factor binding.

As used herein, the term "single-chain" refers to a molecule comprising amino acid monomers linearly linked by peptide bonds. In certain embodiments, one of the antigen binding moieties is a scFv fragment, i.e., a VH domain and a VL domain connected by a peptide linker. In certain embodiments, one of the antigen binding moieties is a single-chain Fab molecule, i.e., a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

The term "SSD" as used herein refers to stimulatory signaling domain.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

In the context of the present invention, the term "tag" refers to a molecule attached or engrafted to or onto a biomolecule such as a protein, particularly an antigen binding molecule. The function of a tag is to mark or label the "tagged" protein (e.g., an immunoglobulin or fragment thereof) such that it can be recognized by a specific antigen binding moiety capable of binding to the tag but not capable of binding to the untagged protein. The term is synonymous to "molecular tag" and comprises without being limited to fluorescent tags, protein tags, affinity tags, solubilization tags, chromatography tags, epitope tags and small molecule tags such as hapten tags. Small molecule tags, e.g., haptens, can be chemically coupled covalently or non-covalently to the biomolecule whereas "protein tags" or "polypeptide tags" are peptide sequences which can be genetically grafted onto a protein and subsequently be recognized by specific antigen binding moieties capable of binding to the tag but not capable of binding to the untagged protein. Hapten tags are able to elicit an immune response when attached to a carrier protein, and, therefore, are suitable to generate specific antigen binding moieties capable of recognizing the tag on a carrier such as a protein. In preferred embodiments of the present invention, the tag is a hapten tag or a polypeptide tag.

As used herein, the term "target antigenic determinant" is synonymous with "target antigen", "target epitope" and "target cell antigen" and refers to a site (e.g., a contiguous stretch of amino acids or a conformational configuration made up of different regions of non-contiguous amino acids) on a polypeptide macromolecule to which an antibody binds, forming an antigen binding moiety-antigen complex. Useful antigenic determinants can be found, for example, on the surfaces of tumor cells (e.g., "tumor target antigens"), on the surfaces of virus-infected cells, on the surfaces of other diseased cells, on the surface of immune cells, free in blood serum, and/or in the extracellular matrix (ECM). The proteins referred to as antigens herein (e.g., CD20, CD38, CD138, CEA, EGFR, FolR1, HER2, LeY, MCSP, STEAP1, TYRP1, and WT1) can be any native form of the proteins from any vertebrate source, including mammals such as primates (e.g., humans) and rodents (e.g., mice and rats), unless otherwise indicated. In a particular embodiment the target antigen is a human protein. Where reference is made to a specific target protein herein, the term encompasses the "full-length", unprocessed target protein as well as any form of the target protein that results from processing in the target cell. The term also encompasses naturally occurring variants of the target protein, e.g., splice variants or allelic variants. Exemplary human target proteins useful as antigens include, but are not limited to: CD20, CD38, CD138, CEA, EGFR, FolR1, HER2, LeY, MCSP, STEAP1, TYRP1, and WT1.

Antibodies may have one, two, three or more binding domains and may be monospecific, bispecific or multispecific. The antibodies can be full length from a single species, or be chimerized or humanized. For an antibody with more than two antigen binding domains, some binding domains may be identical and/or have the same specificity.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

In accordance with this invention, the term "T cell receptor" or "TCR" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subjected to be treated. In this context, suitable T cell receptors which fulfill the above mentioned three criteria are known in the art such as receptors recognizing NY-ESO-1 (for sequence information(s) see, e.g., PCT/GB2005/001924) and/or HER2neu (for sequence information(s) see WO-A1 2011/0280894). Major histocompatibility complex (MHC) class I molecules present peptides from endogenous antigens to CD8+ cytotoxic T cells, and therefore, MHC-peptide complexes are a suitable target for immunotherapeutic approaches. The MHC-peptide complexes can be targeted by recombinant T-cell receptors (TCRs). However, most TCRs may have affinities which are too low for immunotherapy whereas high affinity binding moieties with TCR specificity would be beneficial. Towards this end, high-affinity soluble antibody molecules with TCR-like specificity can be generated, e.g., by generating phage display libraries (e.g., combinatorial libraries) and screening such libraries as further described herein. These soluble antigen binding moieties e.g., scFv or Fab, with TCR-like specificity as described herein are referred to as "T cell receptor like antigen binding moieties" or "TCRL antigen binding moieties".

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode antigen binding receptors of the invention or fragments thereof.

In this context, provided herein are diagnostic methods, particularly in vitro methods, for detecting target antigens on cells, in particular tumor cells (i.e. tumor target antigens), in a sample. In a preferred embodiment, the sample is a patient sample, e.g., deriving from a biopsy or a body fluid in which aberrant cells need to be detected. The assays of the present invention combine the high specificity of chimeric antigen receptors (CARs) comprising antigen binding moieties, in particular scFv and/or Fab fragments, with the sensitivity of luminescence detection of a reporter signal. In the herein described diagnostic methods and assays, the target antigen binding molecule as herein described mediates the contact between a target cell, in particular a cancer cell, and a reporter cell, in particular a T cell. In this context, the methods as described herein are useful to detect a cancer cell based on the specificity of binding of an antigen binding molecule and a CAR capable of specific interaction with the antigen binding molecule wherein the CAR is introduced in a suitable reporter cells, preferably a reporter T cell, e.g., a Jurkat cell.

Accordingly, in one embodiment, provided is a diagnostic assay for determining the presence of a tumor cell in a sample, the diagnostic assay comprising the steps of:
a) contacting the sample with an antigen binding molecule comprising an antigen binding domain and a recognition domain, wherein the antigen binding domain comprises a target antigen binding moiety capable of specific binding to the tumor cell;
b) contacting the sample with a chimeric antigen receptor (CAR) expressing reporter T (CAR-T) cell wherein the reporter CAR-T cell comprises:
  i. a CAR capable of specific binding to the recognition domain, wherein the CAR is operationally coupled to a response element;
  ii. a reporter gene under the control of the response element; and c) determining T cell activation by measuring the expression of the reporter gene to establish the presence of the tumor cell.

Further provided are transduced T cells capable of expression of the herein described CAR molecule(s). The transduced T cells further comprise a reporter gene under the control of a response element, wherein the CAR is operationally coupled to the response element as herein described. Upon binding of the target antigen binding moiety to the target cell, e.g., the tumor cell, and binding of the CAR to the recognition domain, the reporter CAR-T cell becomes activated and the reporter gene is expressed. Expression of the reporter gene is therefore indicative for (specific) binding of the antigen binding molecule comprising the target antigen binding moiety in the context of T cell activation induced by interaction of a T cell to a target antigen, e.g., on a tumor cell.

Binding of the reporter CAR-T cell to the target cell is mediated by an antigen binding molecule capable of specific binding to the target cell, wherein the antigen binding molecules can be specifically detected by the reporter CAR-T cells. In this context further described and used for the diagnostic assay of the present invention are CARs capable of specific binding to an antigen binding molecule. In one embodiment, the antigen binding molecule comprises an antigen binding domain and a recognition domain, wherein the antigen binding domain comprises the target antigen binding moiety, and wherein the CAR is capable of specific binding to the recognition domain. In this context further described and used for the diagnostic assay of the present invention are CARs capable of specific binding to the recognition domain of the antigen binding molecule comprising the target antigen binding moiety. The recognition domain can be any polypeptide domain capable of stable folding into a protein domain which can be tagged by a molecular tag, e.g., a hapten tag or a polypeptide tag. Alternatively, the recognition domain can comprise a mutation which is specifically detected by an antigen binding moiety. Tagging, e.g., with a hapten tag or polypeptide tag, and mutating the recognition domain renders the recognition domain distinct from a non-modified domain, therefore providing an identifiable epitope for detection by an antigen binding moiety. The identifiable epitope does not naturally occur in the sample wherein target cells need to be specifically recognized.

In certain embodiments, the recognition domain is an immunoglobulin domain. Immunoglobulins typically comprise variable and constant domains capable of stable folding wherein the variable domains confer the specificity of the immunoglobulin molecule towards a target antigen. Accordingly, the variable domains are the parts of an immunoglobulin with the highest degree of sequence variance. On the other hand, the constant domains are parts of minimal variance among immunoglobulins of the same class and, therefore, are particularly suited in the context of this invention as recognition domain for methods of the present invention. However, it may also be favorable to reduce the size of the antigen binding molecule as far as possible, in such embodiments, the variable domain of an immunoglobulin, which confer the specificity to a target antigen, can also exert the function of the recognition domain, i.e., the antigen binding domain and the recognition domain can be the same domain, e.g., the variable domain can be coupled with, e.g., a hapten tag or a polypeptide tag, or alternatively, the hapten tag is coupled to the constant region of a Fab fragment. In one embodiment, the antigen binding molecule comprises a Fab domain, particularly an IgG Fab domain, most particularly an IgG1 Fab domain. In one embodiment, the antigen binding molecule comprises a modified Fab domain, particularly a Fab domain comprising a tag (e.g., a hapten tag or a polypeptide tag) for specific recognition by the CAR.

In another embodiment, the antigen binding molecule comprises a modified Fc region, e.g., a mutated Fc region or an Fc region comprising a tag (e.g., a hapten tag or a polypeptide tag) for specific recognition by the CAR. In such embodiments, the CAR used according to the present invention is capable of specific binding to the modified Fc region.

In one embodiment, the modified Fc region is a mutated Fc. In a particular embodiment, the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G, P331G and/or H435A. Further provided herein is the use of antigen binding moieties capable of specific binding to the mutated Fc domain but not capable of specific binding to the non-mutated parent Fc domain. The antigen binding molecule preferably is an IgG class antibody, particularly an IgG1 or IgG4 isotype antibody, or a fragment thereof. In one particular embodiment, the antigen binding molecule is an IgG1 class antibody comprising an IgG1 Fc domain. In one embodiment, the IgG1 Fc domain is a human IgG1 Fc domain.

Accordingly, in one embodiment, the human IgG1 Fc domain is mutated. In one embodiment, the mutant human IgG1 Fc domain comprises an amino acid substitution at a position selected from the group consisting of residue 117, 118, 136, 180, 193, 212, 214, and 318 of human IgG1 Fc (SEQ ID NO:132). In one embodiment, the mutant human IgG1 Fc comprises the amino acid substitution leucine to alanine at residue 117, leucine to alanine at residue 118, isoleucine to alanine at position 136, asparagine to alanine at residue 180, histidine to alanine at residue 193, proline to glycine at residue 212, proline to glycine at residue 214, and/or or histidine to alanine at residue 318 of human IgG1 Fc (SEQ ID NO:132). In one embodiment, the mutant human IgG1 Fc domain comprises an amino acid substitution at the position of residue 212 of human IgG1 Fc (SEQ ID NO:132). In one embodiment, the mutant human IgG1 Fc domain comprises the amino acid substitution proline to glycine at residue 212 of human IgG1 Fc (SEQ ID NO:132).

In another embodiment, the modified Fc domain comprises a hapten tag. In particular embodiments, the hapten tag is selected from the group consisting of Biotin, Digoxigenin (DIG) and Fluorescein (FITC).

In another embodiment, modified Fc domain comprises a polypeptide tag. In one embodiment, the polypeptide tag has a length of from 1 to 30 amino acids, from 1 to 25 amino acids, from 1 to 20 amino acids, from 1 to 15 amino acids or from 1 to 10 amino acids. In particular embodiments, the polypeptide tag is selected from the group consisting of myc-tag, HA-tag, AviTag, FLAG-tag, His-tag, GCN4-tag, and NE-tag.

The present invention further describes the transduction and use of T cells, such as CD8+ T cells, CD4+ T cells, CD3+ T cells, γδ T cells or natural killer (NK) T cells and immortalized cell lines, e.g., Jurkat cells, to introduce a reporter system as described herein and (a) CAR(s) as described herein and their targeted recruitment through an antigen binding molecule, comprising the target antigen binding moiety and the recognition domain, preferably an Fc domain or a Fab domain, e.g., a modified Fc domain or Fab fragment as herein described. In one embodiment, the antigen binding molecule, e.g., the modified IgG1 antibody or tagged Fab fragment, is capable of specific binding to a tumor-specific antigen that is naturally occurring on the surface of a target cell, e.g., a cancer cell. In an alternative embodiment, the herein described CAR is capable of direct binding to a target antigen on the surface of the target cell, e.g., on the surface of a tumor cell.

Accordingly, the invention provides a versatile diagnostic platform wherein CARs may be used as a guidance for immune cells (e.g., T cells), in particular wherein T cells are specifically targeted toward the tumor cells by the CARs and antigen binding molecules as described herein. After engagement of the CAR to the target antigen on the surface of a tumor cell (mediated by the antigen binding molecule), the reporter T cell becomes activated wherein the activation can be measured, e.g., by read-out of a fluorescent or luminescent signal. The platform is flexible and specific by allowing the use of diverse existing or newly developed target antigen binding moieties or co-application of multiple antibodies with different antigen specificity but comprising the same recognition domain.

Antigen binding moieties capable of specific binding to a target antigen, e.g., a tumor antigen or a recognition domain, e.g., a modified Fc domain, may be generated by immunization of e.g., a mammalian immune system. Such methods are known in the art and e.g., are described in Burns in Methods in Molecular Biology 295:1-12 (2005). Alternatively, antigen binding moieties of desired activity may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antigen binding moieties possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178:1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992) and in Marks and Bradbury in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). In certain phage display methods, repertoires of VH and VL genes are separately cloned by polymerase chain reaction (PCR) and recombined randomly in phage libraries, which can then be screened for antigen-binding phage as described in Winter et al. in Annual Review of Immunology 12: 433-455 (1994). Phage typically display antibody fragments, either as single-chain Fv (scFv) fragments or as Fab fragments. Libraries from immunized sources provide high-affinity antigen binding moieties to the immunogen without the requirement of constructing hybridomas. Alternatively, the naive repertoire can be cloned (e.g., from human) to provide a single source of antigen binding moieties to a wide range of non-self and also self antigens without any immunization as described by Griffiths et al. in EMBO Journal 12: 725-734 (1993). Naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764, 2007/0292936 and 2009/0002360. Further examples of methods known in the art for screening combinatorial libraries for antigen binding moieties with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319:155-175 (2015) as well as in the Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997).

In a first illustrative embodiments of the present invention, as a proof of concept, CARs are provided comprising an extracellular domain comprising at least one antigen binding moiety, wherein the at least one antigen binding moiety is capable of specific binding to a mutated immunoglobulin domain (e.g., a Fc domain or a Fab domain) but not capable of specific binding to the non-mutated immunoglobulin domain, wherein the mutated immunoglobulin domain comprises one or more amino acid substitutions. In one embodiment, the mutated immunoglobulin is an Fc domain, in particular a human IgG1 Fc domain. The mutated Fc domain comprises at least one amino acid substitution compared to the non-mutated parent Fc domain, wherein the CAR is capable of specific binding to the mutated Fc domain but not capable of specific binding to the non-mutated parent Fc domain.

In a particular embodiment, the mutated Fc domain comprises the P329G mutation. The P329G mutation corresponds to the amino acid substitution proline to glycine at residue 212 of human IgG1 Fc (SEQ ID NO:132). The mutated Fc domain comprising the P329G mutation binds to Fcγ receptors with reduced or abolished affinity compared to the non-mutated Fc domain.

In one particular embodiment the CAR capable of specific binding to an Fc domain comprising the P329G mutation comprises the heavy chain complementarity determining regions (CDRs) of SEQ ID NO:1, SEQ ID NO:2 and SEQ ID NO:3 and the light chain CDRs of SEQ ID NO:4, SEQ ID NO:5 and SEQ ID NO:6.

In one preferred embodiment the CAR capable of specific binding to an Fc domain comprising the P329G mutation comprises a heavy chain variable region comprising:
 (a) a heavy chain complementarity determining region (CDR H) 1 amino acid sequence of RYWMN (SEQ ID NO:1);
 (b) a CDR H2 amino acid sequence of EITPDSSTINYTPSLKD (SEQ ID NO:2);
 (c) a CDR H3 amino acid sequence of PYDYGAWFAS (SEQ ID NO:3);
and a light chain variable region comprising:
 (d) a light chain (CDR L)1 amino acid sequence of RSSTGAVTTSNYAN (SEQ ID NO:4);
 (e) a CDR L2 amino acid sequence of GTNKRAP (SEQ ID NO:5); and (f) a CDR L3 amino acid sequence of ALWYSNHWV (SEQ ID NO:6).

In one embodiment the CAR capable of specific binding to an Fc domain comprising the P329G mutation comprises a heavy chain variable region (VH) comprising an amino acid sequence that is at least about 95%, 96%, 97%, 98%, 99% or 100% identical to the amino acid sequence of SEQ ID NO:8 and a light chain variable region (VL) comprising an amino acid sequence that is at least about 95%, 96%, 97%, 98%, 99% or 100% identical to the amino acid sequence of SEQ ID NO:9.

In one embodiment the CAR capable of specific binding to an Fc domain comprising the P329G mutation comprises a heavy chain variable region (VH) comprising the amino acid sequence of SEQ ID NO:8, and a light chain variable region (VL) comprising the amino acid sequence of SEQ ID NO:9.

In one embodiment, the at least one antigen binding moiety is a scFv, a Fab, a crossFab or a scFab fragment. In one embodiment the CAR capable of specific binding to an Fc domain comprising the P329G mutation comprises a Fab fragment.

In one embodiment the CAR capable of specific binding to an Fc domain comprising the P329G mutation comprises a Fab fragment. In a preferred embodiment the CAR capable of specific binding to an Fc domain comprising the P329G mutation comprises a Fab fragment comprising a heavy chain of SEQ ID NO:31 and a light chain of SEQ ID NO:33

In one embodiment the antigen binding moiety capable of specific binding to an Fc domain comprising the P329G mutation is a Fab fragment comprising a heavy chain comprising or consisting of an amino acid sequence of SEQ ID NO:31 and a light chain comprising or consisting of the amino acid sequence of SEQ ID NO:33.

In a particular embodiment, the antigen binding moiety is a Fab fragment capable of specific binding to an Fc domain comprising the P329G mutation, wherein the antigen binding receptor comprises a heavy chain fusion polypeptide comprising an amino acid sequence that is at least about 95%, 96%, 97%, 98%, 99% or 100% identical to the amino acid sequence of SEQ ID NO:30 and a light chain polypeptide comprising an amino acid sequence that is at least about 95%, 96%, 97%, 98%, 99% or 100% identical to the amino acid sequence of SEQ ID NO:33.

In a preferred embodiment, the antigen binding moiety is a Fab capable of specific binding to an Fc domain comprising the P329G mutation, wherein the antigen binding receptor comprises a heavy chain fusion polypeptide comprising the amino acid sequence of SEQ ID NO:30 and a light chain polypeptide comprising the amino acid sequence of SEQ ID NO:33.

In one embodiment the CAR capable of specific binding to an Fc domain comprising the P329G mutation comprises a scFv fragment. A scFv fragment is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In a preferred embodiment the CAR capable of specific binding to an Fc domain comprising the P329G mutation comprises an scFv fragment comprising the amino acid sequence of SEQ ID NO:10.

In a particular embodiment, the antigen binding moiety is a scFv fragment capable of specific binding to an Fc domain comprising the P329G mutation, wherein the antigen binding receptor comprises a polypeptide comprising an amino acid sequence that is at least about 95%, 96%, 97%, 98%, 99% or 100% identical to the amino acid sequence of SEQ ID NO:7. In a preferred embodiment, the antigen binding moiety is a scFv capable of specific binding to an Fc domain comprising the P329G mutation, wherein the antigen binding receptor comprises a polypeptide comprising the amino acid sequence of SEQ ID NO:7 (as encoded by the nucleotide sequence of SEQ ID NO:19).

In further embodiments according to the invention the antigen binding moiety comprised in the extracellular domain is a single chain Fab fragment or scFab.

In another particular embodiment, the mutated Fc domain comprises the I253A, H310A and H435A ("AAA") mutations. The AAA mutation corresponds to the amino acid substitutions isoleucine to alanine at position 136, histidine to alanine at residue 193 and histidine to alanine at residue 318 of human IgG1 Fc (SEQ ID NO:132). The AAA mutations reduce binding to the neonatal Fc receptor (FcRn). Accordingly, the mutated Fc domain comprising the AAA mutations binds to FcRn with reduced or abolished affinity compared to the non-mutated Fc domain.

In one embodiment the CAR capable of specific binding to an Fc domain comprising the AAA mutation comprises the heavy chain complementarity determining regions (CDRs) of SEQ ID NO:44, SEQ ID NO:45 and SEQ ID NO:46 and at least one light chain CDR selected from the group of SEQ ID NO:47, SEQ ID NO:48 and SEQ ID NO:49.

In a preferred embodiment the CAR capable of specific binding to an Fc domain comprising the I253A, H310A and H435A mutations comprises a heavy chain variable region comprising:
  (a) a heavy chain complementarity determining region (CDR H) 1 amino acid sequence of SYGMS (SEQ ID NO:44);
  (b) a CDR H2 amino acid sequence of SSGGSY (SEQ ID NO:45);
  (c) a CDR H3 amino acid sequence of LGMITTG-YAMDY (SEQ ID NO:46); and a light chain variable region comprising:
  (d) a light chain (CDR L)1 amino acid sequence of RSSQTIVHSTGHTYLE (SEQ ID NO:47);
  (e) a CDR L2 amino acid sequence of KVSNRFS (SEQ ID NO:48); and
  (f) a CDR L3 amino acid sequence of FQGSHVPYT (SEQ ID NO:49).

In one embodiment the CAR capable of specific binding to an Fc domain comprising the I253A, H310A and H435A mutations comprises a heavy chain variable region (VH) comprising an amino acid sequence that is at least about 95%, 96%, 97%, 98%, 99% or 100% identical to the amino acid sequence of SEQ ID NO:52 and a light chain variable region (VL) comprising an amino acid sequence that is at least about 95%, 96%, 97%, 98%, 99% or 100% identical to the amino acid sequence selected of SEQ ID NO:53.

In one embodiment the CAR capable of specific binding to an Fc domain comprising the I253A, H310A and H435A mutations comprises a heavy chain variable region (VH) comprising the amino acid sequence of SEQ ID NO:52, and a light chain variable region (VL) comprising the amino acid sequence of SEQ ID NO:53.

In one embodiment, the at least one antigen binding moiety is a scFv, a Fab, a crossFab or a scFab fragment. In one embodiment the CAR capable of specific binding to an Fc domain comprising the I253A, H310A and H435A mutations comprises a Fab fragment. In a particular embodiment the extracellular domain of the antigen binding receptor comprises an antigen binding moiety capable of specific binding to an Fc domain comprising the I253A, H310A and H435A mutations, wherein the Fab fragment comprises a heavy chain of SEQ ID NO:55 and a light chain of SEQ ID NO:56.

In a particular embodiment, the antigen binding moiety is a Fab fragment capable of specific binding to an Fc domain comprising the AAA mutation, wherein the antigen binding receptor comprises a heavy chain fusion polypeptide comprising an amino acid sequence that is at least about 95%, 96%, 97%, 98%, 99% or 100% identical to the amino acid sequence of SEQ ID NO:54 and a light chain polypeptide comprising an amino acid sequence that is at least about 95%, 96%, 97%, 98%, 99% or 100% identical to the amino acid sequence of SEQ ID NO:56.

In a preferred embodiment, the antigen binding moiety is a Fab capable of specific binding to an Fc domain comprising the AAA mutation, wherein the antigen binding receptor comprises a heavy chain fusion polypeptide comprising the amino acid sequence of SEQ ID NO:54 and a light chain polypeptide comprising the amino acid sequence of SEQ ID NO:56.

In one embodiment the CAR capable of specific binding to an Fc domain comprising the I253A, H310A and H435A mutations comprises a scFv fragment. In a preferred embodiment the CAR capable of specific binding to an Fc domain comprising the AAA mutation comprises an scFv fragment comprising the amino acid sequence of SEQ ID NO:51.

In a particular embodiment, the antigen binding moiety is a scFv fragment capable of specific binding to an Fc domain comprising the AAA mutation, wherein the antigen binding receptor comprises a polypeptide comprising an amino acid sequence that is at least about 95%, 96%, 97%, 98%, 99% or 100% identical to the amino acid sequence of SEQ ID NO:50. In a preferred embodiment, the antigen binding moiety is a scFv capable of specific binding to an Fc domain comprising the AAA mutation, wherein the antigen binding receptor comprises a polypeptide comprising the amino acid sequence of SEQ ID NO:50.

In further embodiments according to the invention the antigen binding moiety comprised in the extracellular domain is a single chain Fab fragment or scFab.

In further illustrative embodiments of the present invention, as a proof of concept, CARs are provided comprising an extracellular domain comprising at least one antigen binding moiety, wherein the at least one antigen binding moiety is capable of specific binding to a modified immunoglobulin domain (e.g., a Fc domain or a Fab domain) but not capable of specific binding to the non-modified immunoglobulin domain, wherein the modified immunoglobulin domain comprises a hapten tag.

Figure 1A:
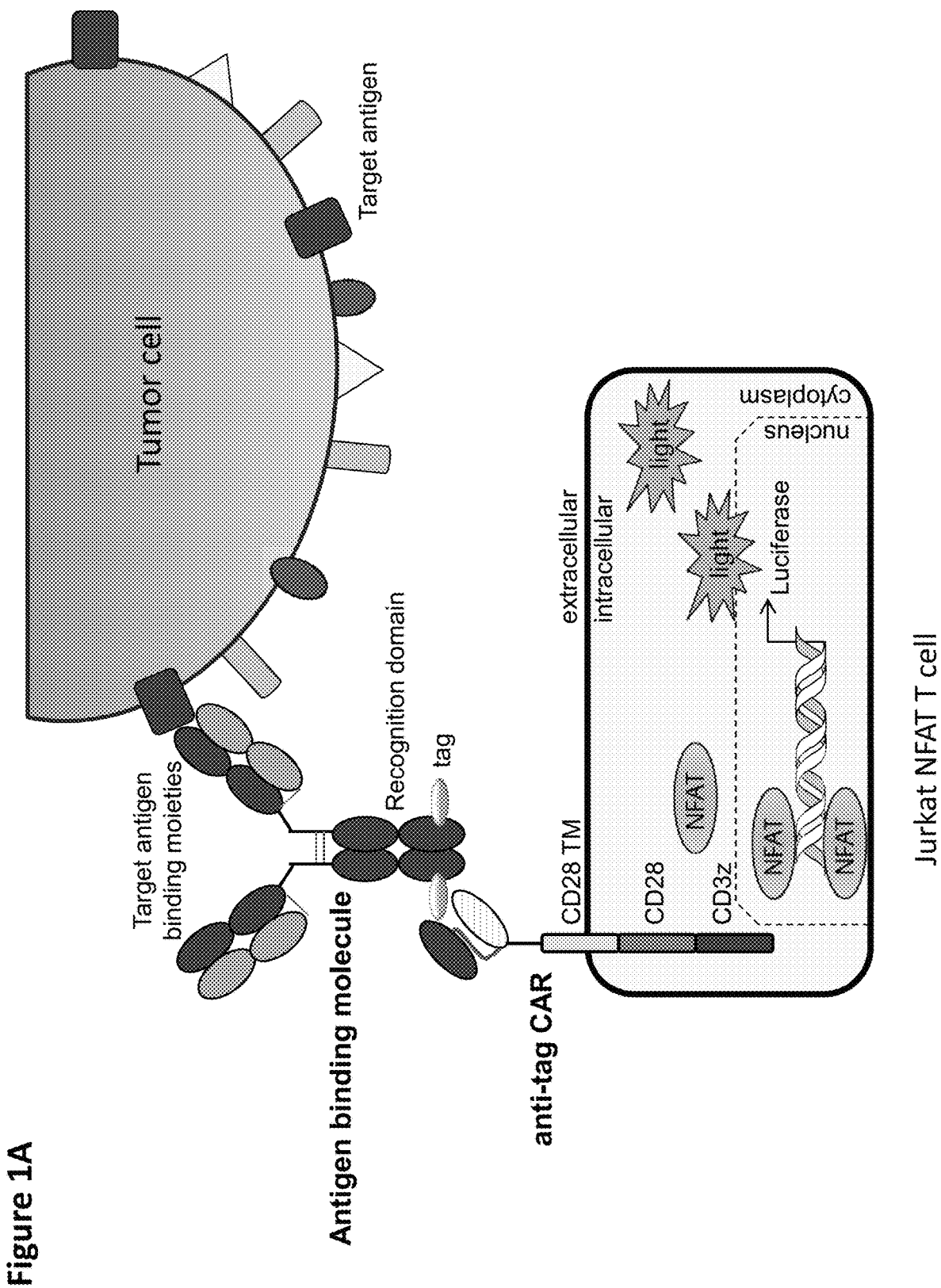
Figure 1B:
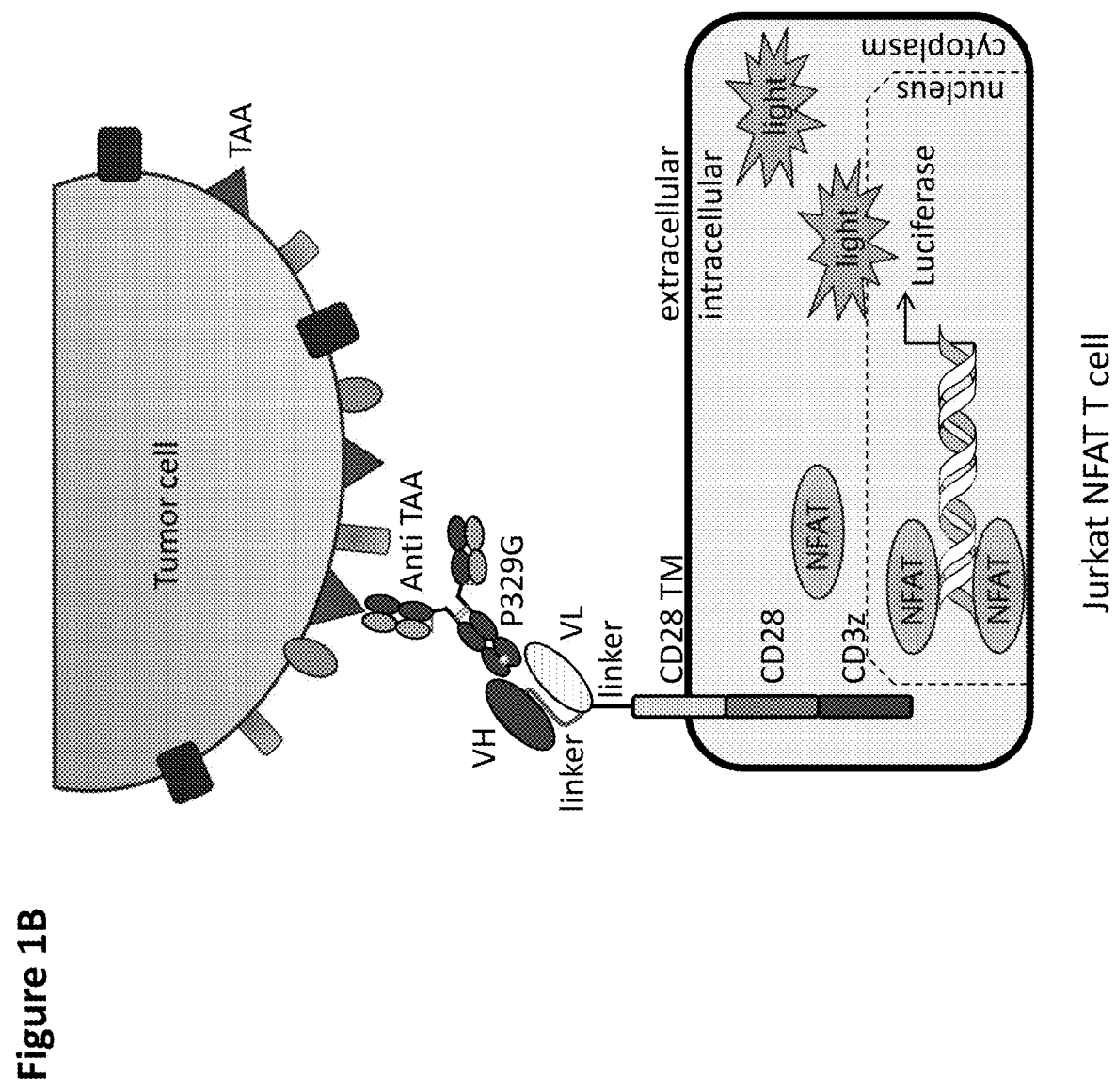
Figure 4:
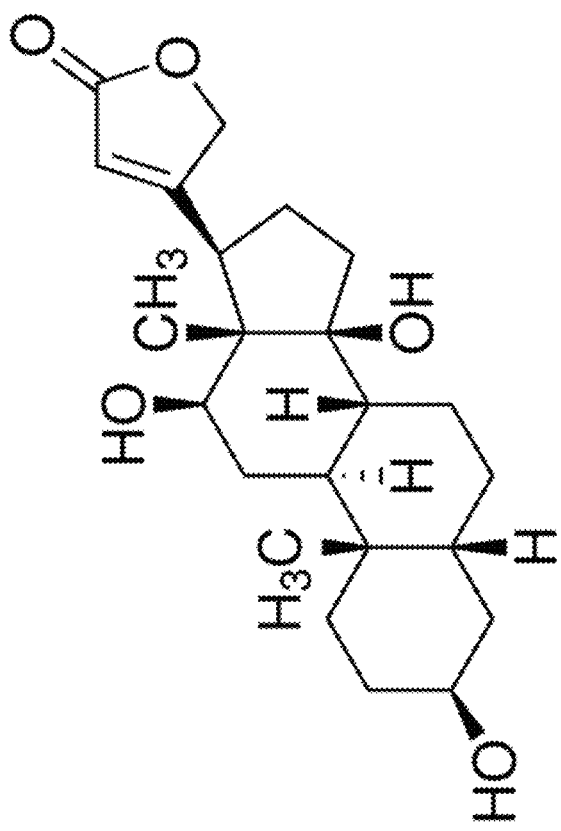
FIG. 4 depicts the structural formula of the Digoxigenin (DIG) molecule.
Figure 5:
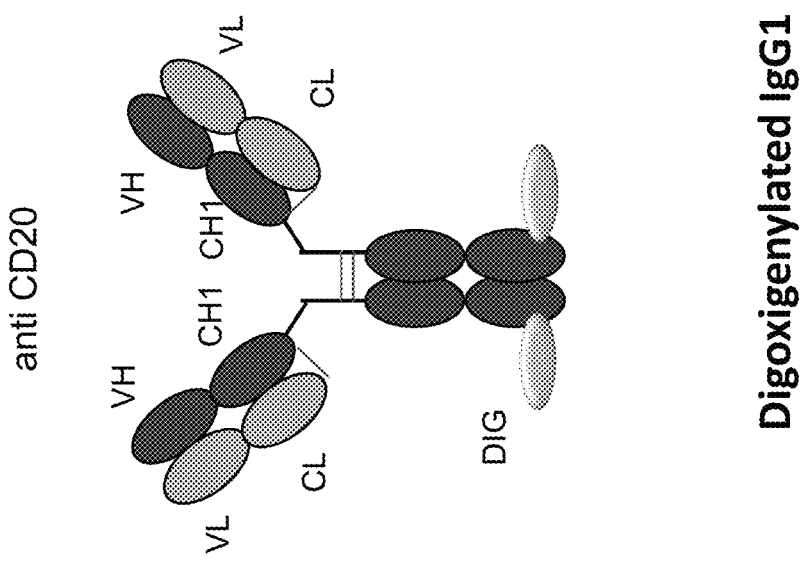
FIG. 5 depicts an exemplary digoxigeninylated IgG1 molecule which can be specifically recognized by an anti-Digoxigenin CAR.

In an illustrative embodiment of the present invention, as a proof of concept, provided are CARs capable of specific binding to a modified immunoglobulin domain comprising the hapten tag Digoxigenin (DIG). The structure of the DIG molecule is depicted in FIG. 4.

In one embodiment the CAR capable of specific binding to an immunoglobulin domain comprising the hapten tag DIG comprises the heavy chain complementarity determining regions (CDRs) of SEQ ID NO:57, SEQ ID NO:58 and SEQ ID NO:59 and the light chain CDRs of SEQ ID NO:60, SEQ ID NO:61 and SEQ ID NO:62.

In one preferred embodiment the CAR capable of specific binding to an immunoglobulin domain comprising the hapten tag DIG comprises a heavy chain variable region comprising:
(a) a heavy chain complementarity determining region (CDR H) 1 amino acid sequence of RYWMN (SEQ ID NO:57);
(b) a CDR H2 amino acid sequence of EITPDSSTINYTPSLKD (SEQ ID NO:58);
(c) a CDR H3 amino acid sequence of PYDYGAWFAS (SEQ ID NO:59);
and a light chain variable region comprising:
(d) a light chain (CDR L)1 amino acid sequence of RSSTGAVTTSNYAN (SEQ ID NO:60);
(e) a CDR L2 amino acid sequence of GTNKRAP (SEQ ID NO:61); and
(f) a CDR L3 amino acid sequence of ALWYSNHWV (SEQ ID NO:62).

In one embodiment the CAR capable of specific binding to an immunoglobulin domain comprising the hapten tag DIG comprises a heavy chain variable region (VH) comprising an amino acid sequence that is at least about 95%, 96%, 97%, 98%, 99% or 100% identical to the amino acid sequence of SEQ ID NO:64 and a light chain variable region (VL) comprising an amino acid sequence that is at least about 95%, 96%, 97%, 98%, 99% or 100% identical to the amino acid sequence of SEQ ID NO:65.

In one embodiment the CAR capable of specific binding to an immunoglobulin domain comprising the hapten tag DIG comprises a heavy chain variable region (VH) comprising the amino acid sequence of SEQ ID NO:64 and a light chain variable region (VL) comprising the amino acid sequence of SEQ ID NO:65.

In one embodiment, the at least one antigen binding moiety is a scFv, a Fab, a crossFab or a scFab fragment. In one embodiment the CAR capable of specific binding to an immunoglobulin domain comprising the hapten tag DIG comprises a Fab fragment. In a preferred embodiment the CAR capable of specific binding to an immunoglobulin domain comprising the hapten tag DIG comprises a Fab fragment comprising a heavy chain of SEQ ID NO:68 and a light chain of SEQ ID NO:69.

In one embodiment the CAR capable of specific binding to an immunoglobulin domain comprising the hapten tag DIG comprises a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In a preferred embodiment the CAR capable of specific binding to an immunoglobulin domain comprising the hapten tag DIG comprises an scFv fragment comprising the amino acid sequence of SEQ ID NO:66.

In another illustrative embodiment of the present invention, as a proof of concept, provided are CARs capable of specific binding to a modified immunoglobulin domain comprising the hapten tag Fluorescein isothiocyanate (FITC).

In one embodiment the CAR capable of specific binding to an immunoglobulin domain comprising the hapten tag FITC comprises the heavy chain complementarity determining regions (CDRs) of SEQ ID NO:72, SEQ ID NO:73 and SEQ ID NO:74 and the light chain CDRs of SEQ ID NO:75, SEQ ID NO:76 and SEQ ID NO:77.

In one preferred embodiment the CAR capable of specific binding to an immunoglobulin domain comprising the hapten tag FITC comprises a heavy chain variable region comprising:
(a) a heavy chain complementarity determining region (CDR H) 1 amino acid sequence of RYWMN (SEQ ID NO:72);
(b) a CDR H2 amino acid sequence of EITPDSSTI-NYTPSLKD (SEQ ID NO:73);
(c) a CDR H3 amino acid sequence of PYDYGAWFAS (SEQ ID NO:74);
and a light chain variable region comprising:
(d) a light chain (CDR L)1 amino acid sequence of RSSTGAVTTSNYAN (SEQ ID NO:75);
(e) a CDR L2 amino acid sequence of GTNKRAP (SEQ ID NO:76); and
(f) a CDR L3 amino acid sequence of ALWYSNHWV (SEQ ID NO:77).

In one embodiment the CAR capable of specific binding to an immunoglobulin domain comprising the hapten tag FITC comprises a heavy chain variable region (VH) comprising an amino acid sequence that is at least about 95%, 96%, 97%, 98%, 99% or 100% identical to the amino acid sequence of SEQ ID NO:80 and a light chain variable region (VL) comprising an amino acid sequence that is at least about 95%, 96%, 97%, 98%, 99% or 100% identical to the amino acid sequence of SEQ ID NO:81.

In one embodiment the CAR capable of specific binding to an immunoglobulin domain comprising the hapten tag FITC comprises a heavy chain variable region (VH) comprising the amino acid sequence of SEQ ID NO:80, and a light chain variable region (VL) comprising the amino acid sequence of SEQ ID NO:81.

In one embodiment, the at least one antigen binding moiety is a scFv, a Fab, a crossFab or a scFab fragment.

In one embodiment the CAR capable of specific binding to an immunoglobulin domain comprising the hapten tag FITC comprises a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In a preferred embodiment the CAR capable of specific binding to an immunoglobulin domain comprising the hapten tag FITC comprises an scFv fragment comprising the amino acid sequence of SEQ ID NO:78.

In further illustrative embodiments of the present invention, as a proof of concept, CARs are provided comprising an extracellular domain comprising at least one antigen binding moiety, wherein the at least one antigen binding moiety is capable of specific binding to a modified immunoglobulin domain (e.g., a Fc domain or a Fab domain) but not capable of specific binding to the non-modified immunoglobulin domain, wherein the modified immunoglobulin domain comprises a polypeptide tag.

In one illustrative embodiment of the present invention, as a proof of concept, provided are CARs capable of specific binding to a modified immunoglobulin domain comprising a polypeptide tag from the influenza hemagglutinin (HA) glycoprotein. In one embodiment, the polypeptide tag from the HA protein comprises the amino acid sequence of YPYDVPDYA (SEQ ID NO:103).

In one embodiment the CAR capable of specific binding to an immunoglobulin domain comprising the HA tag comprises the heavy chain complementarity determining regions (CDRs) of SEQ ID NO:82, SEQ ID NO:83 and SEQ ID NO:84 and the light chain CDRs of SEQ ID NO:85, SEQ ID NO:86 and SEQ ID NO:87.

In one preferred embodiment the CAR capable of specific binding to an immunoglobulin domain comprising the HA tag comprises a heavy chain variable region comprising:
(a) a heavy chain complementarity determining region (CDR H) 1 amino acid sequence of RYWMN (SEQ ID NO:82);
(b) a CDR H2 amino acid sequence of EITPDSSTI-NYTPSLKD (SEQ ID NO:83);
(c) a CDR H3 amino acid sequence of PYDYGAWFAS (SEQ ID NO:84);
and a light chain variable region comprising:
(d) a light chain (CDR L)1 amino acid sequence of RSSTGAVTTSNYAN (SEQ ID NO:85);
(e) a CDR L2 amino acid sequence of GTNKRAP (SEQ ID NO:86); and
(l) a CDR L3 amino acid sequence of ALWYSNHWV (SEQ ID NO:87).

In one embodiment the CAR capable of specific binding to an immunoglobulin domain comprising the HA tag comprises a heavy chain variable region (VH) comprising an amino acid sequence that is at least about 95%, 96%, 97%, 98%, 99% or 100% identical to the amino acid sequence of SEQ ID NO:90 and a light chain variable region (VL) comprising an amino acid sequence that is at least about 95%, 96%, 97%, 98%, 99% or 100% identical to the amino acid sequence of SEQ ID NO:91.

In one embodiment the CAR capable of specific binding to an immunoglobulin domain comprising the HA tag comprises a heavy chain variable region (VH) comprising the amino acid sequence of SEQ ID NO:90, and a light chain variable region (VL) comprising the amino acid sequence of SEQ ID NO:91.

In one embodiment, the at least one antigen binding moiety is a scFv, a Fab, a crossFab or a scFab fragment. In one embodiment the CAR capable of specific binding to an immunoglobulin domain comprising the HA tag comprises a Fab fragment.

In one embodiment the CAR capable of specific binding to an immunoglobulin domain comprising the HA tag comprises a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In a preferred embodiment the CAR capable of specific binding to an immunoglobulin domain comprising the HA tag comprises an scFv fragment comprising the amino acid sequence of SEQ ID NO:89.

In another illustrative embodiment of the present invention, as a proof of concept, provided are CARs capable of specific binding to a modified immunoglobulin domain comprising a polypeptide tag from the human c-myc protein. In one embodiment, the polypeptide tag from the human c-myc protein comprises the amino acid sequence of EQKLISEEDL (SEQ ID NO:104).

In one embodiment the CAR capable of specific binding to an immunoglobulin domain comprising the myc tag comprises the heavy chain complementarity determining regions (CDRs) of SEQ ID NO:92, SEQ ID NO:93 and SEQ ID NO:94 and the light chain CDRs of SEQ ID NO:95, SEQ ID NO:96 and SEQ ID NO:97.

In one preferred embodiment the CAR capable of specific binding to an immunoglobulin domain comprising the myc tag comprises a heavy chain variable region comprising:
  (a) a heavy chain complementarity determining region (CDR H) 1 amino acid sequence of RYWMN (SEQ ID NO:92);
  (b) a CDR H2 amino acid sequence of EITPDSSTI-NYTPSLKD (SEQ ID NO:93);
  (c) a CDR H3 amino acid sequence of PYDYGAWFAS (SEQ ID NO:94);
and a light chain variable region comprising:
  (d) a light chain (CDR L)1 amino acid sequence of RSSTGAVTTSNYAN (SEQ ID NO:95);
  (e) a CDR L2 amino acid sequence of GTNKRAP (SEQ ID NO:96); and
  (f) a CDR L3 amino acid sequence of ALWYSNHWV (SEQ ID NO:97).

In one embodiment the CAR capable of specific binding to an immunoglobulin domain comprising the myc tag comprises a heavy chain variable region (VH) comprising an amino acid sequence that is at least about 95%, 96%, 97%, 98%, 99% or 100% identical to the amino acid sequence of SEQ ID NO:101 and a light chain variable region (VL) comprising an amino acid sequence that is at least about 95%, 96%, 97%, 98%, 99% or 100% identical to the amino acid sequence of SEQ ID NO:102.

In one embodiment the CAR capable of specific binding to an immunoglobulin domain comprising the myc tag comprises a heavy chain variable region (VH) comprising the amino acid sequence of SEQ ID NO:101, and a light chain variable region (VL) comprising the amino acid sequence of SEQ ID NO:102.

In one embodiment, the at least one antigen binding moiety is a scFv, a Fab, a crossFab or a scFab fragment. In one embodiment the CAR capable of specific binding to an immunoglobulin domain comprising the myc tag comprises a Fab fragment. In a preferred embodiment the CAR capable of specific binding to an immunoglobulin domain comprising the myc tag comprises a Fab fragment comprising a heavy chain of SEQ ID NO:99 and a light chain of SEQ ID NO:100.

In a particular embodiment, the antigen binding moiety is a Fab fragment capable of specific binding to an immunoglobulin domain comprising the myc tag, wherein the antigen binding receptor comprises a heavy chain fusion polypeptide comprising an amino acid sequence that is at least about 95%, 96%, 97%, 98%, 99% or 100% identical to the amino acid sequence of SEQ ID NO:98 and a light chain polypeptide comprising an amino acid sequence that is at least about 95%, 96%, 97%, 98%, 99% or 100% identical to the amino acid sequence of SEQ ID NO:100.

In a preferred embodiment, the antigen binding moiety is a Fab capable of specific binding to an immunoglobulin domain comprising the myc tag, wherein the antigen binding receptor comprises a heavy chain fusion polypeptide comprising the amino acid sequence of SEQ ID NO:98 and a light chain polypeptide comprising the amino acid sequence of SEQ ID NO:100.

In one embodiment the CAR capable of specific binding to an immunoglobulin domain comprising the myc tag comprises a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

Fab and scFab fragments are stabilized via the natural disulfide bond between the CL domain and the CH1 domain. Antigen binding moieties comprising a heavy chain variable domain (VH) and a light chain variable domain (VL), such as the Fab, crossFab, scFv and scFab fragments as described herein might be further stabilized by introducing interchain disulfide bridges between the VH and the VL domain. Accordingly, in one embodiment, the Fab fragment(s), the crossFab fragment(s), the scFv fragment(s) and/or the scFab fragment(s) comprised in the antigen binding receptors according to the invention might be further stabilized by generation of interchain disulfide bonds via insertion of cysteine residues (e.g., position 44 in the variable heavy chain and position 100 in the variable light chain according to Kabat numbering). Such stabilized antigen binding moieties are herein referred to by the term "ds".

Haptens can be coupled covalently or non-covalently to the recognition domain according to methods known in the art. For example biotinylation is widely used in the art to couple the hapten Biotin to a polypeptide, e.g., an immunoglobulin. Biotin is typically conjugated to proteins via primary amines (e.g., lysine). For IgG antibodies, usually, between 3 and 6 biotin molecules are conjugated per antibody molecule. Alternatively, carbohydrates can be biotinylated according to methods known in the art.

In one embodiment, the hapten molecule is coupled to the recognition domain using site-directed coupling. In one embodiment, introduction of a polypeptide tag in the antigen binding molecule is combined with site-directed coupling of a hapten molecule to the polypeptide tag. In such embodiments of the present invention, the number of hapten molecules coupled to the antigen binding molecule can be controlled, e.g., by providing a defined number of coupling sites in the polypeptide tag. An example of a site-directed coupling technology is the AviTag system which is known in the art. The polypeptide tag AviTag of GLNDIFEAQK-IEWH (SEQ ID NO:106) comprises a natural biotinylation site which can be selectively biotinylated using the BirA Biotin-protein ligase. In one embodiment, the recognition domain comprises a defined number of hapten molecules. In one embodiment, the recognition domain does not comprise more than 1, 2, 3 or 4 hapten molecules. In a preferred embodiment, the recognition domain comprises two hapten molecules, e.g., the recognition domain is a Fc domain composed of two polypeptide molecules each comprising one hapten molecule. In another preferred embodiment, the recognition domain comprises one hapten molecule, e.g., the recognition domain is a Fab fragment comprising a hapten molecule either coupled to the heavy chain or the light chain fragment.

The CARs as provided and used herein comprise an extracellular domain comprising an antigen binding moiety capable of specific binding to the recognition domain, an anchoring transmembrane domain and at least one intracellular signaling and/or at least one co-stimulatory signaling domain. The anchoring transmembrane domain mediates confinement of the CAR to the cell membrane of the reporter cell, e.g., the T cell. The intracellular signaling and/or at least one co-stimulatory signaling domain transfer the binding of the CAR to an intracellular signal, e.g., T cell activation, which can be assessed by measuring reporter gene expression. In the context of the present invention, expression of the reporter gene as described herein is indicative for binding of the target antigen binding moiety to the target antigen and resulting T cell activation as described herein.

The anchoring transmembrane domain of the CAR may be characterized by not having a cleavage site for mammalian proteases. Proteases refer to proteolytic enzymes that are able to hydrolyze the amino acid sequence of a transmembrane domain comprising a cleavage site for the protease. The term proteases include both endopeptidases and exopeptidases. In the context of the present invention any anchoring transmembrane domain of a transmembrane protein as laid down among others by the CD-nomenclature may be used to generate a CAR suitable according to the invention, which activates T cells, upon binding, e.g., target cell or a modified immunoglobulin domain, as defined herein.

Accordingly, in the context of the present invention, the anchoring transmembrane domain may comprise part of a murine/mouse or preferably of a human transmembrane domain. An example for such an anchoring transmembrane domain is a transmembrane domain of CD28, for example, having the amino acid sequence as shown herein in SEQ ID NO:11 (as encoded by the DNA sequence shown in SEQ ID NO:23). In the context of the present invention, the transmembrane domain of the CAR may comprise/consist of an amino acid sequence as shown in SEQ ID NO:11 (as encoded by the DNA sequence shown in SEQ ID NO:23).

Alternatively, any protein having a transmembrane domain, as provided among others by the CD nomenclature, may be used as an anchoring transmembrane domain of the CAR provided and used in the invention. As described above, the CAR may comprise the anchoring transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO:112 (as encoded by the cDNA shown in SEQ ID NO:111). Accordingly, in context of the present invention the anchoring transmembrane domain may comprise or consist of an amino acid sequence as shown in SEQ ID NO:11 (as encoded by the DNA sequence shown in SEQ ID NO:23).

As described herein, the CAR used according to the invention comprises at least one stimulatory signaling and/or co-stimulatory signaling domain. The stimulatory signaling and/or co-stimulatory signaling domain transduce the binding of the antigen binding molecule comprising the target antigen binding moiety to an intracellular signal in the reporter CAR-T cell. Accordingly, the CAR preferably comprises a stimulatory signaling domain, which provides T cell activation. In a preferred embodiment, binding of the target antigen binding moiety to the target antigen and/or binding of the reporter CAR-T cell to the antigen binding molecule comprising the target antigen binding moiety leads to activation of the intracellular signaling and/or co-signaling domain. In certain embodiments, the herein provided CAR comprises a stimulatory signaling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is O54709 (version number 132 with sequence number 2)). Thus, the stimulatory signaling domain which is comprised in the CAR may be a fragment/polypeptide part of the full length of CD3z, FCGR3A or NKG2D. The amino acid sequence of the murine/mouse full length of CD3z is shown herein as SEQ ID NO:109 (murine/mouse as encoded by the DNA sequence shown in SEQ ID NO:110). The amino acid sequence of the human full length CD3z is shown herein as SEQ ID NO:107 (human as encoded by the DNA sequence shown in SEQ ID NO:108). The CAR provided and used according to the present invention may comprise fragments of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the CAR comprises polypeptides which are derived from human origin. Preferably, the CAR comprises the amino acid sequence as shown herein as SEQ ID NO:107 (CD3z) (human as encoded by the DNA sequences shown in SEQ ID NO:108 (CD3z)). For example, the fragment/polypeptide part of the human CD3z which may be comprised in the CAR may comprise or consist of the amino acid sequence shown in SEQ ID NO:13 (as encoded by the DNA sequence shown in SEQ ID NO:25). Accordingly, in one embodiment the CAR comprises the sequence as shown in SEQ ID NO:13 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO:13 and which is characterized by having a stimulatory signaling activity. Specific configurations of CARs comprising a stimulatory signaling domain are provided herein below and in the Examples and Figures. The stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

The CAR preferably comprises at least one co-stimulatory signaling domain which provides additional activity to the reporter CAR-T cell. The CAR may comprise a co-stimulatory signaling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the Uniprot Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)), DAP10 (the UniProt Entry of the human DAP10 is Q9UBJ5 (version number 25 with sequence number 1); the UniProt entry of the murine/mouse DAP10 is Q9QUJ0 (primary citable accession number) or Q9R1E7 (secondary citable accession number) with the version number 101 and the sequence number 1)) or DAP12 (the UniProt Entry of the human DAP12 is O43914 (version number 146 and the sequence number 1); the UniProt entry of the murine/mouse DAP12 is O054885 (primary citable accession number) or Q9R1E7 (secondary citable accession number) with the version number 123 and the sequence number 1). In certain embodiments the CAR may comprise one or more, i.e., 1, 2, 3, 4, 5, 6 or 7 of the herein defined co-stimulatory signaling domains. Accordingly, in the context of the present invention, the CAR may comprise a fragment/polypeptide part of a murine/mouse or preferably of a human CD28 as first co-stimulatory signaling domain and the second co-stimulatory signaling domain is selected from the group consisting of the murine/mouse or preferably of the human CD27, CD28, CD137, OX40, ICOS, DAP10 and DAP12, or fragments thereof. Preferably, the CAR comprises a co-stimulatory signaling domain which is derived from a human origin. Thus, more preferably, the co-stimulatory signaling domain(s) which is (are) comprised in the CAR may comprise or consist of the amino acid sequence as shown in SEQ ID NO:12 (as encoded by the DNA sequence shown in SEQ ID NO:24).

Thus, the co-stimulatory signaling domain which may be optionally comprised in the CAR is a fragment/polypeptide part of the full length CD27, CD28, CD137, OX40, ICOS, DAP10 and DAP12. The amino acid sequence of the murine/mouse full length CD28 is shown herein as SEQ ID NO:114 (murine/mouse as encoded by the DNA sequences shown in SEQ ID NO:113). However, because human sequences are most preferred in the context of the present invention, the co-stimulatory signaling domain which may be optionally comprised in the CAR protein is a fragment/polypeptide part of the human full length CD27, CD28, CD137, OX40, ICOS, DAP10 or DAP12. The amino acid sequence of the human full length CD28 is shown herein as SEQ ID NO:112 (human as encoded by the DNA sequence shown in SEQ ID NO:111).

In one preferred embodiment, the CAR comprises CD28 or a fragment thereof as co-stimulatory signaling domain. The CAR may comprise a fragment of CD28 as co-stimulatory signaling domain, provided that at least one signaling domain of CD28 is comprised. In particular, any part/fragment of CD28 is suitable for the CAR as long as at least one of the signaling motives of CD28 is comprised. For example, the CD28 polypeptide which is comprised in the CAR may comprise or consist of the amino acid sequence shown in SEQ ID NO:12 (as encoded by the DNA sequence shown in SEQ ID NO:24). In the present invention the intracellular domain of CD28, which functions as a co-stimulatory signaling domain, may comprise a sequence derived from the intracellular domain of the CD28 polypeptide having the sequence(s) YMNM (SEQ ID NO:115) and/or PYAP (SEQ ID NO:116). Preferably, the CAR comprises polypeptides which are derived from human origin. For example, the fragment/polypeptide part of the human CD28 which may be comprised in the CAR may comprise or consist of the amino acid sequence shown in SEQ ID NO:12 (as encoded by the DNA sequence shown in SEQ ID NO:24). Accordingly, in one embodiment, the CAR comprises the sequence as shown in SEQ ID NO:12 or a sequence which has up to 1, 2, 3, 4, 5, 6, 7, 8, 9 or 10 substitutions, deletions or insertions in comparison to SEQ ID NO:12 and which is characterized by having a co-stimulatory signaling activity. Specific configurations of CARs comprising a co-stimulatory signaling domain (CSD) are provided herein below and in the Examples and Figures. The co-stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

As mentioned above, in an embodiment of the present invention, the co-stimulatory signaling domain of the CAR may be derived from the human CD28 gene (Uni Prot Entry No: P10747 (accession number with the entry version: 173 and version 1 of the sequence)) and provides CD28 activity, defined as cytokine production, proliferation and lytic activity of the transduced cell described herein, like a transduced T cell. CD28 activity can be measured by release of cytokines by ELISA or flow cytometry of cytokines such as interferon-gamma (IFN-γ) or interleukin 2 (IL-2), proliferation of T cells measured e.g., by ki67-measurement, cell quantification by flow cytometry, or lytic activity as assessed by real time impedence measurement of the target cell (by using e.g., an ICELLligence instrument as described e.g., in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Düwell et al., Cell Death Differ. 21(12) (2014), 1825-1837, Erratum in: Cell Death Differ. 21(12) (2014), 161). The co-stimulatory signaling domains PYAP and YMNM are beneficial for the function of the CD28 polypeptide and the functional effects enumerated above. The amino acid sequence of the YMNM domain is shown in SEQ ID NO:115; the amino acid sequence of the PYAP domain is shown in SEQ ID NO:116. Accordingly, in the CAR as provided and used herein, the CD28 polypeptide preferably comprises a sequence derived from intracellular domain of a CD28 polypeptide having the sequences YMNM (SEQ ID NO:115) and/or PYAP (SEQ ID NO:116). These signaling motives may, be present at any site within the intracellular domain of the CARs.

The extracellular domain comprising at least one antigen binding moiety capable of specific binding to the recognition domain, the anchoring transmembrane domain that does not have a cleavage site for mammalian proteases, the co-stimulatory signaling domain and the stimulatory signaling domain may be comprised in a single-chain multi-functional polypeptide. A single-chain fusion construct e.g., may consist of (a) polypeptide(s) comprising (an) extracellular domain(s) comprising at least one antigen binding moiety, (an) anchoring transmembrane domain(s), (a) co-stimulatory signaling domain(s) and/or (a) stimulatory signaling domain(s). In alternative embodiments, the CAR comprises an antigen binding moiety which is not a single chain fusion construct, i.e., the antigen binding moiety is a Fab or a crossFab fragment. In such embodiments the CAR is not a single chain fusion construct comprising only one polypeptide chain. Preferably such constructs will comprise a single chain heavy chain fusion polypeptide combined with an immunoglobulin light chain, e.g., the heavy chain fusion polypeptide comprises (an) immunoglobulin heavy chain(s), (an) anchoring transmembrane domain(s), (a) co-stimulatory signaling domain(s) and/or (a) stimulatory signaling domain(s) and is combined with (an) immunoglobulin light chain(s). Accordingly, the extracellular domain, the anchoring transmembrane domain, the co-stimulatory signaling domain and the stimulatory signaling domain may be connected by one or more identical or different peptide linker.

For example, the linker between the extracellular domain comprising at least one antigen binding moiety capable of specific binding to the recognition domain and the anchoring transmembrane domain may comprise or consist of the amino acid sequence as shown in SEQ ID NO:17. Accordingly, the anchoring transmembrane domain, the co-stimulatory signaling domain and/or the stimulatory domain may be connected to each other by peptide linkers or alternatively, by direct fusion of the domains.

In some embodiments, the antigen binding moiety comprised in the extracellular domain is a single-chain variable fragment (scFv) which is a fusion protein of the variable regions of the heavy (VH) and light chains (VL) of an antibody, connected with a short linker peptide of 10 to about 25 amino acids. The linker is usually rich in glycine for flexibility, as well as serine or threonine for solubility, and can either connect the N-terminus of the VH with the C-terminus of the VL, or vice versa. For example, the linker may have the amino and amino acid sequence as shown in SEQ ID NO:16. A scFv antigen binding moiety retains the specificity of the original antibody, despite removal of the constant regions and the introduction of the linker. scFv antibodies are, e.g., described in Houston, J. S., Methods in Enzymol. 203 (1991) 46-96).

The CAR or parts thereof may comprise a signal peptide. Such a signal peptide will bring the protein to the surface of the T cell membrane. For example, the signal peptide may have the amino and amino acid sequence as shown in SEQ ID NO:117 (as encoded by the DNA sequence shown in SEQ ID NO:118).

The components of the CARs can be fused to each other in a variety of configurations to generate T cell activating CARs. In some embodiments, the CAR comprises an extracellular domain composed of a heavy chain variable domain (VH) and a light chain variable domain (VL) connected to an anchoring transmembrane domain. In some embodiments, the VH domain is fused at the C-terminus to the N-terminus of the VL domain, optionally through a peptide linker. In other embodiments, the CAR further comprises a stimulatory signaling domain and/or a co-stimulatory signaling domain. In a specific such embodiment, the CAR essentially consists of a VH domain and a VL domain, an anchoring transmembrane domain, and optionally a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain. Optionally, the CAR further comprises a co-stimulatory signaling domain. In one such specific embodiment, the antigen binding receptor essentially consists of a VH domain and a VL domain, an anchoring transmembrane domain, a stimulatory signaling domain and a co-stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain, wherein the stimulatory signaling domain is fused at the C-terminus to the N-terminus of the co-stimulatory signaling domain. In an alternative embodiment, the co-stimulatory signaling domain is connected to the anchoring transmembrane domain instead of the stimulatory signaling domain. In a preferred embodiment, the CAR essentially consists of a VH domain and a VL domain, an anchoring transmembrane domain, a co-stimulatory signaling domain and a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the co-stimulatory signaling domain, wherein the co-stimulatory signaling domain is fused at the C-terminus to the N-terminus of the stimulatory signaling domain.

In preferred embodiments, one of the binding moieties is a Fab fragment or a crossFab fragment. In one preferred embodiment, the antigen binding moiety is fused at the C-terminus of the Fab or crossFab heavy chain to the N-terminus of the anchoring transmembrane domain, optionally through a peptide linker. In an alternative embodiment, the antigen binding moiety is fused at the C-terminus of the Fab or crossFab light chain to the N-terminus of the anchoring transmembrane domain, optionally through a peptide linker. In other embodiments, the CAR further comprises a stimulatory signaling domain and/or a co-stimulatory signaling domain. In a specific such embodiment, the CAR essentially consists of a Fab or crossFab fragment, an anchoring transmembrane domain, and optionally a stimulatory signaling domain connected by one or more peptide linkers, wherein the Fab or crossFab fragment is fused at the C-terminus of the heavy or light chain to the N-terminus of the anchoring transmembrane domain, wherein the anchoring transmembrane domain is fused at the C-terminus to the N-terminus of the stimulatory signaling domain. Preferably, the CAR further comprises a co-stimulatory signaling domain. In one such embodiment, the CAR essentially consists of a Fab or crossFab fragment, an anchoring transmembrane domain, a stimulatory signaling domain and a co-stimulatory signaling domain connected by one or more peptide linkers, wherein the Fab or crossFab fragment is fused at the C-terminus of the heavy or light chain to the N-terminus of the anchoring transmembrane domain, wherein the stimulatory signaling domain is fused at the C-terminus to the N-terminus of the co-stimulatory signaling domain. In a preferred embodiment, the co-stimulatory signaling domain is connected to the anchoring transmembrane domain instead of the stimulatory signaling domain. In a most preferred embodiment, the CAR essentially consists of a Fab or crossFab fragment, an anchoring transmembrane domain, a co-stimulatory signaling domain and a stimulatory signaling domain, wherein the Fab or crossFab fragment is fused at the C-terminus of the heavy chain to the N-terminus of the anchoring transmembrane domain through a peptide linker, wherein the anchoring transmembrane domain is fused at the C-terminus to the N-terminus of the co-stimulatory signaling domain, wherein the co-stimulatory signaling domain is fused at the C-terminus to N-terminus of the stimulatory signaling domain.

The antigen binding moiety, the anchoring transmembrane domain and the stimulatory signaling and/or co-stimulatory signaling domains may be fused to each other directly or through one or more peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers, wherein "n" is generally a number between 1 and 10, typically between 2 and 4. A preferred peptide linker for connecting the antigen binding moiety and the anchoring transmembrane moiety is GGGGS ($G_4S$) according to SEQ ID NO 20. An exemplary peptide linker suitable for connecting variable heavy chain (VH) and the variable light chain (VL) is GGGSGGGSGGGSGGGS ($(G_4S)_4$) according to SEQ ID NO 19.

Additionally, linkers may comprise (a portion of) an immunoglobulin hinge region. Particularly where an antigen binding moiety is fused to the N-terminus of an anchoring transmembrane domain, it may be fused via an immunoglobulin hinge region or a portion thereof, with or without an additional peptide linker.

As described herein, the CARs provided and used according to the present invention comprise an extracellular domain comprising at least one antigen binding moiety. A CAR with a single antigen binding moiety is useful and preferred, particularly in cases where high expression of the CAR is needed. In such cases, the presence of more than one antigen binding moiety may limit the expression efficiency of the CAR. In other cases, however, it will be advantageous to have a CAR comprising two or more antigen binding moieties, for example to optimize targeting to the target site or to allow crosslinking of target cell antigens.

In the context of the methods according to the invention, contacting the reporter CAR-T cell with the antigen binding molecule comprising the target antigen binding moiety and binding of the target antigen binding moiety to the target cell (e.g., the tumor cell) comprising the target antigen on the surface leads to expression of the reporter gene as described herein. Accordingly, in one embodiment, activation of the intracellular signaling and/or co-signaling domain as described herein leads to activation of a response element as herein described. In a preferred embodiment, the response element controls the expression of the reporter gene. In a preferred embodiment, activation of the response element leads to expression of the reporter gene. Accordingly, the reporter gene in the reporter cells (e.g., the reporter CAR-T cell) is expressed upon binding of the target antigen binding moiety to the target. In one embodiment, the expression of the reporter gene is indicative for binding of the target antigen binding moiety to the target antigen. In this context, the binding of the CAR to its target elicits a cellular response which results in a modulation of the activity of the response element, either directly or through a cascade of cell signaling. The response element is a DNA element which can be silenced or activated by transcription factors or the like. Response elements are known in the art and are commercially available, e.g., in reporter vectors. Usually the response element comprises DNA repeat elements and is a cis-acting enhancer element located upstream of a minimal promotor which drives expression of a reporter gene upon transcription factor binding.

Binding of the CAR to the recognition domain, e.g., the modified Fc domain or Fab fragment, activates the response element. In one embodiment the response element is a nuclear response element located in the nucleus of the cell. In another embodiment said response element is located on a plasmid in the reporter cell. In one embodiment the assay comprises the preliminary step of transfection of the reporter cells, e.g., a CAR-T cell, with an expression vector comprising the DNA sequence coding for the reporter gene under the control of the response element. Additionally, the reporter cells can be transfected with an expression vector comprising the DNA sequence coding for the CAR. The reporter cells can be transfected with an expression vector comprising all elements of the signaling cascade or with different vectors individually expressing the different components. In one embodiment, the reporter cells comprise the DNA sequence coding for the reporter gene under the control of the response element, and the DNA sequence coding for the CAR.

Accordingly, as described herein, the CAR is functionally linked to a response element. In one embodiment, the response element controls the expression of the reporter gene. In one embodiment the response element is part of the NFAT pathway, the NF-κB pathway or the AP-1 pathway, preferably, the NFAT pathway.

In one embodiment the reporter gene is selected from a gene coding for a fluorescent protein or a gene coding for an enzyme whose catalytic activity can be detected. In one embodiment, the reporter gene is coding for a luminescent protein. In further embodiments the fluorescent protein is selected from the group consisting of green fluorescent protein (GFP), yellow fluorescent protein (YFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Oruro et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) enhanced green fluorescent protein (EGFP) and can be measured e.g., by live cell imaging (e.g., Incucyte) or fluorescent spectrophotometry. In one embodiment the enzyme whose catalytic activity can be detected is selected from the group consisting of luciferase, beta Galactosidase and Alkaline Phosphatase. In one embodiment the reporter gene is encoding for GFP. In a preferred embodiment the reporter gene is encoding for luciferase. The activity of luciferase can be detected by commercially available assays, e.g., by the Luciferase 1000 Assay System or the ONE-Glo™ Luciferase Assay System (both Promega). The Luciferase 1000 Assay System contains coenzyme A (CoA) besides luciferin as a substrate, resulting in a strong light intensity lasting for at least one minute. For assaying the intracellular luciferase, it is necessary to lyse the cells prior to detection. The light which is produced as a by-product of the reaction is collected by the luminometer from the entire visible spectrum. In the examples shown herein the signal was proportional to the amount of produced luciferase and therefore proportional to the strength of the activation of the NFAT promotor. In another embodiment a Luciferase assay is used wherein the luciferase is secreted from the cells. Hence the assay can be performed without lysis of the cells.

As described herein, the expression of the reporter gene can be directly correlated with the binding of the target antigen binding moiety to the target antigen on the target cell and the resulting activation of the reporter cell, e.g., the Jurkat cell. For example when using a gene encoding for luciferase as a reporter gene, the amount of light detected from the cells correlates directly with the target antigen binding and is indicative for the target antigen binding when compared to appropriate control situations. In one embodiment the antigen binding molecule comprising the target antigen binding moiety is applied in different concentrations and the half maximal effective concentration (EC50) of reporter gene activation is determined. EC50 refers to the concentration of the antigen binding molecule (e.g. the antibody) or ligand at which the antigen binding molecule activates or inhibits the reporter gene halfway between the baseline and maximum after a specified exposure time. The EC50 of the dose response curve therefore represents the concentration of the target antigen binding moiety where 50% of its maximal activating or inhibitory effect on the target antigen is observed.

In one embodiment, the target antigen binding moiety is capable of specific binding to a tumor target antigen on the surface of the tumor cell. In one embodiment, the tumor target antigen is selected from the group consisting of CD20, CD38, CD138, CEA, EGFR, FolR1, HER2, LeY, MCSP, STEAP1, TYRP1, and WT1, or a fragment thereof. However, the target antigen is not limited to proteins which are primarily or exclusively located on the cell surface but may also derive from polypeptides or proteins which are temporarily or permanently located intracellularly. In such cases, the target antigen deriving from an intracellular polypeptide or protein can be presented on the (tumor) cell surface by one or several molecules of the major histocompatibility complex (MHC). In one embodiment, the tumor target antigen is a peptide bound to a molecule of the MHC. In one embodiment, the MHC is a human MHC. In one embodiment, the peptide bound to a molecule of the MHC has an overall length of between 8 and 100, preferably between 8 and 30, and more preferred between 8 and 16 amino acids. In one embodiment, the tumor target antigen derives from a protein which is exclusively or mainly expressed in tumor tissue. In one embodiment, the protein is an intracellular protein and the peptide is generated by the MHC-I or MHC-II pathway and presented by a MHC class I or MHC class II complex. In one embodiment, the peptide is generated by the MHC-I pathway and presented by a MHC class I complex. In one embodiment, the target antigen binding moiety is a T cell receptor like (TCRL) antigen binding moiety. A TCRL antigen binding moiety is capable of specific binding to a peptide antigen which is exclusively or mainly expressed in tumor tissue, wherein the peptide antigen is bound to a molecule of the MHC located on the surface of a target cell, particularly a cancer cell. In this context, the method of the present invention is particularly suitable to detect the presence of a target cell, e.g., a tumor cell, based on presence of a specific peptide/MHC complex on the surface of the target cell using established or novel TCRL target antigen binding moieties. Indeed, currently available diagnostic assay formats are limited in their ability to specifically detect tumor specific peptide/MHC complex. The present invention provides a specific and sensitive assay format for the detection of peptide/MHC complex with the specific detection of peptide/MHC complex by TCRL antigen binding moieties. In such embodiments of the present invention, at least one TCRL antigen binding moiety is comprised in the antigen binding molecule comprising the recognition domain, e.g., the modified or mutation Fc domain.

The binding of the antigen binding molecule comprising the target antigen binding moiety to the target antigen can be determined qualitatively or qualitatively, i.e., by the presence or absence of the expression of the reporter gene; with the absence of any fluorescence or luminescence being indicative of no binding. For quantitative measurement of binding and activation the amount of reporter gene activation can be compared to a reference. Accordingly, the diagnostic assay as described herein may additionally comprise the step of comparing the level of expression of the reporter gene to a reference. A suitable reference usually comprises a negative control which is substantially identical to the referenced assay omitting one or several essential component(s) of the assay or method. For the methods of the invention the omitted component may be, e.g., omitting addition of the antigen binding molecule or omitting the target cell. Alternatively, a reporter CAR-T cell not capable of binding to the target cell and/or the recognition domain of the antigen binding molecule can be used. In one embodiment, the reference is expression of the reporter gene in absence of the antigen binding molecule. In another embodiment, the reference is expression of the reporter gene in absence of the target cell, in particular in absence of the tumor cell. In specific embodiments, the expression of the reporter gene is at least 2×, 3×, 4×, 5×, 10×, 100×, 1000×, or 10000×, higher compared to the expression of the reporter gene in presence of the reference.

Alternatively, the absence of reporter gene expression can be defined by a certain threshold, i.e., after deduction of a background signal. The background signal is usually determined by performing the assay with all reagents but without the antigen binding molecule or in absence of the target cell. A positive signal from the diagnostic assay according to the invention is given if the level of expression of the reporter gene in the presence of the target cell in relation to the expression of the reporter gene in absence of the target cell is higher than a predefined threshold value. In specific embodiments, the threshold value is 2, 3, 4, 5, 10, 100, 1000, or 10000.

The novel diagnostic assay as described herein is robust, suitable for use in high-throughput format and efficient in terms of hands-on time needed to accomplish the assay. Furthermore, the diagnostic assay of the present invention tolerates the presence of dead cells in the sample to be analyzed. This is in contrast to cell assays wherein the binding and functionality of an antigen binding molecule is determined by measuring cell viability or cell death.

One further advantage of the new diagnostic assay described herein is that no washing steps are required. The reporter cells and/or the antigen binding molecule to be tested can be added to the target cells, e.g., tumor cells, in either order or at the same time. In one embodiment, reporter CAR-T cells and the tumor sample is added to the cell culture medium which may contain the diluted antigen binding molecule in a suitable cell culture format, e.g., in a well of a 24 well plate or in a well of a 96 well plate. Preferably the testing medium is a medium that provides conditions for cells to be viable for up to 48 hours. In one embodiment the diagnostic assay is performed in a microtiter plate. In one embodiment the microtiter plate is suitable for high throughput screening. The diagnostic assay of the present invention can be performed in any format that allows for rapid preparation, processing, and analysis of multiple reactions. This can be, for example, in multi-well assay plates (e.g., 24 wells, 96 wells or 384 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting fluorescent and/or luminescent signals.

In one embodiment about 100000 to about 1000000 reporter CAR-T cells per well of a 24-well plate are provided in step c). In a preferred embodiment about 300000 to about 700000 cells or about 400000 to about 600000 reporter CAR-T cells per well of a 24-well plate are provided in step c). In one embodiment about 500000 reporter CAR-T cells per well of a 24-well plate are provided in step c). In one embodiment about 10000 to about 100000 reporter CAR-T per well of a 96-well plate are provided in step c). In a preferred embodiment about 30000 to about 70000 reporter CAR-T or about 40000 to about 60000 reporter CAR-T per well of a 96-well plate are provided in step c). In one embodiment about 50000 reporter CAR-T per well of a 96-well plate are provided in step c). In one embodiment about 3000 to about 30000 reporter CAR-T cells per well of a 384-well plate are provided in step c). In a preferred embodiment about 5000 to about 15000 cells or about 8000 to about 12000 reporter CAR-T cells per well of a 384-well plate are provided in step c). In one embodiment about 10000 reporter CAR-T cells per well of a 384-well plate are provided in step c). In one embodiment about 200000 to about 2000000 reporter CAR-T per ml of cell culture medium are provided in step c). In a preferred embodiment about 600000 to about 1400000 reporter CAR-T or about 800000 to about 1200000 reporter CAR-T per ml of cell culture medium are provided in step c). In one embodiment about 1000000 reporter CAR-T per ml of cell culture medium are provided in step c).

In one embodiment the antigen binding molecule is provided in step b) to achieve a final concentration of about 0.1 fg/ml to 10 µg/ml. In further embodiments the antigen binding molecule is provided in step b) to achieve a final concentration of about 1 fg/ml to about 1 µg/ml or about 1 pg/ml to about 1 µg/ml. In further embodiments the antigen binding molecule is provided in step b) to achieve a final concentration of about 0.1 ng/ml. In one embodiment the antigen binding molecule is provided in step b) to achieve a final concentration of about 1 nM to about 1000 nM. In further embodiments the antigen binding molecule is provided in step b) to achieve a final concentration of about 5 nM to about 200 nM or about 10 nM to about 100 nM. In further embodiments the antigen binding molecule is provided in step b) to achieve a final concentration of about 50 nM. The antigen binding molecule can be diluted in cell culture medium. The antigen binding molecule diluted to the final concentration as described herein is added to the target cells before or after adding the reporter cells. In one embodiment, the antigen binding molecule diluted to the final concentration as described herein is added to the target cells before adding the reporter cells.

Furthermore provided are transduced T cells, i.e., reporter CAR-T cells (e.g., Jurkat cells), capable of expressing a CAR as described herein and their use in the diagnostic assay according to the invention. The CAR relates to a molecule which is naturally not comprised in and/or on the surface of T cells and which is not (endogenously) expressed in or on normal (non-transduced) T cells. Thus, the CAR as used herein in and/or on T cells is artificially introduced into T cells. The CAR molecule, artificially introduced and subsequently presented in and/or on the surface of said T cells, e.g., reporter CAR-T cells, comprises domains comprising one or more antigen binding moiety accessible (in vitro or in vivo) to antigens and/or (Ig-derived) immunoglobulins, preferably antibodies, e.g., to the Fc domain or Fab fragment of the antigen binding molecules used according to the invention. In this context, these artificially introduced molecules are presented in and/or on the surface of said T cells after transduction as described herein below. Accordingly, after transduction, T cells according to the disclosure can be activated by the target antigen and/or immunoglobulins.

Herein provided are also transduced T cells expressing a CAR encoded by (a) nucleic acid molecule(s) encoding the CAR as described herein. Accordingly, in the context of the present invention, the transduced cell may comprise a nucleic acid molecule encoding the CAR as provided and used herein.

In the context of the present invention, the term "transduced T cell" relates to a genetically modified T cell (i.e., a T cell wherein a nucleic acid molecule has been introduced deliberately). In particular, the nucleic acid molecule encoding the CAR as described herein can be stably integrated into the genome of the T cell by using a retroviral or lentiviral transduction. The extracellular domain of the CAR may comprise the complete extracellular domain of an antigen binding moiety as described herein but also parts thereof. The minimal size required being the antigen binding site of the antigen binding moiety in the CAR. The extracellular portion of the CAR (i.e., the extracellular domain comprising the antigen binding moiety) can be detected on the cell surface, while the intracellular portion (i.e., the co-stimulatory signaling domain(s) and the stimulatory signaling domain) are not detectable on the cell surface. The detection of the extracellular domain of the CAR can be carried out by using an antibody which specifically binds to this extracellular domain or by the recognition domain, e.g., the modified immunoglobulin domain, which the extracellular domain is capable to bind. The extracellular domain can be detected using these antibodies, antigens or recognition domains by flow cytometry or microscopy.

The transduced cells may be any immune cell. These include but are not limited to B-cells, T cells, Natural Killer (NK) cells, Natural Killer (NK) T cells, γδ T cells, innate lymphoid cells, macrophages, monocytes, dendritic cells, or neutrophils and immortalized cell lines thereof. Preferentially, said immune cell would be a lymphocyte, preferentially a NK or T cells or immortalized cell lines deriving thereof. The said T cells include CD4 T cells and CD8 T cells. Triggering of the CAR on the surface of the leukocyte will render the cell responsive against a target cell irrespective of the lineage the cell originated from. Activation will happen irrespective of the stimulatory signaling domain or co-stimulatory signaling domain chosen for the CAR and is not dependent on the exogenous supply of additional cytokines.

The transduced cell may be co-transduced with further nucleic acid molecules, e.g., with a nucleic acid molecule encoding a response element as described herein.

The transduced cell/cells is/are preferably grown under controlled conditions, outside of their natural environment. In particular, the term "culturing" means that cells (e.g., the transduced cell(s)) are in vitro. Culturing cells is a laboratory technique of keeping cells alive which are separated from their original tissue source. Herein, the transduced cell used according to the present invention is cultured under conditions allowing the expression of the introduced gene in or on said transduced cells. Conditions which allow the expression of a transgene are commonly known in the art.

Further provided herein are nucleic acids and vectors encoding one or several CARs used according to the present invention. The nucleic acid molecules may be under the control of regulatory sequences. For example, promoters, transcriptional enhancers and/or sequences which allow for induced expression of the CARs may be employed. In the context of the present invention, the nucleic acid molecules are expressed under the control of constitutive or inducible promoter. Suitable promoters are e.g., the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24). Herein the term vector relates to a circular or linear nucleic acid molecule which can autonomously replicate in a cell (i.e., in a transduced cell) into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors can be reconstituted into liposomes for delivery to target cells. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT. The vector can be polycistronic. Such regulatory sequences (control elements) are known to the skilled person and may include a promoter, a splice cassette, translation initiation codon, and translation and insertion site for introducing an insert into the vector(s). In the context of the present invention, said nucleic acid molecule(s) is (are) operatively linked to said expression control sequences allowing expression in eukaryotic or prokaryotic cells. It is envisaged that said vector(s) is (are) an expression vector(s) comprising the nucleic acid molecule(s) encoding the CAR as defined herein. Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector (s) is (are) an expression vector(s). An expression vector is a construct that can be used to transform a selected cell and provides for expression of a coding sequence in the selected cell. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in *E. coli*, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences encoding signal peptides capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a CAR including an N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (Invitrogene), pEF-DHFR, pEF-ADA or pEF-neo (Raum et al. Cancer Immunol Immunother 50 (2001), 141-150) or pSPORT1 (GIBCO BRL).

The described nucleic acid molecule(s) or vector(s) which is (are) introduced in the T cell or its precursor cell may either integrate into the genome of the cell or it may be maintained extrachromosomally.

Exemplary Embodiments

1. A diagnostic assay for determining the presence of a tumor cell in a sample, the diagnostic assay comprising the steps of:
    a) contacting the sample with an antigen binding molecule comprising an antigen binding domain and a recognition domain, wherein the antigen binding domain comprises a target antigen binding moiety capable of specific binding to the tumor cell;
    b) contacting the sample with a chimeric antigen receptor (CAR) expressing reporter T (CAR-T) cell wherein the reporter CAR-T cell comprises:
        i. a CAR capable of specific binding to the recognition domain, wherein the CAR is operationally coupled to a response element;
        ii. a reporter gene under the control of the response element; and
    c) determining T cell activation by measuring the expression of the reporter gene to establish the presence of the tumor cell.
2. The diagnostic assay of embodiment 1, wherein the CAR comprises an antigen binding moiety capable of specific binding to the recognition domain.
3. The diagnostic assay of any one of embodiments 1 or 2, wherein the antigen binding molecule comprises an antigen binding domain and a recognition domain, wherein the antigen binding domain comprises the target antigen binding moiety, and wherein the CAR is capable of specific binding to the recognition domain.
4. The diagnostic assay of any one of embodiments 1 to 3, wherein the antigen binding domain and the recognition domain are immunoglobulin domains, or fragments thereof
5. The diagnostic assay of any one of embodiments 1 to 4, wherein the antigen binding domain and the recognition domain are individually selected from the group consisting of an antibody, an Fc domain, a Fab fragment, a crossover Fab fragment, a single chain Fab fragment, a Fv fragment, a scFv fragment, a single-domain antibody, an aVH, or fragments thereof.
6. The diagnostic assay of any one of embodiments 1 to 5, wherein the antigen binding domain is a Fab fragment and the recognition domain is an Fc domain.
7. The diagnostic assay of any one of embodiments 1 to 6, wherein the antigen binding molecule is an IgG class antibody, particularly an IgG1 or IgG4 isotype antibody.
8. The diagnostic assay of embodiments 1 to 7, wherein the recognition domain is a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.
9. The diagnostic assay of embodiment 8, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G, P331G and/or H435A.
10. The diagnostic assay of any one of embodiments 8 or 9, wherein the mutant Fc domain comprises an amino acid substitution at a position selected from the group consisting of residue 117, 118, 136, 180, 193, 212, 214, and 318 of human IgG1 Fc (SEQ ID NO:132), in particular wherein the mutant human IgG1 Fc comprises the amino acid substitution leucine to alanine at residue 117, leucine to alanine at residue 118, isoleucine to alanine at position 136, asparagine to alanine at residue 180, histidine to alanine at residue 193, proline to glycine at residue 212, proline to glycine at residue 214, and/or or histidine to alanine at residue 318 of human IgG1 Fc (SEQ ID NO:132).
11. The diagnostic assay of any one of embodiments 8 to 10, wherein mutant Fc domain comprises an amino acid substitution at the position of residue 212 of human IgG1 Fc (SEQ ID NO:138), in particular wherein the mutant Fc domain comprises the amino acid substitution proline to glycine at residue 212 of human IgG1 Fc (SEQ ID NO:132).
12. The diagnostic assay of any one of embodiment 8 to 11, wherein the mutated Fc domain comprises the amino acid mutation P329G according to EU numbering.
13. The diagnostic assay of any one of embodiments 1 to 5, wherein the antigen binding domain and the recognition domain are the same domain, in particular a Fab fragment.
14. The diagnostic assay of embodiments 1 to 13, wherein the recognition domain comprises a tag.
15. The diagnostic assay of embodiment 14, wherein the CAR is capable of specific binding to the recognition domain comprising the tag but not capable of specific binding to the recognition domain not comprising the tag.
16. The diagnostic assay of any one of embodiments 14 or 15, wherein the tag is a hapten molecule.
17. The diagnostic assay of embodiment 16, wherein the hapten molecule is coupled to the recognition domain.
18. The diagnostic assay of any one of embodiments 16 or 17, wherein the hapten molecule is covalently coupled to the recognition domain.
19. The diagnostic assay of any one of embodiments 16 to 18, wherein the hapten molecule is non-covalently coupled to the recognition domain.
20. The diagnostic assay of any one of embodiments 16 to 19, wherein the hapten molecule is selected from the group consisting of Biotin, Digoxigenin (DIG) and Fluorescein (FITC).
21. The diagnostic assay of any one of embodiments 14 or 15, wherein the tag is a polypeptide tag.
22. The diagnostic assay of embodiment 21, wherein the polypeptide tag has a length of from 1 to 30 amino acids, from 1 to 25 amino acids, from 1 to 20 amino acids, from 1 to 15 amino acids or from 1 to 10 amino acids.
23. The diagnostic assay of any one of embodiments 21 or 22, wherein the polypeptide tag is connected at the C-terminus to the N-terminus of the recognition domain, optionally through a peptide linker.
24. The diagnostic assay of any one of embodiments 21 or 22, wherein the polypeptide tag is connected at the N-terminus to the C-terminus of the recognition domain, optionally through a peptide linker.
25. The diagnostic assay of any one of embodiments 22 to 24, wherein the polypeptide tag is selected from the group consisting of myc-tag, HA-tag, AviTag, FLAG-tag, His-tag, GCN4-tag, and NE-tag.
26. The diagnostic assay of any one of embodiments 1 to 25, wherein the CAR comprises at least one intracellular stimulatory signaling and/or co-stimulatory signaling domain.
27. The diagnostic assay of embodiment 26, wherein binding of the target antigen binding moiety to the target antigen and binding of the antigen binding moiety to the recognition domain leads to activation of the intracellular signaling and/or co-signaling domain.
28. The diagnostic assay of any one of embodiments 26 or 27, wherein activation of the intracellular signaling and/or co-signaling domain leads to activation of the response element.
29. The diagnostic assay of any one of embodiments 1 to 28, wherein the response element controls the expression of the reporter gene.
30. The diagnostic assay of any one of embodiments 1 to 29, wherein activation of the response element leads to expression of the reporter gene.
31. The diagnostic assay of any one of embodiments 1 to 30, wherein the response element is part of the NFAT pathway, the NF-κB pathway or the AP-1 pathway.
32. The diagnostic assay of any one of embodiments 1 to 31, wherein the reporter gene is coding for a luminescent protein.
33. The diagnostic assay of any one of embodiments 1 to 32, wherein the reporter gene is coding for green fluorescent protein (GFP) or luciferase.
34. The diagnostic assay of any one of embodiments 1 to 33, wherein the target antigen binding moiety is capable of specific binding to a tumor target antigen on the surface of the tumor cell.
35. The diagnostic assay of embodiment 34, wherein the tumor target antigen is a cell surface antigen and/or a cell surface receptor.
36. The diagnostic assay of any one of embodiments 34 or 35, wherein the tumor target antigen is selected from the group consisting of CD20, CD38, CD138, CEA, EGFR, FolR1, HER2, LeY, MCSP, STEAP1, TYRP1, and WT1, or a fragment thereof 37. The diagnostic assay of any one of embodiments 34 to 36, wherein the tumor target antigen is a peptide bound to a molecule of the human major histocompatibility complex (MHC).
38. The diagnostic assay of embodiment 37, wherein the target antigen binding moiety is a T cell receptor like (TCRL) antigen binding moiety.
39. The diagnostic assay of any one of embodiments 1 to 38, wherein the sample is a patient sample derived from an individual suffering from a disease, in particular wherein the disease is cancer.
40. The diagnostic assay of any one of embodiments 1 to 39, additionally comprising the step of:
   c) comparing the expression of the reporter gene to a reference.
41. The diagnostic assay of embodiment 40, wherein the reference is expression of the reporter gene in the presence of a reference sample, wherein the reference sample does not comprise the tumor cell.
42. The diagnostic assay of embodiment 41, wherein expression of the reporter gene in the presence of the patient sample is at least 2×, 3×, 4×, 5×, 10×, 100×, 1000×, or 10000×, higher compared to the expression of the reporter gene in the presence of the reference sample.
43. The diagnostic assay of any one of embodiments 1 to 42, wherein the sample is a patient sample.
44. The diagnostic assay of embodiment 43, additionally comprising the step of:
   d) establishing the presence of a tumor cell if the expression of the reporter gene in the presence of the patient sample in relation to the expression of the reporter gene in the presence of a reference is higher than a predefined threshold value.
45. The diagnostic assay of embodiment 44, wherein the reference is expression of the reporter gene in the presence of a reference sample, wherein the reference sample does not comprise the tumor cell.
46. The diagnostic assay of embodiment 44 or 45, wherein the threshold value is 2, 3, 4, 5, 10, 100, 1000, or 10000.
47. The diagnostic assay of any one of embodiment 1 to 46, wherein the patient is a mammal, in particular wherein the patient is a human.
48. A diagnostic kit comprising
   (a) an antigen binding molecule capable of specific binding to a tumor cell; and
   (b) a transduced T cell comprising (i) a CAR capable of specific binding to the antigen binding molecule and (ii) a reporter gene under the control of the response element, wherein the CAR is operationally coupled to a response element.
49. The diagnostic kit of embodiment 48, wherein the antigen binding molecule comprises a target antigen binding moiety capable of specific binding to a tumor target antigen on the surface of the tumor cell.
50. The diagnostic kit of embodiment 49, wherein the tumor target antigen is a cell surface antigen and/or a cell surface receptor.
51. The diagnostic kit of any one of embodiments 49 or 50, wherein the tumor target antigen is selected from the group consisting of CD20, CD38, CD138, CEA, EGFR, FolR1, HER2, LeY, MCSP, STEAP1, TYRP1, and WT1, or a fragment thereof
52. The diagnostic kit of any one of embodiments 49 to 51, wherein the tumor target antigen is a peptide bound to a molecule of the human major histocompatibility complex (MHC).
53. The diagnostic kit assay of embodiment 52, wherein the target antigen binding moiety is a T cell receptor like (TCRL) antigen binding moiety.
54. The diagnostic kit of any one of embodiment 48 to 53, wherein the antigen binding molecule is an IgG class antibody, particularly an IgG1 or IgG4 isotype antibody, or a fragment thereof
55. The diagnostic kit of any one of embodiments 48 or 54, wherein the antigen binding molecule comprises a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.
56. The diagnostic kit of embodiment 55, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G, P331G and/or H435A.
57. The diagnostic kit of any one of embodiments 55 or 56, wherein the mutant Fc domain comprises an amino acid substitution at a position selected from the group consisting of residue 117, 118, 136, 180, 193, 212, 214, and 318 of human IgG1 Fc (SEQ ID NO:132), in particular wherein the mutant human IgG1 Fc comprises the amino acid substitution leucine to alanine at residue 117, leucine to alanine at residue 118, isoleucine to alanine at position 136, asparagine to alanine at residue 180, histidine to alanine at residue 193, proline to glycine at residue 212, proline to glycine at residue 214, and/or or histidine to alanine at residue 318 of human IgG1 Fc (SEQ ID NO:132).
58. The diagnostic kit of any one of embodiments 55 to 57, wherein the mutant Fc domain comprises an amino acid substitution at the position of residue 212 of human IgG1 Fc (SEQ ID NO:132), in particular wherein the mutant Fc domain comprises the amino acid substitution proline to glycine at residue 212 of human IgG1 Fc (SEQ ID NO:132).
59. The diagnostic kit of any one of embodiment 55 to 58, wherein the mutated Fc domain comprises the amino acid mutation P329G according to EU numbering.
60. The diagnostic kit of any one embodiments 48 to 54, wherein the antigen binding molecule comprises a tag and wherein the CAR is capable of specific binding to the antigen binding molecule comprising the tag but not capable of specific binding to the antigen binding molecule not comprising the tag.
61. The diagnostic kit of embodiment 60, wherein the tag is a hapten molecule.
62. The diagnostic kit of embodiment 61, wherein the hapten molecule is selected from the group consisting of Biotin, Digoxigenin (DIG) and Fluorescein (FITC).
63. The diagnostic kit of embodiment 62, wherein the tag is a polypeptide tag.
64. The diagnostic kit of embodiment 63, wherein the polypeptide tag has a length of from 1 to 30 amino acids, from 1 to 25 amino acids, from 1 to 20 amino acids, from 1 to 15 amino acids or from 1 to 10 amino acids.

65. The diagnostic kit of any one of embodiments 63 or 64, wherein the polypeptide tag is selected from the group consisting of myc-tag, HA-tag, AviTag, FLAG-tag, His-tag, GCN4-tag, and NE-tag.

66. The diagnostic kit of any one of embodiments 48 to 65 for use in the diagnosis of cancer.

67. A method for monitoring the efficacy of an antitumor treatment, comprising providing a sample from a subject having received antitumor treatment, and determining the presence of tumor cells using the diagnostic assay of any one of embodiments 1 to 47 or the diagnostic kit of any one of embodiments 48 to 66.

68. A method for predicting the efficacy of an antitumor treatment by administration of a T cell activating antigen binding molecule to a patient suffering from a tumor, comprising providing a sample from the subject, and determining expression of the reporter gene using the diagnostic assay of any one of embodiments 1 to 47, or the diagnostic kit of any one of embodiments 48 to 66, wherein the T cell activating antigen binding molecule is used as the antigen binding molecule in the assay or kit and wherein expression of the reporter gene is indicative for predicting the efficacy of the antitumor treatment.

69. The diagnostic assays and methods as herein before described with reference to any of the Examples or to any one of the accompanying drawings.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g., by SDS-PAGE and size exclusion chromatography (SEC).

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Antibody Production

The respective antibodies were produced by co-transfecting HEK293-EBNA cells with the mammalian expression vectors using polyethylenimine. The cells were transfected with the corresponding expression vectors for heavy and light chains in a 1:1 ratio.

Lentiviral Transduction of Jurkat NFAT CAR-T Cells

To produce lentiviral vectors, respective DNA sequences for the correct assembly of the CAR were cloned in frame in a lentiviral polynucleotide vector under a constitutively active human cytomegalovirus immediate early promoter (CMV). The retroviral vector contained a woodchuck hepatitis virus posttranscriptional regulatory element (WPRE), a central polypurine tract (cPPT) element, a pUC origin of replication and a gene encoding for antibiotic resistance facilitating the propagation and selection in bacteria.

To produce functional virus particles, Lipofectamine LTX™ based transfection was performed using 60-70% confluent Hek293T cells (ATCC CRL3216) and CAR containing vectors as well as pCMV-VSV-G:pRSV-REV: pCgpV transfer vectors at 3:1:1:1 ratio. After 48 h supernatant was collected, centrifuged for 5 minutes at 250 g to remove cell debris and filtrated through 0.45 µm or 0.22 µm polyethersulfon filters. Concentrated virus particles (Lenti-x-Concentrator, Takara) were used to transduce Jurkat NFAT cells (Signosis). Positive transduced cells were sorted as pool or single clones using a FACS-ARIA sorter (BD Bioscience). After cell expansion to appropriate density Jurkat NFAT reporter CAR-T cells were used for experiments.

Example 1

The anti-CD20 antibody GA101 was digoxigenylated and the incorporation of Digoxigenin (DIG) molecules verified by Western Blot analysis. For the coupling reaction of antibody and Digoxigenin, the antibody, which was dissolved in 20 mM His 140 mM NaCl, pH6 was first desalted and the buffer exchanged to 0.1M sodium bicarbonate (pH8) buffer using Zeba™ Spin Desalting Columns (ThermoFisher Cat.-No 89889). Equimolar or higher (1:3 ratio) amounts of antibody and Digoxigenin-3-O-methylcarbonyl-e-aminocaproic acid-N-hydroxysuccinimide ester (Sigma Aldrich Cat-No. 11333054001) were incubated for 1 hour at room temperature on a shaker at 300 rpm. Antibody-Digoxigenin conjugates were desalted again and the buffer was exchanged to 20 mM His 140 mM NaCl pH6. Unconjugated Dig-NHS was removed in the same step (cut-off 7 kDa).

Digoxigeninylation was detected by anti-Digoxigenin-AP Fab fragments (Sigma Aldrich Cat.-No 11093274910) in a Western Blot. 1 µg of the respective (un-)conjugated antibody was mixed with NuPAGE™ LDS Sample Buffer (4× (ThermoFisher Cat.-No. NP0007) in a total volume of 20 µl and boiled for 5 min at 95° C. 10 µl were loaded on a NuPAGE™ 4-12% Bis-Tris Protein Gel, 1.0 mm, 10-well (ThermoFisher Cat.-No. NP0321) and run for 1 hour at 170V in 1×NuPAGE™ MES SDS Running Buffer (Cat. No. NP0002). Subsequently, the gel was blotted onto a 0.2 µm PVDF membrane (Trans-Blot® Turbo™ Pack, Bio-Rad Cat.-No. 1704156) using the Trans-Blot® Turbo™ Transfer System (Bio-Rad, Cat.-No 1704150, mixed molecular weight standard protocol). The membrane was blocked with 5% milk in 1×TBS-T buffer for 1 hour at RT on an orbital shaker. Anti-Digoxigenin-AP Fab fragments were diluted 1:2000 in 5% milk/TBS-T and incubated for 1 hour on an orbital shaker at room temperature. The membrane was washed three times with 1×TBS-T for 10 minutes each. The membrane was then incubated for 1 min in 2 ml of BCIP®/NBT-Blue Liquid Substrate System for Membranes (Sigma Aldrich Cat.-No. B3804). After washing three times with bidistilled, the membrane was dried and documented (FIG. 7).

Example 2

The expression of anti-Digoxigenin-ds-scFv-CD28ATD-CD28CSDCD3zSSD in Jurkat NFAT reporter CAR-T cells and the binding of Digoxigenin-Cy5 to the CAR was confirmed by FACS. Anti-Digoxigenin-ds-scFv-CD28ATD-CD28CSDCD3zSSD transduced Jurkat NFAT reporter CAR-T cells were pelleted at 300 g for 3 min at room temperature and resuspended in fresh RPMI-1640+10% FCS+1% Glutamax (growth medium) in an appropriate volume. $3 \times 10^5$ cells were then added to each well in a 96-well plate, spun down once at 300 g for 5 min and resuspended in 100 µl in PBS with 2% FCS. Dig-Cy5 was added to a final concentration of 20 nM and incubated on ice for 45 minutes. Cells were then pelleted and resuspended in ice-cold PBS. The washing step was repeated two more times. Cells were then analyzed for Cy5 signal (APC channel) via flow cytometry (FIG. 8). As a negative control, untransduced Jurkat NFAT cells were treated and analyzed equally.

Example 3

Described herein is a reporter CAR-T cell assay using CD20 expressing SUDHDL4 tumor cells as target cells and a sorted pool of anti-Digoxigenin-ds-scFv-CD28ATD-CD28CSDCD3zSSD expressing Jurkat NFAT reporter CAR-T cells as reporter cells (FIG. 9). Digoxygeninylated GA101 IgG (antibody:Dig-NHS ratio 1:10) was used as IgG, which on one hand recognizes the tumor antigen and on the other hand is recognized by the transduced Jurkat NFAT reporter CAR-T cells. As positive control a 96 well plate (Cellstar Greiner-bio-one, CAT-No. 655185) was coated with 10 µg/ml CD3 antibody (from Biolegend®) in phosphate buffered saline (PBS) either for 4° C. over night or for at least 1 h at 37° C. The CD3 coated wells were washed twice with PBS, after the final washing step PBS was fully removed. Reporter cells or Jurkat NFAT wild type cells were counted and checked for their viability using Cedex HiRes. The cell number was adjusted to $1 \times 10^6$ viable cells/ml. Therefore, an appropriate aliquot of the cell suspension was pelleted at 210 g for 5 min at room temperature (RT) and resuspended in fresh RPMI-1640+10% FCS+1% Glutamax (growth medium). Target cells expressing the antigen of interest, were counted and checked for their viability as well. The cell number was adjusted to $1 \times 10^6$ viable cells/ml in growth medium. Target cells and reporter (effector) cells were plated in either 5:1 E:T ratio (110.000 cells per well in total) in triplicates in a 96-well suspension culture plate (Greiner-bio one). As a next step a serial dilution of digoxigeninylated GA101 antibody, targeting the antigen of interest, was prepared in growth medium using a 2 ml deep well plate (Axygen®). To obtain final concentrations ranging from 1 µg/ml to 0.01 pg/ml in a final volume of 200 µl per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 hours incubation the content of each well was mixed by pipetting up and down 10 times using a multichannel pipette. 100 µl cell suspension was transferred to a new white flat clear bottom 96 well plate (Greiner-bio-one) and 100 µl ONE-Glo™ Luciferase Assay (Promega) was added. After 15 min incubation in the dark on a rotary shaker at 300 rpm and room temperature, luminescence was measured using a Tecan® Spark10M plate reader, at 1 sec/well as detection time. Upon co-cultivation of target and reporter cells in a ratio 5:1 (grey dots) for 20 hours, the graphs show a dose-dependent activation of anti-Digoxigenin-ds-scFv-CD28ATD-CD28CSDCD3zSSD expressing Jurkat NFAT reporter CAR-T cells when digoxigenylated GA101 IgG was used as antibody (FIG. 9). When the GA101 IgG without Digoxeninylation (FIG. 9, depicted in grey squares) was used, no activation of the transduced Jurkat NFAT reporter CAR-T cells was detectable. Further Jurkat NFAT wild type cells incubated with 1 µg/ml digoxigeninylated GA101 but without target cells did not show any activation (FIG. 9 black square). In contrast, anti-Digoxigenin-ds-scFv-CD28ATD-CD28CSDCD3zSSD expressing Jurkat NFAT reporter CAR-T cells incubated with 1 µg/ml digoxigeninylated GA101 IgG but without target cells showed activation (FIG. 9 black triangle).

Each point represents the mean value of technical triplicates. All values are depicted as baseline corrected. Standard deviation is indicated by error bars.

Example 4

Described herein is a Jurkat NFAT reporter CAR-T cell assay using CD20 expressing SUDHDL4 tumor cells as target cells and a sorted pool of Anti-P329G-ds-Fab-CD28ATD-CD28CSD-CD3zSSD expressing Jurkat NFAT reporter CAR-T cells (FIG. 11A) or a pool of Anti-P329G-ds-scFv-CD28ATD-CD28CSD-CD3zSSD expressing Jurkat NFAT reporter CAR-T cells (FIG. 11B) as reporter cells. GA101 IgG with P329G LALA mutation was used as IgG, which on one hand recognizes the tumor antigen and on the other hand is recognized by the transduced Jurkat NFAT reporter CAR-T cells. As positive control a 96 well plate (Cellstar Greiner-bio-one, CAT-No. 655185) was coated with 10 μg/ml CD3 antibody (from Biolegend®) in phosphate buffered saline (PBS) either for 4° C. over night or for at least 1 h at 37° C. The CD3 coated wells were washed twice with PBS, after the final washing step PBS was fully removed. Reporter cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the reporter cells, to $1\times10^6$ viable cells/ml in growth medium. Target cells and reporter cells were plated in either 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and reporter cells in a ratio 5:1 (dots) or 1:1 (squares) for 20 h the graphs show a dose-dependent activation of Anti-P329G-ds-Fab-CD28ATD-CD28CSD-CD3zSSD expressing Jurkat NFAT reporter CAR-T cells as well as Anti-P329G-ds-scFv-CD28ATD-CD28CSD-CD3zSSD expressing Jurkat NFAT reporter CAR-T cells when GA101 IgG with P329G LALA mutation was used as antibody (FIGS. 11 A and B, depicted in black). If the GA101 IgG without P329G LALA mutation (FIGS. 11 A and B, depicted in grey) was used, no activation of the transduced Jurkat NFAT reporter CAR-T cells was detectable. Each point represents the mean value of biological duplicates, each performed as technical duplicate. All values are depicted as baseline corrected. Standard deviation is indicated by error bars.

Example 5

Described herein is a Jurkat NFAT reporter CAR-T cell assay using CD20 expressing SUDHDL4 (FIGS. 12C and 12D) or WSUDLCL2 (FIGS. 12A and 12B) tumor cells as target cells and single clone Jurkat NFAT cells expressing Anti-P329G-ds-Fab-CD28ATD-CD28CSD-CD3zSSD as reporter cells. GA101 IgG with P329G LALA mutation was used as IgG which on one hand recognizes the tumor antigen and on the other hand is recognized by the Jurkat NFAT reporter CAR-T cells. Reporter cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the reporter cells, to $1\times10^6$ viable cells/ml in growth medium. Target cells and reporter cells were plated in either 10:1, 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 10:1 (dots), 5:1 (squares) or 1:1 (triangles) for 20 h the graphs show a GA101 IgG with P329G LALA dose-dependent activation of Anti-P329G-ds-Fab-CD28ATD-CD28CSD-CD3zSSD expressing Jurkat NFAT reporter CAR-T cells (FIG. 12A-D, depicted in black). If the GA101 IgG without P329G LALA mutation (FIG. 12A-D, depicted in grey) was used, then only little activation of the transduced Jurkat NFAT reporter CAR-T cells was detectable at the highest antibody concentration of 1 μg/ml. Each point represents the mean value of technical duplicate. All values are depicted as baseline corrected. Standard deviation is indicated by error bars.

Example 6

Described herein is a Jurkat NFAT reporter CAR-T cell assay performed using adherent FAP expressing NIH/3T3-huFAP cl 19 tumor cells as target cells. As reporter cells a sorted pool of Anti-P329G-ds-Fab-CD28ATD-CD28CSD-CD3zSSD expressing Jurkat NFAT reporter CAR-T cells (FIG. 13A) or Anti-P329G-ds-scFv-CD28ATD-CD28CSD-CD3zSSD expressing Jurkat NFAT reporter CAR-T cells (FIG. 13C) were used. FAP 4B9 IgG with P329G LALA mutation was used as IgG which on one hand recognizes the tumor antigen and on the other hand is recognized by the Jurkat NFAT reporter CAR-T cells. IgG DP47/vk3 harboring P329G LALA mutation was included as isotype control. As positive control wells of a 96 well plate (Greiner-bio-one, CAT-No. 655185) were coated with 10 μg/ml CD3 antibody (from Biolegend®) in phosphate buffered saline (PBS) for at least 1 h at 37° C. The CD3 coated wells were washed twice with PBS, after the final washing step PBS was fully removed. Adherent NIH/3T3-huFAP cl 19 target cells were washed once with PBS and detached using Trypsin. Detached cells were resuspended in DMEM+4.5 g LD-Glucose+L-Glutamine+25 mM HEPES+10% FCS and 1% Glutamax. Reporter cells or Jurkat NFAT wild type T cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the reporter cells, to $1\times10^6$ viable cells/ml in growth medium. Target cells and reporter cells were plated in 5:1 E:T ratio (110.000 cells per well in total) in triplicates in a 96-well suspension culture plate (Greiner-bio one). As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml, in a final volume of 200 ul per well, a 50 µl aliquot of the different dilutions was pipetted to the respective wells. The 96-well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

FIGS. 13B and 13D, represent data of Anti-P329G-ds-Fab-CD28ATD-CD28CSD-CD3zSSD expressing Jurkat NFAT reporter CAR-T cells (FIG. 13D) or Anti-P329G-ds-scFv-CD28ATD-CD28CSD-CD3zSSD expressing Jurkat NFAT reporter CAR-T cells (FIG. 13 B) both co-cultivated with target cells and 1 µg/ml of FAP 4B9 antibody compared to different control conditions.

Upon incubation with 1 µg/ml FAP 4B9 P329G LALA, Jurkat NFAT reporter CAR-T cells (FIGS. 13B and 13D black triangle) as well as target cells only (FIGS. 13B and 13D upside down black triangle) do not show any detectable luminescence signal.

Also Jurkat NFAT reporter CAR-T cells show no luminescence signal upon co-cultivation with target cells and 1 µg/ml of FAP 4B9 antibody (FIG. 13B and FIG. 13D black diamond). Whereas CD3 dependent activation of Jurkat NFAT cells co-cultivated with target cells and 1 µg/ml of FAP 4B9 antibody proofs their functionality through a detectable luminescence signal (withe dots).

CD3 dependent activation of Anti-P329G-ds-Fab-CD28ATD-CD28CSD-CD3zSSD expressing Jurkat NFAT reporter CAR-T cells (FIG. 13B white squares) and activation of Anti-P329G-ds-scFv-CD28ATD-CD28CSD-CD3zSSD expressing Jurkat NFAT reporter CAR-T cells (FIG. 13D depicted in white squares) co-cultivated with target cells and 1 µg/ml of FAP 4B9 antibody shows the highest luminescence signals of all, since it combines the CAR mediated activation with CD3 mediated activation. CD3 mediated luminescence signal is also visible when CARs are incubated with target cells and 1 µg/ml of DP47/vk3 antibody (FIG. 13B and FIG. 13D upside down white triangles). Each point represents the mean value of technical triplicates. All values are depicted as baseline corrected. Standard deviation is indicated by error bars.

Example 7

Described herein is a Jurkat NFAT reporter CAR-T cell assay using adherent CEA expressing MKN45 tumor cells as target cells. As reporter cells a sorted pool of Anti-P329G-ds-Fab-CD28ATD-CD28CSD-CD3zSSD expressing Jurkat NFAT reporter CAR-T cells (FIG. 14A) or Anti-P329G-ds-scFv-CD28ATD-CD28CSD-CD3zSSD expressing Jurkat NFAT reporter CAR-T cells (FIG. 14C) were used. Either CEA A5B7 IgG or CEA T84 LCHA IgG both with P329G LALA mutation were used. Further IgG DP47/vk3 harboring P329G LALA mutation was included as isotype control.

As positive control wells of a 96 well plate (Greiner-bioone, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine+25 mM HEPES+10% FCS and 1% Glutamax.

Reporter cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1\times10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 5:1 (FIGS. 14A and 14C, dots) for 20 h the graphs show a dose-dependent activation of Anti-P329G-ds-Fab-CD28ATD-CD28CSD-CD3zSSD expressing Jurkat NFAT reporter CAR-T cells as well Anti-P329G-ds-scFv-CD28ATD-CD28CSD-CD3zSSD expressing Jurkat NFAT reporter CAR-T cells when CEA A5B7 with P329G LALA mutation was used as antibody (FIGS. 14A and 14C grey dots). The use of CEA T84 LCHA with P329G LALA mutation showed only for Anti-P329G-ds-Fab-CD28ATD-CD28CSD-CD3zSSD expressing Jurkat NFAT reporter CAR-T cells a dose dependent activation (FIG. 14A black dots). Whereas, when using the antibody with P329G LALA mutation an activation of Anti-P329G-ds-scFv-CD28ATD-CD28CSD-CD3zSSD expressing Jurkat NFAT reporter CAR-T cells was detectable only at the highest antibody concentration of 1 µg/ml.

If the control antibody DP47/vk3 IgG with P329G LALA mutation (FIGS. 14A and 14C, black triangles) was used, no activation of Anti-P329G-ds-scFv-CD28ATD-CD28CSD-CD3zSSD Jurkat NFAT reporter CAR-T cells or Anti-P329G-ds-Fab-CD28ATD-CD28CSD-CD3zSSD expressing Jurkat NFAT reporter CAR-T cells was detectable. Each point represents the mean value of technical triplicates. Standard deviation is indicated by error bars.

Figure 14B:
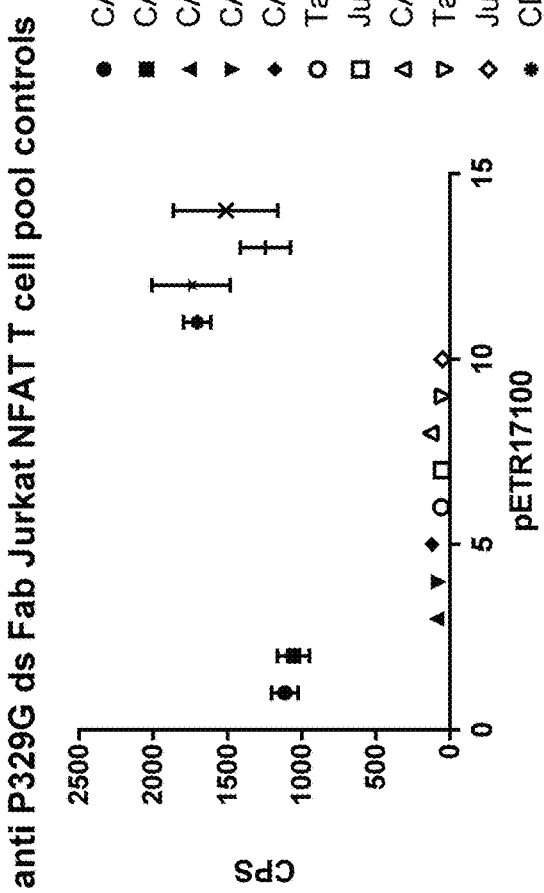
Figure 14C:
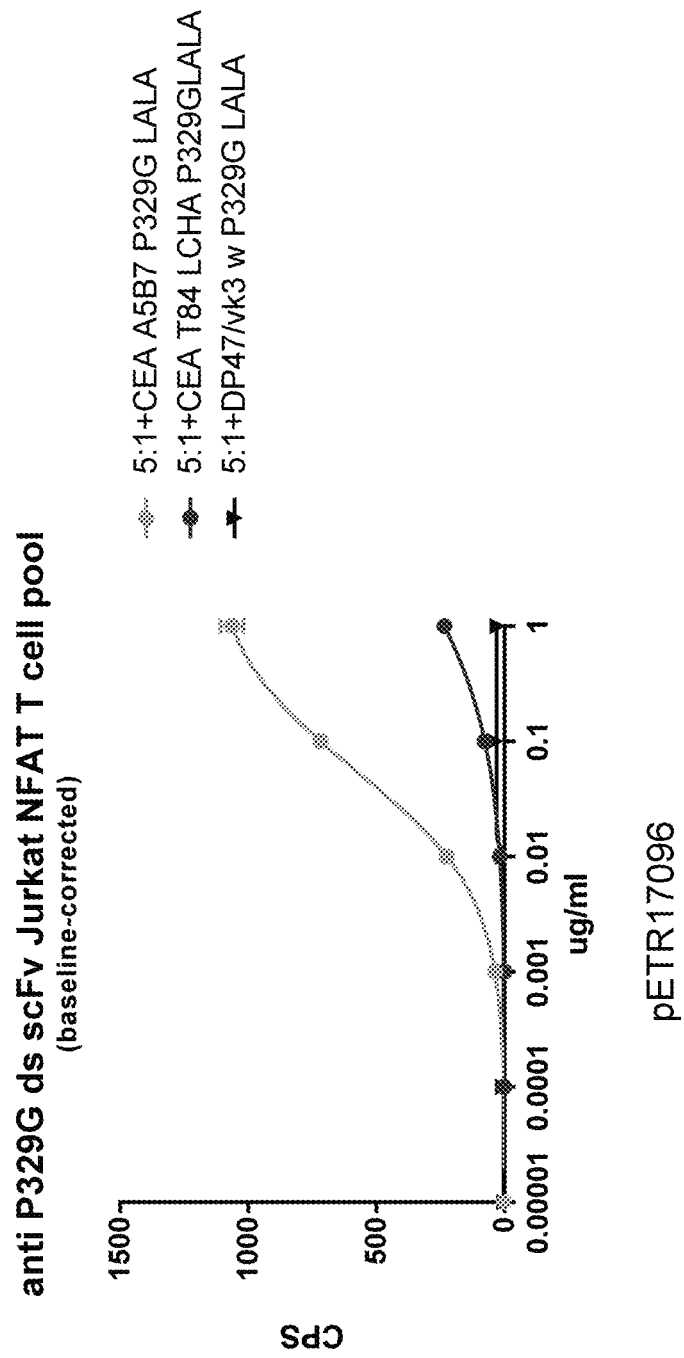
Figure 14D:
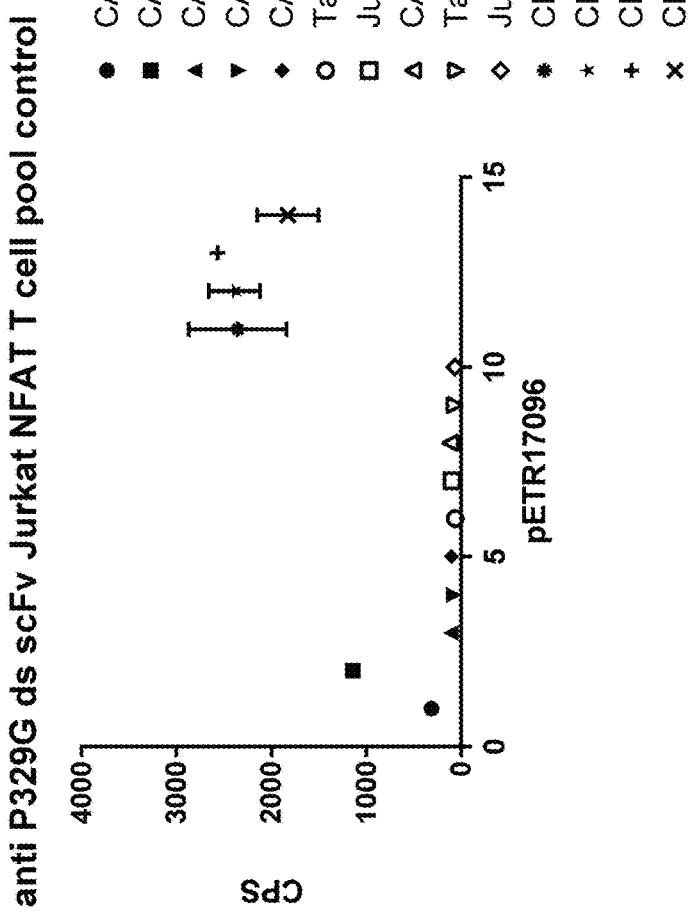

FIGS. 14B and 14D, represent data of Anti-P329G-ds-Fab-CD28ATD-CD28CSD-CD3zSSD expressing Jurkat NFAT reporter CAR-T cells (FIG. 14B) or Anti-P329G-ds-scFv-CD28ATD-CD28CSD-CD3zSSD expressing Jurkat NFAT reporter CAR-T cells (FIG. 14D) both co-cultivated with target cells and 1 µg/ml of CEA T8 LCHA P329G LALA or CEA A5B7 P329G LALA antibody compared to different control conditions.

Upon incubation with 1 µg/ml CEA T8 LCHA P329G LALA, Jurkat NFAT CAR T cells alone (FIGS. 14B and 14D black diamond) as well as target cells alone (FIGS. 14B and 14D white circle) do not show any detectable luminescence signal.

Also Jurkat NFAT reporter CAR-T cells do not show a detectable luminescence signal upon co-cultivation with target cells and 1 µg/ml IgG (FIG. 14B and FIG. 14D white square and white diamond). Whereas CD3 dependent activation of Jurkat NFAT reporter CAR-T cells co-cultivated with target cells and 1 µg/ml IgG proofs their functionality through a detectable luminescence signal (FIGS. 14B and D grey cross).

CD3 dependent activation of Anti-P329G-ds-Fab-CD28ATD-CD28CSD-CD3zSSD Jurkat NFAT reporter CAR-T cells (FIG. 14B black star and grey star) and activation of Anti-P329G-ds-scFv-CD28ATD-CD28CSD-CD3zSSD expressing NFAT T cells (FIG. 14D black star and grey star) co-cultivated with target cells and 1 µg/ml IgG show the highest luminescence signals of all, since CAR mediated activation and CD3 mediated activation is combined. CD3 mediated luminescence signal is also visible when CARs are incubated with target cells and 1 µg/ml of DP47/vk3 antibody (FIG. 14B and FIG. 14D, grey plus). Each point represents the mean value of technical triplicates. Standard deviation is indicated by error bars.

Example 8

Described herein is a Jurkat NFAT reporter CAR-T cell assay using adherent TNC expressing CT26TNC cl 19 tumor cells as target cells. As reporter cells, a sorted pool of Anti-P329G-ds-Fab-CD28ATD-CD28CSD-CD3zSSD expressing Jurkat NFAT reporter CAR-T cells (FIG. 15C) or Anti-P329G-ds-scFv-CD28ATD-CD28CSD-CD3zSSD expressing Jurkat NFAT reporter CAR-T cells (FIG. 15A) were used. TNCA2B10 with P329G LALA mutation was used as IgG. Further IgG DP47/vk3 harboring P329G LALA mutation was included as isotype control.

As positive control wells of a 96 well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+ 15 µg/ml Puromycin.

Reporter cells or Jurkat NFAT wild type T cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1\times10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 5:1 (FIGS. 15A and 16C black dots) for 20 h the graphs show a dose-dependent activation of Anti-P329G-ds-Fab-CD28ATD-CD28CSD-CD3zSSD expressing Jurkat NFAT reporter CAR-T cells as well as of Anti-P329G-ds-scFv-CD28ATD-CD28CSD-CD3zSSD expressing Jurkat NFAT reporter CAR-T cells when TNC A2B10 with P329G LALA mutation was used as antibody. If the control antibody DP47/vk3 IgG with P329G LALA mutation (FIGS. 15A and 15C black dots) was used, neither the activation of Anti-P329G-ds-scFv-CD28ATD-CD28CSD-CD3zSSD expressing Jurkat NFAT reporter CAR-T cells nor Anti-P329G-ds-Fab-CD28ATD-CD28CSD-CD3zSSD expressing Jurkat NFAT reporter CAR-T cells was detectable. Each point represents the mean value of technical triplicates. All values are depicted as baseline corrected. Standard deviation is indicated by error bars.

Figure 15D:
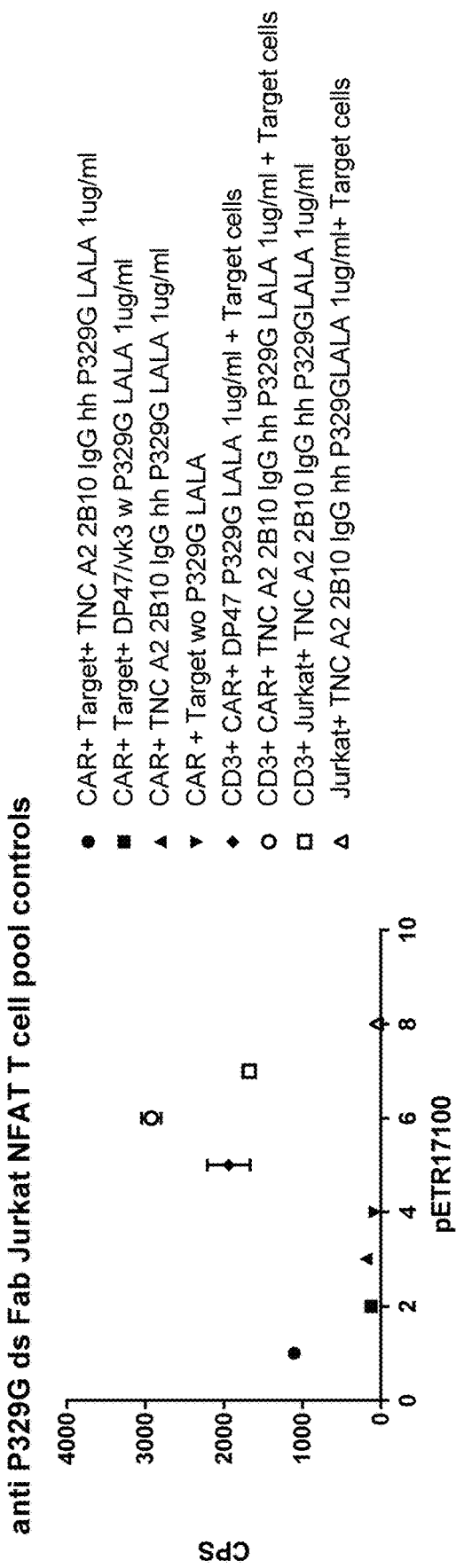

FIGS. 15B and 15D, represent data of Anti-P329G-ds-Fab-CD28ATD-CD28CSD-CD3zSSD expressing Jurkat NFAT reporter CAR-T cells (FIG. 15D) or Anti-P329G-ds-scFv-CD28ATD-CD28CSD-CD3zSSD expressing Jurkat NFAT reporter CAR-T cells (FIG. 15B) both co-cultivated with target cells and 1 µg/ml of TNC A2B10 compared to different control conditions.

Jurkat NFAT reporter CAR-T cells do not show any detectable luminescence signal upon co-cultivation with target cells and 1 µg/ml IgG (FIG. 15B and FIG. 15D white triangle). Whereas CD3 dependent activation of Jurkat NFAT cells co-cultivated with target cells and 1 µg/ml IgG proofs their functionality through a detectable luminescence signal (FIG. 15B and FIG. 15D white square).

CD3 dependent activation of Anti-P329G-ds-Fab-CD28ATD-CD28CSD-CD3zSSD expressing Jurkat NFAT reporter CAR-T cells (FIG. 15B white circle) and activation of Anti-P329G-ds-scFv-CD28ATD-CD28CSD-CD3zSSD expressing Jurkat NFAT reporter CAR-T cells (FIG. 15D white circle) co-cultivated with target cells and 1 µg/ml IgG show the highest luminescence signals of all, since CAR mediated activation and CD3 mediated activation is combined. CD3 mediated luminescence signal is also visible when CARs are incubated with target cells and 1 μg/ml of DP47/vk3 antibody (FIG. 15B and FIG. 15D, black diamond). Each point represents the mean value of technical triplicates. Standard deviation is indicated by error bars.

Example 9

Described herein is a Jurkat NFAT reporter CAR-T cell assay using adherent TNC expressing CT26TNC cl 19 tumor cells as target cells. As reporter cells, a sorted pool of Anti-P329G-Fab-CD28ATD-CD28CSD-CD3zSSD expressing Jurkat NFAT reporter CAR-T cells (FIG. 16A) was used. TNCA2B10 with P329G LALA mutation was used as IgG. Further IgG DP47/vk3 harboring P329G LALA mutation was included as isotype control.

As positive control wells of a 96-well plate (Greiner-bio-one, CAT-No. 655185) were coated with 10 μg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+ 15 μg/ml Puromycin.

Reporter cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1 \times 10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 μl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 5:1 (FIG. 16A black dots) for 20 h the graphs show a dose-dependent activation of Anti-P329G-Fab-CD28ATD-CD28CSD-CD3zSSD expressing Jurkat NFAT reporter CAR-T cells beginning with 0.01 μg/ml of TNC A2B10 with P329G LALA mutation. If the control antibody DP47/vk3 IgG with P329G LALA mutation (FIGS. 16A and 17C grey dots) was used, no activation of Anti-P329G-Fab-CD28ATD-CD28CSD-CD3zSSD expressing Jurkat NFAT reporter CAR-T cells was detectable. Each point represents the mean value of technical triplicates. All values are depicted as baseline corrected. Standard deviation is indicated by error bars.

FIG. 16B, represents data of Anti-P329G-Fab-CD28ATD-CD28CSD-CD3zSSD expressing Jurkat NFAT reporter CAR-T cells co-cultivated with target cells and 1 μg/ml of TNC A2B10 antibody compared to different control conditions.

Anti-P329G-Fab-CD28ATD-CD28CSD-CD3zSSD expressing Jurkat NFAT reporter CAR-T cells incubated with target cells but without antibody (FIG. 16B black square) as well as Jurkat NFAT cells incubated with target cells and 1 μg/ml of TNC A2B10 antibody (FIG. 16B white dots) show no detectable luminescence signal. Whereas Jurkat NFAT cells co-cultured with target cells and 1 μg/ml of TNC A2B10 plated in CD3 coated wells, show a clear luminescence signal.

Further Anti-P329G-CD28ATD-CD28CSD-CD3zSSD Fab expressing Jurkat NFAT reporter CAR-T cells incubated with target cells and either 1 μg/ml of TNC A2B10 or 1 μg/ml DP47/vk3 antibody, in CD3 coated wells, show a high luminescence signal. Each point represents the mean value of technical triplicates. Standard deviation is indicated by error bars.

Example 10

Described herein is a Jurkat NFAT reporter CAR-T cell assay using peptide-pulsed T2 cells as target cells in order to assess the specificity of HLA-A2/WT1-peptide-binders 33F05 (SEQ ID NOs: 139 and 140), 11D06 (SEQ ID NOs: 141 and 142), 33H09 (SEQ ID NOs: 143 and 144) and 5E11 (SEQ ID NOs: 145 and 146). As reporter cells, a sorted pool of Anti-P329G-ds-Fab-CD28ATD-CD28CSD-CD3zSSD expressing Jurkat NFAT reporter CAR-T cells were used. The HLA-A2/WT1-peptide-binders with P329G LALA mutation were used as IgG. Prior to incubation with the HLA-A2/WT1-peptide-binding antibodies and the reporter cells, T2 cells were pulsed with the respective peptide at $10^{-5}$ M for 2 hours at 37° C., or left unpulsed. Target cells and reporter cells were plated in 5:1 E:T ratio (10.000 effector cells per 2000 target cells per well) in triplicates in a 384-well white flat clear bottom plate (Greiner-bio-one). As a next step serial dilutions of the IgGs in question were prepared in growth medium. Incubation of reporter cells, T2 cells and IgGs was allowed for 16 hours at 37° C., followed by addition of 6 μl per well of ONE-Glo™ luciferase substrate (Promega) and direct measurement of luminescence using a TECAN infinite M1000Pro plate reader.

The resulting graphs (FIG. 18A to FIG. 18D) show a dose-dependent activation of anti-P329G-ds-Fab-CD28ATD-CD28CSD-CD3zSSD expressing Jurkat NFAT reporter CAR-T cells. Importantly, this activation appears selectively on RMF-peptide-pulsed T2 cells only for binders 11D06 and 33H09, but unspecifically on RMF- and VLD-peptide-pulsed T2 cells for binders 33F05 and 5E11, indicating the unselective nature of T cell activation for these latter two antibodies.

Example 11

Described herein is a Jurkat NFAT reporter CAR-T cell assay with a sorted pool of anti-P329G-ds-Fab-CD28ATD-CD28CSD-CD3zSSD expressing Jurkat NFAT CAR-T cells as reporter cells. The reporter cells bind the HLA-A2/WT1-peptide binders in IgG format with P329G LALA mutation, which in turn do recognize the tested HLA-A2/WT1 peptides (RMF or VLD, respectively) to different degrees.

The four different antibodies in question (33F05 (SEQ ID NOs: 139 and 140), 11D06 (SEQ ID NOs: 141 and 142), 33H09 (SEQ ID NOs: 143 and 144) and 5E11 (SEQ ID NOs: 145 and 146), respectively) were present at 10 nM. Prior to co-incubation with the Jurkat NFAT reporter cells and the IgGs, T2 cells were pulsed with RMF- or VLD-peptide, respectively, like described in Example 10, or left without peptide. Jurkat NFAT reporter cells and target cells were coincubated for 6 hours at 37° C. at an E:T-ratio of 5:1 with 10000 to 2000 cells in 20 µl per well of a 384-well plate (white flat clear bottom 384 well plate (Greiner bio-one)) and an IgG concentration of 10 nM, followed by addition of 6 µl per well of ONE-Glo™ luciferase substrate (Promega) and direct measurement of luminescence using a TECAN infinite M1000Pro plate reader. The activation of CAR-NFAT-signaling from triplicate measurements of the respective experimental settings is expressed as column graph (FIG. 19) with error bars indicating standard deviations. Comparison of signals on RMF-peptide (target) vs. signal on VLD-peptide (off-target) helps to assess specificity of activation of the respective binder. Signal strength on T2 cells without peptide indicates unspecific binding for candidate binders 35F05 and 05E11. Candidate binders 33H09 and 11D06 prove specific and selective for HLA-A2/WT1-peptide RMF, only, since the signal on off-target peptide VLD is low, especially with regard to the assessed background ("T2 w/o peptide", effector cells "without T2" and effector and target cell co-incubation "without addition of IgG").

Example 12

Described herein is the assessment of specificity of HLA-A2/WT1-peptide-binders 5E11 (SEQ ID NOs: 102 and 103) and 33H09 (SEQ ID NOs: 100 and 101) by means of flow cytometry with T2 cells pulsed with RMF-peptide or VLD-peptide. Prior to incubation with the HLA-A2/WT1-peptide-binding antibodies, T2 cells were pulsed with the respective peptide at $10^{-5}$ M for 2 hours at 37° C., or left unpulsed. Binding of the respective IgG to cell aliquots of 100000 cells, each, at different concentrations of the antibody in question was allowed for 1 h on ice, followed by two washing steps with PBS, and assessed via anti-huFc-detection (anti-human F(ab)2_AF647 from Jackson ImmunoResearch) at a concentration of 90 nM in flow cytometry on a Fortessa analyzer (BD Biosciences). Both binders 5E11 and 33H09 give clear concentration-dependent binding signal on RMF-peptide-pulsed, but not on VLD-peptide-pulsed T2 cells (FIG. 20A and FIG. 20B). According to this flow cytometry-based assessment, both antibody candidates appear to bind specifically to RMF-peptide-pulsed, but not to VLD-peptide-pulsed T2 cells.

Example 13

Described herein is a Jurkat NFAT reporter CAR-T cell assay using a primary, patient derived tumor sample (lung metastasis of colon carcinoma). The tumor sample was characterized by fluorescence activated cell sorting (FACS) showing the expression of CEA and FAP antigen levels. FACS analysis showed that about 80% the CD45 positive cells express CEA and about 16% express FAP on their surface (FIG. 22A). As reporter cells, a sorted pool of Anti-P329G-ds-Fab-CD28ATD-CD28CSD-CD3zSSD expressing Jurkat NFAT reporter CAR-T cells (FIG. 22B) or a sorted pool of Anti-P329G-ds-scFv-CD28ATD-CD28CSD-CD3zSSD expressing Jurkat NFAT reporter CAR-T cells (FIG. 22C) were used. Human IgG1 anti-CEA T84 LCHA, or anti-FAP (4B9) antibodies with P329G LALA mutation were used as IgGs. Tumor cells and reporter cells were plated in 5:1 E:T ratio (20.000 effector cells per 200.000 target cells per well) in duplicates in a 96-well white flat clear bottom plate. As a next step 1 µg/ml serial dilutions of the IgGs in question were prepared in growth medium. Incubation of reporter cells, target cells and IgGs was allowed for 8 h hours at 37° C., followed by addition of 50 µl per well of ONE-Glo™ luciferase substrate (Promega) and direct measurement of luminescence using a TECAN infinite M1000Pro plate reader.

The resulting graphs (FIG. 22B and FIG. 22C) show an antigen dependent activation of anti-P329G-ds-Fab-CD28ATD-CD28CSD-CD3zSSD or ds-scFv-CD28ATD-CD28CSD-CD3zSSD expressing Jurkat NFAT reporter CAR-T cells respectively. Importantly, this activation appears only in the presence of the respective antibody that recognizes the tumor antigen present in the provided sample.

Exemplary Sequences

TABLE 2

| Anti-P329G-ds-scFv amino acid sequences: | | |
|---|---|---|
| Construct | Amino acid sequence | SEQ ID NO |
| Anti-P329G CDR H1 Kabat | RYWMN | 1 |
| Anti-P329G CDR H2 Kabat | EITPDSSTINYTPSLKD | 2 |
| Anti-P329G CDR H3 Kabat | PYDYGAWFAS | 3 |
| Anti-P329G CDR L1 Kabat | RSSTGAVTTSNYAN | 4 |
| Anti-P329G CDR L2 Kabat | GTNKRAP | 5 |
| Anti-P329G CDR L3 Kabat | ALWYSNHWV | 6 |

TABLE 2-continued

Anti-P329G-ds-scFv amino acid sequences:

| Construct | Amino acid sequence | SEQ ID NO |
|---|---|---|
| Anti-P329G-ds-scFv-CD28ATD-CD28CSD-CD3zSSD fusion | EVKLLESGGGLVQPGGSLKLSCAASGFDFSRYWMN WVRQAPGKCLEWIGEITPDSSTINYTPSLKDKFIISRD NAKNTLYLQMIKVRSEDTALYYCVRPYDYGAWFAS WGQGTLVTVSAGGGGSGGGGSGGGGSGGGGSQAV VTQESALTTSPGETVTLTCRSSTGAVTTSNYANWVQ EKPDHLFTGLIGGTNKRAPGVPARFSGSLIGDKAALTI TGAQTEDEAIYFCALWYSNHWVFGCGTKLTVLGGG GSFWVLVVVGGVLACYSLLVTVAFIIFWVRSKRSRL LHSDYMNMTPRRPGPTRKHYQPYAPPRDFAAYRSR VKFSRSADAPAYQQGQNQLYNELNLGRREEYDVLD KRRGRDPEMGGKPRRKNPQEGLYNELQKDKMAEA YSEIGMKGERRRGKGHDGLYQGLSTATKDTYDALH MQALPPR | 7 |
| Anti-P329G-ds VH | EVKLLESGGGLVQPGGSLKLSCAASGFDFSRYWMN WVRQAPGKCLEWIGEITPDSSTINYTPSLKDKFIISRD NAKNTLYLQMIKVRSEDTALYYCVRPYDYGAWFAS WGQGTLVTVSA | 8 |
| Anti-P329G-ds VL | QAVVTQESALTTSPGETVTLTCRSSTGAVTTSNYAN WVQEKPDHLFTGLIGGTNKRAPGVPARFSGSLIGDK AALTITGAQTEDEAIYFCALWYSNHWVFGCGTKLTVL | 9 |
| Anti-P329G-ds-scFv | EVKLLESGGGLVQPGGSLKLSCAASGFDFSRYWMN WVRQAPGKCLEWIGEITPDSSTINYTPSLKDKFIISRD NAKNTLYLQMIKVRSEDTALYYCVRPYDYGAWFAS WGQGTLVTVSAGGGGSGGGGSGGGGSGGGGSQAV VTQESALTTSPGETVTLTCRSSTGAVTTSNYANWVQ EKPDHLFTGLIGGTNKRAPGVPARFSGSLIGDKAALTI TGAQTEDEAIYFCALWYSNHWVFGCGTKLTVL | 10 |
| CD28ATD | FWVLVVVGGVLACYSLLVTVAFIIFWV | 11 |
| CD28CSD | RSKRSRLLHSDYMNMTPRRPGPTRKHYQPYAPPRDF AAYRS | 12 |
| CD3zSSD | RVKFSRSADAPAYQQGQNQLYNELNLGRREEYDVL DKRRGRDPEMGGKPRRKNPQEGLYNELQKDKMAE AYSEIGMKGERRRGKGHDGLYQGLSTATKDTYDAL HMQALPPR | 13 |
| CD28ATD-CD28CSD-CD3zSSD | FWVLVVVGGVLACYSLLVTVAFIIFWVRSKRSRLLH SDYMNMTPRRPGPTRKHYQPYAPPRDFAAYRSRVKF SRSADAPAYQQGQNQLYNELNLGRREEYDVLDKRR GRDPEMGGKPRRKNPQEGLYNELQKDKMAEAYSEI GMKGERRRGKGHDGLYQGLSTATKDTYDALHMQA LPPR | 14 |
| eGFP | VSKGEELFTGVVPILVELDGDVNGHKFSVSGEGEGD ATYGKLTLKFICTTGKLPVPWPTLVTTLTYGVQCFSR YPDHMKQHDFFKSAMPEGYVQERTIFFKDDGNYKT RAEVKFEGDTLVNRIELKGIDFKEDGNILGHKLEYNY NSHNVYIMADKQKNGIKVNFKIRHNIEDGSVQLADH YQQNTPIGDGPVLLPDNHYLSTQSALSKDPNEKRDH MVLLEFVTAAGITLGMDELYK | 15 |
| (G4S)4 linker | GGGGSGGGGSGGGGSGGGGS | 16 |
| G4S linker | GGGGS | 17 |
| T2A linker | GEGRGSLLTCGDVEENPGP | 18 |

TABLE 3 anti-P329G-ds-scFv DNA sequences:

| Construct | DNA sequence | SEQ ID NO |
|---|---|---|
| Anti-P329G-ds-scFv-CD28ATD-CD28CSD-CD3zSSD fusion | ATGGGATGGAGCTGTATCATCCTCTTCTTGGTAGC AACAGCTACCGGTGTGCATTCCGAGGTGAAGCTGC TGGAGAGCGGCGGCGGCCTGGTGCAGCCCGGCGG CAGCCTGAAGCTGAGCTGCGCCGCCAGCGGCTTCG ACTTCAGCAGGTACTGGATGAACTGGGTGAGGCA GGCCCCCGGCAAGTGTCTGGAGTGGATCGGCGAG ATCACCCCCGACAGCAGCACCATCAACTACACCCC CAGCCTGAAGGACAAGTTCATCATCAGCAGGGAC AACGCCAAGAACACCCTGTACCTGCAGATGATCAA GGTGAGGAGCGAGGACACCGCCCTGTACTACTGC GTGAGGCCCTACGACTACGGCGCCTGGTTCGCCAG CTGGGGCCAGGGCACCCTGGTGACCGTGAGCGCC GGAGGGGGCGGAAGTGGTGGCGGGGGAAGCGGCG GGGTGGCAGCGGAGGGGGCGGATCTCAGGCCGT GGTGACCCAGGAGAGCGCCCTGACCACCAGCCCC GGCGAGACCGTGACCCTGACCTGCAGGAGCAGCA CCGGCGCCGTGACCACCAGCAACTACGCCAACTGG GTGCAGGAGAAGCCCGACCACCTGTTCACCGGCCT GATCGGCGGCACCAACAAGAGGGCCCCCGGCGTG CCCGCCAGGTTCAGCGGCAGCCTGATCGGCGACAA GGCCGCCCTGACCATCACCGGCGCCCAGACCGAG GACGAGGCCATCTACTTCTGCGCCCTGTGGTACAG CAACCACTGGGTGTTCGGCTGTGGCACCAAGCTGA CCGTGCTGGGAGGGGGCGGATCCTTCTGGGTGCTG GTGGTGGTGGGCGGCGTGCTGGCCTGCTACAGCCT GCTGGTGACCGTGGCCTTCATCATCTTCTGGGTGA GGAGCAAGAGGAGCAGGCTGCTGCACAGCGACTA CATGAACATGACCCCCAGGAGGCCCGGCCCCACC AGGAAGCACTACCAGCCCTACGCCCCCCCCAGGG ACTTCGCCGCCTACAGGAGCAGGGTGAAGTTCAGC AGGAGCGCCGACGCCCCCGCCTACCAGCAGGGCC AGAACCAGCTGTATAACGAGCTGAACCTGGGCAG GAGGGAGGAGTACGACGTGCTGGACAAGAGGAGG GGCAGGGACCCCGAGATGGGCGGCAAGCCCAGGA GGAAGAACCCCCAGGAGGGCCTGTATAACGAGCT GCAGAAGGACAAGATGGCCGAGGCCTACAGCGAG ATCGGCATGAAGGGCGAGAGGAGGAGGGGCAAGG GCCACGACGGCCTGTACCAGGGCCTGAGCACCGCC ACCAAGGACACCTACGACGCCCTGCACATGCAGG CCCTGCCCCCCAGG | 19 |
| Anti-P329G-ds VH | GAGGTGAAGCTGCTGGAGAGCGGCGGCGGCCTGG TGCAGCCCGGCGGCAGCCTGAAGCTGAGCTGCGCC GCCAGCGGCTTCGACTTCAGCAGGTACTGGATGAA CTGGGTGAGGCAGGCCCCCGGCAAGTGTCTGGAGT GGATCGGCGAGATCACCCCCGACAGCAGCACCAT CAACTACACCCCCAGCCTGAAGGACAAGTTCATCA TCAGCAGGGACAACGCCAAGAACACCCTGTACCT GCAGATGATCAAGGTGAGGAGCGAGGACACCGCC CTGTACTACTGCGTGAGGCCCTACGACTACGGCGC CTGGTTCGCCAGCTGGGGCCAGGGCACCCTGGTGA CCGTGAGCGCC | 20 |
| Anti-P329G-ds VL | CAGGCCGTGGTGACCCAGGAGAGCGCCCTGACCA CCAGCCCCGGCGAGACCGTGACCCTGACCTGCAGG AGCAGCACCGGCGCCGTGACCACCAGCAACTACG CCAACTGGGTGCAGGAGAAGCCCGACCACCTGTTC ACCGGCCTGATCGGCGGCACCAACAAGAGGGCCC CCGGCGTGCCCGCCAGGTTCAGCGGCAGCCTGATC GGCGACAAGGCCGCCCTGACCATCACCGGCGCCC AGACCGAGGACGAGGCCATCTACTTCTGCGCCCTG TGGTACAGCAACCACTGGGTGTTCGGCTGTGGCAC CAAGCTGACCGTGCTG | 21 |
| Anti-P329G-ds-scFv | ATGGGATGGAGCTGTATCATCCTCTTCTTGGTAGC AACAGCTACCGGTGTGCATTCCGAGGTGAAGCTGC TGGAGAGCGGCGGCGGCCTGGTGCAGCCCGGCGG CAGCCTGAAGCTGAGCTGCGCCGCCAGCGGCTTCG ACTTCAGCAGGTACTGGATGAACTGGGTGAGGCA GGCCCCCGGCAAGTGTCTGGAGTGGATCGGCGAG ATCACCCCCGACAGCAGCACCATCAACTACACCCC CAGCCTGAAGGACAAGTTCATCATCAGCAGGGAC AACGCCAAGAACACCCTGTACCTGCAGATGATCAA GGTGAGGAGCGAGGACACCGCCCTGTACTACTGC GTGAGGCCCTACGACTACGGCGCCTGGTTCGCCAG CTGGGGCCAGGGCACCCTGGTGACCGTGAGCGCC | 22 |

TABLE 3-continued anti-P329G-ds-scFv DNA sequences:

| Construct | DNA sequence | SEQ ID NO |
|---|---|---|
| | GGAGGGGGCGGAAGTGGTGGCGGGGGAAGCGGCG GGGGTGGCAGCGGAGGGGGCGGATCTCAGGCCGT GGTGACCCAGGAGAGCGCCCTGACCACCAGCCCC GGCGAGACCGTGACCCTGACCTGCAGGAGCAGCA CCGGCGCCGTGACCACCAGCAACTACGCCAACTGG GTGCAGGAGAAGCCCGACCACCTGTTCACCGGCCT GATCGGCGGCACCAACAAGAGGGCCCCCGGCGTG CCCGCCAGGTTCAGCGGCAGCCTGATCGGCGACAA GGCCGCCCTGACCATCACCGGCGCCCAGACCGAG GACGAGGCCATCTACTTCTGCGCCCTGTGGTACAG CAACCACTGGGTGTTCGGCTGTGGCACCAAGCTGA CCGTGCTG | |
| CD28ATD | TTCTGGGTGCTGGTGGTGGTGGGCGGCGTGCTGGC CTGCTACAGCCTGCTGGTGACCGTGGCCTTCATCA TCTTCTGGGTG | 23 |
| CD28CSD | AGGAGCAAGAGGAGCAGGCTGCTGCACAGCGACT ACATGAACATGACCCCCAGGAGGCCCGGCCCCAC CAGGAAGCACTACCAGCCCTACGCCCCCCCCAGGG ACTTCGCCGCCTACAGGAGC | 24 |
| CD3zSSD | AGGGTGAAGTTCAGCAGGAGCGCCGACGCCCCCG CCTACCAGCAGGGCCAGAACCAGCTGTATAACGA GCTGAACCTGGGCAGGAGGGAGGAGTACGACGTG CTGGACAAGAGGAGGGGCAGGGACCCCGAGATGG GCGGCAAGCCCAGGAGGAAGAACCCCCAGGAGGG CCTGTATAACGAGCTGCAGAAGGACAAGATGGCC GAGGCCTACAGCGAGATCGGCATGAAGGGCGAGA GGAGGAGGGGCAAGGGCCACGACGGCCTGTACCA GGGCCTGAGCACCGCCACCAAGGACACCTACGAC GCCCTGCACATGCAGGCCCTGCCCCCCAGG | 25 |
| CD28ATD-CD28CSD-CD3zSSD | TTCTGGGTGCTGGTGGTGGTGGGCGGCGTGCTGGC CTGCTACAGCCTGCTGGTGACCGTGGCCTTCATCA TCTTCTGGGTGAGGAGCAAGAGGAGCAGGCTGCT GCACAGCGACTACATGAACATGACCCCCAGGAGG CCCGGCCCCACCAGGAAGCACTACCAGCCCTACGC CCCCCCCAGGGACTTCGCCGCCTACAGGAGCAGGG TGAAGTTCAGCAGGAGCGCCGACGCCCCCGCCTAC CAGCAGGGCCAGAACCAGCTGTATAACGAGCTGA ACCTGGGCAGGAGGGAGGAGTACGACGTGCTGGA CAAGAGGAGGGGCAGGGACCCCGAGATGGGCGGC AAGCCCAGGAGGAAGAACCCCCAGGAGGGCCTGT ATAACGAGCTGCAGAAGGACAAGATGGCCGAGGC CTACAGCGAGATCGGCATGAAGGGCGAGAGGAGG AGGGGCAAGGGCCACGACGGCCTGTACCAGGGCC TGAGCACCGCCACCAAGGACACCTACGACGCCCTG CACATGCAGGCCCTGCCCCCCAGG | 26 |
| T2A element | TCCGGAGAGGGCAGAGGAAGTCTTCTAACATGCG GTGACGTGGAGGAGAATCCCGGCCCTAGG | 27 |
| eGFP | GTGAGCAAGGGCGAGGAGCTGTTCACCGGGGTGG TGCCCATCCTGGTCGAGCTGGACGGCGACGTAAAC GGCCACAAGTTCAGCGTGTCCGGCGAGGGCGAGG GCGATGCCACCTACGGCAAGCTGACCCTGAAGTTC ATCTGCACCACCGGCAAGCTGCCCGTGCCCTGGCC CACCCTCGTGACCACCCTGACCTACGGCGTGCAGT GCTTCAGCCGCTACCCCGACCACATGAAGCAGCAC GACTTCTTCAAGTCCGCCATGCCCGAAGGCTACGT CCAGGAGCGCACCATCTTCTTCAAGGACGACGGCA ACTACAAGACCCGCGCCGAGGTGAAGTTCGAGGG CGACACCCTGGTGAACCGCATCGAGCTGAAGGGC ATCGACTTCAAGGAGGACGGCAACATCCTGGGGC ACAAGCTGGAGTACAACTACAACAGCCACAACGT CTATATCATGGCCGACAAGCAGAAGAACGGCATC AAGGTGAACTTCAAGATCCGCCACAACATCGAGG ACGGCAGCGTGCAGCTCGCCGACCACTACCAGCA GAACACCCCCATCGGCGACGGCCCCGTGCTGCTGC CCGACAACCACTACCTGAGCACCCAGTCCGCCCTG AGCAAAGACCCCAACGAGAAGCGCGATCACATGG TCCTGCTGGAGTTCGTGACCGCCGCCGGGATCACT CTCGGCATGGACGAGCTGTACAAGTGA | 28 |

TABLE 3-continued anti-P329G-ds-scFv DNA sequences:

| Construct | DNA sequence | SEQ ID NO |
|---|---|---|
| Anti-P329G-ds-scFv-CD28ATD-CD28CSD-CD3zSSD-eGFP fusion | ATGGGATGGAGCTGTATCATCCTCTTCTTGGTAGC<br>AACAGCTACCGGTGTGCATTCCGAGGTGAAGCTGC<br>TGGAGAGCGGCGGCGGCCTGGTGCAGCCCGGCGG<br>CAGCCTGAAGCTGAGCTGCGCCGCCAGCGGCTTCG<br>ACTTCAGCAGGTACTGGATGAACTGGGTGAGGCA<br>GGCCCCCGGCAAGTGTCTGGAGTGGATCGGCGAG<br>ATCACCCCCGACAGCAGCACCATCAACTACACCCC<br>CAGCCTGAAGGACAAGTTCATCATCAGCAGGGAC<br>AACGCCAAGAACACCCTGTACCTGCAGATGATCAA<br>GGTGAGGAGCGAGGACACCGCCCTGTACTACTGC<br>GTGAGGCCCTACGACTACGGCGCCTGGTTCGCCAG<br>CTGGGGCCAGGGCACCCTGGTGACCGTGAGCGCC<br>GGAGGGGGCGGAAGTGGTGGCGGGGGAAGCGGCG<br>GGGGTGGCAGCGGAGGGGGCGGATCTCAGGCCGT<br>GGTGACCCAGGAGAGCGCCCTGACCACCAGCCCC<br>GGCGAGACCGTGACCCTGACCTGCAGGAGCAGCA<br>CCGGCGCCGTGACCACCAGCAACTACGCCAACTGG<br>GTGCAGGAGAAGCCCGACCACCTGTTCACCGGCCT<br>GATCGGCGGCACCAACAAGAGGGCCCCCGGCGTG<br>CCCGCCAGGTTCAGCGGCAGCCTGATCGGCGACAA<br>GGCCGCCCTGACCATCACCGGCGCCCAGACCGAG<br>GACGAGGCCATCTACTTCTGCGCCCTGTGGTACAG<br>CAACCACTGGGTGTTCGGCTGTGGCACCAAGCTGA<br>CCGTGCTGGGAGGGGGCGGATCCTTCTGGGTGCTG<br>GTGGTGGTGGGCGGCGTGCTGGCCTGCTACAGCCT<br>GCTGGTGACCGTGGCCTTCATCATCTTCTGGGTGA<br>GGAGCAAGAGGAGCAGGCTGCTGCACAGCGACTA<br>CATGAACATGACCCCCAGGAGGCCCGGCCCCACC<br>AGGAAGCACTACCAGCCCTACGCCCCCCCCAGGG<br>ACTTCGCCGCCTACAGGAGCAGGGTGAAGTTCAGC<br>AGGAGCGCCGACGCCCCCGCCTACCAGCAGGGCC<br>AGAACCAGCTGTATAACGAGCTGAACCTGGGCAG<br>GAGGGAGGAGTACGACGTGCTGGACAAGAGGAGG<br>GGCAGGGACCCCGAGATGGGCGGCAAGCCCAGGA<br>GGAAGAACCCCCAGGAGGGCCTGTATAACGAGCT<br>GCAGAAGGACAAGATGGCCGAGGCCTACAGCGAG<br>ATCGGCATGAAGGGCGAGAGGAGGAGGGGCAAGG<br>GCCACGACGGCCTGTACCAGGGCCTGAGCACCGCC<br>ACCAAGGACACCTACGACGCCCTGCACATGCAGG<br>CCCTGCCCCCCAGGTCCGGAGAGGGCAGAGGAAG<br>TCTTCTAACATGCGGTGACGTGGAGGAGAATCCCG<br>GCCCTAGGGTGAGCAAGGGCGAGGAGCTGTTCAC<br>CGGGGTGGTGCCCATCCTGGTCGAGCTGGACGGCG<br>ACGTAAACGGCCACAAGTTCAGCGTGTCCGGCGA<br>GGGCGAGGGCGATGCCACCTACGGCAAGCTGACC<br>CTGAAGTTCATCTGCACCACCGGCAAGCTGCCCGT<br>GCCCTGGCCCACCCTCGTGACCACCCTGACCTACG<br>GCGTGCAGTGCTTCAGCCGCTACCCCGACCACATG<br>AAGCAGCACGACTTCTTCAAGTCCGCCATGCCCGA<br>AGGCTACGTCCAGGAGCGCACCATCTTCTTCAAGG<br>ACGACGGCAACTACAAGACCCGCGCCGAGGTGAA<br>GTTCGAGGGCGACACCCTGGTGAACCGCATCGAGC<br>TGAAGGGCATCGACTTCAAGGAGGACGGCAACAT | 29 |

TABLE 4

8: Anti-P329G-Fab amino acid sequences:

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |

TABLE 4-continued

8: Anti-P329G-Fab amino acid sequences:

| Construct | Amino acid sequence | SEQ ID NO |
|---|---|---|
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-Fab-heavy chain-CD28ATD-CD28CSD-CD3zSSD fusion | EVKLLESGGGLVQPGGSLKLSCAASGFDFSRYWMN WVRQAPGKGLEWIGEITPDSSTINYTPSLKDKFIISRD NAKNTLYLQMIKVRSEDTALYYCVRPYDYGAWFAS WGQGTLVTVSAASTKGPSVFPLAPSSKSTSGGTAAL GCLVKDYFPEPVTVSWNSGALTSGVHTFPAVLQSSG LYSLSSVVTVPSSSLGTQTYICNVNHKPSNTKVDKKV EPKSCGGGGSFWVLVVVGGVLACYSLLVTVAFIIFW VRSKRSRLLHSDYMNMTPRRPGPTRKHYQPYAPPRD FAAYRSRVKFSRSADAPAYQQGQNQLYNELNLGRR EEYDVLDKRRGRDPEMGGKPRRKNPQEGLYNELQK DKMAEAYSEIGMKGERRRGKGHDGLYQGLSTATKD TYDALHMQALPPR | 30 |
| Anti-P329G-Fab heavy chain | EVKLLESGGGLVQPGGSLKLSCAASGFDFSRYWMN WVRQAPGKGLEWIGEITPDSSTINYTPSLKDKFIISRD NAKNTLYLQMIKVRSEDTALYYCVRPYDYGAWFAS WGQGTLVTVSAASTKGPSVFPLAPSSKSTSGGTAAL GCLVKDYFPEPVTVSWNSGALTSGVHTFPAVLQSSG LYSLSSVVTVPSSSLGTQTYICNVNHKPSNTKVDKKV EPKSC | 31 |
| Anti-P329G-Fab light chain | QAVVTQESALTTSPGETVTLTCRSSTGAVTTSNYAN WVQEKPDHLFTGLIGGTNKRAPGVPARFSGSLIGDK AALTITGAQTEDEAIYFCALWYSNHWVFGGGTKLTV LRTVAAPSVFIFPPSDEQLKSGTASVVCLLNNFYPRE AKVQWKVDNALQSGNSQESVTEQDSKDSTYSLSSTL TLSKADYEKHKVYACEVTHQGLSSPVTKSFNRGEC | 32 |
| Anti-P329G VL | QAVVTQESALTTSPGETVTLTCRSSTGAVTTSNYAN WVQEKPDHLFTGLIGGTNKRAPGVPARFSGSLIGDK AALTITGAQTEDEAIYFCALWYSNHWVFGGGTKLTV L | 33 |
| CL | RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC | 34 |
| Anti-P329G VH | EVKLLESGGGLVQPGGSLKLSCAASGFDFSRYWMN WVRQAPGKGLEWIGEITPDSSTINYTPSLKDKFIISRD NAKNTLYLQMIKVRSEDTALYYCVRPYDYGAWFAS WGQGTLVTVSA | 35 |
| CH1 | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSC | 36 |

TABLE 5

9: Anti-P329G-Fab DNA sequences:

| Construct | DNA Sequenz | SEQ ID NO |
|---|---|---|
| Anti-P329G-Fab-heavy chain-CD28ATD-CD28CSD-CD3zSSD fusion | ATGGGATGGAGCTGTATCATCCTCTTCTTGGTAGC AACAGCTACGGGTGTGCATTCCCAGGCCGTGGTGA CCCAGGAGAGCGCCCTGACCACCAGCCCCGGCGA GACCGTGACCCTGACCTGCAGGAGCAGCACCGGC GCCGTGACCACCAGCAACTACGCCAACTGGGTGCA GGAGAAGCCCGACCACCTGTTCACCGGCCTGATCG GCGGCACCAACAAGAGGGCCCCCGGCGTGCCCGC CAGGTTCAGCGGCAGCCTGATCGGCGACAAGGCC GCCCTGACCATCACCGGCGCCCAGACCGAGGACG AGGCCATCTACTTCTGCGCCCTGTGGTACAGCAAC | 37 |

TABLE 5-continued

9: Anti-P329G-Fab DNA sequences:

| Construct | DNA Sequenz | SEQ ID NO |
|---|---|---|
| | CACTGGGTGTTCGGCGGTGGCACCAAGCTGACCGT<br>GCTGCGTACGGTGGCTGCACCATCTGTCTTCATCTT<br>CCCGCCATCTGATGAGCAGTTGAAATCTGGAACTG<br>CCTCTGTTGTGTGCCTGCTGAATAACTTCTATCCCA<br>GAGAGGCCAAAGTACAGTGGAAGGTGGATAACGC<br>CCTCCAATCGGGTAACTCCCAGGAGAGTGTCACAG<br>AGCAGGACAGCAAGGACAGCACCTACAGCCTCAG<br>CAGCACCCTGACGCTGAGCAAAGCAGACTACGAG<br>AAACACAAAGTCTACGCCTGCGAAGTCACCCATCA<br>GGGCCTGAGCTCGCCCGTCACAAAGAGCTTCAACA<br>GGGGAGAGTGTTAGGAATTCCCCGAAGTAACTTAG<br>AAGCTGTAAATCAACGATCAATAGCAGGTGTGGC<br>ACACCAGTCATACCTTGATCAAGCACTTCTGTTTCC<br>CCGGACTGAGTATCAATAGGCTGCTCGCGCGGCTG<br>AAGGAGAAAACGTTCGTTACCCGACCAACTACTTC<br>GAGAAGCTTAGTACCACCATGAACGAGGCAGGGT<br>GTTTCGCTCAGCACAACCCCAGTGTAGATCAGGCT<br>GATGAGTCACTGCAACCCCCATGGGCGACCATGGC<br>AGTGGCTGCGTTGGCGGCCTGCCCATGGAGAAATC<br>CATGGGACGCTCTAATTCTGACATGGTGTGAAGTG<br>CCTATTGAGCTAACTGGTAGTCCTCCGGCCCCTGA<br>TTGCGGCTAATCCTAACTGCGGAGCACATGCTCAC<br>AAACCAGTGGGTGGTGTCGTAACGGGCAACTCT<br>GCAGCGGAACCGACTACTTTGGGTGTCCGTGTTTC<br>CTTTTATTCCTATATTGGCTGCTTATGGTGACAATC<br>AAAAAGTTGTTACCATATAGCTATTGGATTGGCCA<br>TCCGGTGTGCAACAGGGCAACTGTTTACCTATTTA<br>TTGGTTTTGTACCATTATCACTGAAGTCTGTGATCA<br>CTCTCAAATTCATTTTGACCCTCAACACAATCAAA<br>CGCCACCATGGGATGGAGCTGTATCATCCTCTTCT<br>TGGTAGCAACAGCTACCGGTGTGCACTCCGAGGTG<br>AAGCTGCTGGAGAGCGGCGGCGCCTGGTGCAGC<br>CCGGCGGCAGCCTGAAGCTGAGCTGCGCCGCCAG<br>CGGCTTCGACTTCAGCAGGTACTGGATGAACTGGG<br>TGAGGCAGGCCCCCGGCAAGGGTCTGGAGTGGAT<br>CGGCGAGATCACCCCCGACAGCAGCACCATCAACT<br>ACACCCCCAGCCTGAAGGACAAGTTCATCATCAGC<br>AGGGACAACGCCAAGAACACCCTGTACCTGCAGA<br>TGATCAAGGTGAGGAGCGAGGACACCGCCCTGTA<br>CTACTGCGTGAGGCCCTACGACTACGGCGCCTGGT<br>TCGCCAGCTGGGGCCAGGGCACCCTGGTGACCGTG<br>AGCGCCGCTAGCACCAAGGGCCCCTCCGTGTTCCC<br>CCTGGCCCCCAGCAGCAAGAGCACCAGCGGCGGC<br>ACAGCCGCTCTGGGCTGCCTGGTCAAGGACTACTT<br>CCCCGAGCCCGTGACCGTGTCCTGGAACAGCGGAG<br>CCCTGACCTCCGGCGTGCACACCTTCCCCGCCGTG<br>CTGCAGAGTTCTGGCCTGTATAGCCTGAGCAGCGT<br>GGTCACCGTGCCTTCTAGCAGCCTGGGCACCCAGA<br>CCTACATCTGCAACGTGAACCACAAGCCCAGCAAC<br>ACCAAGGTGGACAAGAAGGTGGAGCCCAAGAGCT<br>GCGGAGGGGGCGGATCCTTCTGGGTGCTGGTGGTG<br>GTGGGCGGCGTGCTGGCCTGCTACAGCCTGCTGGT<br>GACCGTGGCCTTCATCATCTTCTGGGTGAGGAGCA<br>AGAGGAGCAGGCTGCTGCACAGCGACTACATGAA<br>CATGACCCCCAGGAGGCCCGGCCCCACCAGGAAG<br>CACTACCAGCCCTACGCCCCCCCCAGGGACTTCGC<br>CGCCTACAGGAGCAGGGTGAAGTTCAGCAGGAGC<br>GCCGACGCCCCCGCCTACCAGCAGGGCCAGAACC<br>AGCTGTATAACGAGCTGAACCTGGGCAGGAGGGA<br>GGAGTACGACGTGCTGGACAAGAGGAGGGGCAGG<br>GACCCCGAGATGGGCGGCAAGCCCAGGAGGAAGA<br>ACCCCCAGGAGGGCCTGTATAACGAGCTGCAGAA<br>GGACAAGATGGCCGAGGCCTACAGCGAGATCGGC<br>ATGAAGGGCGAGAGGAGGAGGGGCAAGGGCCAC<br>GACGGCCTGTACCAGGGCCTGAGCACCGCCACCA<br>AGGACACCTACGACGCCCTGCACATGCAGGCCCTG<br>CCCCCCAGG | |
| Anti-P329G VL | CAGGCCGTGGTGACCCAGGAGAGCGCCCTGACCA<br>CCAGCCCCGGCGAGACCGTGACCCTGACCTGCAGG<br>AGCAGCACCGGCGCCGTGACCACCAGCAACTACG<br>CCAACTGGGTGCAGGAGAAGCCCGACCACCTGTTC<br>ACCGGCCTGATCGGCGGCACCAACAAGAGGGCCC<br>CCGGCGTGCCCGCCAGGTTCAGCGGCAGCCTGATC<br>GGCGACAAGGCCGCCCTGACCATCACCGGCGCCC<br>AGACCGAGGACGAGGCCATCTACTTCTGCGCCCTG | 38 |

TABLE 5-continued

9: Anti-P329G-Fab DNA sequences:

| Construct | DNA Sequenz | SEQ ID NO |
|---|---|---|
| | TGGTACAGCAACCACTGGGTGTTCGGCGGTGGCAC CAAGCTGACCGTGCTG | |
| CL | CGTACGGTGGCTGCACCATCTGTCTTCATCTTCCCG CCATCTGATGAGCAGTTGAAATCTGGAACTGCCTC TGTTGTGTGCCTGCTGAATAACTTCTATCCCAGAG AGGCCAAAGTACAGTGGAAGGTGGATAACGCCCT CCAATCGGGTAACTCCCAGGAGAGTGTCACAGAG CAGGACAGCAAGGACAGCACCTACAGCCTCAGCA GCACCCTGACGCTGAGCAAAGCAGACTACGAGAA ACACAAAGTCTACGCCTGCGAAGTCACCCATCAGG GCCTGAGCTCGCCCGTCACAAAGAGCTTCAACAGG GGAGAGTGTTAG | 39 |
| Anti-P329G VH | GAGGTGAAGCTGCTGGAGAGCGGCGGCGGCCTGG TGCAGCCCGGCGGCAGCCTGAAGCTGAGCTGCGCC GCCAGCGGCTTCGACTTCAGCAGGTACTGGATGAA CTGGGTGAGGCAGGCCCCCGGCAAGGGTCTGGAG TGGATCGGCGAGATCACCCCCGACAGCAGCACCAT CAACTACACCCCCAGCCTGAAGGACAAGTTCATCA TCAGCAGGGACAACGCCAAGAACACCCTGTACCT GCAGATGATCAAGGTGAGGAGCGAGGACACCGCC CTGTACTACTGCGTGAGGCCCTACGACTACGGCGC CTGGTTCGCCAGCTGGGGCCAGGGCACCCTGGTGA CCGTGAGCGCC | 40 |
| CH1 | GCTAGCACCAAGGGCCCCTCCGTGTTCCCCCTGGC CCCCAGCAGCAAGAGCACCAGCGGCGGCACAGCC GCTCTGGGCTGCCTGGTCAAGGACTACTTCCCCGA GCCCGTGACCGTGTCCTGGAACAGCGGAGCCCTGA CCTCCGGCGTGCACACCTTCCCCGCCGTGCTGCAG AGTTCTGGCCTGTATAGCCTGAGCAGCGTGGTCAC CGTGCCTTCTAGCAGCCTGGGCACCCAGACCTACA TCTGCAACGTGAACCACAAGCCCAGCAACACCAA GGTGGACAAGAAGGTGGAGCCCAAGAGCTGC | 41 |
| IRES EV71, internal ribosomal entry side | CCCGAAGTAACTTAGAAGCTGTAAATCAACGATCA ATAGCAGGTGTGGCACACCAGTCATACCTTGATCA AGCACTTCTGTTTCCCCGGACTGAGTATCAATAGG CTGCTCGCGCGGCTGAAGGAGAAAACGTTCGTTAC CCGACCAACTACTTCGAGAAGCTTAGTACCACCAT GAACGAGGCAGGGTGTTTCGCTCAGCACAACCCCA GTGTAGATCAGGCTGATGAGTCACTGCAACCCCCA TGGGCGACCATGGCAGTGGCTGCGTTGGCGGCCTG CCCATGGAGAAATCCATGGGACGCTCTAATTCTGA CATGGTGTGAAGTGCCTATTGAGCTAACTGGTAGT CCTCCGGCCCCTGATTGCGGCTAATCCTAACTGCG GAGCACATGCTCACAAACCAGTGGGTGGTGTGTCG TAACGGGCAACTCTGCAGCGGAACCGACTACTTTG GGTGTCCGTGTTTCCTTTTATTCCTATATTGGCTGC TTATGGTGACAATCAAAAAGTTGTTACCATATAGC TATTGGATTGGCCATCCGGTGTGCAACAGGGCAAC TGTTTACCTATTTATTGGTTTTGTACCATTATCACT GAAGTCTGTGATCACTCTCAAATTCATTTTGACCCT CAACACAATCAAAC | 42 |
| CD28ATD-CD28CSD-CD3zSSD | see Table 3 | 27 |
| Anti-P329G-Fab-heavy chain-CD28ATD-CD28CSD-CD3zSSD-eGFP fusion | ATGGGATGGAGCTGTATCATCCTCTTCTTGGTAGC AACAGCTACGGGTGTGCATTCCCAGGCCGTGGTGA CCCAGGAGAGCGCCCTGACCACCAGCCCCGGCGA GACCGTGACCCTGACCTGCAGGAGCAGCACCGGC GCCGTGACCACCAGCAACTACGCCAACTGGGTGCA GGAGAAGCCCGACCACCTGTTCACCGGCCTGATCG GCGGCACCAACAAGAGGGCCCCCGGCGTGCCCGC CAGGTTCAGCGGCAGCCTGATCGGCGACAAGGCC GCCCTGACCATCACCGGCGCCCAGACCGAGGACG AGGCCATCTACTTCTGCGCCCTGTGGTACAGCAAC CACTGGGTGTTCGGCGGTGGCACCAAGCTGACCGT GCTGCGTACGGTGGCTGCACCATCTGTCTTCATCTT CCCGCCATCTGATGAGCAGTTGAAATCTGGAACTG CCTCTGTTGTGTGCCTGCTGAATAACTTCTATCCCA GAGAGGCCAAAGTACAGTGGAAGGTGGATAACGC CCTCCAATCGGGTAACTCCCAGGAGAGTGTCACAG AGCAGGACAGCAAGGACAGCACCTACAGCCTCAG | 43 |

TABLE 5-continued

9: Anti-P329G-Fab DNA sequences:

| Construct | DNA Sequenz | SEQ ID NO |
|---|---|---|
| | CAGCACCCTGACGCTGAGCAAAGCAGACTACGAG | |
| | AAACACAAAGTCTACGCCTGCGAAGTCACCCATCA | |
| | GGGCCTGAGCTCGCCCGTCACAAAGAGCTTCAACA | |
| | GGGGAGAGTGTTAGGAATTCCCCGAAGTAACTTAG | |
| | AAGCTGTAAATCAACGATCAATAGCAGGTGTGGC | |
| | ACACCAGTCATACCTTGATCAAGCACTTCTGTTTCC | |
| | CCGGACTGAGTATCAATAGGCTGCTCGCGCGGCTG | |
| | AAGGAGAAAACGTTCGTTACCCGACCAACTACTTC | |
| | GAGAAGCTTAGTACCACCATGAACGAGGCAGGGT | |
| | GTTTCGCTCAGCACAACCCCAGTGTAGATCAGGCT | |
| | GATGAGTCACTGCAACCCCATGGGCGACCATGGC | |
| | AGTGGCTGCGTTGGCGGCCTGCCCATGGAGAAATC | |
| | CATGGGACGCTCTAATTCTGACATGGTGTGAAGTG | |
| | CCTATTGAGCTAACTGGTAGTCCTCCGGCCCCTGA | |
| | TTGCGGCTAATCCTAACTGCGGAGCACATGCTCAC | |
| | AAACCAGTGGGTGGTGTGTCGTAACGGGCAACTCT | |
| | GCAGCGGAACCGACTACTTTGGGTGTCCGTGTTTC | |
| | CTTTTATTCCTATATTGGCTGCTTATGGTGACAATC | |
| | AAAAAGTTGTTACCATATAGCTATTGGATTGGCCA | |
| | TCCGGTGTGCAACAGGGCAACTGTTTACCTATTTA | |
| | TTGGTTTTGTACCATTATCACTGAAGTCTGTGATCA | |
| | CTCTCAAATTCATTTTGACCCTCAACACAATCAAA | |
| | CGCCACCATGGGATGGAGCTGTATCATCCTCTTCT | |
| | TGGTAGCAACAGCTACCGGTGTGCACTCCGAGGTG | |
| | AAGCTGCTGGAGAGCGGCGGCGGCCTGGTGCAGC | |
| | CCGGCGGCAGCCTGAAGCTGAGCTGCGCCGCCAG | |
| | CGGCTTCGACTTCAGCAGGTACTGGATGAACTGGG | |
| | TGAGGCAGGCCCCCGGCAAGGGTCTGGAGTGGAT | |
| | CGGCGAGATCACCCCCGACAGCAGCACCATCAACT | |
| | ACACCCCCAGCCTGAAGGACAAGTTCATCATCAGC | |
| | AGGGACAACGCCAAGAACACCCTGTACCTGCAGA | |
| | TGATCAAGGTGAGGAGCGAGGACACCGCCCTGTA | |
| | CTACTGCGTGAGGCCCTACGACTACGGCGCCTGGT | |
| | TCGCCAGCTGGGGCCAGGGCACCCTGGTGACCGTG | |
| | AGCGCCGCTAGCACCAAGGGCCCCTCCGTGTTCCC | |
| | CCTGGCCCCCAGCAGCAAGAGCACCAGCGGCGGC | |
| | ACAGCCGCTCTGGGCTGCCTGGTCAAGGACTACTT | |
| | CCCCGAGCCCGTGACCGTGTCCTGGAACAGCGGAG | |
| | CCCTGACCTCCGGCGTGCACACCTTCCCCGCCGTG | |
| | CTGCAGAGTTCTGGCCTGTATAGCCTGAGCAGCGT | |
| | GGTCACCGTGCCTTCTAGCAGCCTGGGCACCCAGA | |
| | CCTACATCTGCAACGTGAACCACAAGCCCAGCAAC | |
| | ACCAAGGTGGACAAGAAGGTGGAGCCCAAGAGCT | |
| | GCGGAGGGGCGGATCCTTCTGGGTGCTGGTGGTG | |
| | GTGGGCGGCGTGCTGGCCTGCTACAGCCTGCTGGT | |
| | GACCGTGGCCTTCATCATCTTCTGGGTGAGGAGCA | |
| | AGAGGAGCAGGCTGCTGCACAGCGACTACATGAA | |
| | CATGACCCCCAGGAGGCCCGGCCCCACCAGGAAG | |
| | CACTACCAGCCCTACGCCCCCCCCAGGGACTTCGC | |
| | CGCCTACAGGAGCAGGGTGAAGTTCAGCAGGAGC | |
| | GCCGACGCCCCCGCCTACCAGCAGGGCCAGAACC | |
| | AGCTGTATAACGAGCTGAACCTGGGCAGGAGGGA | |
| | GGAGTACGACGTGCTGGACAAGAGGAGGGGCAGG | |
| | GACCCCGAGATGGGCGGCAAGCCCAGGAGGAAGA | |
| | ACCCCCAGGAGGGCCTGTATAACGAGCTGCAGAA | |
| | GGACAAGATGGCCGAGGCCTACAGCGAGATCGGC | |
| | ATGAAGGGCGAGAGGAGGAGGGGCAAGGGCCAC | |
| | GACGGCCTGTACCAGGGCCTGAGCACCGCCACCA | |
| | AGGACACCTACGACGCCCTGCACATGCAGGCCCTG | |
| | CCCCCCAGGTCCGGAGAGGGCAGAGGAAGTCTTCT | |
| | AACATGCGGTGACGTGGAGGAGAATCCCGGCCCT | |
| | AGGGTGAGCAAGGGCGAGGAGCTGTTCACCGGGG | |
| | TGGTGCCCATCCTGGTCGAGCTGGACGGCGACGTA | |
| | AACGGCCACAAGTTCAGCGTGTCCGGCGAGGGCG | |
| | AGGGCGATGCCACCTACGGCAAGCTGACCCTGAA | |
| | GTTCATCTGCACCACCGGCAAGCTGCCCGTGCCCT | |
| | GGCCCACCCTCGTGACCACCCTGACCTACGGCGTG | |
| | CAGTGCTTCAGCCGCTACCCCGACCACATGAAGCA | |
| | GCACGACTTCTTCAAGTCCGCCATGCCCGAAGGCT | |
| | ACGTCCAGGAGCGCACCATCTTCTTCAAGGACGAC | |
| | GGCAACTACAAGACCCGCGCCGAGGTGAAGTTCG | |
| | AGGGCGACACCCTGGTGAACCGCATCGAGCTGAA | |
| | GGGCATCGACTTCAAGGAGGACGGCAACATCCTG | |
| | GGGCACAAGCTGGAGTACAACTACAACAGCCACA | |
| | ACGTCTATATCATGGCCGACAAGCAGAAGAACGG | |
| | CATCAAGGTGAACTTCAAGATCCGCCACAACATCG | |

TABLE 5-continued

9: Anti-P329G-Fab DNA sequences:

| Construct | DNA Sequenz | SEQ ID NO |
|---|---|---|
| | AGGACGGCAGCGTGCAGCTCGCCGACCACTACCA<br>GCAGAACACCCCCATCGGCGACGGCCCCGTGCTGC<br>TGCCCGACAACCACTACCTGAGCACCCAGTCCGCC<br>CTGAGCAAAGACCCCAACGAGAAGCGCGATCACA<br>TGGTCCTGCTGGAGTTCGTGACCGCCGCCGGGATC<br>ACTCTCGGCATGGACGAGCTGTACAAGTGA | |

TABLE 6

10: Anti-AAA-scFv amino acid sequences

| Construct | Amino acid sequence | SEQ ID NO |
|---|---|---|
| Anti-AAA CDR H1 Kabat | SYGMS | 44 |
| Anti-AAA CDR H2 Kabat | SSGGSY | 45 |
| Anti-AAA CDR H3 Kabat | LGMITTGYAMDY | 46 |
| Anti-AAA CDR L1 Kabat | RSSQTIVHSTGHTYLE | 47 |
| Anti-AAA CDR L2 Kabat | KVSNRFS | 48 |
| Anti-AAA CDR L3 Kabat | FQGSHVPYT | 49 |
| Anti-AAA-scFv-<br>CD28ATD-<br>CD28CSD-<br>CD3zSSD fusion | MNFGLSLVFLALILKGVQCEVQLVESGGDLVKPGGS<br>LKLSCAASGFTFSSYGMSWVRQTPDKRLEWVATISS<br>GGSYIYYPDSVKGRFTISRDNAKNTLYLQMSSLKSED<br>TAMYYCARLGMITTGYAMDYWGQGTSVTVSSGGG<br>GSGGGGSGGGGSGGGGSDVLMTQTPLSLPVSLGDQ<br>ASISCRSSQTIVHSTGHTYLEWFLQKPGQSPKLLIYKV<br>SNRFSGVPDRFSGSGSGTDFTLKISRVEAEDLGVYYC<br>FQGSHVPYTFGGGTKLEIKGGGGSFWVLVVVGGVL<br>ACYSLLVTVAFIIFWVRSKRSRLLHSDYMNMTPRRP<br>GPTRKHYQPYAPPRDFAAYRSRVKFSRSADAPAYQQ<br>GQNQLYNELNLGRREEYDVLDKRRGRDPEMGGKPR<br>RKNPQEGLYNELQKDKMAEAYSEIGMKGERRRGKG<br>HDGLYQGLSTATKDTYDALHMQALPPR | 50 |
| Anti-AAA-scFv | MNFGLSLVFLALILKGVQCEVQLVESGGDLVKPGGS<br>LKLSCAASGFTFSSYGMSWVRQTPDKRLEWVATISS<br>GGSYIYYPDSVKGRFTISRDNAKNTLYLQMSSLKSED<br>TAMYYCARLGMITTGYAMDYWGQGTSVTVSSGGG<br>GSGGGGSGGGGSGGGGSDVLMTQTPLSLPVSLGDQ<br>ASISCRSSQTIVHSTGHTYLEWFLQKPGQSPKLLIYKV<br>SNRFSGVPDRFSGSGSGTDFTLKISRVEAEDLGVYYC<br>FQGSHVPYTFGGGTKLEIK | 51 |
| Anti-AAA VH | MNFGLSLVFLALILKGVQCEVQLVESGGDLVKPGGS<br>LKLSCAASGFTFSSYGMSWVRQTPDKRLEWVATISS<br>GGSYIYYPDSVKGRFTISRDNAKNTLYLQMSSLKSED<br>TAMYYCARLGMITTGYAMDYWGQGTSVTVSS | 52 |
| Anti-AAA VL | DVLMTQTPLSLPVSLGDQASISCRSSQTIVHSTGHTYL<br>EWFLQKPGQSPKLLIYKVSNRFSGVPDRFSGSGSGTD<br>FTLKISRVEAEDLGVYYCFQGSHVPYTFGGGTKLEIK | 53 |

TABLE 7

| 11: Anti-AAA-Fab amino acid sequences | | |
|---|---|---|
| Construct | Protein Sequence | SEQ ID NO |
| Anti-AAA CDR H1 Kabat | see Table 6 | 44 |
| Anti-AAA CDR H2 Kabat | see Table 6 | 45 |
| Anti-AAA CDR H3 Kabat | see Table 6 | 46 |
| Anti-AAA CDR L1 Kabat | see Table 6 | 47 |
| Anti-AAA CDR L2 Kabat | see Table 6 | 48 |
| Anti-AAA CDR L3 Kabat | see Table 6 | 49 |
| Anti-AAA-Fab-heavy chain-CD28ATD-CD28CSD-CD3zSSD fusion | MNFGLSLVFLALILKGVQCEVQLVESGGDLVKPGGS LKLSCAASGFTFSSYGMSWVRQTPDKRLEWVATISS GGSYIYYPDSVKGRFTISRDNAKNTLYLQMSSLKSED TAMYYCARLGMITTGYAMDYWGQGTSVTVSSASTK GPSVFPLAPSSKSTSGGTAALGCLVKDYFPEPVTVSW NSGALTSGVHTFPAVLQSSGLYSLSSVVTVPSSSLGT QTYICNVNHKPSNTKVDKKVEPKSCGGGGSFWVLV VVGGVLACYSLLVTVAFIIFWVRSKRSRLLHSDYMN MTPRRPGPTRKHYQPYAPPRDFAAYRSRVKFSRSAD APAYQQGQNQLYNELNLGRREEYDVLDKRRGRDPE MGGKPRRKNPQEGLYNELQKDKMAEAYSEIGMKGE RRRGKGHDGLYQGLSTATKDTYDALHMQALPPR | 54 |
| Anti-AAA-Fab heavy chain | MNFGLSLVFLALILKGVQCEVQLVESGGDLVKPGGS LKLSCAASGFTFSSYGMSWVRQTPDKRLEWVATISS GGSYIYYPDSVKGRFTISRDNAKNTLYLQMSSLKSED TAMYYCARLGMITTGYAMDYWGQGTSVTVSSASTK GPSVFPLAPSSKSTSGGTAALGCLVKDYFPEPVTVSW NSGALTSGVHTFPAVLQSSGLYSLSSVVTVPSSSLGT QTYICNVNHKPSNTKVDKKVEPKSC | 55 |
| Anti-AAA-Fab light chain | DVLMTQTPLSLPVSLGDQASISCRSSQTIVHSTGHTYL EWFLQKPGQSPKLLIYKVSNRFSGVPDRFSGSGSGTD FTLKISRVEAEDLGVYYCFQGSHVPYTFGGGTKLEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC | 56 |
| Anti-AAA VL | see Table 6 | 53 |
| CL | see Table 4 | 35 |
| Anti-AAA VH | see Table 6 | 52 |
| CH1 | see Table 4 | 37 |

TABLE 8

| 8: Anti-DIG-ds-scFv amino acid sequences: | | |
|---|---|---|
| Construct | Amino acid sequence | SEQ ID NO |
| Anti-DIG CDR H1 Kabat | DYAMS | 57 |
| Anti-DIG CDR H2 Kabat | SINIGATYIYYADSVKG | 58 |
| Anti-DIG CDR H3 Kabat | PGSPYEYDKAYYSMAY | 59 |
| Anti-DIG CDR L1 Kabat | RASQDIKNYLN | 60 |

TABLE 8-continued

8: Anti-DIG-ds-scFv amino acid sequences:

| Construct | Amino acid sequence | SEQ ID NO |
|---|---|---|
| Anti-DIG CDR L2 Kabat | YSSTLLS | 61 |
| Anti-DIG CDR L3 Kabat | QQSITLPPT | 62 |
| Anti-DIG-ds-scFv-CD28ATD-CD28CSD-CD3zSSD fusion | QVQLVESGGGLVKPGGSLRLSCAASGFTFSDYAMSW IRQAPGKCLEWVSSINIGATYIYYADSVKGRFTISRDN AKNSLYLQMNSLRAEDTAVYYCARPGSPYEYDKAY YSMAYWGQGTTVTVSSGGGGSGGGGSGGGGSGGG GSDIQMTQSPSSLSASVGDRVTITCRASQDIKNYLNW YQQKPGKAPKLLIYYSSTLLSGVPSRFSGSGSGTDFTL TISSLQPEDFATYYCQQSITLPPTFGCGTKVEIKGGGG SFWVLVVVGGVLACYSLLVTVAFIIFWVRSKRSRLL HSDYMNMTPRRPGPTRKHYQPYAPPRDFAAYRSRV KFSRSADAPAYQQGQNQLYNELNLGRREEYDVLDK RRGRDPEMGGKPRRKNPQEGLYNELQKDKMAEAYS EIGMKGERRRGKGHDGLYQGLSTATKDTYDALHMQ ALPPR | 63 |
| Anti-DIG-ds VH | QVQLVESGGGLVKPGGSLRLSCAASGFTFSDYAMSW IRQAPGKCLEWVSSINIGATYIYYADSVKGRFTISRDN AKNSLYLQMNSLRAEDTAVYYCARPGSPYEYDKAY YSMAYWGQGTTVTVSS | 64 |
| Anti-DIG-ds VL | DIQMTQSPSSLSASVGDRVTITCRASQDIKNYLNWYQ QKPGKAPKLLIYYSSTLLSGVPSRFSGSGSGTDFTLTI SSLQPEDFATYYCQQSITLPPTFGCGTKVEIK | 65 |
| Anti-DIG-ds-scFv | QVQLVESGGGLVKPGGSLRLSCAASGFTFSDYAMSW IRQAPGKCLEWVSSINIGATYIYYADSVKGRFTISRDN AKNSLYLQMNSLRAEDTAVYYCARPGSPYEYDKAY YSMAYWGQGTTVTVSSGGGGSGGGGSGGGGSGGG GSDIQMTQSPSSLSASVGDRVTITCRASQDIKNYLNW YQQKPGKAPKLLIYYSSTLLSGVPSRFSGSGSGTDFTL TISSLQPEDFATYYCQQSITLPPTFGCGTKVEIK | 66 |

TABLE 9

9: Anti-DIG-Fab amino acid sequences:

| Construct | Amino acid sequence | SEQ ID NO |
|---|---|---|
| Anti-DIG CDR H1 Kabat | see Table 8 | 57 |
| Anti-DIG CDR H2 Kabat | see Table 8 | 58 |
| Anti-DIG CDR H3 Kabat | see Table 8 | 59 |
| Anti-DIG CDR L1 Kabat | see Table 8 | 60 |
| Anti-DIG CDR L2 Kabat | see Table 8 | 61 |
| Anti-DIG CDR L3 Kabat | see Table 8 | 62 |

TABLE 9-continued

9: Anti-DIG-Fab amino acid sequences:

| Construct | Amino acid sequence | SEQ ID NO |
|---|---|---|
| Anti-DIG-Fab-heavy chain-CD28ATD-CD28CSD-CD3zSSD fusion | QVQLVESGGGLVKPGGSLRLSCAASGFTFSDYAMSW IRQAPGKGLEWVSSINIGATYIYYADSVKGRFTISRDN AKNSLYLQMNSLRAEDTAVYYCARPGSPYEYDKAY YSMAYWGQGTTVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNTK VDKKVEPKSCGGGGSFWVLVVVGGVLACYSLLVTV AFIIFWVRSKRSRLLHSDYMNMTPRRPGPTRKHYQP YAPPRDFAAYRSRVKFSRSADAPAYQQGQNQLYNEL NLGRREEYDVLDKRRGRDPEMGGKPRRKNPQEGLY NELQKDKMAEAYSEIGMKGERRRGKGHDGLYQGLS TATKDTYDALHMQALPPR | 67 |
| Anti-DIG-Fab heavy chain | QVQLVESGGGLVKPGGSLRLSCAASGFTFSDYAMSW IRQAPGKGLEWVSSINIGATYIYYADSVKGRFTISRDN AKNSLYLQMNSLRAEDTAVYYCARPGSPYEYDKAY YSMAYWGQGTTVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNTK VDKKVEPKSC | 68 |
| Anti-DIG-Fab light chain | DIQMTQSPSSLSASVGDRVTITCRASQDIKNYLNWYQ QKPGKAPKLLIYYSSTLLSGVPSRFSGSGSGTDFTLTI SSLQPEDFATYYCQQSITLPPTFGGGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC | 69 |
| Anti-DIG VH | QVQLVESGGGLVKPGGSLRLSCAASGFTFSDYAMSW IRQAPGKGLEWVSSINIGATYIYYADSVKGRFTISRDN AKNSLYLQMNSLRAEDTAVYYCARPGSPYEYDKAY YSMAYWGQGTTVTVSS | 70 |
| Anti-DIG VL | DIQMTQSPSSLSASVGDRVTITCRASQDIKNYLNWYQ QKPGKAPKLLIYYSSTLLSGVPSRFSGSGSGTDFTLTI SSLQPEDFATYYCQQSITLPPTFGGGTKVEIK | 71 |

TABLE 10

10: Anti-FITC- scFv amino acid sequences

| Construct | Amino acid sequence | SEQ ID NO |
|---|---|---|
| Anti-FITC CDR H1 Kabat | HYWMN | 72 |
| Anti-FITC CDR H2 Kabat | QFRNKPYNYETYYSDSVKG | 73 |
| Anti-FITC CDR H3 Kabat | ASYGMEY | 74 |
| Anti-FITC CDR L1 Kabat | RSSQSLVHSNGNTYLR | 75 |
| Anti-FITC CDR L2 Kabat | KVSNRVS | 76 |
| Anti-FITC CDR L3 Kabat | SQSTHVPWT | 77 |
| Anti-FITC-scFv-CD28ATD-CD28CSD-CD3zSSD fusion | GVKLDETGGGLVQPGGAMKLSCVTSGFTFGHYWM NWVRQSPEKGLEWVAQFRNKPYNYETYYSDSVKGR FTISRDDSKSSVYLQMNNLRVEDTGIYYCTGASYGM EYLGQGTSVTVSSGGGGSGGGGSGGGGSGGGGSDV VMTQTPLSLPVSLGDQASISCRSSQSLVHSNGNTYLR WYLQKPGQSPKVLIYKVSNRVSGVPDRFSGSGSGTD FTLKINRVEAEDLGVYFCSQSTHVPWTFGGGTKLEIK RGGGGSFWVLVVVGGVLACYSLLVTVAFIIFWVRSK RSRLLHSDYMNMTPRRPGPTRKHYQPYAPPRDFAAY RSRVKFSRSADAPAYQQGQNQLYNELNLGRREEYD VLDKRRGRDPEMGGKPRRKNPQEGLYNELQKDKM | 78 |

TABLE 10-continued

10: Anti-FITC- scFv amino acid sequences

| Construct | Amino acid sequence | SEQ ID NO |
|---|---|---|
| | AEAYSEIGMKGERRRGKGHDGLYQGLSTATKDTYD<br>ALHMQALPPR | |
| Anti-FITC-scFv | GVKLDETGGGLVQPGGAMKLSCVTSGFTFGHYWM<br>NWVRQSPEKGLEWVAQFRNKPYNYETYYSDSVKGR<br>FTISRDDSKSSVYLQMNNLRVEDTGIYYCTGASYGM<br>EYLGQGTSVTVSSGGGGSGGGGSGGGGSGGGGSDV<br>VMTQTPLSLPVSLGDQASISCRSSQSLVHSNGNTYLR<br>WYLQKPGQSPKVLIYKVSNRVSGVPDRFSGSGSGTD<br>FTLKINRVEAEDLGVYFCSQSTHVPWTFGGGTKLEIK | 79 |
| Anti-FITC VH | GVKLDETGGGLVQPGGAMKLSCVTSGFTFGHYWM<br>NWVRQSPEKGLEWVAQFRNKPYNYETYYSDSVKGR<br>FTISRDDSKSSVYLQMNNLRVEDTGIYYCTGASYGM<br>EYLGQGTSVTVSS | 80 |
| Anti-FITC VL | DVVMTQTPLSLPVSLGDQASISCRSSQSLVHSNGNTY<br>LRWYLQKPGQSPKVLIYKVSNRVSGVPDRFSGSGSG<br>TDFTLKINRVEAEDLGVYFCSQSTHVPWTFGGGTKL<br>EIK | 81 |

TABLE 11

11: Anti-HA-scFv amino acid sequences

| Construct | Amino acid sequence | SEQ ID NO |
|---|---|---|
| Anti-HA CDR H1 Kabat | NYDMA | 82 |
| Anti-HA CDR H2 Kabat | TISHDGRNTNYRD SVKG | 83 |
| Anti-HA CDR H3 Kabat | PGFAH | 84 |
| Anti-HA CDR L1 Kabat | RS SKTLLNTRGIT SLY | 85 |
| Anti-HA CDR L2 Kabat | RMSNLAS | 86 |
| Anti-HA CDR L3 Kabat | AQFLEFPLT | 87 |
| Anti-HA-scFv-<br>CD28ATD-<br>CD28CSD-<br>CD3zSSD fusion | EVQLVE SGGGLVQPGRSMKLSCAVSGFIFSNYDMA<br>WVRQAPKKCLEWVATISHDGRNTNYRDSVKGRFTG<br>SRDSAQSTLYLQMDSLRSEDTAIYFCAGPGFAHWGQ<br>GTLVTVSSGGGGSGGGGSGGGGSGGGGSDIVLTQAP<br>LSVSVSPGESASISCRSSKTLLNTRGITSLYWYLQKPG<br>KSPQLLIYRMSNLASGIPDRFSGSGSETHFTLQISKVE<br>TEDVGIYYCAQFLEFPLTFGCGTKLEIKGGGGSFWVL<br>VVVGGVLACYSLLVTVAFIIFWVRSKRSRLLHSDYM<br>NMTPRRPGPTRKHYQPYAPPRDFAAYRSRVKFSRSA<br>DAPAYQQGQNQLYNELNLGRREEYDVLDKRRGRDP<br>EMGGKPRRKNPQEGLYNELQKDKMAEAYSEIGMKG<br>ERRRGKGHDGLYQGLSTATKDTYDALHMQALPPR | 88 |
| Anti-HA-scFv | EVQLVESGGGLVQPGRSMKLSCAVSGFIFSNYDMA<br>WVRQAPKKCLEWVATISHDGRNTNYRDSVKGRFTG<br>SRDSAQSTLYLQMDSLRSEDTAIYFCAGPGFAHWGQ<br>GTLVTVSSGGGGSGGGGSGGGGSGGGGSDIVLTQAP<br>LSVSVSPGESASISCRSSKTLLNTRGITSLYWYLQKPG<br>KSPQLLIYRMSNLASGIPDRFSGSGSETHFTLQISKVE<br>TEDVGIYYCAQFLEFPLTFGCGTKLEIK | 89 |
| Anti-HA VH | EVQLVESGGGLVQPGRSMKLSCAVSGFIFSNYDMA<br>WVRQAPKKCLEWVATISHDGRNTNYRDSVKGRFTG<br>SRDSAQSTLYLQMDSLRSEDTAIYFCAGPGFAHWGQ<br>GTLVTVSS | 90 |

TABLE 11-continued

11: Anti-HA-scFv amino acid sequences

| Construct | Amino acid sequence | SEQ ID NO |
|---|---|---|
| Anti-HA VL | DIVLTQAPLSVSVSPGESASISCRSSKTLLNTRGIT-SLY WYLQKPGKSPQLLIYRMSNLASGIPDRFSGSGSETHF TLQISKVETEDVGIYYCAQFLEFPLTFGCGTKLEIK | 91 |

TABLE 12

12: Anti-myc-Fab amino acid sequences

| Construct | Protein Sequence | SEQ ID NO |
|---|---|---|
| Anti-myc CDR Kabat | H1 HYGMS | 92 |
| Anti-myc CDR Kabat | H2 TIGSRGTYTHYPDSVKG | 93 |
| Anti-myc CDR Kabat | H3 RSEFYYYGNTYYYSAMDY | 94 |
| Anti-myc CDR Kabat | L1 RASESVDNYGFSFMN | 95 |
| Anti-myc CDR Kabat | L2 AISNRGS | 96 |
| Anti-myc CDR Kabat | L3 QQTKEVPWT | 97 |
| Anti-myc-Fab-heavy chain-CD28ATD-CD28CSD-CD3zSSD fusion | EVHLVESGGDLVKPGGSLKLSCAASGFTFSHYGMSW VRQTPDKRLEWVATIGSRGTYTHYPDSVKGRFTISRD NDKNALYLQMNSLKSEDTAMYYCARRSEFYYYGNT YYYSAMDYWGQGASVTVSSAKTTPPSVYPLAPGSA AQTNSMVTLGCLVKGYFPEPVTVTWNSGSLSSGVHT FPAVLQSDLYTLSSSVTVPSSTWPSETVTCNVAHPAS STKVDKKIVPRDCGGGGSFWVLVVVGGVLACYSLL VTVAFIIFWVRSKRSRLLHSDYMNMTPRRPGPTRKH YQPYAPPRDFAAYRSRVKFSRSADAPAYQQGQNQL YNELNLGRREEYDVLDKRRGRDPEMGGKPRRKNPQ EGLYNELQKDKMAEAYSEIGMKGERRRGKGHDGLY QGLSTATKDTYDALHMQALPPR | 98 |
| Anti-myc-Fab heavy chain | EVHLVESGGDLVKPGGSLKLSCAASGFTFSHYGMSW VRQTPDKRLEWVATIGSRGTYTHYPDSVKGRFTISRD NDKNALYLQMNSLKSEDTAMYYCARRSEFYYYGNT YYYSAMDYWGQGASVTVSSAKTTPPSVYPLAPGSA AQTNSMVTLGCLVKGYFPEPVTVTWNSGSLSSGVHT FPAVLQSDLYTLSSSVTVPSSTWPSETVTCNVAHPAS STKVDKKIVPRDC | 99 |
| Anti-myc-Fab light chain | DIVLTQSPASLAVSLGQRATISCRASESVDNYGFSFM NWFQQKPGQPPKLLIYAISNRGSGVPARFSGSGSGTD FSLNIHPVEEDDPAMYFCQQTKEVPWTFGGGTKLEIK RADAAPTVSIFPPSSEQLTSGGASVVCFLNNFYPKDIN VKWKIDGSERQNGVLNSWTDQDSKDSTYSMSSTLTL TKDEYERHNSYTCEATHKTSTSPIVKSFNRNEC | 100 |
| Anti-myc VH | EVHLVESGGDLVKPGGSLKLSCAASGFTFSHYGMSW VRQTPDKRLEWVATIGSRGTYTHYPDSVKGRFTISRD NDKNALYLQMNSLKSEDTAMYYCARRSEFYYYGNT YYYSAMDYWGQGASVTVSS | 101 |
| Anti-myc VL | DIVLTQSPASLAVSLGQRATISCRASESVDNYGFSFM NWFQQKPGQPPKLLIYAISNRGSGVPARFSGSGSGTD FSLNIHPVEEDDPAMYFCQQTKEVPWTFGGGTKLEIK | 102 |

TABLE 13

13: Polypeptide tag sequences

| Construct | Amino acid sequence | SEQ ID NO |
|---|---|---|
| HA tag | YPYDVPDYA | 103 |
| Myc tag | EQKLISEEDL | 104 |
| GCN4 tag | YHLENEVARLKK | 105 |
| AviTag | GLNDIFEAQKIEWHE | 106 |

TABLE 14

| Construct | Amino acid sequence | SEQ ID NO |
|---|---|---|
| Human CD3z | MKWKALFTAAILQAQLPITEAQSFGLLDPKLCYLLDGI LFIYGVILTALFLRVKFSRSADAPAYQQGQNQLYNELN LGRREEYDVLDKRRGRDPEMGGKPQRRKNPQEGLYN ELQKDKMAEAYSEIGMKGERRRGKGHDGLYQGLSTA TKDTYDALHMQALPPR | 107 |
| Human CD3z | ATGAAGTGGAAGGCGCTTTTCACCGCGGCCATCCTG CAGGCACAGTTGCCGATTACAGAGGCACAGAGCTTT GGCCTGCTGGATCCCAAACTCTGCTACCTGCTGGAT GGAATCCTCTTCATCTATGGTGTCATTCTCACTGCCT TGTTCCTGAGAGTGAAGTTCAGCAGGAGCGCAGAG CCCCCCGCGTACCAGCAGGGCCAGAACCAGCTCTAT AACGAGCTCAATCTAGGACGAAGAGAGGAGTACGA TGTTTTGGACAAGAGACGTGGCCGGGACCCTGAGAT GGGGGGAAAGCCGAGAAGGAAGAACCCTCAGGAA GGCCTGTACAATGAACTGCAGAAAGATAAGATGGC GGAGGCCTACAGTGAGATTGGGATGAAAGGCGAGC GCCGGAGGGGCAAGGGGCACGATGGCCTTTACCAG GTCTCAGTACAGCCACCAAGGACACCTACGACGCC CTTCACATGCAGGCCCTGCCCCCTCGCTAA | 108 |
| Murine CD3z | MKWKVSVLACILHVRFPGAEAQSFGLLDPKLCYLLDG ILFIYGVIITALYLRAKFSRSAETAANLQDPNQLYNELN LGRREEYDVLEKKRARDPEMGGKQQRRRNPQEGVYN ALQKDKMAEAYSEIGTKGERRRGKGHDGLYQGLSTA TKDTYDALHMQTLAPR | 109 |
| Murine CD3z | ATGAAGTGGAAAGTGTCTGTTCTCGCCTGCATCCTC CACGTGCGGTTCCCAGGAGCAGAGGCACAGAGCTTT GGTCTGCTGGATCCCAAACTCTGCTACTTGCTAGAT GGAATCCTCTTCATCTACGGAGTCATCATCACAGCC CTGTACCTGAGAGCAAAATTCAGCAGGAGTGCAGA GACTGCTGCCAACCTGCAGGACCCCAACCAGCTCTA CAATGAGCTCAATCTAGGGCGAAGAGAGGAATATG ACGTCTTGGAGAAGAAGCGGGCTCGGGATCCAGAG ATGGGAGGCAAACAGCAGAGGAGGAGGAACCCCCA GGAAGGCGTATACAATGCACTGCAGAAAGACAAGA TGGCAGAAGCCTACAGTGAGATCGGCACAAAGGC GAGAGGCGGAGAGGCAAGGGGCACGATGGCCTTTA CCAGGGTCTCAGCACTGCCACCAAGGACACCTATGA TGCCCTGCATATGCAGACCCTGGCCCCTCGCTAA | 110 |
| Human CD28 | ATGCTGCGCCTGCTGCTGGCGCTGAACCTGTTTCCG AGCATTCAGGTGACCGGCAACAAAATTCTGGTGAA ACAGAGCCCGATGCTGGTGGCGTATGATAACGCGGT GAACCTGAGCTGCAAATATAGCTATAACCTGTTTAG CCGCGAATTTCGCGCGAGCCTGCATAAAGGCCTGGA TAGCGCGGTGGAAGTGTGCGTGGTGTATGGCAACTA TAGCCAGCAGCTGCAGGTGTATAGCAAAACCGGCTT TAACTGCGATGGCAAACTGGGCAACGAAAGCGTGA CCTTTTATCTGCAGAACCTGTATGTGAACCAGACCG ATATTTATTTTTGCAAAATTGAAGTGATGTATCCGCC GCCGTATCTGGATAACGAAAAAAGCAACGGCACCA TTATTCATGTGAAAGGCAAACATCTGTGCCCCGAGCC CGCTGTTTCCGGGCCCGAGCAAACCGTTTTGGGTGC TGGTGGTGGTGGGCGGCGTGCTGGCGTGCTATAGCC TGCTGGTGACCGTGGCGTTTATTATTTTTTGGGTGCG CAGCAAACGCAGCCGCCTGCTGCATAGCGATTATAT GAACATGACCCCGCGCCGCCCGGGCCCGACCCGCA AACATTATCAGCCGTATGCGCCGCCGCGCGATTTTG CGGCGTATCGCAGC | 111 |

TABLE 14-continued

| Construct | Amino acid sequence | SEQ ID NO |
|---|---|---|
| Human CD28 | MLRLLLALNLFPSIQVTGNKILVKQSPMLVAYDNAVN LSCKYSYNLFSREFRASLHKGLDSAVEVCVVYGNYSQ QLQVYSKTGFNCDGKLGNESVTFYLQNLYVNQTDIYF CKIEVMYPPPYLDNEKSNGTIIHVKGKHLCPSPLFPGPS KPFWVLVVVGGVLACYSLLVTVAFIIFWVRSKRSRLL HSDYMNMTPRRPGPTRKHYQPYAPPRDFAAYRS | 112 |
| Murine CD28 | ATGACCCTGCGCCTGCTGTTTCTGGCGCTGAACTTTT TTAGCGTGCAGGTGACCGAAAACAAAATTCTGGTGA AACAGAGCCCGCTGCTGGTGGTGGATAGCAACGAA GTGAGCCTGAGCTGCCGCTATAGCTATAACCTGCTG GCGAAAGAATTTCGCGCGAGCCTGTATAAAGGCGT GAACAGCGATGTGGAAGTGTGCGTGGGCAACGGCA ACTTTACCTATCAGCCGCAGTTTCGCAGCAACGCGG AATTTAACTGCGATGGCGATTTTGATAACGAAACCG TGACCTTTCGCCTGTGGAACCTGCATGTGAACCATA CCGATATTTATTTTTGCAAAATTGAATTTATGTATCC GCCGCCGTATCTGGATAACGAACGCAGCAACGGCA CCATTATTCATATTAAAGAAAAACATCTGTGCCATA CCCAGAGCAGCCCGAAACTGTTTTGGGCGCTGGTGG TGGTGGCGGGCGTGCTGTTTTGCTATGGCCTGCTGG TGACCGTGGCGCTGTGCGTGATTTGGACCAACAGCC GCCGCAACCGCCTGCTGCAGAGCGATTATATGAACA TGACCCCGCGCCGCCCGGGCCTGACCCGCAAACCGT ATCAGCCGTATGCGCCGGCGCGCGATTTTGCGGCGT ATCGCCCG | 113 |
| Murine CD28 | MTLRLLFLALNFFSVQVTENKILVKQSPLLVVDSNEVS LSCRYSYNLLAKEFRASLYKGVNSDVEVCVGNGNFTY QPQFRSNAEFNCDGDFDNETVTFRLWNLHVNHTDIYF CKIEFMYPPPYLDNERSNGTIIHIKEKHLCHTQSSPKLF WALVVVAGVLFCYGLLVTVALCVIWTNSRRNRLLQS DYMNMTPRRPGLTRKPYQPYAPARDFAAYRP | 114 |
| CD28 YMNM | YMNM | 115 |
| CD28 PYAP | PYAP | 116 |
| Signal peptide | ATGGGATGGAGCTGTATCATCCTCTTCTTGGTAGCA | 117 |
| Signal peptide DNA sequence | ATGGGATGGAGCTGTATCATCCTCTTCTTGGTAGCA ACAGCTACCGGTGTGCACTCC | 118 |
| Anti-CD20 (GA101) PGLALA heavy chain | QVQLVQSGAEVKKPGSSVKVSCKASGYAFSYSWINW VRQAPGQGLEWMGRIFPGDGDTDYNGKFKGRVTITA DKSTSTAYMELSSLRSEDTAVYYCARNVFDGYWLVY WGQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPKS CDKTHTCPPCPAPEAAGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALG APIEKTISKAKGQPREPQVYTLPPSRDELTKNQVSLTCL VKGFYPSDIAVEWESNGQPENNYKTTPPVLDSDGSFFL YSKLTVDKSRWQQGNVFSCSVMHEALHNHYTQKSLS LSPGK | 119 |
| Anti-CD20 (GA101) light chain | DIVMTQTPLSLPVTPGEPASISCRSSKSLLHSNGITYLY WYLQKPGQSPQLLIYQMSNLVSGVPDRFSGSGSGTDF TLKISRVEAEDVGVYYCAQNLELPYTFGGGTKVEIKRT VAAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC | 120 |
| Anti-CEA (CH1A1A98/992F1) PGLALA heavy chain | QVQLVQSGAEVKKPGASVKVSCKASGYTFTEFGMNW VRQAPGQGLEWMGWINTKTGEATYVEEFKGRVTFTT DTSTSTAYMELRSLRSDDTAVYYCARWDFAYYVEAM DYWGQGTTVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVEP KSCDKTHTCPPCPAPEAAGGPSVFLFPPKPKDTLMISRT PEVTCVVVDVSHEDPEVKFNWYVDGVEVHNAKTKPR EEQYNSTYRVVSVLTVLHQDWLNGKEYKCKVSNKAL GAPIEKTISKAKGQPREPQVCTLPPSRDELTKNQVSLSC AVKGFYPSDIAVEWESNGQPENNYKTTPPVLDSDGSFF | 121 |

TABLE 14-continued

| Construct | Amino acid sequence | SEQ ID NO |
|---|---|---|
| | LVSKLTVDKSRWQQGNVFSCSVMHEALHNHYTQKSL SLSPGK | |
| Anti-CEA (CH1A1A98/992F1) light chain | DIQMTQSPSSLSASVGDRVTITCKASAAVGTYVAWYQ QKPGKAPKLLIYSASYRKRGVPSRFSGSGSGTDFTLTIS SLQPEDFATYYCHQYYTYPLFTFGQGTKLEIKRTVAAP SVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 122 |
| Human IgG1 Fc | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCP APELLGGPSVFLFPPKPKDTLMISRTPEVTCVVVDVSH EDPEVKFNWYVDGVEVHNAKTKPREEQYNSTYRVVS VLTVLHQDWLNGKEYKCKVSNKALPAPIEKTISKAKG QPREPQVYTLPPSRDELTKNQVSLTCLVKGFYPSDIAV EWESNGQPENNYKTTPPVLDSDGSFFLYSKLTVDKSR WQQGNVFSCSVMHEALHNHYTQKSLSLSPGK | 123 |
| Anti-WT1 (33F05) PGLALA heavy chain | QVQLQESGPGLVKPSETLSLTCTVSGGSINSYYWSWIR QPPGKGLEWIGYIYYSGSTNYNPSLKSRVTISVDTSKN QFSLKLSSVTAADTAVYYCARSYYEAFDYWGQGTLV TVSSSLGTQTYICNVNHKPSNTKVDKKVEPKSCDKTH TCPPCPAPEAAGGPSVFLFPPKPKDTLMISRTPEVTCVV VDVSHEDPEVKFNWYVDGVEVHNAKTKPREEQYNST YRVVSVLTVLHQDWLNGKEYKCKVSNKALGAPIEKTI SKAKGQPREPQVCTLPPSRDELTKNQVSLSCAVKGFYP SDIAVEWESNGQPENNYKTTPPVLDSDGSFFLVSKLTV DKSRWQQGNVFSCSVMHEALHNHYTQKSLSLSPGK | 124 |
| Anti-WT1 (33F05) light chain | SSELTQDPAVSVALGQTVRITCQGDSLRSYYASWYQQ KPGQAPVLVIYGKNNRPSGIPDRFSGSSSGNTASLTITG AQAEDEADYYCNSPDMNGNAVFGGGTKLTVLRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 125 |
| Anti-WT1 (11D06) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARSIELWWGGFDYWG QGTTVTVSSSLGTQTYICNVNHKPSNTKVDKKVEPKS CDKTHTCPPCPAPEAAGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALG APIEKTISKAKGQPREPQVCTLPPSRDELTKNQVSLSCA VKGFYPSDIAVEWESNGQPENNYKTTPPVLDSDGSFFL VSKLTVDKSRWQQGNVFSCSVMHEALHNHYTQKSLS LSPGK | 126 |
| Anti-WT1 (11D06) light chain | DIQMTQSPSTLSASVGDRVTITCRASQSISSWLAWYQQ KPGKAPKLLIYDASSLESGVPSRFSGSGSGTEFTLTIGSL QPDDFATYYCQQYEDYTTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKV YACEVTHQGLSSPVTKSFNRGEC | 127 |
| Anti-WT1 (33H09) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARGSYDLFSLDYWGQG TTVTVSSSLGTQTYICNVNHKPSNTKVDKKVEPKSCD KTHTCPPCPAPEAAGGPSVFLFPPKPKDTLMISRTPEVT CVVVDVSHEDPEVKFNWYVDGVEVHNAKTKPREEQY NSTYRVVSVLTVLHQDWLNGKEYKCKVSNKALGAPI EKTISKAKGQPREPQVCTLPPSRDELTKNQVSLSCAVK GFYPSDIAVEWESNGQPENNYKTTPPVLDSDGSFFLVS KLTVDKSRWQQGNVFSCSVMHEALHNHYTQKSLSLS PGK | 128 |
| Anti-WT1 (33H09) light chain | DIQMTQSPSTLSASVGDRVTITCRASQSISSWLAWYQQ KPGKAPKLLIYDASSLESGVPSRFSGSGSGTEFTLTISSL QPDDFATYYCQQYYDGITFGQGTKVEIKRTVAAPSVFI FPP SDEQLKSGTASVVCLLNNFYPREAKVQWKVDNAL QSGNSQESVTEQDSKDSTYSLSSTLTLSKADYEKHKV YACEVTHQGLSSPVTKSFNRGEC | 129 |

TABLE 14-continued

| Construct | Amino acid sequence | SEQ ID NO |
|---|---|---|
| Anti-WT1 (5E11) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARSSYDLYSFDYWGQG TTVTVSSSLGTQTYICNVNHKPSNTKVDKKVEPKSCD KTHTCPPCPAPEAAGGPSVFLFPPKPKDTLMISRTPEVT CVVVDVSHEDPEVKFNWYVDGVEVHNAKTKPREEQY NSTYRVVSVLTVLHQDWLNGKEYKCKVSNKALGAPI EKTISKAKGQPREPQVCTLPPSRDELTKNQVSLSCAVK GFYPSDIAVEWESNGQPENNYKTTPPVLDSDGSFFLVS KLTVDKSRWQQGNVFSCSVMHEALHNHYTQKSLSLS PGK | 130 |
| Anti-WT1 (5E11) light chain | DIQMTQSPSTLSASVGDRVTITCRASQSISSWLAWYQQ KPGKAPKLLIYDASSLESGVPSRFSGSGSGTEFTLTISSL QPDDFATYYCQQYSFPPMITFGQGTKVEIKRTVAAPSV FIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC | 131 |
| Human IgG1 Fc | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GK | 132 |

The invention claimed is:

1. A diagnostic assay for determining the presence of a tumor cell in a sample, the diagnostic assay comprising the steps of:
   a) contacting the sample with an antigen binding molecule comprising an antigen binding domain and a recognition domain, wherein the antigen binding domain comprises a target antigen binding moiety capable of specific binding to the tumor cell;
   b) contacting the sample with a chimeric antigen receptor (CAR) expressing reporter T (CAR-T) cell wherein the reporter CAR-T cell comprises:
      i. a CAR capable of specific binding to the recognition domain, wherein the CAR is operationally coupled to a response element;
      ii. a reporter gene under the control of the response element; and
   c) determining T cell activation by measuring the expression of the reporter gene to establish the presence of the tumor cell
      wherein the antigen binding domain is a Fab fragment and the recognition domain is an Fc domain, wherein the antigen binding molecule is an IgG class antibody, and wherein the mutant Fc domain comprises an amino acid substitution at the position of residue 212 of human IgG1 Fc (SEQ ID NO:132).

2. The diagnostic assay of claim 1, wherein the recognition domain is a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.

3. The diagnostic assay of claim 2, wherein the mutant Fc domain comprises an amino acid substitution at a position selected from the group consisting of residue 117, 118, 136, 180, 193, 212, 214, and 318 of human IgG1 Fc (SEQ ID NO:132).

4. The diagnostic assay of claim 1, wherein the recognition domain comprises a tag, wherein the CAR is capable of specific binding to the recognition domain comprising the tag but not capable of specific binding to the recognition domain not comprising the tag.

5. The diagnostic assay of claim 4, wherein the tag is a hapten molecule.

6. The diagnostic assay of claim 4, wherein the tag is a polypeptide tag.

7. The diagnostic assay of claim 1, wherein the CAR comprises at least one intracellular stimulatory signaling and/or co-stimulatory signaling domain.

8. The diagnostic assay of claim 7, wherein activation of the intracellular stimulatory signaling and/or co-stimulatory signaling domain leads to activation of the response element.

9. The diagnostic assay of claim 1, wherein activation of the response element leads to expression of the reporter gene.

10. The diagnostic assay of claim 1, wherein the sample is a patient sample derived from an individual suffering from a disease.

11. A diagnostic kit for determining the presence of a tumor cell in a sample, the diagnostic kit comprising:
  (a) an antigen binding molecule capable of specific binding to a tumor cell, wherein the antigen binding molecule comprises a mutated Fc domain, wherein the mutated Fc domain comprises at least one amino acid substitution compared to the non-mutated parent Fc domain; and
  (b) a transduced T cell comprising (i) a CAR capable of specific binding to the antigen binding molecule, wherein the CAR is capable of specific binding to the mutated Fc domain but not capable of specific binding to the non-mutated parent Fc domain and (ii) a reporter gene under the control of the response element, wherein the CAR is operationally coupled to a response element.

12. A diagnostic kit for determining the presence of a tumor cell in a sample, the diagnostic kit comprising:
  (a) an antigen binding molecule capable of specific binding to a tumor cell, wherein the antigen binding molecule comprises a tag; and
  (b) a transduced T cell comprising (i) a CAR capable of specific binding to the antigen binding molecule, wherein the CAR is capable of specific binding to the antigen binding molecule comprising the tag but not capable of specific binding to the antigen binding molecule not comprising the tag, and
  (ii) a reporter gene under the control of the response element, wherein the CAR is operationally coupled to a response element.

13. The diagnostic assay of claim 1, wherein the IgG class antibody is an IgG1 or IgG4 isotype antibody.

14. The diagnostic assay of claim 3, wherein the mutant Fc domain comprises the amino acid substitution leucine to alanine at residue 117, leucine to alanine at residue 118, isoleucine to alanine at position 136, asparagine to alanine at residue 180, histidine to alanine at residue 193, proline to glycine at residue 212, proline to glycine at residue 214, and/or or histidine to alanine at residue 318 of human IgG1 Fc (SEQ ID NO:132).

15. The diagnostic assay of claim 2, wherein the mutant Fc domain comprises the amino acid substitution proline to glycine at residue 212 of human IgG1 Fc (SEQ ID NO:132).

16. The diagnostic assay of claim 5, wherein the hapten molecule is selected from the group consisting of Biotin, Digoxigenin (DIG) and Fluorescein (FITC).

17. The diagnostic assay of claim 6, wherein the polypeptide tag is selected from the group consisting of myc-tag, HA-tag, AviTag, FLAG-tag, His-tag, GCN4-tag, and NE-tag.

18. The diagnostic assay of claim 10, wherein the disease is cancer.

* * * * *

SEQUENCE LISTING

<160> NUMBER OF SEQ ID NOS: 132

<210> SEQ ID NO 1
<211> LENGTH: 5
<212> TYPE: PRT
<213> ORGANISM: Artificial sequence
<220> FEATURE:
<223> OTHER INFORMATION: Anti-P329G CDR H1 Kabat

<400> SEQUENCE: 1

Arg Tyr Trp Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: Anti-P329G CDR H2

<400> SEQUENCE: 2

Glu Ile Thr Pro Asp Ser Ser Thr Ile Asn Tyr Thr Pro Ser Leu Lys
1               5                   10                  15

Asp

<210> SEQ ID NO 3
<211> LENGTH: 10
<212> TYPE: PRT
<213> ORGANISM: Artificial sequence
<220> FEATURE:
<223> OTHER INFORMATION: Anti-P329G CDR H3 Kabat

<400> SEQUENCE: 3

```
Pro Tyr Asp Tyr Gly Ala Trp Phe Ala Ser
1               5                   10

<210> SEQ ID NO 4
<211> LENGTH: 14
<212> TYPE: PRT
<213> ORGANISM: Artificial sequence
<220> FEATURE:
<223> OTHER INFORMATION: Anti-P329G CDR L1 Kabat

<400> SEQUENCE: 4

Arg Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Artificial sequence
<220> FEATURE:
<223> OTHER INFORMATION: Anti-P329G CDR L2 Kabat

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Artificial sequence
<220> FEATURE:
<223> OTHER INFORMATION: Anti-P329G CDR L3 Kabat

<400> SEQUENCE: 6

Ala Leu Trp Tyr Ser Asn His Trp Val
1               5

<210> SEQ ID NO 7
<211> LENGTH: 433
<212> TYPE: PRT
<213> ORGANISM: Artificial sequence
<220> FEATURE:
<223> OTHER INFORMATION: Anti-P329G-ds-scFv-CD28ATD-CD28CSD-CD3zSSD
      fusion

<400> SEQUENCE: 7

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
                100                 105                 110

Thr Leu Val Thr Val Ser Ala Gly Gly Gly Gly Ser Gly Gly Gly Gly
            115                 120                 125

Ser Gly Gly Gly Gly Ser Gly Gly Gly Gly Ser Gln Ala Val Val Thr
```

```
                130             135             140
Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Cys Gly Thr Lys Leu Thr Val Leu Gly Gly Gly Ser Phe Trp Val
                245                 250                 255

Leu Val Val Val Gly Val Leu Ala Cys Tyr Ser Leu Leu Val Thr
                260                 265                 270

Val Ala Phe Ile Ile Phe Trp Val Arg Ser Lys Arg Ser Arg Leu Leu
    275                 280                 285

His Ser Asp Tyr Met Asn Met Thr Pro Arg Arg Pro Gly Pro Thr Arg
290                 295                 300

Lys His Tyr Gln Pro Tyr Ala Pro Pro Arg Asp Phe Ala Ala Tyr Arg
305                 310                 315                 320

Ser Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
                340                 345                 350

Tyr Asp Val Leu Asp Lys Arg Arg Gly Arg Asp Pro Glu Met Gly Gly
                355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
                420                 425                 430

Arg

<210> SEQ ID NO 8
<211> LENGTH: 119
<212> TYPE: PRT
<213> ORGANISM: Artificial sequence
<220> FEATURE:
<223> OTHER INFORMATION: Anti-P329G-ds VH

<400> SEQUENCE: 8

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60
```

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala
        115

<210> SEQ ID NO 9
<211> LENGTH: 109
<212> TYPE: PRT
<213> ORGANISM: Artificial sequence
<220> FEATURE:
<223> OTHER INFORMATION: Anti-P329G-ds VL

<400> SEQUENCE: 9

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Cys Gly Thr Lys Leu Thr Val Leu
            100                 105

<210> SEQ ID NO 10
<211> LENGTH: 248
<212> TYPE: PRT
<213> ORGANISM: Artificial sequence
<220> FEATURE:
<223> OTHER INFORMATION: Anti-P329G-ds-scFv

<400> SEQUENCE: 10

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Gly Gly Gly Gly Ser Gly Gly Gly Gly
            115                 120                 125

Ser Gly Gly Gly Gly Ser Gly Gly Gly Gly Ser Gln Ala Val Val Thr

```
                130                 135                 140
Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Cys Gly Thr Lys Leu Thr Val Leu
                245

<210> SEQ ID NO 11
<211> LENGTH: 27
<212> TYPE: PRT
<213> ORGANISM: Artificial sequence
<220> FEATURE:
<223> OTHER INFORMATION: CD28ATD

<400> SEQUENCE: 11

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 12
<211> LENGTH: 41
<212> TYPE: PRT
<213> ORGANISM: Artificial sequence
<220> FEATURE:
<223> OTHER INFORMATION: CD28CSD

<400> SEQUENCE: 12

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 13
<211> LENGTH: 112
<212> TYPE: PRT
<213> ORGANISM: Artificial sequence
<220> FEATURE:
<223> OTHER INFORMATION: CD3zSSD

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60
```

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
                100                 105                 110

<210> SEQ ID NO 14
<211> LENGTH: 180
<212> TYPE: PRT
<213> ORGANISM: Artificial sequence
<220> FEATURE:
<223> OTHER INFORMATION: CD28ATD-CD28CSD-CD3zSSD

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
    130                 135                 140

Lys Gly Glu Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180

<210> SEQ ID NO 15
<211> LENGTH: 238
<212> TYPE: PRT
<213> ORGANISM: Artificial sequence
<220> FEATURE:
<223> OTHER INFORMATION: eGFP

<400> SEQUENCE: 15

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln

```
                65                  70                  75                  80
His Asp Phe Phe Lys Ser Ala Met Pro Glu Gly Tyr Val Gln Glu Arg
                    85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 16
<211> LENGTH: 20
<212> TYPE: PRT
<213> ORGANISM: Artificial sequence
<220> FEATURE:
<223> OTHER INFORMATION: (G4S)4 linker

<400> SEQUENCE: 16

Gly Gly Gly Gly Ser Gly Gly Gly Gly Ser Gly Gly Gly Gly Ser Gly
1               5                   10                  15

Gly Gly Gly Ser
            20

<210> SEQ ID NO 17
<211> LENGTH: 5
<212> TYPE: PRT
<213> ORGANISM: Artificial sequence
<220> FEATURE:
<223> OTHER INFORMATION: G4S linker

<400> SEQUENCE: 17

Gly Gly Gly Gly Ser
1               5

<210> SEQ ID NO 18
<211> LENGTH: 19
<212> TYPE: PRT
<213> ORGANISM: Artificial sequence
<220> FEATURE:
<223> OTHER INFORMATION: T2A linker

<400> SEQUENCE: 18

Gly Glu Gly Arg Gly Ser Leu Leu Thr Cys Gly Asp Val Glu Glu Asn
1               5                   10                  15

Pro Gly Pro

<210> SEQ ID NO 19
<211> LENGTH: 1356
```

```
<212> TYPE: DNA
<213> ORGANISM: Artificial sequence
<220> FEATURE:
<223> OTHER INFORMATION: Anti-P329G-ds-scFv-CD28ATD-CD28CSD-CD3zSSD
      fusion

<400> SEQUENCE: 19
atgggatgga gctgtatcat cctcttcttg gtagcaacag ctaccggtgt gcattccgag      60
gtgaagctgc tggagagcgg cggcggcctg gtgcagcccg gcggcagcct gaagctgagc     120
tgcgccgcca gcggcttcga cttcagcagg tactggatga actgggtgag gcaggccccc     180
ggcaagtgtc tggagtggat cggcgagatc accccgaca gcagcaccat caactacacc      240
cccagcctga aggacaagtt catcatcagc agggacaacg ccaagaacac cctgtacctg     300
cagatgatca aggtgaggag cgaggacacc gccctgtact actgcgtgag gccctacgac     360
tacggcgcct ggttcgccag ctggggccag ggcaccctgg tgaccgtgag cgccggaggg     420
ggcggaagtg gtggcggggg aagcggcggg ggtggcagcg aggggggcgg atctcaggcc     480
gtggtgaccc aggagagcgc cctgaccacc agccccggcg agaccgtgac cctgacctgc     540
aggagcagca ccggcgccgt gaccaccagc aactacgcca actgggtgca ggagaagccc     600
gaccacctgt tcaccggcct gatcggcggc accaacaaga gggcccccgg cgtgcccgcc     660
aggttcagcg gcagcctgat cggcgacaag gccgccctga ccatcaccgg cgcccagacc     720
gaggacgagg ccatctactt ctgcgccctg tggtacagca ccactgggt gttcggctgt      780
ggcaccaagc tgaccgtgct ggggggggc ggatccttct gggtgctggt ggtggtgggc      840
ggcgtgctgg cctgctacag cctgctggtg accgtggcct tcatcatctt ctgggtgagg     900
agcaagagga gcaggctgct gcacagcgac tacatgaaca tgacccccag gaggcccggc     960
cccaccagga gcactacca gcctacgcc cccccaggg acttcgccgc ctacaggagc        1020
agggtgaagt tcagcaggag cgccgacgcc cccgcctacc agcagggcca gaaccagctg     1080
tataacgagc tgaacctggg caggaggagg agtacgacg tgctggacaa gaggaggggc      1140
agggaccccg agatgggcgg caagcccagg aggaagaacc cccaggaggg cctgtataac     1200
gagctgcaga aggacaagat ggccgaggcc tacagcgaga tcggcatgaa gggcgagagg     1260
aggaggggca agggccacga cggcctgtac cagggcctga gcaccgccac caaggacacc     1320
tacgacgccc tgcacatgca ggccctgccc cccagg                               1356

<210> SEQ ID NO 20
<211> LENGTH: 357
<212> TYPE: DNA
<213> ORGANISM: Artificial sequence
<220> FEATURE:
<223> OTHER INFORMATION: Anti-P329G-ds VH

<400> SEQUENCE: 20
gaggtgaagc tgctggagag cggcggcggc ctggtgcagc ccggcggcag cctgaagctg      60
agctgcgccg ccagcggctt cgacttcagc aggtactgga tgaactgggt gaggcaggcc     120
cccggcaagt gtctggagtg gatcggcgag atcaccccg acagcagcac catcaactac       180
accccagcc tgaaggacaa gttcatcatc agcaggga cgccaagaa caccctgtac          240
ctgcagatga tcaaggtgag gagcgaggac accgccctgt actactgcgt gaggccctac     300
gactacggcg cctggttcgc cagctggggc cagggcaccc tggtgaccgt gagcgcc        357

<210> SEQ ID NO 21
<211> LENGTH: 327
```

```
<212> TYPE: DNA
<213> ORGANISM: Artificial sequence
<220> FEATURE:
<223> OTHER INFORMATION: Anti-P329G-ds VL

<400> SEQUENCE: 21
caggccgtgg tgacccagga gagcgccctg accaccagcc ccggcgagac cgtgaccctg    60
acctgcagga gcagcaccgg cgccgtgacc accagcaact acgccaactg ggtgcaggag   120
aagcccgacc acctgttcac cggcctgatc ggcggcacca acaagagggc ccccggcgtg   180
cccgccaggt tcagcggcag cctgatcggc gacaaggccg ccctgaccat caccggcgcc   240
cagaccgagg acgaggccat ctacttctgc gccctgtggt acagcaacca ctgggtgttc   300
ggctgtggca ccaagctgac cgtgctg                                       327

<210> SEQ ID NO 22
<211> LENGTH: 801
<212> TYPE: DNA
<213> ORGANISM: Artificial sequence
<220> FEATURE:
<223> OTHER INFORMATION: Anti-P329G-ds-scFv

<400> SEQUENCE: 22
atgggatgga gctgtatcat cctcttcttg gtagcaacag ctaccggtgt gcattccgag    60
gtgaagctgc tggagagcgg cggcggcctg gtgcagcccg gcggcagcct gaagctgagc   120
tgcgccgcca gcggcttcga cttcagcagg tactggatga ctgggtgag gcaggccccc   180 ggcaagtgtc tggagtggat cggcgagatc accccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag gccctacgac   360
tacggcgcct ggttcgccag ctggggccag ggcaccctgg tgaccgtgag cgccggaggg   420
ggcggaagtg gtggcggggg aagcggcggg ggtggcagcg gaggggcgg atctcaggcc   480 gtggtgaccc aggagagcgc cctgaccacc agccccggcg agaccgtgac cctgacctgc   540
aggagcagca ccggcgccgt gaccaccagc aactacgcca actgggtgca ggagaagccc   600
gaccacctgt tcaccggcct gatcggcggc accaacaaga gggcccccgg cgtgcccgcc   660
aggttcagcg gcagcctgat cggcgacaag gccgccctga ccatcaccgg cgcccagacc   720
gaggacgagg ccatctactt ctgcgccctg tggtacagca accactgggt gttcggctgt   780
ggcaccaagc tgaccgtgct g                                             801

<210> SEQ ID NO 23
<211> LENGTH: 81
<212> TYPE: DNA
<213> ORGANISM: Artificial sequence
<220> FEATURE:
<223> OTHER INFORMATION: CD28ATD

<400> SEQUENCE: 23
ttctgggtgc tggtggtggt gggcggcgtg ctggcctgct acagcctgct ggtgaccgtg    60
gccttcatca tcttctgggt g                                              81

<210> SEQ ID NO 24
<211> LENGTH: 123
<212> TYPE: DNA
<213> ORGANISM: Artificial sequence
<220> FEATURE:
<223> OTHER INFORMATION: CD28CSD
```

```
<400> SEQUENCE: 24
aggagcaaga ggagcaggct gctgcacagc gactacatga acatgacccc caggaggccc    60
ggccccacca ggaagcacta ccagccctac gccccccca gggacttcgc cgcctacagg   120
agc                                                                 123

<210> SEQ ID NO 25
<211> LENGTH: 336
<212> TYPE: DNA
<213> ORGANISM: Artificial sequence
<220> FEATURE:
<223> OTHER INFORMATION: CD3zSSD

<400> SEQUENCE: 25
agggtgaagt tcagcaggag cgccgacgcc cccgcctacc agcagggcca gaaccagctg    60
tataacgagc tgaacctggg caggagggag gagtacgacg tgctggacaa gaggagggc   120 agggaccccg agatgggcgg caagcccagg aggaagaacc cccaggaggg cctgtataac   180
gagctgcaga aggacaagat ggccgaggcc tacagcgaga tcggcatgaa gggcgagagg   240
aggaggggca agggccacga cggcctgtac cagggcctga gcaccgccac caaggacacc   300
tacgacgccc tgcacatgca ggccctgccc cccagg                             336

<210> SEQ ID NO 26
<211> LENGTH: 540
<212> TYPE: DNA
<213> ORGANISM: Artificial sequence
<220> FEATURE:
<223> OTHER INFORMATION: CD28ATD-CD28CSD-CD3zSSD

<400> SEQUENCE: 26
ttctgggtgc tggtggtggt gggcggcgtg ctggcctgct acagcctgct ggtgaccgtg    60
gccttcatca tcttctgggt gaggagcaag aggagcaggc tgctgcacag cgactacatg   120
aacatgaccc ccaggaggcc cggccccacc aggaagcact accagcccta cgccccccc   180 agggacttcg ccgcctacag gagcagggtg aagttcagca ggagcgccga cgcccccgcc   240
taccagcagg gccagaacca gctgtataac gagctgaacc tgggcaggag ggaggagtac   300
gacgtgctgg acaagaggag gggcagggac cccgagatgg gcggcaagcc caggaggaag   360 aaccccccagg agggcctgta taacgagctg cagaaggaca agatggccga ggcctacagc   420
gagatcggca tgaagggcga ggaggaggag ggcaagggcc acgacggcct gtaccagggc   480
ctgagcaccg ccaccaagga cacctacgac gccctgcaca tgcaggccct gccccccagg   540

<210> SEQ ID NO 27
<211> LENGTH: 63
<212> TYPE: DNA
<213> ORGANISM: Artificial sequence
<220> FEATURE:
<223> OTHER INFORMATION: T2A element

<400> SEQUENCE: 27
tccggagagg gcagaggaag tcttctaaca tgcggtgacg tggaggagaa tcccggccct    60
agg                                                                  63

<210> SEQ ID NO 28
<211> LENGTH: 717
<212> TYPE: DNA
<213> ORGANISM: Artificial sequence
<220> FEATURE:
<223> OTHER INFORMATION: eGFP
```

<400> SEQUENCE: 28

```
gtgagcaagg gcgaggagct gttcaccggg gtggtgccca tcctggtcga gctggacggc        60
gacgtaaacg gccacaagtt cagcgtgtcc ggcgagggcg agggcgatgc cacctacggc       120
aagctgaccc tgaagttcat ctgcaccacc ggcaagctgc ccgtgccctg cccaccctc        180
gtgaccaccc tgacctacgg cgtgcagtgc ttcagccgct accccgacca catgaagcag       240
cacgacttct tcaagtccgc catgcccgaa ggctacgtcc aggagcgcac catcttcttc       300
aaggacgacg gcaactacaa gacccgcgcc gaggtgaagt tcgagggcga caccctggtg       360
aaccgcatcg agctgaaggg catcgacttc aaggaggacg gcaacatcct ggggcacaag       420
ctggagtaca actacaacag ccacaacgtc tatatcatgg ccgacaagca gaagaacggc       480
atcaaggtga acttcaagat ccgccacaac atcgaggacg gcagcgtgca gctcgccgac       540
cactaccagc agaacacccc catcggcgac ggccccgtgc tgctgcccga caaccactac       600
ctgagcaccc agtccgccct gagcaaagac cccaacgaga gcgcgatca  catggtcctg       660
ctggagttcg tgaccgccgc cgggatcact ctcggcatgg acgagctgta caagtga         717
```

<210> SEQ ID NO 29
<211> LENGTH: 2136
<212> TYPE: DNA
<213> ORGANISM: Artificial sequence
<220> FEATURE:
<223> OTHER INFORMATION: Anti-P329G-ds-scFv-CD28ATD-CD28CSD-CD3zSSD-eGFP
       fusion

<400> SEQUENCE: 29

```
atgggatgga gctgtatcat cctcttcttg gtagcaacag ctaccggtgt gcattccgag        60
gtgaagctgc tggagagcgg cggcggcctg gtgcagcccg gcggcagcct gaagctgagc       120
tgcgccgcca gcggcttcga cttcagcagg tactggatga actgggtgag caggcccccc       180
ggcaagtgtc tggagtggat cggcgagatc accccccgaca gcagcaccat caactacacc       240
cccagcctga aggacaagtt catcatcagc agggacaacg ccaagaacac cctgtacctg       300
cagatgatca aggtgaggag cgaggacacc gccctgtact actgcgtgag gccctacgac       360
tacggcgcct ggttcgccag ctggggccag ggcaccctgg tgaccgtgag cgccggaggg       420
ggcggaagtg gtggcggggg aagcggcggg ggtggcagcg gagggggcgg atctcaggcc       480
gtggtgaccc aggagagcgc cctgaccacc agccccggcg agaccgtgac cctgacctgc       540
aggagcagca ccggcgccgt gaccaccagc aactacgcca actgggtgca ggagaagccc       600
gaccacctgt tcaccggcct gatcggcggc accaacaaga gggcccccgg cgtgccccgcc      660
aggttcagcg gcagcctgat cggcgacaag gccgccctga ccatcaccgg cgcccagacc       720
gaggacgagg ccatctactt ctgcgccctg tggtacagca ccactgggt gttcggctgt        780
ggcaccaagc tgaccgtgct ggagggggc ggatccttct gggtgctggt ggtggtgggc        840
ggcgtgctgg cctgctacag cctgctggtg accgtggcct tcatcatctt ctgggtgagg       900
agcaagagga gcaggctgct gcacagcgac tacatgaaca tgaccccag gaggccggc         960
cccaccagga gcactaccag gcctacgcc ccccaggg acttcgccgc ctacaggagc        1020
agggtgaagt tcagcaggag cgccgacgcc cccgcctacc agcagggcca gaaccagctg      1080
tataacgagc tgaacctggg caggagggag gagtacgacg tgctggacaa gaggagggc       1140
agggacccccg atgggcggg caagcccagg aggaagaacc cccaggaggg cctgtataac       1200
gagctgcaga aggacaagat ggccgaggcc tacagcgaga tcggcatgaa gggcgagagg      1260
```

-continued

```
aggagggca agggccacga cggcctgtac cagggcctga gcaccgccac caaggacacc      1320
tacgacgccc tgcacatgca ggccctgccc cccaggtccg gagagggcag aggaagtctt      1380
ctaacatgcg gtgacgtgga ggagaatccc ggccctaggg tgagcaaggg cgaggagctg      1440
ttcaccgggg tggtgcccat cctggtcgag ctggacggcg acgtaaacgg ccacaagttc      1500
agcgtgtccg gcgagggcga gggcgatgcc acctacggca agctgaccct gaagttcatc      1560
tgcaccaccg gcaagctgcc cgtgccctgg cccaccctcg tgaccaccct gacctacggc      1620
gtgcagtgct tcagccgcta ccccgaccac atgaagcagc acgacttctt caagtccgcc      1680
atgcccgaag ctacgtcca ggagcgcacc atcttcttca aggacgacgg caactacaag      1740
acccgcgccg aggtgaagtt cgagggcgac accctggtga accgcatcga gctgaagggc      1800
atcgacttca aggaggacgg caacatcctg gggcacaagc tggagtacaa ctacaacagc      1860
cacaacgtct atatcatggc cgacaagcag aagaacggca tcaaggtgaa cttcaagatc      1920
cgccacaaca tcgaggacgg cagcgtgcag ctcgccgacc actaccagca gaacacccc       1980 atcggcgacg gccccgtgct gctgcccgac aaccactacc tgagcaccca gtccgccctg      2040
agcaaagacc ccaacgagaa gcgcgatcac atggtcctgc tggagttcgt gaccgccgcc      2100
gggatcactc tcggcatgga cgagctgtac aagtga                                2136
```

<210> SEQ ID NO 30
<211> LENGTH: 407
<212> TYPE: PRT
<213> ORGANISM: Artificial sequence
<220> FEATURE:
<223> OTHER INFORMATION: Anti-P329G-Fab-heavy chain- CD28ATD-CD28CSD-
      CD3zSSD fusion

<400> SEQUENCE: 30

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
            195                 200                 205
Ser Asn Thr Lys Val Asp Lys Lys Val Glu Pro Lys Ser Cys Gly Gly
    210                 215                 220

Gly Gly Ser Phe Trp Val Leu Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Val Lys Phe Ser Arg Ser Ala Asp
    290                 295                 300

Ala Pro Ala Tyr Gln Gln Gly Gln Asn Gln Leu Tyr Asn Glu Leu Asn
305                 310                 315                 320

Leu Gly Arg Arg Glu Glu Tyr Asp Val Leu Asp Lys Arg Arg Gly Arg
                325                 330                 335

Asp Pro Glu Met Gly Gly Lys Pro Arg Arg Lys Asn Pro Gln Glu Gly
            340                 345                 350

Leu Tyr Asn Glu Leu Gln Lys Asp Lys Met Ala Glu Ala Tyr Ser Glu
        355                 360                 365

Ile Gly Met Lys Gly Glu Arg Arg Arg Gly Lys Gly His Asp Gly Leu
    370                 375                 380

Tyr Gln Gly Leu Ser Thr Ala Thr Lys Asp Thr Tyr Asp Ala Leu His
385                 390                 395                 400

Met Gln Ala Leu Pro Pro Arg
                405

<210> SEQ ID NO 31
<211> LENGTH: 222
<212> TYPE: PRT
<213> ORGANISM: Artificial sequence
<220> FEATURE:
<223> OTHER INFORMATION: Anti-P329G-Fab heavy chain

<400> SEQUENCE: 31

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
                145                 150                 155                 160
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys
                210                 215                 220

<210> SEQ ID NO 32
<211> LENGTH: 216
<212> TYPE: PRT
<213> ORGANISM: Artificial sequence
<220> FEATURE:
<223> OTHER INFORMATION: Anti-P329G-Fab light chain

<400> SEQUENCE: 32

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
                35                  40                  45

Leu Ile Gly Gly Thr Asn Lys Arg Ala Pro Gly Val Pro Ala Arg Phe
            50                  55                  60

Ser Gly Ser Leu Ile Gly Asp Lys Ala Ala Leu Thr Ile Thr Gly Ala
65              70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
                210                 215

<210> SEQ ID NO 33
<211> LENGTH: 109
<212> TYPE: PRT
<213> ORGANISM: Artificial sequence
<220> FEATURE:
<223> OTHER INFORMATION: Anti-P329G VL

<400> SEQUENCE: 33

Gln Ala Val Val Thr Gln Glu Ser Ala Leu Thr Thr Ser Pro Gly Glu
1               5                   10                  15
```

```
Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105
```

<210> SEQ ID NO 34
<211> LENGTH: 107
<212> TYPE: PRT
<213> ORGANISM: Artificial sequence
<220> FEATURE:
<223> OTHER INFORMATION: CL

<400> SEQUENCE: 34

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 35
<211> LENGTH: 119
<212> TYPE: PRT
<213> ORGANISM: Artificial sequence
<220> FEATURE:
<223> OTHER INFORMATION: Anti-P329G VH

<400> SEQUENCE: 35

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110
```

Thr Leu Val Thr Val Ser Ala
        115

<210> SEQ ID NO 36
<211> LENGTH: 103
<212> TYPE: PRT
<213> ORGANISM: Artificial sequence
<220> FEATURE:
<223> OTHER INFORMATION: CH1

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 37
<211> LENGTH: 2645
<212> TYPE: DNA
<213> ORGANISM: Artificial sequence
<220> FEATURE:
<223> OTHER INFORMATION: Anti-P329G-Fab-heavy chain- CD28ATD-CD28CSD-
      CD3zSSD fusion

<400> SEQUENCE: 37

| | | |
|---|---|---|
| atgggatgga gctgtatcat cctcttcttg gtagcaacag ctacgggtgt gcattcccag | 60 |
| gccgtggtga cccaggagag cgccctgacc accagccccg cgagaccgt gaccctgacc | 120 |
| tgcaggagca gcaccggcgc cgtgaccacc agcaactacg ccaactgggt gcaggagaag | 180 |
| cccgaccacc tgttcaccgg cctgatcggc ggcaccaaca gagggcccc cggcgtgccc | 240 |
| gccaggttca gcggcagcct gatcggcgac aaggccgccc tgaccatcac cggcgcccag | 300 |
| accgaggacg aggccatcta cttctgcgcc ctgtggtaca gcaaccactg ggtgttcggc | 360 |
| ggtggcacca agctgaccgt gctgcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca aagcagacta cgagaaacac aaagtctacg cctgcgaagt cacccatcag | 660 |
| ggcctgagct cgcccgtcac aaagagcttc aacaggggag agtgttagga attccccgaa | 720 |
| gtaacttaga agctgtaaat caacgatcaa tagcaggtgt ggcacaccag tcataccttg | 780 |
| atcaagcact tctgtttccc cggactgagt atcaataggc tgctcgcgcg gctgaaggag | 840 |
| aaaacgttcg ttacccgacc aactacttcg agaagcttag taccaccatg aacgaggcag | 900 |
| ggtgtttcgc tcagcacaac cccagtgtag atcaggctga tgagtcactg caaccccat | 960 |
| gggcgaccat ggcagtggct cgttggcgg cctgcccatg gagaaatcca tgggacgctc | 1020 |

```
taattctgac atggtgtgaa gtgcctattg agctaactgg tagtcctccg gcccctgatt    1080
gcggctaatc ctaactgcgg agcacatgct cacaaaccag tgggtggtgt gtcgtaacgg    1140
gcaactctgc agcggaaccg actactttgg gtgtccgtgt ttccttttat tcctatattg    1200
gctgcttatg gtgacaatca aaagttgtt accatatagc tattggattg gccatccggt     1260
gtgcaacagg gcaactgttt acctatttat tggttttgta ccattatcac tgaagtctgt    1320
gatcactctc aaattcattt tgaccctcaa cacaatcaaa cgccaccatg ggatggagct    1380
gtatcatcct cttcttggta gcaacagcta ccggtgtgca ctccgaggtg aagctgctgg    1440
agagcggcgg cggcctggtg cagcccggcg gcagcctgaa gctgagctgc cgccagcg     1500 gcttcgactt cagcaggtac tggatgaact gggtgaggca ggcccccggc aagggtctgg    1560
agtggatcgg cgagatcacc cccgacagca gcaccatcaa ctacaccccc agcctgaagg    1620
acaagttcat catcagcagg gacaacgcca agaacaccct gtacctgcag atgatcaagg    1680
tgaggagcga ggacaccgcc ctgtactact gcgtgaggcc ctacgactac ggcgcctggt    1740
tcgccagctg gggccagggc accctggtga ccgtgagcgc cgctagcacc aagggcccct    1800
ccgtgttccc cctggccccc agcagcaaga gcaccagcgg cggcacagcc gctctgggct    1860
gcctggtcaa ggactacttc cccgagcccg tgaccgtgtc ctggaacagc ggagccctga    1920
cctccggcgt gcacaccttc cccgccgtgc tgcagagttc tggcctgtat agcctgagca    1980
gcgtggtcac cgtgccttct agcagcctgg gcacccagac ctacatctgc aacgtgaacc    2040
acaagcccag caacaccaag gtggacaaga aggtggagcc caagagctgc ggaggggcg     2100 gatccttctg ggtgctggtg gtggtgggcg gcgtgctggc ctgctacagc ctgctggtga    2160
ccgtggcctt catcatcttc tgggtgagga gcaagaggag caggctgctg cacagcgact    2220
acatgaacat gaccccagg aggcccggcc ccaccaggaa gcactaccag ccctacgccc     2280
cccccaggga cttcgccgcc tacaggagca gggtgaagtt cagcaggagc gccgacgccc    2340
ccgcctacca gcagggccag aaccagctgt ataacgagct gaacctgggc aggagggagg    2400
agtacgacgt gctggacaag aggagggca gggaccccga gatgggcggc aagcccagga    2460
ggaagaaccc ccaggagggc ctgtataacg agctgcagaa ggacaagatg gccgaggcct    2520
acagcgagat cggcatgaag ggcgagagga gaggggcaa gggccacgac ggcctgtacc    2580
agggcctgag caccgccacc aaggacacct acgacgccct gcacatgcag gccctgcccc    2640
ccagg                                                                2645
```

<210> SEQ ID NO 38
<211> LENGTH: 327
<212> TYPE: DNA
<213> ORGANISM: Artificial sequence
<220> FEATURE:
<223> OTHER INFORMATION: Anti-P329G VL

<400> SEQUENCE: 38

```
caggccgtgg tgacccagga gagcgccctg accaccagcc ccggcgagac cgtgaccctg      60
acctgcagga gcagcaccgg cgccgtgacc accagcaact acgccaactg ggtgcaggag     120
aagcccgacc acctgttcac cggcctgatc ggcggcacca caagagggc cccggcgtg      180 ccgccaggt tcagcggcag cctgatcggc gacaaggccg ccctgaccat caccggcgcc     240
cagaccgagg acgaggccat ctacttctgc gccctgtggt acagcaacca ctgggtgttc    300
ggcggtggca ccaagctgac cgtgctg                                         327
```

<210> SEQ ID NO 39
<211> LENGTH: 324
<212> TYPE: DNA
<213> ORGANISM: Artificial sequence
<220> FEATURE:
<223> OTHER INFORMATION: CL

<400> SEQUENCE: 39

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                         324
```

<210> SEQ ID NO 40
<211> LENGTH: 357
<212> TYPE: DNA
<213> ORGANISM: Artificial sequence
<220> FEATURE:
<223> OTHER INFORMATION: Anti-P329G VH

<400> SEQUENCE: 40

```
gaggtgaagc tgctggagag cggcggcggc ctggtgcagc ccggcggcag cctgaagctg    60
agctgcgccg ccagcggctt cgacttcagc aggtactgga tgaactgggt gaggcaggcc   120
cccggcaagg gtctggagtg gatcggcgag atcaccccg acagcagcac catcaactac   180 accccagcc tgaaggacaa gttcatcatc agcagggaca acgccaagaa caccctgtac   240
ctgcagatga tcaaggtgag gagcgaggac accgccctgt actactgcgt gaggccctac   300
gactacggcg cctggttcgc cagctggggc cagggcaccc tggtgaccgt gagcgcc     357
```

<210> SEQ ID NO 41
<211> LENGTH: 309
<212> TYPE: DNA
<213> ORGANISM: Artificial sequence
<220> FEATURE:
<223> OTHER INFORMATION: CH1

<400> SEQUENCE: 41

```
gctagcacca agggcccctc cgtgttcccc ctggccccca gcagcaagag caccagcggc    60
ggcacagccg ctctgggctg cctggtcaag gactacttcc ccgagcccgt gaccgtgtcc   120
tggaacagcg gagccctgac ctccggcgtg cacaccttcc ccgccgtgct gcagagttct   180
ggcctgtata gcctgagcag cgtggtcacc gtgccttcta gcagcctggg cacccagacc   240
tacatctgca acgtgaacca caagcccagc aacaccaagg tggacaagaa ggtggagccc   300
aagagctgc                                                         309
```

<210> SEQ ID NO 42
<211> LENGTH: 647
<212> TYPE: DNA
<213> ORGANISM: Artificial sequence
<220> FEATURE:
<223> OTHER INFORMATION: IRES EV71, internal ribosomal entry side

<400> SEQUENCE: 42

```
cccgaagtaa cttagaagct gtaaatcaac gatcaatagc aggtgtggca caccagtcat    60
accttgatca agcacttctg tttccccgga ctgagtatca ataggctgct cgcgcggctg   120
```

```
aaggagaaaa cgttcgttac ccgaccaact acttcgagaa gcttagtacc accatgaacg      180
aggcagggtg tttcgctcag cacaaccccca gtgtagatca ggctgatgag tcactgcaac     240
ccccatgggc gaccatggca gtggctgcgt tggcggcctg cccatggaga atccatggg       300 acgctctaat tctgacatgg tgtgaagtgc ctattgagct aactggtagt cctccggccc      360
ctgattgcgg ctaatcctaa ctgcggagca catgctcaca accagtgggt ggtgtgtcg       420 taacgggcaa ctctgcagcg gaaccgacta ctttgggtgt ccgtgtttcc ttttattcct      480
atattggctg cttatggtga caatcaaaaa gttgttacca tatagctatt ggattggcca      540
tccggtgtgc aacagggcaa ctgtttacct atttattggt tttgtaccat tatcactgaa      600
gtctgtgatc actctcaaat tcattttgac cctcaacaca atcaaac                    647
```

<210> SEQ ID NO 43
<211> LENGTH: 3425
<212> TYPE: DNA
<213> ORGANISM: Artificial sequence
<220> FEATURE:
<223> OTHER INFORMATION: Anti-P329G-Fab-heavy chain- CD28ATD-CD28CSD-
      CD3zSSD-eGFP fusion

<400> SEQUENCE: 43

```
atgggatgga gctgtatcat cctcttcttg gtagcaacag ctacgggtgt gcattcccag       60
gccgtggtga cccaggagag cgccctgacc accagccccg cgagaccgt gaccctgacc       120 tgcaggagca gcaccggcgc cgtgaccacc agcaactacg ccaactgggt gcaggagaag      180
cccgaccacc tgttcaccgg cctgatcggc ggcaccaaca gagggcccc cggcgtgccc       240 gccaggttca gcggcagcct gatcggcgac aaggccgccc tgaccatcac cggcgcccag      300
accgaggacg aggccatcta cttctgcgcc ctgtggtaca gcaaccactg ggtgttcggc      360
ggtggcacca agctgaccgt gctgcgtacg gtggctgcac catctgtctt catcttcccg      420
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca aagcagacta cgagaaacac aaagtctacg cctgcgaagt cacccatcag      660
ggcctgagct cgcccgtcac aaaagagctt aacaggggag agtgttagga attccccgaa      720
gtaacttaga agctgtaaat caacgatcaa tagcaggtgt ggcacaccag tcataccttg      780
atcaagcact tctgtttccc cggactgagt atcaataggc tgctcgcgcg gctgaaggag      840
aaaacgttcg ttacccgacc aactacttcg agaagcttag taccaccatg aacgaggcag      900
ggtgtttcgc tcagcacaac cccagtgtag atcaggctga tgagtcactg caaccccccat     960 gggcgaccat ggcagtggct gcgttggcgg cctgcccatg gagaaatcca tgggacgctc     1020
taattctgac atggtgtgaa gtgcctattg agctaactgg tagtcctccg gcccctgatt     1080
gcggctaatc ctaactgcgg agcacatgct cacaaaccag tgggtggtgt gtcgtaacgg     1140
gcaactctgc agcggaaccg actactttgg gtgtccgtgt tccttttat tcctatattg      1200 gctgcttatg gtgacaatca aaagttgtt accatatagc tattggattg ccatccggt       1260 gtgcaacagg gcaactgttt acctatttat tggttttgta ccattatcac tgaagtctgt     1320
gatcactctc aaattcattt tgaccctcaa cacaatcaaa cgccaccatg ggatggagct     1380
gtatcatcct cttcttggta gcaacagcta ccggtgtgca ctcgaggtg aagctgctgg      1440 agagcggcgg cggcctggtg cagcccggcg gcagcctgaa gctgagctgc gccgccagcg     1500
```

```
gcttcgactt cagcaggtac tggatgaact gggtgaggca ggcccccggc aagggtctgg    1560
agtggatcgg cgagatcacc cccgacagca gcaccatcaa ctacaccccc agcctgaagg    1620
acaagttcat catcagcagg gacaacgcca agaacaccct gtacctgcag atgatcaagg    1680
tgaggagcga ggacaccgcc ctgtactact gcgtgaggcc ctacgactac ggcgcctggt    1740
tcgccagctg gggccagggc accctggtga ccgtgagcgc cgctagcacc aagggcccct    1800
ccgtgttccc cctggccccc agcagcaaga gcaccagcgg cggcacagcc gctctgggct    1860
gcctggtcaa ggactacttc cccgagcccg tgaccgtgtc ctggaacagc ggagccctga    1920
cctccggcgt gcacaccttc cccgccgtgc tgcagagttc tggcctgtat agcctgagca    1980
gcgtggtcac cgtgccttct agcagcctgg gcacccagac ctacatctgc aacgtgaacc    2040
acaagcccag caacaccaag gtggacaaga aggtggagcc caagagctgc ggaggggcg    2100 gatccttctg ggtgctggtg gtggtgggcg gcgtgctggc ctgctacagc ctgctggtga    2160
ccgtggcctt catcatcttc tgggtgagga caagaggag caggctgctg cacagcgact    2220
acatgaacat gaccccccagg aggcccggcc ccaccaggaa gcactaccag ccctacgccc    2280
cccccaggga cttcgccgcc tacaggagca gggtgaagtt cagcaggagc gccgacgccc    2340
ccgcctacca gcagggccag aaccagctgt ataacgagct gaacctgggc aggagggagg    2400
agtacgacgt gctggacaag aggaggggca gggaccccga gatgggcggc aagcccagga    2460
ggaagaaccc ccaggagggc ctgtataacg agctgcagaa ggacaagatg gccgaggcct    2520
acagcgagat cggcatgaag ggcgagagga ggaggggcaa gggccacgac ggcctgtacc    2580
agggcctgag caccgccacc aaggacacct acgacgccct gcacatgcag gccctgcccc    2640
ccaggtccgg agagggcaga ggaagtcttc taacatgcgg tgacgtggag gagaatcccg    2700
gcccctaggg t gagcaaggge gaggagctgt tcaccggggt ggtgcccatc ctggtcgagc    2760
tggacggcga cgtaaacggc cacaagttca gcgtgtccgg cgagggcgag ggcgatgcca    2820
cctacggcaa gctgaccctg aagttcatct gcaccaccgg caagctgccc gtgccctggc    2880
ccaccctcgt gaccaccctg acctacggcg tgcagtgctt cagccgctac cccgaccaca    2940
tgaagcagca cgacttcttc aagtccgcca tgcccgaagg ctacgtccag gagcgcacca    3000
tcttcttcaa ggacgacggc aactacaaga cccgcgccga ggtgaagttc gagggcgaca    3060
ccctggtgaa ccgcatcgag ctgaagggca tcgacttcaa ggaggacggc aacatcctgg    3120
ggcacaagct ggagtacaac tacaacagcc acaacgtcta tatcatggcc gacaagcaga    3180
agaacggcat caaggtgaac ttcaagatcc gccacaacat cgaggacggc agcgtgcagc    3240
tcgccgacca ctaccagcag aacacccca tcggcgacgg ccccgtgctg ctgcccgaca    3300
accactacct gagcacccag tccgccctga gcaaagaccc caacgagaag cgcgatcaca    3360
tggtcctgct ggagttcgtg accgccgccg ggatcactct cggcatggac gagctgtaca    3420
agtga                                                                3425
```

<210> SEQ ID NO 44
<211> LENGTH: 5
<212> TYPE: PRT
<213> ORGANISM: Artificial sequence
<220> FEATURE:
<223> OTHER INFORMATION: Anti-AAA CDR H1 Kabat

<400> SEQUENCE: 44

Ser Tyr Gly Met Ser
1               5

<210> SEQ ID NO 45
<211> LENGTH: 6
<212> TYPE: PRT
<213> ORGANISM: Artificial sequence
<220> FEATURE:
<223> OTHER INFORMATION: Anti-AAA CDR H2 Kabat

<400> SEQUENCE: 45

Ser Ser Gly Gly Ser Tyr
1               5

<210> SEQ ID NO 46
<211> LENGTH: 12
<212> TYPE: PRT
<213> ORGANISM: Artificial sequence
<220> FEATURE:
<223> OTHER INFORMATION: Anti-AAA CDR H3 Kabat

<400> SEQUENCE: 46

Leu Gly Met Ile Thr Thr Gly Tyr Ala Met Asp Tyr
1               5                   10

<210> SEQ ID NO 47
<211> LENGTH: 16
<212> TYPE: PRT
<213> ORGANISM: Artificial sequence
<220> FEATURE:
<223> OTHER INFORMATION: Anti-AAA CDR L1 Kabat

<400> SEQUENCE: 47

Arg Ser Ser Gln Thr Ile Val His Ser Thr Gly His Thr Tyr Leu Glu
1               5                   10                  15

<210> SEQ ID NO 48
<211> LENGTH: 7
<212> TYPE: PRT
<213> ORGANISM: Artificial sequence
<220> FEATURE:
<223> OTHER INFORMATION: Anti-AAA CDR L2 Kabat

<400> SEQUENCE: 48

Lys Val Ser Asn Arg Phe Ser
1               5

<210> SEQ ID NO 49
<211> LENGTH: 9
<212> TYPE: PRT
<213> ORGANISM: Artificial sequence
<220> FEATURE:
<223> OTHER INFORMATION: Anti-AAA CDR L3 Kabat

<400> SEQUENCE: 49

Phe Gln Gly Ser His Val Pro Tyr Thr
1               5

<210> SEQ ID NO 50
<211> LENGTH: 457
<212> TYPE: PRT
<213> ORGANISM: Artificial sequence
<220> FEATURE:
<223> OTHER INFORMATION: Anti-AAA-scFv-CD28ATD-CD28CSD-CD3zSSD fusion

<400> SEQUENCE: 50

Met Asn Phe Gly Leu Ser Leu Val Phe Leu Ala Leu Ile Leu Lys Gly
1               5                   10                  15

-continued

```
Val Gln Cys Glu Val Gln Leu Val Glu Ser Gly Gly Asp Leu Val Lys
            20                  25                  30
Pro Gly Gly Ser Leu Lys Leu Ser Cys Ala Ala Ser Gly Phe Thr Phe
        35                  40                  45
Ser Ser Tyr Gly Met Ser Trp Val Arg Gln Thr Pro Asp Lys Arg Leu
    50                  55                  60
Glu Trp Val Ala Thr Ile Ser Ser Gly Gly Ser Tyr Ile Tyr Tyr Pro
65                  70                  75                  80
Asp Ser Val Lys Gly Arg Phe Thr Ile Ser Arg Asp Asn Ala Lys Asn
                85                  90                  95
Thr Leu Tyr Leu Gln Met Ser Ser Leu Lys Ser Glu Asp Thr Ala Met
            100                 105                 110
Tyr Tyr Cys Ala Arg Leu Gly Met Ile Thr Thr Gly Tyr Ala Met Asp
        115                 120                 125
Tyr Trp Gly Gln Gly Thr Ser Val Thr Val Ser Ser Gly Gly Gly Gly
    130                 135                 140
Ser Gly Gly Gly Gly Ser Gly Gly Gly Ser Gly Gly Gly Gly Ser
145                 150                 155                 160
Asp Val Leu Met Thr Gln Thr Pro Leu Ser Leu Pro Val Ser Leu Gly
                165                 170                 175
Asp Gln Ala Ser Ile Ser Cys Arg Ser Ser Gln Thr Ile Val His Ser
            180                 185                 190
Thr Gly His Thr Tyr Leu Glu Trp Phe Leu Gln Lys Pro Gly Gln Ser
        195                 200                 205
Pro Lys Leu Leu Ile Tyr Lys Val Ser Asn Arg Phe Ser Gly Val Pro
    210                 215                 220
Asp Arg Phe Ser Gly Ser Gly Ser Gly Thr Asp Phe Thr Leu Lys Ile
225                 230                 235                 240
Ser Arg Val Glu Ala Glu Asp Leu Gly Val Tyr Tyr Cys Phe Gln Gly
                245                 250                 255
Ser His Val Pro Tyr Thr Phe Gly Gly Gly Thr Lys Leu Glu Ile Lys
            260                 265                 270
Gly Gly Gly Gly Ser Phe Trp Val Leu Val Val Val Gly Gly Val Leu
        275                 280                 285
Ala Cys Tyr Ser Leu Leu Val Thr Val Ala Phe Ile Ile Phe Trp Val
    290                 295                 300
Arg Ser Lys Arg Ser Arg Leu Leu His Ser Asp Tyr Met Asn Met Thr
305                 310                 315                 320
Pro Arg Arg Pro Gly Pro Thr Arg Lys His Tyr Gln Pro Tyr Ala Pro
                325                 330                 335
Pro Arg Asp Phe Ala Ala Tyr Arg Ser Arg Val Lys Phe Ser Arg Ser
            340                 345                 350
Ala Asp Ala Pro Ala Tyr Gln Gln Gly Gln Asn Gln Leu Tyr Asn Glu
        355                 360                 365
Leu Asn Leu Gly Arg Arg Glu Glu Tyr Asp Val Leu Asp Lys Arg Arg
    370                 375                 380
Gly Arg Asp Pro Glu Met Gly Gly Lys Pro Arg Arg Lys Asn Pro Gln
385                 390                 395                 400
Glu Gly Leu Tyr Asn Glu Leu Gln Lys Asp Lys Met Ala Glu Ala Tyr
                405                 410                 415
Ser Glu Ile Gly Met Lys Gly Glu Arg Arg Arg Gly Lys Gly His Asp
            420                 425                 430
Gly Leu Tyr Gln Gly Leu Ser Thr Ala Thr Lys Asp Thr Tyr Asp Ala
```

-continued

```
                435                 440                 445

Leu His Met Gln Ala Leu Pro Pro Arg
    450                 455

<210> SEQ ID NO 51
<211> LENGTH: 272
<212> TYPE: PRT
<213> ORGANISM: Artificial sequence
<220> FEATURE:
<223> OTHER INFORMATION: Anti-AAA-scFv

<400> SEQUENCE: 51

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Ser Gly Gly Gly Gly Ser
145                 150                 155                 160

Asp Val Leu Met Thr Gln Thr Pro Leu Ser Leu Pro Val Ser Leu Gly
                165                 170                 175

Asp Gln Ala Ser Ile Ser Cys Arg Ser Ser Gln Thr Ile Val His Ser
            180                 185                 190

Thr Gly His Thr Tyr Leu Glu Trp Phe Leu Gln Lys Pro Gly Gln Ser
        195                 200                 205

Pro Lys Leu Leu Ile Tyr Lys Val Ser Asn Arg Phe Ser Gly Val Pro
    210                 215                 220

Asp Arg Phe Ser Gly Ser Gly Ser Gly Thr Asp Phe Thr Leu Lys Ile
225                 230                 235                 240

Ser Arg Val Glu Ala Glu Asp Leu Gly Val Tyr Tyr Cys Phe Gln Gly
                245                 250                 255

Ser His Val Pro Tyr Thr Phe Gly Gly Gly Thr Lys Leu Glu Ile Lys
            260                 265                 270

<210> SEQ ID NO 52
<211> LENGTH: 140
<212> TYPE: PRT
<213> ORGANISM: Artificial sequence
<220> FEATURE:
<223> OTHER INFORMATION: Anti-AAA VH

<400> SEQUENCE: 52

Met Asn Phe Gly Leu Ser Leu Val Phe Leu Ala Leu Ile Leu Lys Gly
1               5                   10                  15
```

```
Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
            35                  40                  45

Ser Ser Tyr Gly Met Ser Trp Val Arg Gln Thr Pro Asp Lys Arg Leu
 50                  55                  60

Glu Trp Val Ala Thr Ile Ser Ser Gly Gly Ser Tyr Ile Tyr Tyr Pro
 65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
            115                 120                 125

Tyr Trp Gly Gln Gly Thr Ser Val Thr Val Ser Ser
            130                 135                 140
```

```
<210> SEQ ID NO 53
<211> LENGTH: 112
<212> TYPE: PRT
<213> ORGANISM: Artificial sequence
<220> FEATURE:
<223> OTHER INFORMATION: Anti-AAA VL

<400> SEQUENCE: 53

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
            20                  25                  30

Thr Gly His Thr Tyr Leu Glu Trp Phe Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

```
<210> SEQ ID NO 54
<211> LENGTH: 428
<212> TYPE: PRT
<213> ORGANISM: Artificial sequence
<220> FEATURE:
<223> OTHER INFORMATION: Anti-AAA-Fab-heavy chain-CD28ATD-CD28CSD-
    CD3zSSD fusion

<400> SEQUENCE: 54

Met Asn Phe Gly Leu Ser Leu Val Phe Leu Ala Leu Ile Leu Lys Gly
 1               5                  10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
            35                  40                  45

Ser Ser Tyr Gly Met Ser Trp Val Arg Gln Thr Pro Asp Lys Arg Leu
 50                  55                  60

Glu Trp Val Ala Thr Ile Ser Ser Gly Gly Ser Tyr Ile Tyr Tyr Pro
```

```
            65                  70                  75                  80
Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Val Glu Pro
225                 230                 235                 240

Lys Ser Cys Gly Gly Gly Ser Phe Trp Val Leu Val Val Gly
                245                 250                 255

Gly Val Leu Ala Cys Tyr Ser Leu Leu Val Thr Val Ala Phe Ile Ile
                260                 265                 270

Phe Trp Val Arg Ser Lys Arg Ser Arg Leu Leu His Ser Asp Tyr Met
        275                 280                 285

Asn Met Thr Pro Arg Arg Pro Gly Pro Thr Arg Lys His Tyr Gln Pro
    290                 295                 300

Tyr Ala Pro Pro Arg Asp Phe Ala Ala Tyr Arg Ser Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
            340                 345                 350

Lys Arg Arg Gly Arg Asp Pro Glu Met Gly Gly Lys Pro Arg Arg Lys
        355                 360                 365

Asn Pro Gln Glu Gly Leu Tyr Asn Glu Leu Gln Lys Asp Lys Met Ala
    370                 375                 380

Glu Ala Tyr Ser Glu Ile Gly Met Lys Gly Glu Arg Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
            420                 425

<210> SEQ ID NO 55
<211> LENGTH: 243
<212> TYPE: PRT
<213> ORGANISM: Artificial sequence
<220> FEATURE:
<223> OTHER INFORMATION: Anti-AAA-Fab heavy chain

<400> SEQUENCE: 55

Met Asn Phe Gly Leu Ser Leu Val Phe Leu Ala Leu Ile Leu Lys Gly
```

```
   1               5                  10                 15
Val Gln Cys Glu Val Gln Leu Val Glu Ser Gly Gly Asp Leu Val Lys
            20                 25                 30
Pro Gly Gly Ser Leu Lys Leu Ser Cys Ala Ala Ser Gly Phe Thr Phe
            35                 40                 45
Ser Ser Tyr Gly Met Ser Trp Val Arg Gln Thr Pro Asp Lys Arg Leu
 50                 55                 60
Glu Trp Val Ala Thr Ile Ser Ser Gly Gly Ser Tyr Ile Tyr Tyr Pro
 65                 70                 75                 80
Asp Ser Val Lys Gly Arg Phe Thr Ile Ser Arg Asp Asn Ala Lys Asn
             85                 90                 95
Thr Leu Tyr Leu Gln Met Ser Ser Leu Lys Ser Glu Asp Thr Ala Met
            100                105                110
Tyr Tyr Cys Ala Arg Leu Gly Met Ile Thr Thr Gly Tyr Ala Met Asp
            115                120                125
Tyr Trp Gly Gln Gly Thr Ser Val Thr Val Ser Ala Ser Thr Lys
130                135                140
Gly Pro Ser Val Phe Pro Leu Ala Pro Ser Ser Lys Ser Thr Ser Gly
145                150                155                160
Gly Thr Ala Ala Leu Gly Cys Leu Val Lys Asp Tyr Phe Pro Glu Pro
            165                170                175
Val Thr Val Ser Trp Asn Ser Gly Ala Leu Thr Ser Gly Val His Thr
            180                185                190
Phe Pro Ala Val Leu Gln Ser Ser Gly Leu Tyr Ser Leu Ser Ser Val
            195                200                205
Val Thr Val Pro Ser Ser Ser Leu Gly Thr Gln Thr Tyr Ile Cys Asn
            210                215                220
Val Asn His Lys Pro Ser Asn Thr Lys Val Asp Lys Lys Val Glu Pro
225                230                235                240
Lys Ser Cys

<210> SEQ ID NO 56
<211> LENGTH: 219
<212> TYPE: PRT
<213> ORGANISM: Artificial sequence
<220> FEATURE:
<223> OTHER INFORMATION: Anti-AAA-Fab light chain

<400> SEQUENCE: 56

Asp Val Leu Met Thr Gln Thr Pro Leu Ser Leu Pro Val Ser Leu Gly
 1               5                 10                 15
Asp Gln Ala Ser Ile Ser Cys Arg Ser Ser Gln Thr Ile Val His Ser
            20                 25                 30
Thr Gly His Thr Tyr Leu Glu Trp Phe Leu Gln Lys Pro Gly Gln Ser
            35                 40                 45
Pro Lys Leu Leu Ile Tyr Lys Val Ser Asn Arg Phe Ser Gly Val Pro
 50                 55                 60
Asp Arg Phe Ser Gly Ser Gly Ser Gly Thr Asp Phe Thr Leu Lys Ile
 65                 70                 75                 80
Ser Arg Val Glu Ala Glu Asp Leu Gly Val Tyr Tyr Cys Phe Gln Gly
             85                 90                 95
Ser His Val Pro Tyr Thr Phe Gly Gly Gly Thr Lys Leu Glu Ile Lys
            100                105                110
Arg Thr Val Ala Ala Pro Ser Val Phe Ile Phe Pro Pro Ser Asp Glu
            115                120                125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 57
<211> LENGTH: 5
<212> TYPE: PRT
<213> ORGANISM: Artificial sequence
<220> FEATURE:
<223> OTHER INFORMATION: Anti-DIG CDR H1 Kabat

<400> SEQUENCE: 57

Asp Tyr Ala Met Ser
1               5

<210> SEQ ID NO 58
<211> LENGTH: 17
<212> TYPE: PRT
<213> ORGANISM: Artificial sequence
<220> FEATURE:
<223> OTHER INFORMATION: Anti-DIG CDR H2 Kabat

<400> SEQUENCE: 58

Ser Ile Asn Ile Gly Ala Thr Tyr Ile Tyr Tyr Ala Asp Ser Val Lys
1               5                   10                  15

Gly

<210> SEQ ID NO 59
<211> LENGTH: 16
<212> TYPE: PRT
<213> ORGANISM: Artificial sequence
<220> FEATURE:
<223> OTHER INFORMATION: Anti-DIG CDR H3 Kabat

<400> SEQUENCE: 59

Pro Gly Ser Pro Tyr Glu Tyr Asp Lys Ala Tyr Tyr Ser Met Ala Tyr
1               5                   10                  15

<210> SEQ ID NO 60
<211> LENGTH: 11
<212> TYPE: PRT
<213> ORGANISM: Artificial sequence
<220> FEATURE:
<223> OTHER INFORMATION: Anti-DIG CDR L1 Kabat

<400> SEQUENCE: 60

Arg Ala Ser Gln Asp Ile Lys Asn Tyr Leu Asn
1               5                   10

<210> SEQ ID NO 61
<211> LENGTH: 7
<212> TYPE: PRT
<213> ORGANISM: Artificial sequence
<220> FEATURE:
```

-continued

<223> OTHER INFORMATION: Anti-DIG CDR L2 Kabat

<400> SEQUENCE: 61

Tyr Ser Ser Thr Leu Leu Ser
1               5

<210> SEQ ID NO 62
<211> LENGTH: 9
<212> TYPE: PRT
<213> ORGANISM: Artificial sequence
<220> FEATURE:
<223> OTHER INFORMATION: Anti-DIG CDR L3 Kabat

<400> SEQUENCE: 62

Gln Gln Ser Ile Thr Leu Pro Pro Thr
1               5

<210> SEQ ID NO 63
<211> LENGTH: 437
<212> TYPE: PRT
<213> ORGANISM: Artificial sequence
<220> FEATURE:
<223> OTHER INFORMATION: Anti-DIG-ds-scFv-CD28ATD-CD28CSD-CD3zSSD fusion

<400> SEQUENCE: 63

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Cys Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Asp Ile Gln Met Thr Gln Ser Pro Ser Ser Leu Ser Ala Ser Val
145                 150                 155                 160

Gly Asp Arg Val Thr Ile Thr Cys Arg Ala Ser Gln Asp Ile Lys Asn
                165                 170                 175

Tyr Leu Asn Trp Tyr Gln Gln Lys Pro Gly Lys Ala Pro Lys Leu Leu
            180                 185                 190

Ile Tyr Tyr Ser Ser Thr Leu Leu Ser Gly Val Pro Ser Arg Phe Ser
        195                 200                 205

Gly Ser Gly Ser Gly Thr Asp Phe Thr Leu Thr Ile Ser Ser Leu Gln
    210                 215                 220

Pro Glu Asp Phe Ala Thr Tyr Tyr Cys Gln Gln Ser Ile Thr Leu Pro
225                 230                 235                 240

Pro Thr Phe Gly Cys Gly Thr Lys Val Glu Ile Lys Gly Gly Gly Gly
                245                 250                 255

Ser Phe Trp Val Leu Val Val Val Gly Gly Val Leu Ala Cys Tyr Ser

```
            260                 265                 270
Leu Leu Val Thr Val Ala Phe Ile Ile Phe Trp Val Arg Ser Lys Arg
            275                 280                 285

Ser Arg Leu Leu His Ser Asp Tyr Met Asn Met Thr Pro Arg Arg Pro
            290                 295                 300

Gly Pro Thr Arg Lys His Tyr Gln Pro Tyr Ala Pro Pro Arg Asp Phe
305                 310                 315                 320

Ala Ala Tyr Arg Ser Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
                340                 345                 350

Arg Arg Glu Glu Tyr Asp Val Leu Asp Lys Arg Arg Gly Arg Asp Pro
                355                 360                 365

Glu Met Gly Gly Lys Pro Arg Arg Lys Asn Pro Gln Glu Gly Leu Tyr
            370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
                420                 425                 430

Ala Leu Pro Pro Arg
            435

<210> SEQ ID NO 64
<211> LENGTH: 125
<212> TYPE: PRT
<213> ORGANISM: Artificial sequence
<220> FEATURE:
<223> OTHER INFORMATION: Anti-DIG-ds VH

<400> SEQUENCE: 64

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Ile Arg Gln Ala Pro Gly Lys Cys Leu Glu Trp Val
            35                  40                  45

Ser Ser Ile Asn Ile Gly Ala Thr Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
                100                 105                 110

Ala Tyr Trp Gly Gln Gly Thr Thr Val Thr Val Ser Ser
            115                 120                 125

<210> SEQ ID NO 65
<211> LENGTH: 107
<212> TYPE: PRT
<213> ORGANISM: Artificial sequence
<220> FEATURE:
<223> OTHER INFORMATION: Anti-DIG-ds VL

<400> SEQUENCE: 65
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
            35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Cys Gly Thr Lys Val Glu Ile Lys
                100                 105
```

<210> SEQ ID NO 66
<211> LENGTH: 252
<212> TYPE: PRT
<213> ORGANISM: Artificial sequence
<220> FEATURE:
<223> OTHER INFORMATION: Anti-DIG-ds-scFv

<400> SEQUENCE: 66

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Cys Leu Glu Trp Val
            35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
                100                 105                 110

Ala Tyr Trp Gly Gln Gly Thr Thr Val Thr Val Ser Ser Gly Gly Gly
            115                 120                 125

Gly Ser Gly Gly Gly Gly Ser Gly Gly Gly Gly Ser Gly Gly Gly Gly
    130                 135                 140

Ser Asp Ile Gln Met Thr Gln Ser Pro Ser Ser Leu Ser Ala Ser Val
145                 150                 155                 160

Gly Asp Arg Val Thr Ile Thr Cys Arg Ala Ser Gln Asp Ile Lys Asn
                165                 170                 175

Tyr Leu Asn Trp Tyr Gln Gln Lys Pro Gly Lys Ala Pro Lys Leu Leu
            180                 185                 190

Ile Tyr Tyr Ser Ser Thr Leu Leu Ser Gly Val Pro Ser Arg Phe Ser
            195                 200                 205

Gly Ser Gly Ser Gly Thr Asp Phe Thr Leu Thr Ile Ser Ser Leu Gln
        210                 215                 220

Pro Glu Asp Phe Ala Thr Tyr Tyr Cys Gln Gln Ser Ile Thr Leu Pro
225                 230                 235                 240

Pro Thr Phe Gly Cys Gly Thr Lys Val Glu Ile Lys
                245                 250
```

<210> SEQ ID NO 67
<211> LENGTH: 413
<212> TYPE: PRT
<213> ORGANISM: Artificial sequence
<220> FEATURE:
<223> OTHER INFORMATION: Anti-DIG-Fab-heavy chain-CD28ATD-CD28CSD-CD3zSSD fusion

<400> SEQUENCE: 67

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Gly Gly Gly Ser Phe Trp Val Leu Val Val Val
225                 230                 235                 240

Gly Gly Val Leu Ala Cys Tyr Ser Leu Leu Val Thr Val Ala Phe Ile
                245                 250                 255

Ile Phe Trp Val Arg Ser Lys Arg Ser Arg Leu Leu His Ser Asp Tyr
            260                 265                 270

Met Asn Met Thr Pro Arg Arg Pro Gly Pro Thr Arg Lys His Tyr Gln
        275                 280                 285

Pro Tyr Ala Pro Pro Arg Asp Phe Ala Ala Tyr Arg Ser Arg Val Lys
    290                 295                 300

Phe Ser Arg Ser Ala Asp Ala Pro Ala Tyr Gln Gln Gly Gln Asn Gln
305                 310                 315                 320

Leu Tyr Asn Glu Leu Asn Leu Gly Arg Arg Glu Glu Tyr Asp Val Leu
                325                 330                 335

Asp Lys Arg Arg Gly Arg Asp Pro Glu Met Gly Gly Lys Pro Arg Arg
            340                 345                 350

Lys Asn Pro Gln Glu Gly Leu Tyr Asn Glu Leu Gln Lys Asp Lys Met
        355                 360                 365
```

```
Ala Glu Ala Tyr Ser Glu Ile Gly Met Lys Gly Glu Arg Arg Gly
        370                 375                 380

Lys Gly His Asp Gly Leu Tyr Gln Gly Leu Ser Thr Ala Thr Lys Asp
385                 390                 395                 400

Thr Tyr Asp Ala Leu His Met Gln Ala Leu Pro Pro Arg
                405                 410

<210> SEQ ID NO 68
<211> LENGTH: 228
<212> TYPE: PRT
<213> ORGANISM: Artificial sequence
<220> FEATURE:
<223> OTHER INFORMATION: Anti-DIG-Fab heavy chain

<400> SEQUENCE: 68

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Ile Arg Gln Ala Pro Gly Lys Gly Leu Glu Trp Val
            35                  40                  45

Ser Ser Ile Asn Ile Gly Ala Thr Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 69
<211> LENGTH: 214
<212> TYPE: PRT
<213> ORGANISM: Artificial sequence
<220> FEATURE:
<223> OTHER INFORMATION: Anti-DIG-Fab light chain

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
```

```
                    20                  25                  30
Leu Asn Trp Tyr Gln Gln Lys Pro Gly Lys Ala Pro Lys Leu Leu Ile
            35                  40                  45

Tyr Tyr Ser Ser Thr Leu Leu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 125
<212> TYPE: PRT
<213> ORGANISM: Artificial sequence
<220> FEATURE:
<223> OTHER INFORMATION: Anti-DIG VH

<400> SEQUENCE: 70

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125

<210> SEQ ID NO 71
<211> LENGTH: 107
<212> TYPE: PRT
<213> ORGANISM: Artificial sequence
<220> FEATURE:
<223> OTHER INFORMATION: Anti-DIG VL
```

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys
            100                 105

<210> SEQ ID NO 72
<211> LENGTH: 5
<212> TYPE: PRT
<213> ORGANISM: Artificial sequence
<220> FEATURE:
<223> OTHER INFORMATION: Anti-FITC CDR H1 Kabat

<400> SEQUENCE: 72

His Tyr Trp Met Asn
1               5

<210> SEQ ID NO 73
<211> LENGTH: 19
<212> TYPE: PRT
<213> ORGANISM: Artificial sequence
<220> FEATURE:
<223> OTHER INFORMATION: Anti-FITC CDR H2 Kabat

<400> SEQUENCE: 73

Gln Phe Arg Asn Lys Pro Tyr Asn Tyr Glu Thr Tyr Tyr Ser Asp Ser
1               5                   10                  15

Val Lys Gly

<210> SEQ ID NO 74
<211> LENGTH: 7
<212> TYPE: PRT
<213> ORGANISM: Artificial sequence
<220> FEATURE:
<223> OTHER INFORMATION: Anti-FITC CDR H3 Kabat

<400> SEQUENCE: 74

Ala Ser Tyr Gly Met Glu Tyr
1               5

<210> SEQ ID NO 75
<211> LENGTH: 16
<212> TYPE: PRT
<213> ORGANISM: Artificial sequence
<220> FEATURE:
<223> OTHER INFORMATION: Anti-FITC CDR L1 Kabat

<400> SEQUENCE: 75

Arg Ser Ser Gln Ser Leu Val His Ser Asn Gly Asn Thr Tyr Leu Arg
1               5                   10                  15

```
<210> SEQ ID NO 76
<211> LENGTH: 7
<212> TYPE: PRT
<213> ORGANISM: Artificial sequence
<220> FEATURE:
<223> OTHER INFORMATION: Anti-FITC CDR L2 Kabat

<400> SEQUENCE: 76

Lys Val Ser Asn Arg Val Ser
1               5

<210> SEQ ID NO 77
<211> LENGTH: 9
<212> TYPE: PRT
<213> ORGANISM: Artificial sequence
<220> FEATURE:
<223> OTHER INFORMATION: Anti-FITC CDR L3 Kabat

<400> SEQUENCE: 77

Ser Gln Ser Thr His Val Pro Trp Thr
1               5

<210> SEQ ID NO 78
<211> LENGTH: 436
<212> TYPE: PRT
<213> ORGANISM: Artificial sequence
<220> FEATURE:
<223> OTHER INFORMATION: Anti-FITC-scFv-CD28ATD-CD28CSD-CD3zSSD fusion

<400> SEQUENCE: 78

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
                20                  25                  30

Trp Met Asn Trp Val Arg Gln Ser Pro Glu Lys Gly Leu Glu Trp Val
            35                  40                  45

Ala Gln Phe Arg Asn Lys Pro Tyr Asn Tyr Glu Thr Tyr Tyr Ser Asp
        50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Gly Gly Gly Ser Asp Val Val Met Thr Gln
    130                 135                 140

Thr Pro Leu Ser Leu Pro Val Ser Leu Gly Asp Gln Ala Ser Ile Ser
145                 150                 155                 160

Cys Arg Ser Ser Gln Ser Leu Val His Ser Asn Gly Asn Thr Tyr Leu
                165                 170                 175

Arg Trp Tyr Leu Gln Lys Pro Gly Gln Ser Pro Lys Val Leu Ile Tyr
            180                 185                 190

Lys Val Ser Asn Arg Val Ser Gly Val Pro Asp Arg Phe Ser Gly Ser
        195                 200                 205

Gly Ser Gly Thr Asp Phe Thr Leu Lys Ile Asn Arg Val Glu Ala Glu
    210                 215                 220

Asp Leu Gly Val Tyr Phe Cys Ser Gln Ser Thr His Val Pro Trp Thr
225                 230                 235                 240
```

```
Phe Gly Gly Gly Thr Lys Leu Glu Ile Lys Arg Gly Gly Gly Ser
                245                 250                 255

Phe Trp Val Leu Val Val Gly Val Leu Ala Cys Tyr Ser Leu
                260                 265                 270

Leu Val Thr Val Ala Phe Ile Ile Phe Trp Val Arg Ser Lys Arg Ser
                275                 280                 285

Arg Leu Leu His Ser Asp Tyr Met Asn Met Thr Pro Arg Arg Pro Gly
                290                 295                 300

Pro Thr Arg Lys His Tyr Gln Pro Tyr Ala Pro Pro Arg Asp Phe Ala
305                 310                 315                 320

Ala Tyr Arg Ser Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
                355                 360                 365

Met Gly Gly Lys Pro Arg Arg Lys Asn Pro Gln Glu Gly Leu Tyr Asn
                370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
            435

<210> SEQ ID NO 79
<211> LENGTH: 250
<212> TYPE: PRT
<213> ORGANISM: Artificial sequence
<220> FEATURE:
<223> OTHER INFORMATION: Anti-FITC-scFv

<400> SEQUENCE: 79

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
                20                  25                  30

Trp Met Asn Trp Val Arg Gln Ser Pro Glu Lys Gly Leu Glu Trp Val
                35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
                100                 105                 110

Ser Val Thr Val Ser Ser Gly Gly Gly Ser Gly Gly Gly Ser
                115                 120                 125

Gly Gly Gly Gly Ser Gly Gly Gly Ser Asp Val Val Met Thr Gln
                130                 135                 140

Thr Pro Leu Ser Leu Pro Val Ser Leu Gly Asp Gln Ala Ser Ile Ser
145                 150                 155                 160
```

-continued

Cys Arg Ser Ser Gln Ser Leu Val His Ser Asn Gly Asn Thr Tyr Leu
                165                 170                 175

Arg Trp Tyr Leu Gln Lys Pro Gly Gln Ser Pro Lys Val Leu Ile Tyr
            180                 185                 190

Lys Val Ser Asn Arg Val Ser Gly Val Pro Asp Arg Phe Ser Gly Ser
            195                 200                 205

Gly Ser Gly Thr Asp Phe Thr Leu Lys Ile Asn Arg Val Glu Ala Glu
        210                 215                 220

Asp Leu Gly Val Tyr Phe Cys Ser Gln Ser Thr His Val Pro Trp Thr
225                 230                 235                 240

Phe Gly Gly Gly Thr Lys Leu Glu Ile Lys
            245                 250

<210> SEQ ID NO 80
<211> LENGTH: 118
<212> TYPE: PRT
<213> ORGANISM: Artificial sequence
<220> FEATURE:
<223> OTHER INFORMATION: Anti-FITC VH

<400> SEQUENCE: 80

Gly Val Lys Leu Asp Glu Thr Gly Gly Gly Leu Val Gln Pro Gly Gly
1               5                   10                  15

Ala Met Lys Leu Ser Cys Val Thr Ser Gly Phe Thr Phe Gly His Tyr
            20                  25                  30

Trp Met Asn Trp Val Arg Gln Ser Pro Glu Lys Gly Leu Glu Trp Val
        35                  40                  45

Ala Gln Phe Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Thr Gly Ile Tyr
                85                  90                  95

Tyr Cys Thr Gly Ala Ser Tyr Gly Met Glu Tyr Leu Gly Gln Gly Thr
            100                 105                 110

Ser Val Thr Val Ser Ser
        115

<210> SEQ ID NO 81
<211> LENGTH: 112
<212> TYPE: PRT
<213> ORGANISM: Artificial sequence
<220> FEATURE:
<223> OTHER INFORMATION: Anti-FITC VL

<400> SEQUENCE: 81

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser 85                  90                  95
Thr His Val Pro Trp Thr Phe Gly Gly Gly Thr Lys Leu Glu Ile Lys
                100                 105                 110

<210> SEQ ID NO 82
<211> LENGTH: 5
<212> TYPE: PRT
<213> ORGANISM: Artificial sequence
<220> FEATURE:
<223> OTHER INFORMATION: Anti-HA CDR H1 Kabat

<400> SEQUENCE: 82

Asn Tyr Asp Met Ala
1               5

<210> SEQ ID NO 83
<211> LENGTH: 17
<212> TYPE: PRT
<213> ORGANISM: Artificial sequence
<220> FEATURE:
<223> OTHER INFORMATION: Anti-HA CDR H2 Kabat

<400> SEQUENCE: 83

Thr Ile Ser His Asp Gly Arg Asn Thr Asn Tyr Arg Asp Ser Val Lys
1               5                   10                  15
Gly

<210> SEQ ID NO 84
<211> LENGTH: 5
<212> TYPE: PRT
<213> ORGANISM: Artificial sequence
<220> FEATURE:
<223> OTHER INFORMATION: Anti-HA CDR H3 Kabat

<400> SEQUENCE: 84

Pro Gly Phe Ala His
1               5

<210> SEQ ID NO 85
<211> LENGTH: 16
<212> TYPE: PRT
<213> ORGANISM: Artificial sequence
<220> FEATURE:
<223> OTHER INFORMATION: Anti-HA CDR L1 Kabat

<400> SEQUENCE: 85

Arg Ser Ser Lys Thr Leu Leu Asn Thr Arg Gly Ile Thr Ser Leu Tyr
1               5                   10                  15

<210> SEQ ID NO 86
<211> LENGTH: 7
<212> TYPE: PRT
<213> ORGANISM: Artificial sequence
<220> FEATURE:
<223> OTHER INFORMATION: Anti-HA CDR L2 Kabat

<400> SEQUENCE: 86

Arg Met Ser Asn Leu Ala Ser
1               5

<210> SEQ ID NO 87
<211> LENGTH: 9
<212> TYPE: PRT
<213> ORGANISM: Artificial sequence
<220> FEATURE:
<223> OTHER INFORMATION: Anti-HA CDR L3 Kabat

<400> SEQUENCE: 87

Ala Gln Phe Leu Glu Phe Pro Leu Thr
1               5

<210> SEQ ID NO 88
<211> LENGTH: 431
<212> TYPE: PRT
<213> ORGANISM: Artificial sequence
<220> FEATURE:
<223> OTHER INFORMATION: Anti-HA-scFv-CD28ATD-CD28CSD-CD3zSSD fusion

<400> SEQUENCE: 88

Glu Val Gln Leu Val Glu Ser Gly Gly Gly Leu Val Gln Pro Gly Arg
1               5                   10                  15

Ser Met Lys Leu Ser Cys Ala Val Ser Gly Phe Ile Phe Ser Asn Tyr
                20                  25                  30

Asp Met Ala Trp Val Arg Gln Ala Pro Lys Lys Cys Leu Glu Trp Val
            35                  40                  45

Ala Thr Ile Ser His Asp Gly Arg Asn Thr Asn Tyr Arg Asp Ser Val
        50                  55                  60

Lys Gly Arg Phe Thr Gly Ser Arg Asp Ser Ala Gln Ser Thr Leu Tyr
65                  70                  75                  80

Leu Gln Met Asp Ser Leu Arg Ser Glu Asp Thr Ala Ile Tyr Phe Cys
                85                  90                  95

Ala Gly Pro Gly Phe Ala His Trp Gly Gln Gly Thr Leu Val Thr Val
            100                 105                 110

Ser Ser Gly Gly Gly Gly Ser Gly Gly Gly Ser Gly Gly Gly Gly
        115                 120                 125

Ser Gly Gly Gly Gly Ser Asp Ile Val Leu Thr Gln Ala Pro Leu Ser
130                 135                 140

Val Ser Val Ser Pro Gly Glu Ser Ala Ser Ile Ser Cys Arg Ser Ser
145                 150                 155                 160

Lys Thr Leu Leu Asn Thr Arg Gly Ile Thr Ser Leu Tyr Trp Tyr Leu
                165                 170                 175

Gln Lys Pro Gly Lys Ser Pro Gln Leu Leu Ile Tyr Arg Met Ser Asn
            180                 185                 190

Leu Ala Ser Gly Ile Pro Asp Arg Phe Ser Gly Ser Gly Ser Glu Thr
        195                 200                 205

His Phe Thr Leu Gln Ile Ser Lys Val Glu Thr Glu Asp Val Gly Ile
    210                 215                 220

Tyr Tyr Cys Ala Gln Phe Leu Glu Phe Pro Leu Thr Phe Gly Cys Gly
225                 230                 235                 240

Thr Lys Leu Glu Ile Lys Gly Gly Gly Ser Phe Trp Val Leu Val
                245                 250                 255

Val Val Gly Gly Val Leu Ala Cys Tyr Ser Leu Leu Val Thr Val Ala
            260                 265                 270

Phe Ile Ile Phe Trp Val Arg Ser Lys Arg Ser Arg Leu Leu His Ser
        275                 280                 285

Asp Tyr Met Asn Met Thr Pro Arg Arg Pro Gly Pro Thr Arg Lys His
    290                 295                 300

Tyr Gln Pro Tyr Ala Pro Pro Arg Asp Phe Ala Ala Tyr Arg Ser Arg
305                 310                 315                 320

Val Lys Phe Ser Arg Ser Ala Asp Ala Pro Ala Tyr Gln Gln Gly Gln
                325                 330                 335

Asn Gln Leu Tyr Asn Glu Leu Asn Leu Gly Arg Arg Glu Tyr Asp
                340                 345                 350

Val Leu Asp Lys Arg Arg Gly Arg Asp Pro Glu Met Gly Gly Lys Pro
            355                 360                 365

Arg Arg Lys Asn Pro Gln Glu Gly Leu Tyr Asn Glu Leu Gln Lys Asp
370                 375                 380

Lys Met Ala Glu Ala Tyr Ser Glu Ile Gly Met Lys Gly Glu Arg Arg
385                 390                 395                 400

Arg Gly Lys Gly His Asp Gly Leu Tyr Gln Gly Leu Ser Thr Ala Thr
                405                 410                 415

Lys Asp Thr Tyr Asp Ala Leu His Met Gln Ala Leu Pro Pro Arg
            420                 425                 430

<210> SEQ ID NO 89
<211> LENGTH: 246
<212> TYPE: PRT
<213> ORGANISM: Artificial sequence
<220> FEATURE:
<223> OTHER INFORMATION: Anti-HA-scFv

<400> SEQUENCE: 89

Glu Val Gln Leu Val Glu Ser Gly Gly Gly Leu Val Gln Pro Gly Arg
1               5                   10                  15

Ser Met Lys Leu Ser Cys Ala Val Ser Gly Phe Ile Phe Ser Asn Tyr
            20                  25                  30

Asp Met Ala Trp Val Arg Gln Ala Pro Lys Lys Cys Leu Glu Trp Val
        35                  40                  45

Ala Thr Ile Ser His Asp Gly Arg Asn Thr Asn Tyr Arg Asp Ser Val
    50                  55                  60

Lys Gly Arg Phe Thr Gly Ser Arg Asp Ser Ala Gln Ser Thr Leu Tyr
65                  70                  75                  80

Leu Gln Met Asp Ser Leu Arg Ser Glu Asp Thr Ala Ile Tyr Phe Cys
                85                  90                  95

Ala Gly Pro Gly Phe Ala His Trp Gly Gln Gly Thr Leu Val Thr Val
            100                 105                 110

Ser Ser Gly Gly Gly Gly Ser Gly Gly Gly Ser Gly Gly Gly Gly
            115                 120                 125

Ser Gly Gly Gly Gly Ser Asp Ile Val Leu Thr Gln Ala Pro Leu Ser
130                 135                 140

Val Ser Val Ser Pro Gly Glu Ser Ala Ser Ile Ser Cys Arg Ser Ser
145                 150                 155                 160

Lys Thr Leu Leu Asn Thr Arg Gly Ile Thr Ser Leu Tyr Trp Tyr Leu
                165                 170                 175

Gln Lys Pro Gly Lys Ser Pro Gln Leu Leu Ile Tyr Arg Met Ser Asn
            180                 185                 190

Leu Ala Ser Gly Ile Pro Asp Arg Phe Ser Gly Ser Gly Ser Glu Thr
        195                 200                 205

His Phe Thr Leu Gln Ile Ser Lys Val Glu Thr Glu Asp Val Gly Ile
    210                 215                 220

Tyr Tyr Cys Ala Gln Phe Leu Glu Phe Pro Leu Thr Phe Gly Cys Gly
225                 230                 235                 240

Thr Lys Leu Glu Ile Lys
                245

<210> SEQ ID NO 90
<211> LENGTH: 114

```
<212> TYPE: PRT
<213> ORGANISM: Artificial sequence
<220> FEATURE:
<223> OTHER INFORMATION: Anti-HA VH

<400> SEQUENCE: 90
```

Glu Val Gln Leu Val Glu Ser Gly Gly Gly Leu Val Gln Pro Gly Arg
1               5                   10                  15

Ser Met Lys Leu Ser Cys Ala Val Ser Gly Phe Ile Phe Ser Asn Tyr
            20                  25                  30

Asp Met Ala Trp Val Arg Gln Ala Pro Lys Lys Cys Leu Glu Trp Val
        35                  40                  45

Ala Thr Ile Ser His Asp Gly Arg Asn Thr Asn Tyr Arg Asp Ser Val
    50                  55                  60

Lys Gly Arg Phe Thr Gly Ser Arg Asp Ser Ala Gln Ser Thr Leu Tyr
65                  70                  75                  80

Leu Gln Met Asp Ser Leu Arg Ser Glu Asp Thr Ala Ile Tyr Phe Cys
                85                  90                  95

Ala Gly Pro Gly Phe Ala His Trp Gly Gln Gly Thr Leu Val Thr Val
            100                 105                 110

Ser Ser

```
<210> SEQ ID NO 91
<211> LENGTH: 112
<212> TYPE: PRT
<213> ORGANISM: Artificial sequence
<220> FEATURE:
<223> OTHER INFORMATION: Anti-HA VL

<400> SEQUENCE: 91
```

Asp Ile Val Leu Thr Gln Ala Pro Leu Ser Val Ser Val Ser Pro Gly
1               5                   10                  15

Glu Ser Ala Ser Ile Ser Cys Arg Ser Ser Lys Thr Leu Leu Asn Thr
            20                  25                  30

Arg Gly Ile Thr Ser Leu Tyr Trp Tyr Leu Gln Lys Pro Gly Lys Ser
        35                  40                  45

Pro Gln Leu Leu Ile Tyr Arg Met Ser Asn Leu Ala Ser Gly Ile Pro
    50                  55                  60

Asp Arg Phe Ser Gly Ser Gly Ser Glu Thr His Phe Thr Leu Gln Ile
65                  70                  75                  80

Ser Lys Val Glu Thr Glu Asp Val Gly Ile Tyr Tyr Cys Ala Gln Phe
                85                  90                  95

Leu Glu Phe Pro Leu Thr Phe Gly Cys Gly Thr Lys Leu Glu Ile Lys
            100                 105                 110

```
<210> SEQ ID NO 92
<211> LENGTH: 5
<212> TYPE: PRT
<213> ORGANISM: Artificial sequence
<220> FEATURE:
<223> OTHER INFORMATION: Anti-myc CDR H1 Kabat

<400> SEQUENCE: 92
```

His Tyr Gly Met Ser
1               5

```
<210> SEQ ID NO 93
<211> LENGTH: 17
<212> TYPE: PRT
<213> ORGANISM: Artificial sequence
```

```
<220> FEATURE:
<223> OTHER INFORMATION: Anti-myc CDR H2 Kabat

<400> SEQUENCE: 93

Thr Ile Gly Ser Arg Gly Thr Tyr Thr His Tyr Pro Asp Ser Val Lys
1               5                   10                  15

Gly

<210> SEQ ID NO 94
<211> LENGTH: 18
<212> TYPE: PRT
<213> ORGANISM: Artificial sequence
<220> FEATURE:
<223> OTHER INFORMATION: Anti-myc CDR H3 Kabat

<400> SEQUENCE: 94

Arg Ser Glu Phe Tyr Tyr Tyr Gly Asn Thr Tyr Tyr Tyr Ser Ala Met
1               5                   10                  15

Asp Tyr

<210> SEQ ID NO 95
<211> LENGTH: 15
<212> TYPE: PRT
<213> ORGANISM: Artificial sequence
<220> FEATURE:
<223> OTHER INFORMATION: Anti-myc CDR L1 Kabat

<400> SEQUENCE: 95

Arg Ala Ser Glu Ser Val Asp Asn Tyr Gly Phe Ser Phe Met Asn
1               5                   10                  15

<210> SEQ ID NO 96
<211> LENGTH: 7
<212> TYPE: PRT
<213> ORGANISM: Artificial sequence
<220> FEATURE:
<223> OTHER INFORMATION: Anti-myc CDR L2 Kabat

<400> SEQUENCE: 96

Ala Ile Ser Asn Arg Gly Ser
1               5

<210> SEQ ID NO 97
<211> LENGTH: 9
<212> TYPE: PRT
<213> ORGANISM: Artificial sequence
<220> FEATURE:
<223> OTHER INFORMATION: Anti-myc CDR L3 Kabat

<400> SEQUENCE: 97

Gln Gln Thr Lys Glu Val Pro Trp Thr
1               5

<210> SEQ ID NO 98
<211> LENGTH: 414
<212> TYPE: PRT
<213> ORGANISM: Artificial sequence
<220> FEATURE:
<223> OTHER INFORMATION: Anti-myc-Fab-heavy chain-CD28ATD-CD28CSD-
      CD3zSSD fusion

<400> SEQUENCE: 98

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser His Tyr
```

20                  25                  30
Gly Met Ser Trp Val Arg Gln Thr Pro Asp Lys Arg Leu Glu Trp Val
        35                  40                  45

Ala Thr Ile Gly Ser Arg Gly Thr Tyr Thr His Tyr Pro Asp Ser Val
    50                  55                  60

Lys Gly Arg Phe Thr Ile Ser Arg Asp Asn Lys Asn Ala Leu Tyr
65                  70                  75                  80

Leu Gln Met Asn Ser Leu Lys Ser Glu Asp Thr Ala Met Tyr Tyr Cys
                85                  90                  95

Ala Arg Arg Ser Glu Phe Tyr Tyr Gly Asn Thr Tyr Tyr Ser
            100                 105                 110

Ala Met Asp Tyr Trp Gly Gln Gly Ala Ser Val Thr Val Ser Ser Ala
            115                 120                 125

Lys Thr Thr Pro Pro Ser Val Tyr Pro Leu Ala Pro Gly Ser Ala Ala
    130                 135                 140

Gln Thr Asn Ser Met Val Thr Leu Gly Cys Leu Val Lys Gly Tyr Phe
145                 150                 155                 160

Pro Glu Pro Val Thr Val Thr Trp Asn Ser Gly Ser Leu Ser Ser Gly
                165                 170                 175

Val His Thr Phe Pro Ala Val Leu Gln Ser Asp Leu Tyr Thr Leu Ser
            180                 185                 190

Ser Ser Val Thr Val Pro Ser Ser Thr Trp Pro Ser Glu Thr Val Thr
        195                 200                 205

Cys Asn Val Ala His Pro Ala Ser Ser Thr Lys Val Asp Lys Lys Ile
210                 215                 220

Val Pro Arg Asp Cys Gly Gly Gly Ser Phe Trp Val Leu Val Val
225                 230                 235                 240

Val Gly Gly Val Leu Ala Cys Tyr Ser Leu Leu Val Thr Val Ala Phe
            245                 250                 255

Ile Ile Phe Trp Val Arg Ser Lys Arg Ser Arg Leu Leu His Ser Asp
            260                 265                 270

Tyr Met Asn Met Thr Pro Arg Arg Pro Gly Pro Thr Arg Lys His Tyr
        275                 280                 285

Gln Pro Tyr Ala Pro Pro Arg Asp Phe Ala Ala Tyr Arg Ser Arg Val
    290                 295                 300

Lys Phe Ser Arg Ser Ala Asp Ala Pro Ala Tyr Gln Gln Gly Gln Asn
305                 310                 315                 320

Gln Leu Tyr Asn Glu Leu Asn Leu Gly Arg Arg Glu Glu Tyr Asp Val
                325                 330                 335

Leu Asp Lys Arg Arg Gly Arg Asp Pro Glu Met Gly Gly Lys Pro Arg
            340                 345                 350

Arg Lys Asn Pro Gln Glu Gly Leu Tyr Asn Glu Leu Gln Lys Asp Lys
        355                 360                 365

Met Ala Glu Ala Tyr Ser Glu Ile Gly Met Lys Gly Glu Arg Arg Arg
    370                 375                 380

Gly Lys Gly His Asp Gly Leu Tyr Gln Gly Leu Ser Thr Ala Thr Lys
385                 390                 395                 400

Asp Thr Tyr Asp Ala Leu His Met Gln Ala Leu Pro Pro Arg
                405                 410

<210> SEQ ID NO 99
<211> LENGTH: 229
<212> TYPE: PRT
<213> ORGANISM: Artificial sequence

```
<220> FEATURE:
<223> OTHER INFORMATION: Anti-myc-Fab heavy chain

<400> SEQUENCE: 99
```

| | | | | | | | | | | | | | | |
|---|---|---|---|---|---|---|---|---|---|---|---|---|---|---|
|Glu|Val|His|Leu|Val|Glu|Ser|Gly|Gly|Asp|Leu|Val|Lys|Pro|Gly|
|1| | | |5| | | | |10| | | | |15|
|Ser|Leu|Lys|Leu|Ser|Cys|Ala|Ala|Ser|Gly|Phe|Thr|Phe|Ser|His|Tyr
| | | |20| | | | |25| | | | |30| |
|Gly|Met|Ser|Trp|Val|Arg|Gln|Thr|Pro|Asp|Lys|Arg|Leu|Glu|Trp|Val
| | |35| | | | |40| | | | |45| | |
|Ala|Thr|Ile|Gly|Ser|Arg|Gly|Thr|Tyr|Thr|His|Tyr|Pro|Asp|Ser|Val
| |50| | | | |55| | | | |60| | | |
|Lys|Gly|Arg|Phe|Thr|Ile|Ser|Arg|Asp|Asn|Asp|Lys|Asn|Ala|Leu|Tyr
|65| | | | |70| | | | |75| | | | |80
|Leu|Gln|Met|Asn|Ser|Leu|Lys|Ser|Glu|Asp|Thr|Ala|Met|Tyr|Tyr|Cys
| | | | |85| | | | |90| | | | |95|
|Ala|Arg|Arg|Ser|Glu|Phe|Tyr|Tyr|Tyr|Gly|Asn|Thr|Tyr|Tyr|Tyr|Ser
| | | |100| | | | |105| | | | |110| |
|Ala|Met|Asp|Tyr|Trp|Gly|Gln|Gly|Ala|Ser|Val|Thr|Val|Ser|Ser|Ala
| | |115| | | | |120| | | | |125| | |
|Lys|Thr|Thr|Pro|Pro|Ser|Val|Tyr|Pro|Leu|Ala|Pro|Gly|Ser|Ala|Ala
|130| | | | |135| | | | |140| | | | |
|Gln|Thr|Asn|Ser|Met|Val|Thr|Leu|Gly|Cys|Leu|Val|Lys|Gly|Tyr|Phe
|145| | | | |150| | | | |155| | | | |160
|Pro|Glu|Pro|Val|Thr|Val|Thr|Trp|Asn|Ser|Gly|Ser|Leu|Ser|Ser|Gly
| | | |165| | | | |170| | | | |175| |
|Val|His|Thr|Phe|Pro|Ala|Val|Leu|Gln|Ser|Asp|Leu|Tyr|Thr|Leu|Ser
| | |180| | | | |185| | | | |190| | |
|Ser|Ser|Val|Thr|Val|Pro|Ser|Ser|Thr|Trp|Pro|Ser|Glu|Thr|Val|Thr
| |195| | | | |200| | | | |205| | | |
|Cys|Asn|Val|Ala|His|Pro|Ala|Ser|Ser|Thr|Lys|Val|Asp|Lys|Lys|Ile
|210| | | | |215| | | | |220| | | | |
|Val|Pro|Arg|Asp|Cys| | | | | | | | | | |
|225| | | | | | | | | | | | | | |

```
<210> SEQ ID NO 100
<211> LENGTH: 218
<212> TYPE: PRT
<213> ORGANISM: Artificial sequence
<220> FEATURE:
<223> OTHER INFORMATION: Anti-myc-Fab light chain

<400> SEQUENCE: 100
```

| | | | | | | | | | | | | | | | |
|---|---|---|---|---|---|---|---|---|---|---|---|---|---|---|---|
|Asp|Ile|Val|Leu|Thr|Gln|Ser|Pro|Ala|Ser|Leu|Ala|Val|Ser|Leu|Gly
|1| | | |5| | | | |10| | | | |15| |
|Gln|Arg|Ala|Thr|Ile|Ser|Cys|Arg|Ala|Ser|Glu|Ser|Val|Asp|Asn|Tyr
| | | |20| | | | |25| | | | |30| | |
|Gly|Phe|Ser|Phe|Met|Asn|Trp|Phe|Gln|Gln|Lys|Pro|Gly|Gln|Pro|Pro
| | |35| | | | |40| | | | |45| | | |
|Lys|Leu|Leu|Ile|Tyr|Ala|Ile|Ser|Asn|Arg|Gly|Ser|Gly|Val|Pro|Ala
| |50| | | | |55| | | | |60| | | | |
|Arg|Phe|Ser|Gly|Ser|Gly|Ser|Gly|Thr|Asp|Phe|Ser|Leu|Asn|Ile|His
|65| | | | |70| | | | |75| | | | |80|
|Pro|Val|Glu|Glu|Asp|Asp|Pro|Ala|Met|Tyr|Phe|Cys|Gln|Gln|Thr|Lys
| | | | |85| | | | |90| | | | |95| |
|Glu|Val|Pro|Trp|Thr|Phe|Gly|Gly|Gly|Thr|Lys|Leu|Glu|Ile|Lys|Arg

```
                100                 105                 110
Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 101
<211> LENGTH: 127
<212> TYPE: PRT
<213> ORGANISM: Artificial sequence
<220> FEATURE:
<223> OTHER INFORMATION: Anti-myc VH

<400> SEQUENCE: 101

Glu Val His Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser His Tyr
            20                  25                  30

Gly Met Ser Trp Val Arg Gln Thr Pro Asp Lys Arg Leu Glu Trp Val
        35                  40                  45

Ala Thr Ile Gly Ser Arg Gly Thr Tyr Thr His Tyr Pro Asp Ser Val
    50                  55                  60

Lys Gly Arg Phe Thr Ile Ser Arg Asp Asn Asp Lys Asn Ala Leu Tyr
65                  70                  75                  80

Leu Gln Met Asn Ser Leu Lys Ser Glu Asp Thr Ala Met Tyr Tyr Cys
                85                  90                  95

Ala Arg Arg Ser Glu Phe Tyr Tyr Tyr Gly Asn Thr Tyr Tyr Tyr Ser
            100                 105                 110

Ala Met Asp Tyr Trp Gly Gln Gly Ala Ser Val Thr Val Ser Ser
        115                 120                 125

<210> SEQ ID NO 102
<211> LENGTH: 111
<212> TYPE: PRT
<213> ORGANISM: Artificial sequence
<220> FEATURE:
<223> OTHER INFORMATION: Anti-myc VL

<400> SEQUENCE: 102

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Phe Ser Phe Met Asn Trp Phe Gln Gln Lys Pro Gly Gln Pro Pro
        35                  40                  45

Lys Leu Leu Ile Tyr Ala Ile Ser Asn Arg Gly Ser Gly Val Pro Ala
    50                  55                  60
```

```
Arg Phe Ser Gly Ser Gly Ser Gly Thr Asp Phe Ser Leu Asn Ile His
65                  70                  75                  80

Pro Val Glu Glu Asp Asp Pro Ala Met Tyr Phe Cys Gln Gln Thr Lys
                85                  90                  95

Glu Val Pro Trp Thr Phe Gly Gly Gly Thr Lys Leu Glu Ile Lys
            100                 105                 110
```

<210> SEQ ID NO 103
<211> LENGTH: 9
<212> TYPE: PRT
<213> ORGANISM: Artificial sequence
<220> FEATURE:
<223> OTHER INFORMATION: HA tag

<400> SEQUENCE: 103

```
Tyr Pro Tyr Asp Val Pro Asp Tyr Ala
1               5
```

<210> SEQ ID NO 104
<211> LENGTH: 10
<212> TYPE: PRT
<213> ORGANISM: Artificial sequence
<220> FEATURE:
<223> OTHER INFORMATION: Myc tag

<400> SEQUENCE: 104

```
Glu Gln Lys Leu Ile Ser Glu Glu Asp Leu
1               5                   10
```

<210> SEQ ID NO 105
<211> LENGTH: 12
<212> TYPE: PRT
<213> ORGANISM: Artificial sequence
<220> FEATURE:
<223> OTHER INFORMATION: GCN4 tag

<400> SEQUENCE: 105

```
Tyr His Leu Glu Asn Glu Val Ala Arg Leu Lys Lys
1               5                   10
```

<210> SEQ ID NO 106
<211> LENGTH: 15
<212> TYPE: PRT
<213> ORGANISM: Artificial sequence
<220> FEATURE:
<223> OTHER INFORMATION: AviTag

<400> SEQUENCE: 106

```
Gly Leu Asn Asp Ile Phe Glu Ala Gln Lys Ile Glu Trp His Glu
1               5                   10                  15
```

<210> SEQ ID NO 107
<211> LENGTH: 164
<212> TYPE: PRT
<213> ORGANISM: Homo sapiens

<400> SEQUENCE: 107

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
```

```
                50                  55                  60
Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                 85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 108
<211> LENGTH: 492
<212> TYPE: DNA
<213> ORGANISM: Homo sapiens

<400> SEQUENCE: 108
atgaagtgga aggcgctttt caccgcggcc atcctgcagg cacagttgcc gattacagag      60
gcacagagct ttggcctgct ggatcccaaa ctctgctacc tgctggatgg aatcctcttc     120
atctatggtg tcattctcac tgccttgttc ctgagagtga agttcagcag gagcgcagag     180
ccccccgcgt accagcaggg ccagaaccag ctctataacg agctcaatct aggacgaaga     240
gaggagtacg atgttttgga caagagacgt ggccgggacc ctgagatggg gggaaagccg     300
agaaggaaga accctcagga aggcctgtac aatgaactgc agaaagataa gatggcggag     360
gcctacagtg agattgggat gaaaggcgag cgccggaggg caaggggca cgatggcctt     420 taccagggtc tcagtacagc caccaaggac acctacgacg cccttcacat gcaggccctg     480 cccccctcgct aa                                                       492

<210> SEQ ID NO 109
<211> LENGTH: 164
<212> TYPE: PRT
<213> ORGANISM: Mus musculus

<400> SEQUENCE: 109

Met Lys Trp Lys Val Ser Val Leu Ala Cys Ile Leu His Val Arg Phe
 1               5                  10                  15

Pro Gly Ala Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Thr Ala
            35                  40                  45

Leu Tyr Leu Arg Ala Lys Phe Ser Arg Ser Ala Glu Thr Ala Ala Asn
        50                  55                  60

Leu Gln Asp Pro Asn Gln Leu Tyr Asn Glu Leu Asn Leu Gly Arg Arg
 65                  70                  75                  80

Glu Glu Tyr Asp Val Leu Glu Lys Lys Arg Ala Arg Asp Pro Glu Met
                 85                  90                  95

Gly Gly Lys Gln Gln Arg Arg Arg Asn Pro Gln Glu Gly Val Tyr Asn
                100                 105                 110

Ala Leu Gln Lys Asp Lys Met Ala Glu Ala Tyr Ser Glu Ile Gly Thr
            115                 120                 125
```

Lys Gly Glu Arg Arg Gly Lys Gly His Asp Gly Leu Tyr Gln Gly
                130                 135                 140

Leu Ser Thr Ala Thr Lys Asp Thr Tyr Asp Ala Leu His Met Gln Thr
145                 150                 155                 160

Leu Ala Pro Arg

<210> SEQ ID NO 110
<211> LENGTH: 495
<212> TYPE: DNA
<213> ORGANISM: Mus musculus

<400> SEQUENCE: 110
atgaagtgga aagtgtctgt tctcgcctgc atcctccacg tgcggttccc aggagcagag    60
gcacagagct tggtctgct ggatcccaaa ctctgctact tgctagatgg aatcctcttc    120
atctacggag tcatcatcac agccctgtac ctgagagcaa aattcagcag gagtgcagag    180
actgctgcca acctgcagga ccccaaccag ctctacaatg agctcaatct agggcgaaga    240
gaggaatatg acgtcttgga agaagcgg gctcgggatc agagatggg aggcaaacag      300 cagaggagga ggaacccca ggaaggcgta caatgcac tgcagaaaga caagatggca      360
gaagcctaca gtgagatcgg cacaaaaggc gagaggcgga gaggcaaggg gcacgatggc    420
ctttaccagg gtctcagcac tgccaccaag gacacctatg atgccctgca tatgcagacc    480 ctggccctc gctaa                                                      495

<210> SEQ ID NO 111
<211> LENGTH: 660
<212> TYPE: DNA
<213> ORGANISM: Homo sapiens

<400> SEQUENCE: 111
atgctgcgcc tgctgctggc gctgaacctg tttccgagca ttcaggtgac cggcaacaaa    60
attctggtga acagagccc gatgctggtg gcgtatgata cgcgggtgaa cctgagctgc    120
aaatatagct ataacctgtt tagccgcgaa tttcgcgcga gcctgcataa aggcctggat    180
agcgcggtgg aagtgtgcgt ggtgtatggc aactatagcc agcagctgca ggtgtatagc    240
aaaaccggct ttaactgcga tgcaaactg ggcaacgaaa gcgtgacctt ttatctgcag    300
aacctgtatg tgaaccagac cgatatttat ttttgcaaaa ttgaagtgat gtatccgccg    360
ccgtatctgg ataacgaaaa aagcaacggc accattattc atgtgaaagg caaacatctg    420
tgcccgagcc cgctgttcc gggcccgagc aaaccgtttt gggtgctggt ggtggtgggc    480
ggcgtgctgg cgtgctatag cctgctggtg accgtggcgt ttattatttt tgggtgcgc    540 agcaaacgca gccgcctgct gcatagcgat tatatgaaca tgacccccgcg ccgcccgggc    600 ccgacccgca acattatca gccgtatgcg ccgccgcgcg attttgcggc gtatcgcagc    660

<210> SEQ ID NO 112
<211> LENGTH: 220
<212> TYPE: PRT
<213> ORGANISM: Homo sapiens

<400> SEQUENCE: 112

Met Leu Arg Leu Leu Leu Ala Leu Asn Leu Phe Pro Ser Ile Gln Val
1                 5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
         35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
             100                 105                 110

Lys Ile Glu Val Met Tyr Pro Pro Pro Tyr Leu Asp Asn Glu Lys Ser
         115                 120                 125

Asn Gly Thr Ile Ile His Val Lys Gly Lys His Leu Cys Pro Ser Pro
130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                 165                 170                 175

Phe Trp Val Arg Ser Lys Arg Ser Arg Leu Leu His Ser Asp Tyr Met
             180                 185                 190

Asn Met Thr Pro Arg Arg Pro Gly Pro Thr Arg Lys His Tyr Gln Pro
         195                 200                 205

Tyr Ala Pro Pro Arg Asp Phe Ala Ala Tyr Arg Ser
210                 215                 220

<210> SEQ ID NO 113
<211> LENGTH: 654
<212> TYPE: DNA
<213> ORGANISM: Mus musculus

<400> SEQUENCE: 113
atgaccctgc gcctgctgtt tctggcgctg aactttttta gcgtgcaggt gaccgaaaac      60
aaaattctgg tgaaacagag cccgctgctg gtggtggata gcaacgaagt gagcctgagc     120
tgccgctata gctataacct gctggcgaaa gaatttcgcg cgagcctgta taaaggcgtg     180
aacagcgatg tggaagtgtg cgtgggcaac ggcaacttta cctatcagcc gcagtttcgc     240
agcaacgcgg aatttaactg cgatggcgat tttgataacg aaaccgtgac ctttcgcctg     300
tggaacctgc atgtgaacca taccgatatt tattttgca aaattgaatt tatgtatccg      360
ccgccgtatc tggataacga acgcagcaac ggcaccatta ttcatattaa agaaaaacat     420
ctgtgccata cccagagcag cccgaaactg ttttgggcgc tggtggtggt ggcgggcgtg     480
ctgttttgct atggcctgct ggtgaccgtg gcgctgtgcg tgatttggac caacagccgc     540
cgcaaccgcc tgctgcagag cgattatatg aacatgaccc cgcgccgccc gggcctgacc     600
cgcaaaccgt atcagccgta tgcgccggcg cgcgattttg cggcgtatcg cccg            654

<210> SEQ ID NO 114
<211> LENGTH: 218
<212> TYPE: PRT
<213> ORGANISM: Mus musculus

<400> SEQUENCE: 114

Met Thr Leu Arg Leu Leu Phe Leu Ala Leu Asn Phe Phe Ser Val Gln
 1               5                  10                  15

Val Thr Glu Asn Lys Ile Leu Val Lys Gln Ser Pro Leu Leu Val Val
             20                  25                  30

```
Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
 50                  55                  60

Glu Val Cys Val Gly Asn Gly Asn Phe Thr Tyr Gln Pro Gln Phe Arg
 65                  70                  75                  80

Ser Asn Ala Glu Phe Asn Cys Asp Gly Asp Phe Asp Asn Glu Thr Val
                 85                  90                  95

Thr Phe Arg Leu Trp Asn Leu His Val Asn His Thr Asp Ile Tyr Phe
                100                 105                 110

Cys Lys Ile Glu Phe Met Tyr Pro Pro Tyr Leu Asp Asn Glu Arg
                115                 120                 125

Ser Asn Gly Thr Ile Ile His Ile Lys Glu Lys His Leu Cys His Thr
            130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
                180                 185                 190

Thr Pro Arg Arg Pro Gly Leu Thr Arg Lys Pro Tyr Gln Pro Tyr Ala
                195                 200                 205

Pro Ala Arg Asp Phe Ala Ala Tyr Arg Pro
            210                 215
```

```
<210> SEQ ID NO 115
<211> LENGTH: 4
<212> TYPE: PRT
<213> ORGANISM: Artificial sequence
<220> FEATURE:
<223> OTHER INFORMATION: CD28 YMNM

<400> SEQUENCE: 115

Tyr Met Asn Met
1
```

```
<210> SEQ ID NO 116
<211> LENGTH: 4
<212> TYPE: PRT
<213> ORGANISM: Artificial sequence
<220> FEATURE:
<223> OTHER INFORMATION: CD28 PYAP

<400> SEQUENCE: 116

Pro Tyr Ala Pro
1
```

```
<210> SEQ ID NO 117
<211> LENGTH: 21
<212> TYPE: PRT
<213> ORGANISM: Artificial sequence
<220> FEATURE:
<223> OTHER INFORMATION: Signal peptide

<400> SEQUENCE: 117

Ala Thr Met Gly Trp Ser Cys Ile Ile Leu Phe Leu Val Ala Thr Ala
1               5                   10                  15

Thr Gly Val His Ser
            20
```

<210> SEQ ID NO 118
<211> LENGTH: 57
<212> TYPE: DNA
<213> ORGANISM: Artificial sequence
<220> FEATURE:
<223> OTHER INFORMATION: Signal peptide DNA sequence

<400> SEQUENCE: 118
atgggatgga gctgtatcat cctcttcttg gtagcaacag ctaccggtgt gcactcc      57

<210> SEQ ID NO 119
<211> LENGTH: 449
<212> TYPE: PRT
<213> ORGANISM: Artificial sequence
<220> FEATURE:
<223> OTHER INFORMATION: Anti-CD20 (GA101) PGLALA heavy chain

<400> SEQUENCE: 119

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 120
<211> LENGTH: 219
<212> TYPE: PRT
<213> ORGANISM: Artificial sequence
<220> FEATURE:
<223> OTHER INFORMATION: Anti-CD20 (GA101) light chain

<400> SEQUENCE: 120

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
```

<210> SEQ ID NO 121
<211> LENGTH: 451
<212> TYPE: PRT
<213> ORGANISM: Artificial sequence
<220> FEATURE:
<223> OTHER INFORMATION: Anti-CEA (CH1A1A98/992F1) PGLALA heavy chain

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser

```
                355                 360                 365
Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 122
<211> LENGTH: 215
<212> TYPE: PRT
<213> ORGANISM: Artificial sequence
<220> FEATURE:
<223> OTHER INFORMATION: Anti-CEA (CH1A1A98/992F1) light chain

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
                20                  25                  30

Val Ala Trp Tyr Gln Gln Lys Pro Gly Lys Ala Pro Lys Leu Leu Ile
                35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 123
<211> LENGTH: 330
<212> TYPE: PRT
<213> ORGANISM: Artificial sequence
<220> FEATURE:
<223> OTHER INFORMATION: Human IgG1 Fc
```

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 124
<211> LENGTH: 372
<212> TYPE: PRT
<213> ORGANISM: Artificial sequence
<220> FEATURE:
<223> OTHER INFORMATION: Anti-WT1 (33F05) PGLALA heavy chain

<400> SEQUENCE: 124

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Asn Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Ser Tyr Tyr Glu Ala Phe Asp Tyr Trp Gly Gln Gly Thr Leu Val
             100                 105                 110

Thr Val Ser Ser Leu Gly Thr Gln Thr Tyr Ile Cys Asn Val Asn
         115                 120                 125

His Lys Pro Ser Asn Thr Lys Val Asp Lys Lys Val Glu Pro Lys Ser
     130                 135                 140

Cys Asp Lys Thr His Thr Cys Pro Pro Cys Pro Ala Pro Glu Ala Ala
145                 150                 155                 160

Gly Gly Pro Ser Val Phe Leu Phe Pro Pro Lys Pro Lys Asp Thr Leu
                 165                 170                 175

Met Ile Ser Arg Thr Pro Glu Val Thr Cys Val Val Val Asp Val Ser
             180                 185                 190

His Glu Asp Pro Glu Val Lys Phe Asn Trp Tyr Val Asp Gly Val Glu
         195                 200                 205

Val His Asn Ala Lys Thr Lys Pro Arg Glu Glu Gln Tyr Asn Ser Thr
     210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Gly Ala Pro
                 245                 250                 255

Ile Glu Lys Thr Ile Ser Lys Ala Lys Gly Gln Pro Arg Glu Pro Gln
             260                 265                 270

Val Cys Thr Leu Pro Pro Ser Arg Asp Glu Leu Thr Lys Asn Gln Val
         275                 280                 285

Ser Leu Ser Cys Ala Val Lys Gly Phe Tyr Pro Ser Asp Ile Ala Val
     290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Val Ser Lys Leu Thr
                 325                 330                 335

Val Asp Lys Ser Arg Trp Gln Gln Gly Asn Val Phe Ser Cys Ser Val
             340                 345                 350

Met His Glu Ala Leu His Asn His Tyr Thr Gln Lys Ser Leu Ser Leu
         355                 360                 365

Ser Pro Gly Lys
     370

<210> SEQ ID NO 125
<211> LENGTH: 214
<212> TYPE: PRT
<213> ORGANISM: Artificial sequence
<220> FEATURE:
<223> OTHER INFORMATION: Anti-WT1 (33F05) light chain

<400> SEQUENCE: 125
```

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Pro Asp Met Asn Gly Asn Ala
                85                  90                  95

Val Phe Gly Gly Gly Thr Lys Leu Thr Val Leu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 126
<211> LENGTH: 376
<212> TYPE: PRT
<213> ORGANISM: Artificial sequence
<220> FEATURE:
<223> OTHER INFORMATION: Anti-WT1 (11D06) PGLALA heavy chain

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Glu Leu Trp Trp Gly Gly Phe Asp Tyr Trp Gly Gln
            100                 105                 110

Gly Thr Thr Val Thr Val Ser Ser Leu Gly Thr Gln Thr Tyr Ile
        115                 120                 125

Cys Asn Val Asn His Lys Pro Ser Asn Thr Lys Val Asp Lys Lys Val
130                 135                 140
```

Glu Pro Lys Ser Cys Asp Lys Thr His Thr Cys Pro Pro Cys Pro Ala
145                 150                 155                 160

Pro Glu Ala Ala Gly Gly Pro Ser Val Phe Leu Phe Pro Pro Lys Pro
            165                 170                 175

Lys Asp Thr Leu Met Ile Ser Arg Thr Pro Glu Val Thr Cys Val Val
        180                 185                 190

Val Asp Val Ser His Glu Asp Pro Glu Val Lys Phe Asn Trp Tyr Val
    195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Gly Ala Pro Ile Glu Lys Thr Ile Ser Lys Ala Lys Gly Gln Pro
            260                 265                 270

Arg Glu Pro Gln Val Cys Thr Leu Pro Pro Ser Arg Asp Glu Leu Thr
        275                 280                 285

Lys Asn Gln Val Ser Leu Ser Cys Ala Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Val
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375

<210> SEQ ID NO 127
<211> LENGTH: 213
<212> TYPE: PRT
<213> ORGANISM: Artificial sequence
<220> FEATURE:
<223> OTHER INFORMATION: Anti-WT1 (11D06) light chain

<400> SEQUENCE: 127

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Gly Ser Leu Gln Pro
65                  70                  75                  80

Asp Asp Phe Ala Thr Tyr Tyr Cys Gln Gln Tyr Glu Asp Tyr Thr Thr
            85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 128
<211> LENGTH: 375
<212> TYPE: PRT
<213> ORGANISM: Artificial sequence
<220> FEATURE:
<223> OTHER INFORMATION: Anti-WT1 (33H09) PGLALA heavy chain

<400> SEQUENCE: 128

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Asp Leu Phe Ser Leu Asp Tyr Trp Gly Gln Gly
                100                 105                 110

Thr Thr Val Thr Val Ser Ser Leu Gly Thr Gln Thr Tyr Ile Cys
            115                 120                 125

Asn Val Asn His Lys Pro Ser Asn Thr Lys Val Asp Lys Lys Val Glu
    130                 135                 140

Pro Lys Ser Cys Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
                180                 185                 190

Asp Val Ser His Glu Asp Pro Glu Val Lys Phe Asn Trp Tyr Val Asp
                195                 200                 205

Gly Val Glu Val His Asn Ala Lys Thr Lys Pro Arg Glu Glu Gln Tyr
                210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Gly Ala Pro Ile Glu Lys Thr Ile Ser Lys Ala Lys Gly Gln Pro Arg
                260                 265                 270
```

```
Glu Pro Gln Val Cys Thr Leu Pro Ser Arg Asp Glu Leu Thr Lys
            275                 280                 285

Asn Gln Val Ser Leu Ser Cys Ala Val Lys Gly Phe Tyr Pro Ser Asp
        290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Leu Val Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys
    370                 375

<210> SEQ ID NO 129
<211> LENGTH: 213
<212> TYPE: PRT
<213> ORGANISM: Artificial sequence
<220> FEATURE:
<223> OTHER INFORMATION: Anti-WT1 (33H09) light chain

<400> SEQUENCE: 129

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asp Gly Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 130
<211> LENGTH: 375
<212> TYPE: PRT
<213> ORGANISM: Artificial sequence
<220> FEATURE:
```

<223> OTHER INFORMATION: Anti-WT1 (5E11) PGLALA heavy chain

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Asp Leu Tyr Ser Phe Asp Tyr Trp Gly Gln Gly
            100                 105                 110

Thr Thr Val Thr Val Ser Ser Leu Gly Thr Gln Thr Tyr Ile Cys
        115                 120                 125

Asn Val Asn His Lys Pro Ser Asn Thr Lys Val Asp Lys Lys Val Glu
130                 135                 140

Pro Lys Ser Cys Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
            165                 170                 175

Asp Thr Leu Met Ile Ser Arg Thr Pro Glu Val Thr Cys Val Val Val
        180                 185                 190

Asp Val Ser His Glu Asp Pro Glu Val Lys Phe Asn Trp Tyr Val Asp
    195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Gly Ala Pro Ile Glu Lys Thr Ile Ser Lys Ala Lys Gly Gln Pro Arg
            260                 265                 270

Glu Pro Gln Val Cys Thr Leu Pro Pro Ser Arg Asp Glu Leu Thr Lys
        275                 280                 285

Asn Gln Val Ser Leu Ser Cys Ala Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Val Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
        370                 375

<210> SEQ ID NO 131
<211> LENGTH: 215

```
<212> TYPE: PRT
<213> ORGANISM: Artificial sequence
<220> FEATURE:
<223> OTHER INFORMATION: Anti-WT1 (5E11) light chain

<400> SEQUENCE: 131

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Phe Pro Pro Met
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 132
<211> LENGTH: 330
<212> TYPE: PRT
<213> ORGANISM: Homo sapiens

<400> SEQUENCE: 132

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

-continued

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```